United States Patent
Biggart et al.

(10) Patent No.: US 11,123,348 B2
(45) Date of Patent: *Sep. 21, 2021

(54) COMPOUNDS AND COMPOSITIONS FOR THE TREATMENT OF PARASITIC DISEASES

(71) Applicant: NOVARTIS AG, Basel (CH)

(72) Inventors: Agnes Biggart, Spring Valley, CA (US); Fang Liang, Encinitas, CA (US); Casey Jacob Nelson Mathison, San Diego, CA (US); Valentina Molteni, San Diego, CA (US); Advait Suresh Nagle, San Diego, CA (US); Frantisek Supek, San Diego, CA (US); Vince Yeh, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,628

(22) Filed: Feb. 3, 2020

(65) Prior Publication Data

US 2020/0179391 A1 Jun. 11, 2020

Related U.S. Application Data

(60) Division of application No. 16/116,418, filed on Aug. 29, 2018, now Pat. No. 10,596,175, which is a continuation of application No. 15/600,183, filed on May 19, 2017, now Pat. No. 10,085,989, which is a continuation of application No. 15/051,446, filed on Feb. 23, 2016, now Pat. No. 9,700,559, which is a division of application No. 14/574,775, filed on Dec. 18, 2014, now Pat. No. 9,303,034.

(60) Provisional application No. 61/918,089, filed on Dec. 19, 2013.

(51) Int. Cl.
| | |
|---|---|
| *A61K 31/519* | (2006.01) |
| *C07D 487/04* | (2006.01) |
| *C07D 519/00* | (2006.01) |
| *C07F 5/02* | (2006.01) |
| *C07F 7/08* | (2006.01) |
| *A61K 31/5377* | (2006.01) |
| *A61K 31/695* | (2006.01) |
| *A61K 45/06* | (2006.01) |

(52) U.S. Cl.
CPC ........ *A61K 31/519* (2013.01); *A61K 31/5377* (2013.01); *A61K 31/695* (2013.01); *A61K 45/06* (2013.01); *C07D 487/04* (2013.01); *C07D 519/00* (2013.01); *C07F 5/027* (2013.01); *C07F 7/0814* (2013.01); *Y02A 50/30* (2018.01)

(58) Field of Classification Search
CPC .................................................. A61K 31/519
See application file for complete search history.

(56) References Cited

U.S. PATENT DOCUMENTS

| | | | |
|---|---|---|---|
| 4,038,396 A | 7/1977 | Shen et al. | |
| 4,582,837 A | 4/1986 | Hauel et al. | |
| 5,077,408 A | 12/1991 | Guillaumet et al. | |
| 5,434,150 A | 7/1995 | Austel et al. | |
| 2005/0101647 A1 | 5/2005 | Oda et al. | |
| 2005/0214901 A1 | 9/2005 | Ealick et al. | |
| 2005/0282853 A1 | 12/2005 | Boykin et al. | |
| 2007/0148185 A1 | 6/2007 | Rathore et al. | |
| 2009/0163545 A1 | 6/2009 | Goldfarb | |
| 2010/0168084 A1 | 7/2010 | Huber et al. | |
| 2011/0053915 A1 | 3/2011 | Ivaschenko et al. | |
| 2011/0182812 A1 | 7/2011 | Szardenings et al. | |
| 2014/0274926 A1 | 9/2014 | Chatterjee et al. | |
| 2014/0275013 A1 | 9/2014 | Chatterjee et al. | |
| 2014/0275119 A1 | 9/2014 | Liang et al. | |

FOREIGN PATENT DOCUMENTS

| | | |
|---|---|---|
| CA | 2011222 A1 | 9/1990 |
| DE | 4129603 A1 | 3/1993 |
| DE | 1304650 A1 | 8/1994 |
| EP | 700906 A1 | 3/1996 |

(Continued)

OTHER PUBLICATIONS

Al-Salabi, et al., "Purine Nucleobase Transport in Amastigotes of Leishmania mexicana: Involvement in Allopurinol Uptake", Antimicrobial Agents and Chemotherapy, Sep. 2005, vol. 49, No. 9, pp. 3682-3689, American Society for Microbiology, US.

(Continued)

*Primary Examiner* — Brian E McDowell
(74) *Attorney, Agent, or Firm* — Emily T. Wu

(57) ABSTRACT

The present invention provides compounds of Formula A:

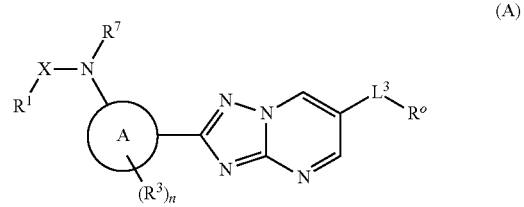

Figure 1:
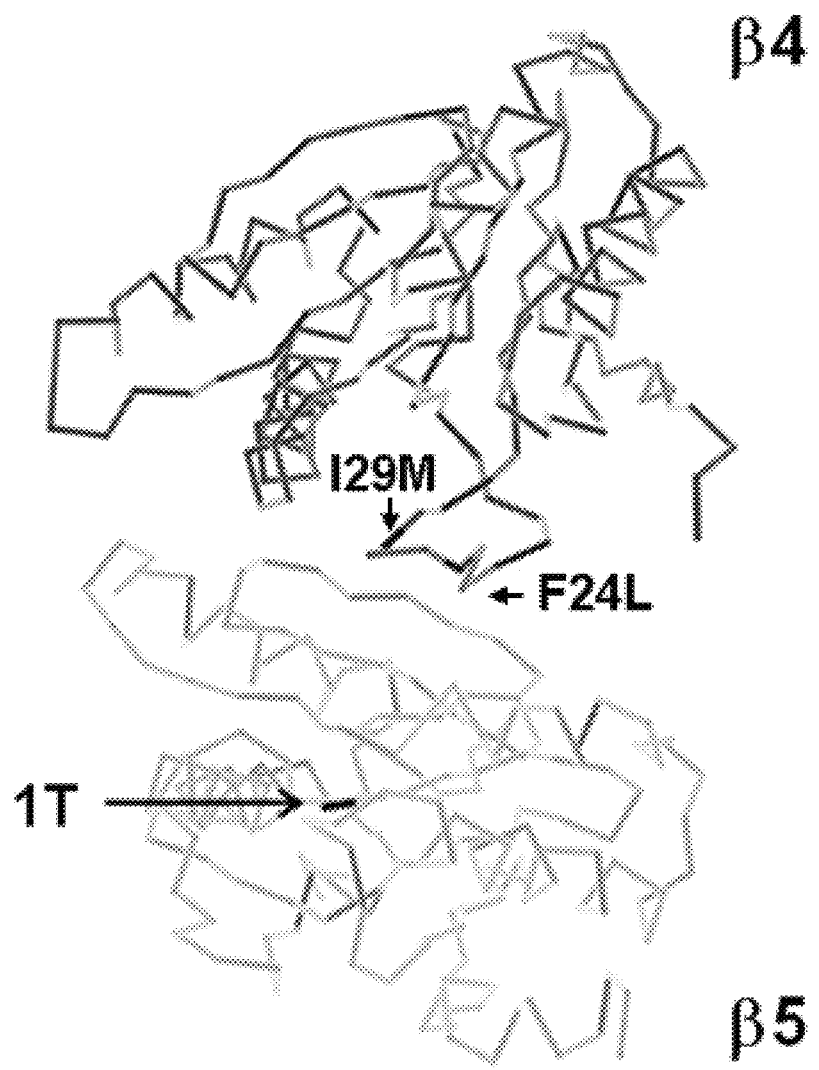

or a pharmaceutically acceptable salt, tautomer, or stereoisomer, thereof, wherein the variables are as defined herein. The present invention further provides pharmaceutical compositions comprising such compounds and methods of using such compounds for treating, preventing, inhibiting, ameliorating, or eradicating the pathology and/or symptomology of a disease caused by a parasite, such as leishmaniasis, human African trypanosomiasis and Chagas disease.

5 Claims, 2 Drawing Sheets

(56) References Cited

FOREIGN PATENT DOCUMENTS

| | | | |
|---|---|---|---|
| EP | 1460067 | A1 | 9/2004 |
| WO | 199806703 | A1 | 2/1998 |
| WO | 9810779 | A1 | 3/1998 |
| WO | 2001070743 | A1 | 9/2001 |
| WO | 2001096336 | A2 | 12/2001 |
| WO | 2002036580 | A2 | 5/2002 |
| WO | 2002038153 | A1 | 5/2002 |
| WO | 2002044126 | A2 | 6/2002 |
| WO | 2002075318 | A2 | 9/2002 |
| WO | 2003011219 | A2 | 2/2003 |
| WO | 2003042185 | A1 | 5/2003 |
| WO | 2003045929 | A1 | 6/2003 |
| WO | 2004024897 | A2 | 3/2004 |
| WO | 2005013950 | A2 | 2/2005 |
| WO | 2005014598 | A1 | 2/2005 |
| WO | 2005023761 | A2 | 3/2005 |
| WO | 2005030206 | A1 | 4/2005 |
| WO | 2006066913 | A2 | 6/2006 |
| WO | 2006066914 | A2 | 6/2006 |
| WO | 2006101456 | A1 | 9/2006 |
| WO | 007017143 | A1 | 2/2007 |
| WO | 2007014707 | A1 | 2/2007 |
| WO | 2007019417 | A1 | 2/2007 |
| WO | 2007028135 | A2 | 3/2007 |
| WO | 2008007900 | A1 | 1/2008 |
| WO | 2008021388 | A1 | 2/2008 |
| WO | 2008048991 | A2 | 4/2008 |
| WO | 2008100376 | A2 | 8/2008 |
| WO | 2008118122 | A2 | 10/2008 |
| WO | 2008128968 | A1 | 10/2008 |
| WO | 2009005551 | A2 | 1/2009 |
| WO | 2009005675 | A1 | 1/2009 |
| WO | 2009006389 | A2 | 1/2009 |
| WO | 2009051454 | A2 | 4/2009 |
| WO | 2009077956 | A2 | 6/2009 |
| WO | 2009112445 | A1 | 9/2009 |
| WO | 2009151546 | A2 | 12/2009 |
| WO | 2010027746 | A2 | 3/2010 |
| WO | 2011027249 | A2 | 3/2011 |
| WO | 2011153377 | A2 | 8/2011 |
| WO | 2012088411 | A1 | 6/2012 |
| WO | 2012130633 | A1 | 10/2012 |
| WO | 2013024282 | A2 | 2/2013 |
| WO | 2013071169 | A1 | 5/2013 |
| WO | 2013078254 | A1 | 5/2013 |
| WO | 2013147711 | A1 | 10/2013 |
| WO | 2013009827 | A1 | 1/2014 |
| WO | 2014003124 | A1 | 1/2014 |
| WO | 2014012511 | A1 | 1/2014 |
| WO | 2014028968 | A1 | 2/2014 |
| WO | 2014151630 | A2 | 9/2014 |
| WO | 2014151729 | A1 | 9/2014 |
| WO | 2014151784 | A1 | 9/2014 |

OTHER PUBLICATIONS

Hwang, et al., "Optimization of Chloronitrobenzamides (CNBs) as Therapeutic Leads for Human African Trypanosomiasis (HAT)", Journal of Medicinal Chemistry, Mar. 13, 2013, vol. 56, pp. 2850-2860.

Lan, et al., "Molecular modeling studies on imidazol [4,5-b]pyridine derivatives as Aurora A kinase inhibitors using 3D-QSAR and docking approaches", European Journal of Medicinal Chemistry, 2011, vol. 46, pp. 77-94.

Middleton, et al., "Synthesis of Imidazo[4,5-b]- and [4,5-c]pyridines", J. Heterocyclic Chem., 1980, vol. 17, pp. 1757-1760.

Savarino, et al., "Aminophenyl-X-azolopyridines as Precursors of Heterocyclic Azo Dyes", J. Heterocyclic Chem., 1989, vol. 26, pp. 289-292.

Verlinde, et al., "Selective Inhibition of Trypanosomal Glyceraldehyde-3-phosphate Dehydrogenase by Protein Structure-Based Design: Toward New Drugs for the Treatment of Sleeping Sickness", J. Med. Chem., 1994, vol. 37, pp. 3605-3613; American Chemical Society.

Ferrins, et al., "3-(Oxazolo[4,5-pyridin-2-yl)anlidies as a novel class of potent inhibitors for the kinetoplastid Trypanosoma brucei, the causative agent for human African trypanosomiasis", European Journal of Medicinal Chemistry, 2013, vol. 66, pp. 450-465, Elsevier Massson SAS.

Wu, et al., "Discovery and Mechanism Study of SIRT1 Activators that Promote the Deacetylation of Fluorophore-Labeled Substrate", Journal of Medicinal Chemistry, 2013, vol. 56, No. 3, pp. 761-780, American Chemical Society.

Bemis, et al., "Discovery of oxazolo[4,5-b]pyridines and related heterocyclic analogs as noval SIRT1 activators", Bioorganic & Medicinal Chemistry Letters, 2009, vol. 19, pp. 2350-2353, Elsevier Ltd.

Cheng, et al., "High-throughput identification of antibacterials against methiciliin-resistant *Staphylococcus aureas* (MRSA) and the transglycosylase", Bioorganic & Medicinal Chemistry, 2010, vol. 18, pp. 8512-8529, Elsevier Ltd.

Park, et al., "3D-QSAR of SIRT1 Activators Targeting Against Diet-Induced Metabolic Syndrome", Bull. Korean Chem. Soc., 2009, vol. 30, No. 9, pp. 2117-2120.

Vu, et al., "Discovery of Imidazo[1,2-b]thiazole Derivatives as Novel SIRT1 Activators", Journal of Medicinal Chemistry, 2009, vol. 52, pp. 1275-1283, American Chemical Society.

Chakraborty, et al., "Studies on omithine decarboxylase of Leishmania donovani: structure modeling and inhibitor docking", Medicinal Chemistry Research, 2013, vol. 22, pp. 466-478.

Tatipaka, et al., "Substituted 2-Phenyl-Imidazopyridines: A New Class of Drug Leads for Human African Trypanosomiasis", Journal of Medicinal Chemistry, Dec. 19, 2013, vol. 57, No. 3, pp. 828-835, American Chemical Society.

Novinson, et al., "Novel Heterocyclic Nitrofurfural Hydrazones. In Vivo Antitryanosomal Activity", Journal of Medicinal Chemistry, 1976, vol. 19, No. 4, pp. 512-516.

Database Registry Chemical Abstracts Service, Columbus, Ohio, US, Aug. 14, 2007, Database accession No. 944581-06-0.

Caballero, et al., "Triazolopyrimidine compounds containing first-row transition metals and their activity against the neglected infectous Chagas disease and leishmaniasis", European Journal of Medicinal Chemistry, 2014, vol. 85, pp. 526-534, Elsevier Masson SAS.

Caballero, et al., "Lanthanide complexes containing 5-methyl-1,2,4-triazolo[1,5-a] pyrimidine-7(4H)-one and their therapeutic potential to fight leishmaniasis and Chagas disease", Journal of Inorganic Biochemistry, 2014, vol. 138, pp. 39-46, Elsevier Inc.

De Rycker, et al., "Comparison of a High-Throughput High-Content Intracellular Leishmania donovani Assay with an Axenic Amastrigote Assay", Antimicrobial Agents and Chemotherapy, 2013, vol. 57, No. 7, pp. 2913-2922.

COMPOUNDS AND COMPOSITIONS FOR THE TREATMENT OF PARASITIC DISEASES

CROSS-REFERENCE TO RELATED APPLICATIONS

This application is a divisional of U.S. application Ser. No. 16/116,418 filed 29 Aug. 2018; which is a continuation of U.S. application Ser. No. 15/600,183 filed 19 May 2017; which is a continuation of U.S. application Ser. No. 15/051,446, filed 23 Feb. 2016; which is a divisional of U.S. application Ser. No. 14/574,775, filed 18 Dec. 2014; which claims the benefit of priority to U.S. Provisional Patent Application No. 61/918,089, filed 19 Dec. 2013. The full disclosure of these applications are incorporated herein by reference in their entirety and for all purposes.

BACKGROUND OF THE INVENTION

Field of the Invention

The invention provides a class of compounds, pharmaceutical compositions comprising such compounds and methods of using such compounds to treat or prevent leishmaniasis, human African trypanosomiasis and Chagas disease.

Background

Leishmaniasis is a disease caused by protozoan parasites that belong to the genus *Leishmania* and is transmitted by the bite of certain species of sand fly.

Leishmaniasis is mostly a disease of the developing world, and is rarely known in the developed world outside a small number of cases, mostly in instances where troops are stationed away from their home countries. Leishmaniasis can be transmitted in many tropical and subtropical countries, and is found in parts of about 88 countries. Approximately 350 million people live in these areas. The settings in which leishmaniasis is found range from rainforests in Central and South America to deserts in West Asia and the Middle East. It affects as many as 12 million people worldwide, with 1.5-2 million new cases each year. The visceral form of leishmaniasis has an estimated incidence of 500,000 new cases and 60,000 deaths each year. More than 90 percent of the world's cases of visceral leishmaniasis are in India, Bangladesh, Nepal, Sudan, and Brazil. Kabul is estimated as the largest center of cutaneous leishmaniasis in the world, with approximately 67,500 cases as of 2004.

There are four main forms of Leishmaniasis. Cutaneous leishmaniasis is the most common form of leishmaniasis. Visceral leishmaniasis, also called kala-azar, is the most serious form in which the parasites migrate to the vital organs. Visceral leishmaniasis is caused by the parasite *Leishmania donovani*, and is potentially fatal if untreated. Currently, no vaccines are in routine use.

The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects. Amphotericin (AmBisome) is now the treatment of choice. Miltefosine (Impavido) and paromomycin are the other treatment alternatives. These drugs are known to produce a definitive cure in >90% of patients. Amphotericin (AmBisome) is expansive and has to be given intravenously; it is not affordable to most patients affected. Paromomycin, although affordable, requires intramuscular injections for 3 weeks; compliance is a major issue. Miltefosine is an oral drug and has shown to be more effective and better tolerated than other drugs. However, there are problems associated with the use of miltefosine that arise from its teratogenicity and pharmacokinetics. Miltefosine was shown to be much slower eliminated from the body and was still detectable five months after the end of treatment. The presence of subtherapeutic miltefosine concentrations in the blood beyond five months after treatment might contribute to the selection of resistant parasites and, moreover, the measures for preventing the teratogenic risks of miltefosine must be reconsidered. This led to some reluctance to taking Miltefosine by affected populations.

The Drugs for Neglected Diseases Initiative is actively facilitating the search for novel therapeutics. Our invention meets that needs.

Human African trypanosomiasis (HAT), also known as African sleeping sickness, is a vector-borne parasitic disease caused by the protozoa *Trypanosoma brucei*. There are two subspecies that infect humans, *T.b. gambiense* and *T.b. rhodesiense*, with the former accounting for over 95% of reported cases and the latter accounting for the remaining reported cases. The parasites are transmitted to humans by tsetse fly (*Glossina* genus) bites which have acquired their infection from human beings or from animals harboring the human pathogenic parasites.

The disease has been recorded as occurring in 36 countries, all in subtropical and equatorial Africa. It is endemic in southeast Uganda and western Kenya. In 1995, the WHO estimated that 300,000 people were afflicted with the disease. In its 2001 report, the WHO set the figure of people at risk of infection at 60 million, of which only 4 to 5 million had access to any kind of medical monitoring. In 2006, the WHO estimated that about 70,000 people could have the disease, and many cases are believed to go unreported. About 48,000 people died of sleeping sickness in 2008. Public health efforts in prevention and the eradication of the tsetse fly population have proven to be successful in controlling the spread of the disease; under 10,000 new cases were reported in 2009 according to WHO figures, which represents a huge decrease from the estimated 300,000 new cases in 1998.

African trypanosomiasis symptoms occur in two stages. In the first stage, known as the haemolymphatic phase, the trypanosomes multiply in subcutaneous tissues, blood and lymph. The haemolymphatic phase is characterized by bouts of fever, headaches, joint pains and itching. In the second stage, the neurological phase, the parasites cross the blood-brain barrier to infect the central nervous system. It is in this stage when more obvious signs and symptoms of the disease appear: changes of behaviour, confusion, sensory disturbances and poor coordination. Disturbance of the sleep cycle, which gives the disease its name, is an important feature of the second stage of the disease. Without treatment, the disease is invariably fatal, with progressive mental deterioration leading to coma, systemic organ failure, and death.

Four drugs are registered for the treatment of sleeping sickness. The protocol depends on the stage of the disease. The current standard treatment for first-stage disease is intravenous or intramuscular pentamidine (for *T.b. gambiense*), or intravenous suramin (for *T.b. rhodesiense*). The current standard treatment for second-stage disease is: Intravenous melarsoprol, or intravenous melarsoprol in combination with oral nifurtimox, intravenous eflornithine only or eflornithine in combination with nifurtimox. All of the drugs have undesirable or sometime serious side effects. For example, 3-10% of patients those injected with Melarsoprol (Arsobal), an organoarsenical, developed reactive encephalopathy (convulsions, progressive coma, or psychotic reactions), and 10-70% of such cases result in death.

Chagas disease, also called American trypanosomiasis, is a tropical parasitic disease caused by the flagellate protozoan *Trypanosoma cruzi*. *T. cruzi* is commonly transmitted to humans and other mammals by the blood-sucking "kissing bugs" of the subfamily Triatominae (family Reduviidae).

Chagas disease is contracted primarily in the Americas. It is endemic in twenty one Cental and Latin American countries; particularly in poor, rural areas of Mexico, Central America, and South America. Large-scale population movements from rural to urban areas of Latin America and to other regions of the world have increased the geographic distribution of Chagas disease, and cases have been noted in many countries, particularly in Europe. Although there are triatomine bugs in the U.S., only very rarely vectorborne cases of Chagas disease have been documented.

Each year, an estimated 10 to 15 million people across the world are infected with Chagas disease, most of whom do not know they are infected. Every year, 14,000 people die as a consequence of the disease. In Central and South America, Chagas kills more people than any other parasite-borne disease, including malaria. By applying published seroprevalence figures to immigrant populations, CDC estimates that more than 300,000 persons with *Trypanosoma cruzi* infection live in the United States. Most people with Chagas disease in the United States acquired their infections in endemic countries.

Chagas disease has an acute and a chronic phase. If untreated, infection is lifelong.

Acute Chagas disease occurs immediately after infection, may last up to a few weeks or months, and parasites may be found in the circulating blood. Infection may be mild or asymptomatic. There may be fever or swelling around the site of inoculation (where the parasite entered into the skin or mucous membrane). Rarely, acute infection may result in severe inflammation of the heart muscle or the brain and lining around the brain. The initial acute phase is responsive to antiparasitic treatments, with 60-90% cure rates.

Following the acute phase, most infected people enter into a prolonged asymptomatic form of disease (called "chronic indeterminate") during which few or no parasites are found in the blood. During this time, most people are unaware of their infection. Many people may remain asymptomatic for life and never develop Chagas-related symptoms. However, an estimated 20-30% of infected people will develop debilitating and sometimes life-threatening medical problems over the course of their lives.

The symptoms of Chagas disease vary over the course of an infection. In the early, acute stage, symptoms are mild and usually produce no more than local swelling at the site of infection. The initial acute phase is responsive to antiparasitic treatments, with 60-90% cure rates. After 4-8 weeks, individuals with active infections enter the chronic phase of Chagas disease that is asymptomatic for 60-80% of chronically infected individuals through their lifetime.

There is no vaccine against Chagas disease. Treatment for Chagas disease focuses on killing the parasite and managing signs and symptoms.

During the acute phase of Chagas disease, the drugs currently available for treatment are benznidazole and nifurtimox. Once Chagas disease reaches the chronic phase, medications aren't effective for curing the disease. Instead, treatment depends on the specific signs and symptoms. However, problems with these current therapies include their diverse side effects, the length of treatment, and the requirement for medical supervision during treatment. Resistance to the two frontline drugs has already occurred. The antifungal agent Amphotericin b has been proposed as a second-line drug, but this drug is costly and relatively toxic.

In view of the foregoing, it is desirable to develop novel compounds as antiparasitic agents.

SUMMARY OF THE INVENTION

The invention therefore provides a compound of Formula (A):

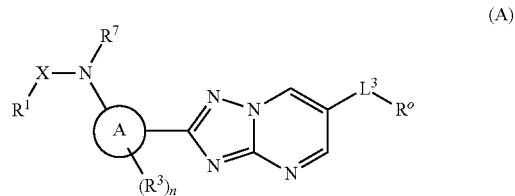

(A)

or a pharmaceutically acceptable salt, or stereoisomer thereof; wherein

Ring A is phenyl or pyridyl;

X is —C(O)— or —S(O)$_2$—;

$R^1$ is selected from nitro, $C_{1-4}$alkyl, $C_{1-6}$alkoxy, amino, $C_{1-6}$alkylamino, di-$C_{1-6}$alkylamino, —N($C_2H_3$)$_2$, $C_{3-6}$cycloalkyl, $C_{4-6}$heterocycloalkyl, $C_{4-8}$heterocycloalkenyl, and $C_{5-9}$heteroaryl, wherein the $C_{1-6}$alkoxy, $C_{1-6}$alkylamino, $C_{3-6}$cycloalkyl, $C_{4-6}$heterocycloalkyl, $C_{4-8}$heterocycloalkenyl, or $C_{5-9}$heteroaryl of $R^1$ is unsubstituted or substituted by 1-2 substituents independently selected from halo, cyano, $C_{1-4}$alkyl, halo$C_{1-4}$alkyl, $C_{1-4}$alkoxy, amino, $C_{1-4}$alkylamino, di$C_{1-4}$alkylamino, and hydroxycarbonyl, and $C_{1-4}$alkylcarbonyl;

$R^3$ is selected from hydrogen, halo, cyano, $C_{1-4}$alkyl, and halo$C_{1-4}$alkyl, and n is 0, 1, or 2;

$R^7$ is selected from hydrogen or $C_{1-4}$alkyl;

$L^3$ is a bond, phenylene, or $C_{5-8}$heteroarylene;

$R^0$ is selected from hydrogen, hydroxyl, halo, nitro, —N═CHN(CH$_3$)$_2$, $C_{1-4}$alkyl, $C_{4-6}$heterocycloalkyl $C_{1-4}$alkyl, $C_{1-4}$alkoxy, —NR$^{2a}$R$^{2b}$, —NR$^5$C(O)R$^6$, —NR$^5$S(O)$_2$R$^8$, —Si(CH$_3$)$_3$, $C_{3-6}$cycloalkyl, $C_{5-6}$cycloalkenyl, $C_{4-6}$heterocycloalkyl, $C_{5-8}$heterocycloalkenyl, $C_{6-10}$aryl, and $C_{5-6}$heteroaryl; wherein the $C_{1-4}$alkyl or $C_{1-4}$alkoxy of $R^0$ is unsubstituted or substituted by 1-2 substituents independently selected from $C_{1-4}$alkoxy, amino, phenyl and $C_{5-6}$heteroaryl; wherein the phenyl or $C_{5-6}$heteroaryl substituent of $R^0$ is unsubstituted or substituted by halo or $C_{1-4}$ alkyl;

the $C_{3-6}$cycloalkyl, $C_{5-6}$cycloalkenyl, $C_{4-8}$heterocycloalkyl, $C_{5-8}$heterocycloalkenyl, $C_{6-10}$aryl, and $C_{5-6}$heteroaryl of $R^0$ is unsubstituted or substituted by 1 to 4 substituents independently selected from halo, oxo, $C_{1-4}$alkyl, hydroxy$C_{1-4}$alkyl, halo$C_{1-4}$alkyl, —(CH$_2$)$_{1-4}$NR$^a$R$^b$, $C_{4-6}$heterocycloalkylC$_{1-4}$alkyl, benzyl, $C_{1-4}$alkoxy, amino, $C_{1-4}$alkylamino, di$C_{1-4}$alkylamino, unsubstituted $C_{4-6}$heterocycloalkyl and $C_{1-4}$alkyl substituted $C_{4-6}$heterocycloalkyl, wherein $R^a$ and $R^b$ are each independently selected from hydrogen, $C_{1-4}$alkyl, and $C_{3-6}$cycloalkyl;

$R^{2a}$ is hydrogen or $C_{1-4}$alkyl;

$R^{2b}$ is selected from hydrogen, $C_{1-4}$alkyl and —C(O)OCH(CH$_3$)$_2$, wherein the $C_{1-4}$alkyl of $R^{2b}$ is unsubstituted or substituted by amino, $C_{4-6}$heterocycloalkyl, phenyl or $C_{5-6}$heteroaryl, wherein the $C_{4-6}$heterocycloalkyl, phenyl or $C_{5-6}$heteroaryl substituent of $R^{2b}$ is unsubstituted or substituted by hydroxyl, halo or $C_{1-4}$alkyl;

$R^5$ is hydrogen or $C_{1-4}$alkyl;

$R^6$ is selected from hydrogen, $C_{1-4}$alkyl, $C_{1-4}$alkoxy, $C_{3-6}$cycloalkyloxy, amino, $C_{3-6}$cycloalkyl, $C_{5-6}$heterocycloalkyl, and $C_{5-6}$heteroaryl, wherein the $C_{1-4}$alkyl, $C_{1-4}$alkoxy, $C_{3-6}$cycloalkyloxy, or amino of $R^6$ is unsubstituted or substituted by to 2 substituents independently selected from halo, hydroxyl, $C_{1-4}$alkyl, halo$C_{1-4}$alkyl, $C_{1-4}$alkoxy, —NR$^{9a}$R$^{9b}$, $C_{3-6}$cycloalkyl, $C_{5-6}$heterocycloalkyl, and $C_{5-6}$heteroaryl, wherein $R^{9a}$ is hydrogen or $C_{1-4}$alkyl, $R^{9b}$ is selected from hydrogen, $C_{1-4}$alkyl, $C_{1-4}$alkylcarbonyl and $C_{1-4}$alkoxycarbonyl, and the $C_{5-6}$heterocycloalkyl or $C_{5-8}$heteroaryl substituent of $R^6$ is each unsubstituted or substituted by 1-2 substituents independently selected from hydroxyl, $C_{1-4}$alkyl and $C_{1-4}$alkoxycarbonyl, the $C_{3-6}$cycloalkyl or $C_{4-6}$heterocycloalkyl of $R^6$ is unsubstituted or substituted by 1 to 2 substituents independently selected from halo, cyano, hydroxyl, $C_{1-4}$alkyl, halo$C_{1-4}$alkyl, $C_{1-4}$alkoxy$C_{1-4}$alkyl, $C_{1-4}$alkoxy, amino, $C_{1-4}$alkylamino, di-$C_{1-4}$alkylamino, aminocarbonyl, $C_{1-4}$alkoxycarbonyl, and $C_{1-4}$alkoxycarbonylamino$C_{1-4}$alkyl, and the $C_{5-6}$heteroaryl of $R^6$ is unsubstituted or substituted by 1 to 2 substituents independently selected from hydroxyl, $C_{1-4}$alkyl, $C_{1-4}$alkoxy, amino, $C_{1-4}$alkylamino, di-$C_{1-4}$alkylamino, and $C_{1-4}$alkoxycarbonyl; and $R^8$ is $C_{1-4}$alkyl or $C_{1-4}$alkylamino.

In a second aspect, the present invention provides a pharmaceutical composition which contains a compound of the invention selected from Formula I, a N-oxide derivative, individual isomers and mixture of isomers thereof; or a pharmaceutically acceptable salt thereof, in admixture with one or more suitable excipients.

In a third aspect, the present invention provides a method of treating a disease in an animal in which a compound of the invention can prevent, inhibit or ameliorate the pathology and/or symptomology of a disease caused by a parasite of the *Leishmania* genus, for example, *Leishmania donovani*, *Leishmania infantum*, *Leishmania braziliensis*, *Leishmania panamensis*, *Leishmania guayanensis*, *Leishmania amazonensis*, *Leishmania mexicana*, *Leishmania tropica*, *Leishmania major*, *Trypanosoma cruzi*, and *Trypanosoma brucei* and a parasite of the *Trypanosoma* genus, for example, *Trypanosoma cruzi* and *Trypanosoma brucei*, which method comprises administering to the animal a therapeutically effective amount of a compound selected from Formula I, an N-oxide derivative, individual isomers and mixture of isomers thereof, or a pharmaceutically acceptable salt thereof.

In a fourth aspect, the present invention provides a compound of Formula I, an N-oxide derivative, individual isomers and mixture of isomers thereof, or a pharmaceutically acceptable salt thereof, for treating, preventing, inhibiting, ameliorating, or eradicating the pathology and/or symptomology of a disease caused by a parasite of the *Leishmania* genus, for example, *Leishmania donovani*, *Leishmania infantum*, *Leishmania braziliensis*, *Leishmania panamensis*, *Leishmania guayanensis*, *Leishmania amazonensis*, *Leishmania mexicana*, *Leishmania tropica*, *Leishmania major*, *Trypanosoma cruzi*, and *Trypanosoma brucei* and a parasite of the *Trypanosoma* genus, such as, for example, *Trypanosoma cruzi* and *Trypanosoma brucei*. Particularly, the parasite is a *Leishmania*, and the disease is Leishmanaisis.

In a fifth aspect, the present invention provides the use of a compound selected from Formula I, an N-oxide derivative, individual isomers and mixture of isomers thereof, or a pharmaceutically acceptable salt thereof, in the manufacture of a medicament for treating a disease caused by a parasite in an animal. The disease may be Leishmaniasis, Human African Trypanosomiasis and/or Chagas disease.

In a sixth aspect, the present invention provides a method for treating, preventing, inhibiting, ameliorating, or eradicating the pathology and/or symptomology of a disease caused by a parasite, the method comprises administering to a subject in need thereof a therapeutically effective amount of an agent capable of inhibiting the activity of the proteasomes of the parasite, wherein the disease is selected from leishmaniasis, human African trypanosomiasis and Chagas disease.

Unless specified otherwise, the term "compounds of the present invention" refers to compounds of Fomula (I) and subformulae thereof, salts of the compound, hydrates or solvates of the compounds, salts, as well as all stereoisomers (including diastereoisomers and enantiomers), tautomers and isotopically labeled compounds (including deuterium substitutions). Compounds of the present invention further comprise polymorphs of compounds of formula I (or subformulae thereof) and salts thereof.

DETAILED DESCRIPTION OF THE FIGURES

FIG. 1. Crystal structure of *S. cerevisiae* proteasome with beta 4 and beta 5 subunits shown. Active site threonine (1T) in beta 5 subunit, which harbors chymotrypsin-like proteolytic activity, is indicated with the arrow. Two resistance mutations located to *T. cruzi* proteasome beta 4 subunit (I29M and F24L), which confer resistance to compounds of the invention, are positioned at the interface of beta 4 and beta 5 subunits.

Figure 2:
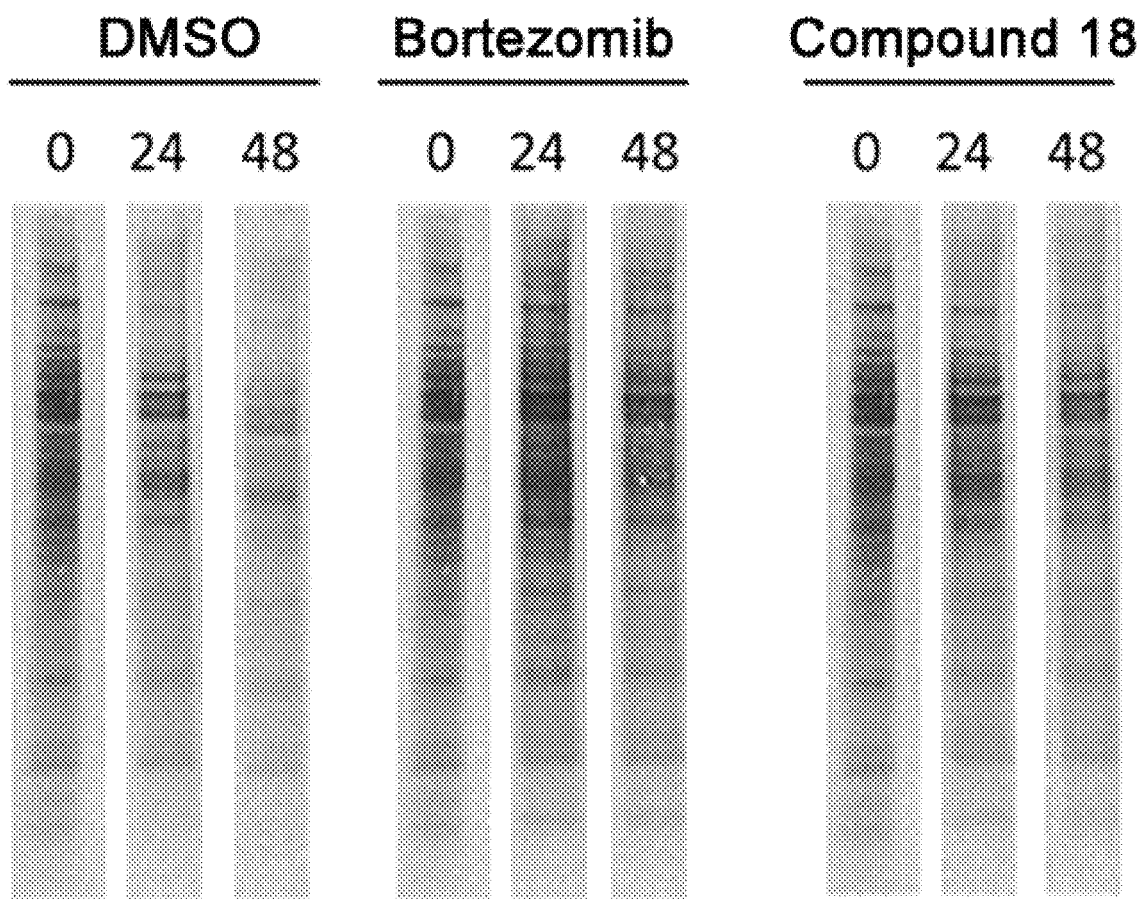

FIG. 2. Effect of Compound 18 on protein turnover in *Trypanosoma cruzi* trypomastigotes. Trypomastigotes were labeled for 2 hours with $^{35}$S methionine, washed and resuspended in a growth medium containing excess of non-radioactive methionine to prevent further protein labeling. Labeled trypomastigotes were incubated in the presence of DMSO, bortezomib (prototypical proteasome inhibitor) or Compound 8, and total cellular labeled proteins were analyzed by PAGE at 0, 24 and 48 hours. Similar to bortezomib, Compound 8 slowed down trypomastigote protein turnover, which can be clearly observed in the control experiment with DMSO.

DETAILED DESCRIPTION OF THE INVENTION

Definitions

For purposes of interpreting this specification, the following definitions will apply and whenever appropriate, terms used in the singular will also include the plural and vice versa.

"Alkoxy" as used herein refers the radical —O-alkyl, wherein the alkyl is as defined herein. $C_X$alkoxy and $C_{X-Y}$alkoxy as used herein describe alkoxy groups where X and Y indicate the number of carbon atoms in the alkyl chain. Representative examples of $C_{1-10}$alkoxy include, but are not limited to, methoxy, ethoxy, propoxy, 2-propoxy, butoxy, tert-butoxy, pentyloxy, hexyloxy, heptyloxy, octyloxy and decyloxy. The alkyl portion of the alkoxy may be unsubstituted or substituted, and the substituents include those described for the alkyl group below.

"Alkyl" as used herein refers to a fully saturated branched or unbranched hydrocarbon chain having up to 10 carbon atoms. $C_X$alkyl and $C_{X-Y}$alkyl as used herein describe alkyl groups where X and Y indicate the number of carbon atoms in the alkyl chain. For example, $C_{1-10}$ alkyl refers to an alkyl radical as defined above containing one to ten carbon atoms. $C_{1-10}$ alkyl includes, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Alkyl represented along with another radical like arylalkyl, heteroarylalkyl, alkoxyalkyl, alkoxyalkyl, alkylamino, where the alkyl portion shall have the same meaning as described for alkyl and is bonded to the other radical. For example, $(C_{6-10})$aryl$(C_{1-3})$alkyl includes, benzyl, phenylethyl, 1-phenylethyl, 3-phenylpropyl, 2-thienylmethyl, 2-pyridinylmethyl and the like.

Unless stated otherwise specifically in the specification, an alkyl group may be unsubstituted or substituted by one or more substituents to the extent that such substitution makes sense chemically. Typical substituents include, but are not limited to halo, hydroxyl, alkoxy, cyano, amino, acyl, aryl, arylalkyl, and cycloalkyl, or an heteroforms of one of these groups, and each of which can be substituted by the substituents that are appropriate for the particular group.

"Alkenyl" as used herein refers to a straight or branched, hydrocarbon chain having up to 10 carbon atoms and at least one carbon-carbon double bond. $C_X$alkenyl and $C_{X-Y}$alkenyl as used herein describe alkenyl groups where X and Y indicate the number of carbon atoms in the alkenyl chain. Examples of $C_{2-7}$alkenyl include vinyl, allyl, isopropenyl, pentenyl, hexenyl, heptenyl, 1-propenyl, 2-butenyl, 2-methyl-2-butenyl, and the like. The alkenyl may be unsubstituted or substituted, and the substituents include those described for the alkyl group descried herein.

"Alkynyl" as used herein refers to a straight or branched, hydrocarbon chain having up to 10 carbon atoms and at least one carbon-carbon triple bond. $C_X$alkynyl and $C_{X-Y}$alkynyl as used herein describe alkynyl groups, where X and Y indicate the number of carbon atoms in the alkynyl chain. For example, $C_{2-7}$alkynyl include, but are not limited to, ethynyl, propargyl, 3-methyl-1-pentynyl, 2-heptynyl and the like. An alkynyl may be unsubstituted or substituted, and the substituents include those described for the alkyl group described herein.

"Alkylene" as used herein refers to a divalent alkyl group defined herein. Examples of $C_{1-10}$alkylene includes, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene. An alkylene group may be unsubstituted or substituted, and the substituents include those described for the alkyl group described herein.

"Amino" as used herein refers to the radical —NH$_2$. When an amino is described as "substituted" or "optionally substituted", the term includes NR'R" wherein each R' and R" is independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl or groups or heteroforms of one of these groups, each of which is optionally substituted with the substituents described herein as suitable for the corresponding group.

The term "amino" also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Alkylamino" as used herein refers to the radical —NR$_a$R$_b$, where at least one of, or both, R$_a$ and R$_b$ are an alkyl group as described herein. A $C_{1-4}$alkylamino group includes —NHC$_{1-4}$alkyl and —N(C$_{1-4}$alkyl)$_2$; e.g., —NHCH$_3$, —N(CH$_3$)$_2$, —NH(CH$_2$CH$_3$), —N(CH$_2$CH$_3$)$_2$, and the like.

"Aromatic" as used herein refers to a moiety wherein the constituent atoms make up an unsaturated ring system, where all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" as used herein refers to a 6-14 membered monocyclic or polycyclic aromatic ring assembly where all the ring atoms are carbon atoms. Typically, the aryl is a 6 membered monocyclic, a 10-12 membered bicyclic or a 14-membered fused tricyclic aromatic ring system. $C_X$aryl and $C_{X-Y}$aryl as used herein describe an aryl group where X and Y indicate the number of carbon atoms in the ring system. $C_{6-14}$aryls include, but are not limited to, phenyl, biphenyl, naphthyl, azulenyl, and anthracenyl.

An aryl may be unsubstituted or substituted by 1-5 (such as one, or two, or three) substituents independently selected from the group consisting of hydroxy, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl, aryl, heteroaryl, cycloalkyl and heterocycloalkyl, wherein each of the aforementioned substitutents may be further substituted by one or more substituents independently selected from halogen, alkyl, hydroxyl or $C_{1-4}$alkoxy groups.

When an "aryl" is represented along with another radical like "arylalkyl", "aryloxyalkyl", "aryloxycarbonyl", "aryloxy-carbonylalkyl", the aryl portion shall have the same meaning as described in the above-mentioned definition of "aryl".

"Alkylene" as used herein refers to a divalent alkyl group defined herein. Examples of $C_{1-10}$alkylene includes, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene. An alkylene group may be optionally substituted, and the substituents include those described for the alkyl group described herein.

"Alkenylene" as used herein refers to a divalent alkenyl group defined herein. Examples of $C_{1-3}$alkenylene include, but are not limited to, ethene-1,2-diyl, propene-1,3-diyl, and methylene-1,1-diyl. An alkenylene may be optionally substituted, and the substituents include those described for the alkyl group described herein.

"Aryloxy" as used herein, refers to the radical —O-aryl, wherein aryl is as defined herein.

"Bicyclic" or "bicyclyl" as used here in refers to a ring assembly of two rings where the two rings are fused together, linked by a single bond or linked by two bridging atoms. The rings may be a carbocyclyl, a heterocyclyl, or a mixture thereof.

"Bridging ring" as used herein refers to a polycyclic ring system where two ring atoms that are common to two rings are not directly bound to each other. One or more rings of the ring system may also comprise heteroatoms as ring atoms. Non-exclusive examples of bridging rings include norbornanyl, 7-oxabicyclo[2.2.1]heptanyl, adamantanyl, azabicyclo[3.2.1]oct-3-en-3-yl, and the like.

"Carbamoyl" as used herein refers to the radical —C(O)NR$_a$— where R$_a$ is H, or is an alkyl, alkenyl, alkynyl, acyl, aryl, or arylalkyl group or a heteroform of one of these groups, and each of the alkyl, alkenyl, alkynyl, acyl, aryl, arylalkyl or heteroforms of one of these groups is optionally substituted with the substituents described herein as suitable for the corresponding group.

"Carbamate" as used herein refers to the radical —OC(O)NR$_a$R$_b$ where R$_a$ and R$_b$ are each independently H, or is an alkyl, alkenyl, alkynyl, acyl, aryl, or arylalkyl group or a heteroform of one of these groups, and each of the alkyl, alkenyl, alkynyl, acyl, aryl, arylalkyl or heteroforms of one of these groups is optionally substituted with the substituents described herein as suitable for the corresponding group.

"Cycloalkyl", as used herein, means a radical comprising a non-aromatic, saturated or partially unsaturated, monocyclic, bicyclic, tricyclic, fused, bridged or spiro polycyclic hydrocarbon ring system of 3-20 carbon atoms. $C_X$cycloalkyl and $C_{X-Y}$cycloalkyl are typically used where X and Y indicate the number of carbon atoms in the ring assembly. For example, $C_{3-6}$cycloalkyl includes cyclopropyl, cyclobutyl, cyclopentyl, cyclohexyl, cyclohexenyl, 2,5-cyclohexadienyl.

Exemplary monocyclic cycloalkyl include, but are not limited to, cyclopropyl, cyclobutyl, cyclopentyl, cyclopentenyl, cyclohexyl and cyclohexenyl and the like.

Exemplary bicyclic cycloalkyls include bornyl, norbornanyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic cycloalkyl groups include, for example, adamantyl.

A cycloalkyl may be unsubstituted or substituted by one, or two, or three, or more substituents independently selected from the group consisting of hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

"Cycloalkoxy" or "cycloalkyloxy", as used herein, refers to —O-cycloalkyl, wherein the cycloalkyl is defined herein. Representative examples of $C_{3-12}$cycloalkyloxy include, but are not limited to, monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyloxy, decahydronaphthyloxy, bicyclo[2.1.1]hexyloxy, bicyclo[2.2.1]heptyloxy, bicyclo[2.2.1]heptenyloxy, 6,6-dimethylbicyclo[3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

"Cyano", as used herein, refers to the radical —CN.

"EC$_{50}$", refers to the molar concentration of an inhibitor or modulator that produces 50% efficacy.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halo" or "halogen" as used herein refers to fluoro, chloro, bromo, and iodo.

"Haloalkyl", or halo-substituted-alkyl" as used herein, refers to an alkyl as defined herein, which is substituted by one or more halo atoms defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. $C_X$haloalkyl and $C_{X-Y}$haloalkyl are typically used where X and Y indicate the number of carbon atoms in the alkyl chain. Non-limiting examples of $C_{1-4}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A $C_{1-4}$perhaloalkyl group refers to a $C_{1-4}$alkyl group having all hydrogen atoms replaced with halo atoms.

"Heteroaryl", as used herein, refers to a 5-14 membered ring assembly (e.g., a 5-7 membered monocycle, an 8-10 membered bicycle, or a 13-14 membered tricyclic ring system) having 1 to 8 heteroatoms selected from N, O and S as ring atoms and the remaining ring atoms are carbon atoms. The nitrogen atoms of such heteroaryl rings can be optionally quaternerized and the sulfur atoms of such heteroaryl rings can be optionally oxidized. $C_X$heteroaryl and $C_{X-Y}$heteroaryl as used herein describe heteroaryls where X and Y indicate the number of ring atoms in the heteroaryl ring. Typical $C_{5-7}$heteroaryl groups include thienyl, furanyl, imidazolyl, pyrazolyl, pyrrolyl, pyrrolinyl, thiazolyl, 1,3,4-thiadiazolyl, isothiazolyl, oxazolyl, oxadiazole isoxazolyl, triazolyl, tetrazolyl, pyridyl, pyridazinyl, pyrazinyl, pyrazinyl, pyrimidinyl, and the like. Bicyclic or tricyclic $C_{8-14}$heteroaryls include, but are not limited to, those derived from benzo[b]furan, benzo[b]thiophene, benzimidazole, imidazo

[4,5-c]pyridine, quinazoline, thieno[2,3-c]pyridine, thieno[3,2-b]pyridine, thieno[2,3-b]pyridine, quinazolinyle, pteridinyl, indolizine, imidazo[1,2a]pyridine, quinoline, quinolinyl, isoquinoline, phthalazine, quinoxaline, naphthyridine, naphthyridinyl, quinolizine, indolyl, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, purinyl, carbazole, acridine, phenazine, phenothiazene, phenoxazine, 1,2-dihydropyrrolo[3,2,1-hi]indole, indolizine, pyrido[1,2-a]indole and 2(1H)-pyridinone.

A heteroaryl may be unsubstituted or substituted with one or more substituents independently selected from hydroxyl, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heteroaryl is represented along with another radical like "heteroaryloxy", "heteroaryloxyalkyl", "heteroaryloxycarbonyl", the heteroaryl portion shall have the same meaning as described in the above-mentioned definition of "heteroaryl".

"Heteroaryloxy", as used herein, refers to an —O-heteroaryl group, wherein the heteroaryl is as defined in this Application.

"Heteroatom", as used herein, refers to an atom that is not a carbon atom. Particular examples of heteroatoms include, but are not limited to nitrogen, oxygen, and sulfur.

"Heterocycloalkyl", as used herein, refers to a 4-20 membered, non-aromatic, saturated or partially unsaturated, monocyclic or polycyclic ring system, comprising 1-8 heteroatoms as ring atoms and that the remaining ring atoms are carbon atoms. The heteroatoms are selected from N, O, and S, preferably O and N. The nitrogen atoms of the heterocycloalkyl can be optionally quaternerized and the sulfur atoms of the heterocycloalkyl can be optionally oxidized. The heterocycloalkyl can include fused or bridged rings as well as spirocyclic rings. $C_X$heterocycloalkyl and $C_{X-Y}$heterocycloalkyl are typically used where X and Y indicate the number of ring atoms in the ring. Typically, the heterocycloalkyl is 4-8-membered monocyclic ring containing 1 to 3 heteroatoms, a 7 to 12-membered bicyclic ring system containing 1-5 heteroatoms, or a 10-15-membered tricyclic ring system containing 1 to 7 heteroatoms. Examples of $C_{4-6}$heterocycloalkyl include azetidinyl, tetrahydrofuran (THF), dihydrofuran, 1, 4-dioxane, morpholine, 1,4-dithiane, piperazine, piperidine, 1,3-dioxolane, imidazolidine, imidazoline, pyrazolidinyl, pyrroline, pyrrolidine, tetrahydropyran, dihydropyran, oxathiolane, dithiolane, 1,3-dioxane, 1,3-dithiane, oxathiane, thiomorpholine, and the like.

A heterocycloalkyl may be unsubstituted or substituted with 1-5 substituents (such as one, or two, or three) each independently selected from hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heterocycloalkyl forms part of other groups like "heterocycloalkyl-alkyl", "heterocycloalkoxy", "heterocycloalkyl-aryl", the heteroaryl portion shall have the same meaning as described in the above-mentioned definition of "heteroaryl".

"Heterocycloalkylene", as used herein, refers to a cycloalkylene, as defined in this Application, provided that one or more of the ring member carbon atoms is replaced by a heteroatom.

"Heterocyclyl", "heterocycle" or "heterocyclo", as used herein, refers to a 3-20 membered, monocyclic or polycyclic ring system containing at least one heteroatom moiety selected from the group consisting of N, O, SO, $SO_2$, (C=O), and S, and preferably N, O, S, optionally containing one to four additional heteroatoms in each ring. $C_X$heterocyclyl and $C_{X-Y}$heterocyclyl are typically used where X and Y indicate the number of ring atoms in the ring system. Unless otherwise specified, a heterocyclyl may be saturated, partially unsaturated, aromatic or partially aromatic.

Hydroxy, as used herein, refers to the radical —OH.

"Hydroxyalkyl" or "hydroxyl-substituted alkyl" as used herein, refers to an alkyl as defined herein, having one or more of the available hydrogen of the alkyl replaced by a hydroxyl group. For example, a hydroxy$C_{1-4}$alkyl includes, but are not limited to, —$CH_2CH_2OH$, —CH(OH)$CH_2CH_2OH$, —CH(OH)$CH_2CH(OH)CH_3$.

"Nitro", as used herein, refers to the radical —$NO_2$.

"Oxo", as used herein, refers to the divalent radical =O.

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Unsubstituted or substituted" or "optionally substituted" as used herein indicate the substituent bound on the available valance of a named group or radical. "Unsubstituted" as used herein indicates that the named group or radical will have no further non-hydrogen substituents. "Substituted" or "optionally substituted" as used herein indicates that at least one of the available hydrogen atoms of named group or radical has been (or may be) replaced by a non-hydrogen substituent.

Unless otherwise specified, examples of substituents may include, but are not limited to, halo, nitro, cyano, thio, oxy, hydroxy, carbonyloxy, $C_{1-6}$alkoxy, $C_{6-10}$aryloxy, hetero$C_{5-10}$aryloxy, carbonyl, oxycarbonyl, aminocarbonyl, amino, $C_{1-6}$alkylamino, sulfonamido, imino, sulfonyl, sulfinyl, $C_{1-6}$alkyl, $C_{1-6}$haloalkyl, hydroxy$C_{1-6}$alkyl, carbonyl$C_{1-6}$alkyl, thiocarbonyl$C_{1-10}$alkyl, sulfonyl$C_{1-6}$alkyl, sulfinyl$C_{1-6}$alkyl, $C_{1-10}$azaalkyl, imino$C_{1-6}$alkyl, $C_{3-12}$cycloalkyl$C_{1-6}$alkyl, $C_{4-15}$heterocycloalkyl$C_{1-6}$alkyl, $C_{6-10}$aryl$C_{1-6}$alkyl, $C_{5-10}$heteroaryl$C_{1-6}$alkyl, $C_{10-12}$bicycloaryl$C_{1-6}$alkyl, $C_{9-12}$heterobicycloaryl$C_{1-6}$alkyl, $C_{3-12}$cycloalkyl, $C_{4-12}$heterocycloalkyl, $C_{9-12}$bicycloalkyl, $C_{3-12}$heterobicycloalkyl, $C_{4-12}$aryl, hetero$C_{1-10}$aryl, $C_{9-12}$bicycloaryl and $C_{4-12}$heterobicycloaryl.

"Sulfanyl" as used herein, means the radical —S—.

"Sulfinyl", as used herein, means the radical —S(O)—. It is noted that the term "sulfinyl" when referring to a monovalent substituent can alternatively refer to a substituted sulfinyl group, —S(=O)R, where R is hydrogen or a non-hydrogen substituent on the sulfur atom forming different sulfinyl groups including sulfinic acids, sulfinamides, sulfinyl esters, and sulfoxides.

"Sulfonyl", as used herein, means the radical —S(O)$_2$—. It is noted that the term "sulfonyl" when referring to a monovalent substituent can alternatively refer to a substituted sulfonyl group, —S(=O)$_2$R, where R is hydrogen or a non-hydrogen substituent on the sulfur atom forming different sulfonyl groups including sulfonic acids, sulfonamides, sulfonate esters, and sulfones.

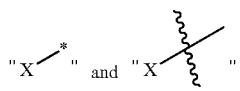

are symbols denoting the point of attachment of X, to other part of the molecule.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

It is noted in regard to all of the definitions provided herein that the definitions should be interpreted as being open ended in the sense that further substituents beyond those specified may be included. Hence, a $C_1$alkyl indicates that there is one carbon atom but does not indicate what are the substituents on the carbon atom. Hence, a $C_1$alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is not a hydrogen atom. Hence, —CF$_3$, —CH$_2$OH and —CH$_2$CN, for example, are all $C_1$alkyls.

DESCRIPTION OF THE PREFERRED EMBODIMENTS

The invention provides a novel class of compounds, pharmaceutical compositions comprising such compounds and methods of using such compounds to treat or prevent diseases or disorders associated with a parasite. In particular, the compounds can be used to treat leishmaniasis, Human Trypanosomiasis and/or Chagas disease. The compounds of the invention are effective in inhibiting, ameliorating, or eradicating the pathology and/or symptomology of the parasite.

In one embodiment, the compounds of the invention is of Formula (A):

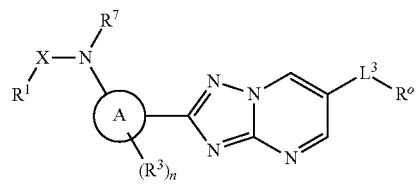

(A)

or a pharmaceutically acceptable salt, or stereoisomer thereof; wherein

Ring A is phenyl or pyridyl;

X is —C(O)— or —S(O)$_2$—;

$R^1$ is selected from nitro, $C_{1-4}$alkyl, $C_{1-6}$alkoxy, amino, $C_{1-6}$alkylamino, di-$C_{1-6}$alkylamino, —N(C$_2$H$_3$)$_2$, $C_{3-6}$cycloalkyl, $C_{4-6}$heterocycloalkyl, $C_{4-8}$heterocycloalkenyl, and $C_{5-9}$heteroaryl, wherein the $C_{1-6}$alkoxy, $C_{1-6}$alkylamino, $C_{3-6}$cycloalkyl, $C_{4-6}$heterocycloalkyl, $C_{4-8}$heterocycloalkenyl, or $C_{5-9}$heteroaryl of $R^1$ is unsubstituted or substituted by 1-2 substituents independently selected from halo, cyano, $C_{1-4}$alkyl, halo$C_{1-4}$alkyl, $C_{1-4}$alkoxy, amino, $C_{1-4}$alkylamino, di$C_{1-4}$alkylamino, and hydroxycarbonyl, and $C_{1-4}$alkylcarbonyl;

$R^3$ is selected from hydrogen, halo, cyano, $C_{1-4}$alkyl, and halo$C_{1-4}$alkyl, and n is 0, 1, or 2;

$R^7$ is selected from hydrogen or $C_{1-4}$alkyl;

$L^3$ is a bond, phenylene, or $C_{5-6}$heteroarylene;

$R^0$ is selected from hydrogen, hydroxyl, halo, nitro, —N=CHN(CH$_3$)$_2$, $C_{1-4}$alkyl, $C_{4-6}$heterocycloalkyl $C_{1-4}$alkyl, $C_{1-4}$alkoxy, —NR$^{2a}$R$^{2b}$, —NR$^5$C(O)R$^6$, —NR$^5$S(O)$_2$R$_8$, —Si(CH$_3$)$_3$, $C_{3-6}$cycloalkyl, $C_{5-6}$cycloalkenyl, $C_{4-6}$heterocycloalkyl, $C_{5-8}$heterocycloalkenyl, $C_{6-10}$aryl, and $C_{5-6}$heteroaryl; wherein the $C_{1-4}$alkyl or $C_{1-4}$alkoxy of $R^0$ is unsubstituted or substituted by 1-2 substituents independently selected from $C_{1-4}$alkoxy, amino, phenyl and $C_{5-6}$heteroaryl; wherein the phenyl or $C_{5-6}$heteroaryl substituent of $R^0$ is unsubstituted or substituted by halo or $C_{1-4}$alkyl;

the $C_{3-6}$cycloalkyl, $C_{5-6}$cycloalkenyl, $C_{4-6}$heterocycloalkyl, $C_{5-8}$heterocycloalkenyl, $C_{6-10}$aryl, and $C_{5-6}$heteroaryl of $R^0$ is unsubstituted or substituted by 1 to 4 substituents independently selected from halo, oxo, $C_{1-4}$alkyl, hydroxy$C_{1-4}$alkyl, halo$C_{1-4}$alkyl, —(CH$_2$)$_{1-4}$NR$^a$R$^b$, $C_{4-6}$heterocycloalkyl$C_{1-4}$alkyl, benzyl, $C_{1-4}$alkoxy, amino, $C_{1-4}$alkylamino, di$C_{1-4}$alkylamino, unsubstituted $C_{4-6}$heterocycloalkyl and $C_{1-4}$alkyl substituted $C_{4-6}$heterocycloalkyl, wherein $R^a$ and $R^b$ are each independently selected from hydrogen, $C_{1-4}$alkyl, and $C_{3-6}$cycloalkyl;

$R^{2a}$ is hydrogen or $C_{1-4}$alkyl;

$R^{2b}$ is selected from hydrogen, $C_{1-4}$alkyl and —C(O)OCH(CH$_3$)$_2$, wherein the $C_{1-4}$ alkyl of $R^{2b}$ is unsubstituted or substituted by amino, $C_{4-6}$heterocycloalkyl, phenyl or $C_{5-6}$heteroaryl, wherein the $C_{4-6}$heterocycloalkyl, phenyl or $C_{5-6}$heteroaryl substituent of $R^{2b}$ is unsubstituted or substituted by hydroxyl, halo or $C_{1-4}$alkyl;

$R^5$ is hydrogen or $C_{1-4}$alkyl;

$R^6$ is selected from hydrogen, $C_{1-4}$alkyl, $C_{1-4}$alkoxy, $C_{3-6}$cycloalkyloxy, amino, $C_{3-6}$cycloalkyl, $C_{5-6}$heterocycloalkyl, and $C_{5-6}$heteroaryl, wherein the $C_{1-4}$alkyl, $C_{1-4}$alkoxy, $C_{3-6}$cycloalkyloxy, or amino of $R^6$ is unsubstituted or substituted by 1 to 2 substituents independently selected from halo, hydroxyl, $C_{1-4}$alkyl, halo$C_{1-4}$alkyl, $C_{1-4}$alkoxy, —NR$^{9a}$R$^{9b}$, C$_{3-6}$cycloalkyl, C$_{5-6}$heterocycloalkyl, and C$_{5-6}$heteroaryl, wherein R$^{9a}$ is hydrogen or C$_{1-4}$alkyl, R$^{9b}$ is selected from hydrogen, C$_{1-4}$alkyl, C$_{1-4}$alkylcarbonyl and C$_{1-4}$alkoxycarbonyl, and the C$_{5-6}$heterocycloalkyl or C$_{5-8}$heteroaryl substituent of R$^6$ is each unsubstituted or substituted by 1-2 substituents independently selected from hydroxyl, C$_{1-4}$alkyl and C$_{1-4}$alkoxycarbonyl, the C$_{3-6}$cycloalkyl or C$_{4-6}$heterocycloalkyl of R$^6$ is unsubstituted or substituted by 1 to 2 substituents independently selected from halo, cyano, hydroxyl, C$_{1-4}$alkyl, haloC$_{1-4}$alkyl, C$_{1-4}$alkoxylC$_{1-4}$alkyl, C$_{1-4}$alkoxy, amino, C$_{1-4}$alkylamino, di-C$_{1-4}$alkylamino, aminocarbonyl, C$_{1-4}$alkoxycarbonyl, and C$_{1-4}$alkoxycarbonylaminoC$_{1-4}$alkyl, and the C$_{5-6}$heteroaryl of R$^6$ is unsubstituted or substituted by 1 to 2 substituents independently selected from hydroxyl, C$_{1-4}$alkyl, C$_{1-4}$alkoxy, amino, C$_{1-4}$alkylamino, di-C$_{1-4}$alkylamino, and C$_{1-4}$alkoxycarbonyl; and R$^8$ is C$_{1-4}$alkyl or C$_{1-4}$alkylamino.

In one embodiment of the above embodiment, Ring A is pyridinyl and n is 0.

In another embodiment of the above embodiment, R$^7$ is methyl.

In another embodiment of the above embodiments, the compound of the invention is of Formula I:

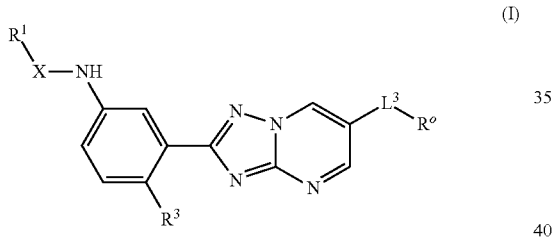

(I)

or a pharmaceutically acceptable salt, or stereoisomer thereof; wherein

X is —C(O)— or —S(O)$_2$—;

R$^1$ is selected from nitro, C$_{1-4}$alkyl, C$_{1-6}$alkoxy, amino, C$_{1-6}$alkylamino, di-C$_{1-6}$alkylamino, —N(C$_2$H$_3$)$_2$, C$_{3-6}$cycloalkyl, C$_{4-6}$heterocycloalkyl, C$_{4-8}$heterocycloalkenyl, and C$_{5-9}$heteroaryl, wherein the C$_{1-6}$alkoxy, C$_{1-6}$alkylamino, C$_{3-6}$cycloalkyl, C$_{4-6}$heterocycloalkyl, C$_{4-8}$heterocycloalkenyl, or C$_{5-9}$heteroaryl of R$^1$ is unsubstituted or substituted by 1-2 substituents independently selected from halo, cyano, C$_{1-4}$alkyl, haloC$_{1-4}$alkyl, C$_{1-4}$alkoxy, amino, C$_{1-4}$alkylamino, diC$_{1-4}$alkylamino, and hydroxycarbonyl, and C$_{1-4}$alkylcarbonyl;

R$^3$ is selected from hydrogen, halo, cyano, C$_{1-4}$alkyl, and haloC$_{1-4}$alkyl;

L$^3$ is a bond, phenylene, or C$_{5-6}$heteroarylene;

R$^0$ is selected from hydrogen, hydroxyl, halo, nitro, —N=CHN(CH$_3$)$_2$, C$_{1-4}$alkyl, C$_{4-6}$heterocycloalkyl C$_{1-4}$alkyl, C$_{1-4}$alkoxy, —NR$^{2a}$R$^{2b}$, —NR$^5$C(O)R$^6$, —NR$^5$S(O)$_2$R$_8$, —Si(CH$_3$)$_3$, C$_{3-6}$cycloalkyl, C$_{5-6}$cycloalkenyl, C$_{4-6}$heterocycloalkyl, C$_{5-6}$heterocycloalkenyl, C$_{6-10}$aryl, and C$_{5-6}$heteroaryl; wherein the C$_{1-4}$alkyl or C$_{1-4}$alkoxy of R$^0$ is unsubstituted or substituted by 1-2 substituents independently selected from C$_{1-4}$alkoxy, amino, phenyl and C$_{5-6}$heteroaryl; wherein the phenyl or C$_{5-6}$heteroaryl substituent of R$^0$ is unsubstituted or substituted by halo or C$_{1-4}$alkyl;

the C$_{3-6}$cycloalkyl, C$_{5-6}$cycloalkenyl, C$_{4-6}$heterocycloalkyl, C$_{5-6}$heterocycloalkenyl, C$_{6-10}$aryl, and C$_{5-6}$heteroaryl of R$^0$ is unsubstituted or substituted by 1 to 4 substituents independently selected from halo, oxo, C$_{1-4}$alkyl, hydroxyC$_{1-4}$alkyl, haloC$_{1-4}$alkyl, —(CH$_2$)$_{1-4}$NR$^a$R$^b$, C$_{4-6}$heterocycloalkylC$_{1-4}$alkyl, benzyl, C$_{1-4}$alkoxy, amino, C$_{1-4}$alkylamino, diC$_{1-4}$alkylamino, unsubstituted C$_{4-6}$heterocycloalkyl and C$_{1-4}$alkyl substituted C$_{4-6}$heterocycloalkyl, wherein R$^a$ and R$^b$ are each independently selected from hydrogen, C$_{1-4}$alkyl, and C$_{3-6}$cycloalkyl;

R$^{2a}$ is hydrogen or C$_{1-4}$alkyl;

R$^{2b}$ is selected from hydrogen, C$_{1-4}$alkyl and —C(O)OCH(CH$_3$)$_2$, wherein the C$_{1-4}$alkyl of R$^{2b}$ is unsubstituted or substituted by amino, C$_{4-6}$heterocycloalkyl, phenyl or C$_{5-6}$heteroaryl, wherein the C$_{4-6}$heterocycloalkyl, phenyl or C$_{5-6}$heteroaryl substituent of R$^{2b}$ is unsubstituted or substituted by hydroxyl, halo or C$_{1-4}$alkyl;

R$^5$ is hydrogen or C$_{1-4}$alkyl;

R$^6$ is selected from hydrogen, C$_{1-4}$alkyl, C$_{1-4}$alkoxy, C$_{3-6}$cycloalkyloxy, amino, C$_{3-6}$cycloalkyl, C$_{5-6}$heterocycloalkyl, and C$_{5-6}$heteroaryl, wherein the C$_{1-4}$alkyl, C$_{1-4}$alkoxy, C$_{3-6}$cycloalkyloxy, or amino of R$^6$ is unsubstituted or substituted by 1 to 2 substituents independently selected from halo, hydroxyl, C$_{1-4}$alkyl, haloC$_{1-4}$alkyl, C$_{1-4}$alkoxy, —NR$^{9a}$R$^{9b}$, C$_{3-6}$cycloalkyl, C$_{5-6}$heterocycloalkyl, and C$_{5-6}$heteroaryl, wherein R$^{9a}$ is hydrogen or C$_{1-4}$alkyl, R$^{9b}$ is selected from hydrogen, C$_{1-4}$alkyl, C$_{1-4}$alkylcarbonyl and C$_{1-4}$alkoxycarbonyl, and the C$_{5-6}$heterocycloalkyl or C$_{5-6}$heteroaryl substituent of R$^6$ is each unsubstituted or substituted by 1-2 substituents independently selected from hydroxyl, C$_{1-4}$alkyl and C$_{1-4}$alkoxycarbonyl, the C$_{3-6}$cycloalkyl or C$_{4-6}$heterocycloalkyl of R$^6$ is unsubstituted or substituted by 1 to 2 substituents independently selected from halo, cyano, hydroxyl, C$_{1-4}$alkyl, haloC$_{1-4}$alkyl, C$_{1-4}$alkoxylC$_{1-4}$alkyl, C$_{1-4}$alkoxy, amino, C$_{1-4}$alkylamino, di-C$_{1-4}$alkylamino, aminocarbonyl, C$_{1-4}$alkoxycarbonyl, and C$_{1-4}$alkoxycarbonylaminoC$_{1-4}$alkyl, and the C$_{5-6}$heteroaryl of R$^6$ is unsubstituted or substituted by 1 to 2 substituents independently selected from hydroxyl, C$_{1-4}$alkyl, C$_{1-4}$alkoxy, amino, C$_{1-4}$alkylamino, di-C$_{1-4}$alkylamino, and C$_{1-4}$alkoxycarbonyl; and R$^8$ is C$_{1-4}$alkyl or C$_{1-4}$alkylamino.

In one embodiment of the above embodiments and variations of the compound of the invention, X is —C(O)—.

In one embodiment of the above embodiments and variations, R$^1$ is selected from C$_{1-4}$alkyl, C$_{1-4}$alkoxy, amino, C$_{1-4}$alkylamino, diC$_{1-4}$alkylamino, —N(C$_2$H$_3$)$_2$, C$_{3-6}$cycloalkyl, C$_{4-6}$heterocycloalkyl, and C$_{5-9}$heteroaryl, wherein the C$_{1-6}$alkoxy or C$_{1-6}$alkylamino of R$^1$ is unsubstituted or substituted by 1 to 2 substituents independently selected from C$_{1-4}$alkyl and C$_{1-4}$alkoxy; and the C$_{3-6}$cycloalkyl, C$_{4-6}$heterocycloalkyl or C$_{5-6}$heteroaryl of R$^1$ is unsubstituted or substituted by 1 to 2 substituents independently selected from halo, cyano, C$_{1-4}$alkyl, haloC$_{1-4}$alkyl, C$_{1-4}$alkoxy, amino, C$_{1-6}$alkylamino, diC$_{1-6}$alkylamino, and hydroxycarbonyl.

In another variation, $R^1$ is selected from $C_{1-4}$alkoxy, di$C_{1-4}$alkylamino, cyclobutyl, azetidinyl, pyrrolidinyl, furanyl and oxazolyl, wherein the cyclobutyl, azetidinyl, pyrrolidinyl, furanyl or oxazolyl is unsubstituted or substituted by 1 to 2 substituents independently selected from halo, $C_{1-4}$alkyl, $C_{1-4}$alkoxy, di$C_{1-4}$alkylamino, and hydroxycarbonyl.

In another variation, $R^1$ is selected from $C_{1-6}$alkoxy and $C_{1-6}$alkylamino, wherein the $C_{1-6}$alkoxy and $C_{1-6}$alkylamino are each unsubstituted or substituted by 1-2 substituents independently selected from $C_{1-4}$alkyl and $C_{1-4}$alkoxy.

In another variation, $R^1$ is selected from —$CH_3$, —$(CH_2)_{1-3}CH_3$, —$CH(CH_3)_2$, —$CH_2CH(CH_3)_2$, —$(CH_2)_2F$, —$(CH_2)_2OCH_3$, —$N(CH_3)_2$, —$N(CH_3)CH_2CH_3$, —$N(CH_2CH_3)_2$, —$N(CH_3)OCH_3$, —$OCH_2CH_3$, —$O(CH_2)_3CH_3$, —$OCH(CH_3)_2$, —$OCH_2CH(CH_3)_2$, —$O(CH_2)_2OCH_3$.

In still another variation, $R^1$ is selected from —$N(CH_3)CH_2CH_3$, —$N(CH_3)_2$, —$N(CH_2CH_3)_2$, —$N(CH_3)OCH_3$, —$OCH_2CH_3$, —$OCH(CH_3)_2$, —$O(CH_2)_2OCH_3$. In still another variation, $R^1$ is selected from $C_{5-9}$heteroaryl, $C_{4-6}$heterocycloalkyl, and $C_{3-6}$cycloalkyl, each of which is independently unsubstituted or substituted by 1-2 substituents independently selected from halo, cyano, $C_{1-4}$alkyl and $C_{1-4}$alkoxy.

In yet another variation, $R^1$ is selected from pyrrolyl, pyrazolyl, imidazolyl, oxazolyl, furanyl, thiophenyl, thiazolyl, phenyl, pyrazinyl, cyclopropyl, cyclopentyl, pyrrolidinyl, and indolyl, each of which is independently unsubstituted or substituted by 1-2 substituents independently selected from halo, cyano, $C_{1-4}$alkyl, halo$C_{1-4}$alkyl, $C_{1-4}$alkoxy, di$C_{1-4}$alkylamino, hydroxycarbonyl. and $C_{1-4}$alkylcarbonyl.

In yet another variation, $R^1$ is selected from cyclobutyl, azetidinyl, pyrrolidinyl, furanyl and oxazolyl, wherein the cyclobutyl, azetidinyl, pyrrolidinyl, furanyl or oxazolyl is unsubstituted or substituted by 1 to 2 substituents independently selected from halo, $C_{1-4}$alkyl, $C_{1-4}$alkoxy, di$C_{1-4}$alkylamino, and hydroxycarbonyl.

In yet another variation, $R^1$ is selected from azetidinyl, pyrrolidinyl, and oxazolyl, wherein the azetidinyl, pyrrolidinyl, or oxazolyl is unsubstituted or substituted by 1 to 2 substituents independently selected from halo or $C_{1-4}$alkyl.

In another embodiment of the above embodiments and variations, in one variation, —X—$R^1$ is selected from —$C(O)CH(CH_3)_2$, —$C(O)(CH_2)_2F$, —$C(O)CH(NH_2)(CH_3)$, —$C(O)N(CH_3)_2$, —$C(O)N(CH_3)CH_2CH_3$, —$C(O)N(CH_2CH_3)_2$, —$C(O)N(CH_3)OCH_3$, —$C(O)OCH_2CH_3$, —$C(O)OCH(CH_3)_2$, —$C(O)OCH(CH_3)(CH_2CH_3)$, —$C(O)O(CH_2)CH(CH_3)_2$, —$C(O)O(CH_2)_2OCH_3$. —$S(O)_2CH_3$, and —$S(O)_2CH(CH_3)_2$.

In another variation, —X—$R^1$ is selected from —$NHC(O)N(CH_3)CH_2CH_3$, —$NHC(O)N(CH_3)OCH_3$, —$NHC(O)N(CH_3)_2$, —$NHC(O)N(CH_2CH_3)_2$, —$NHC(O)OCH_2CH_3$, —$NHC(O)OCH(CH_3)_2$, and —$NHC(O)O(CH_2)_2OCH_3$.

In another variation, —X—$R^1$ is selected from

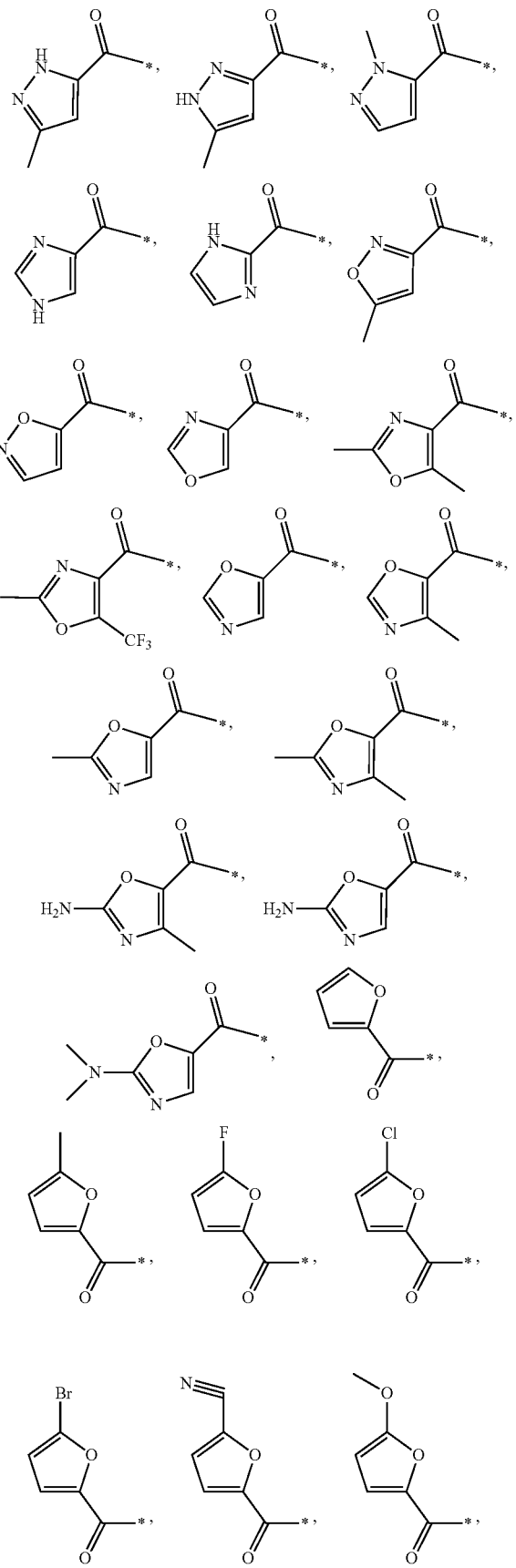

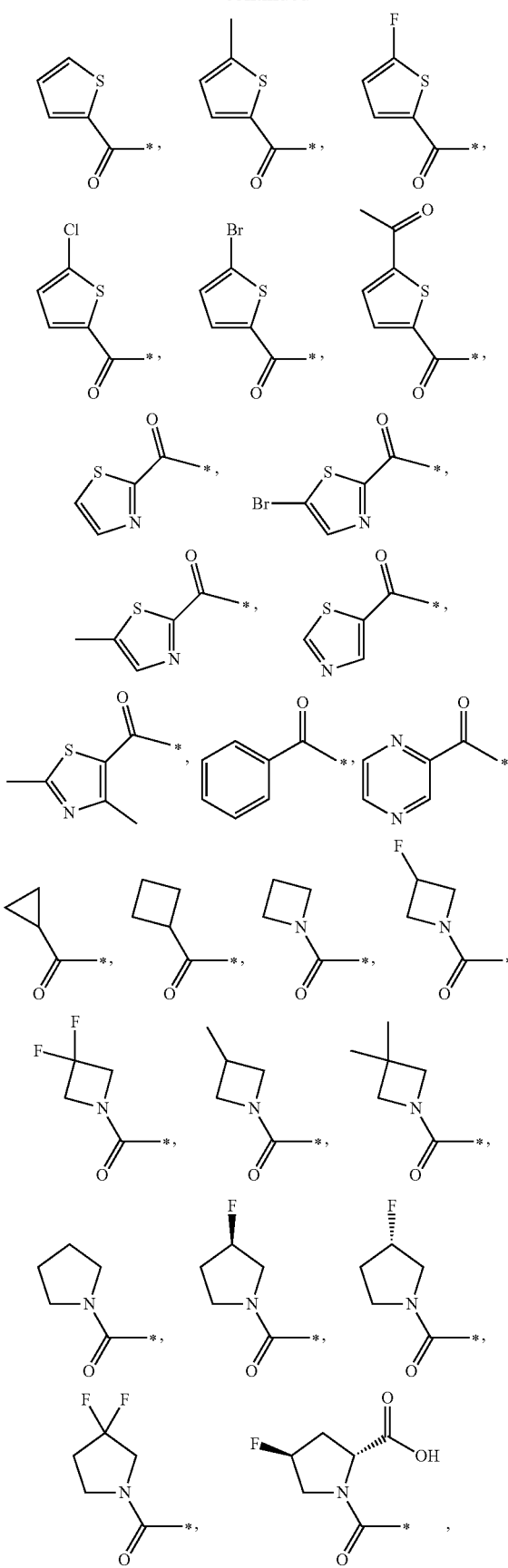
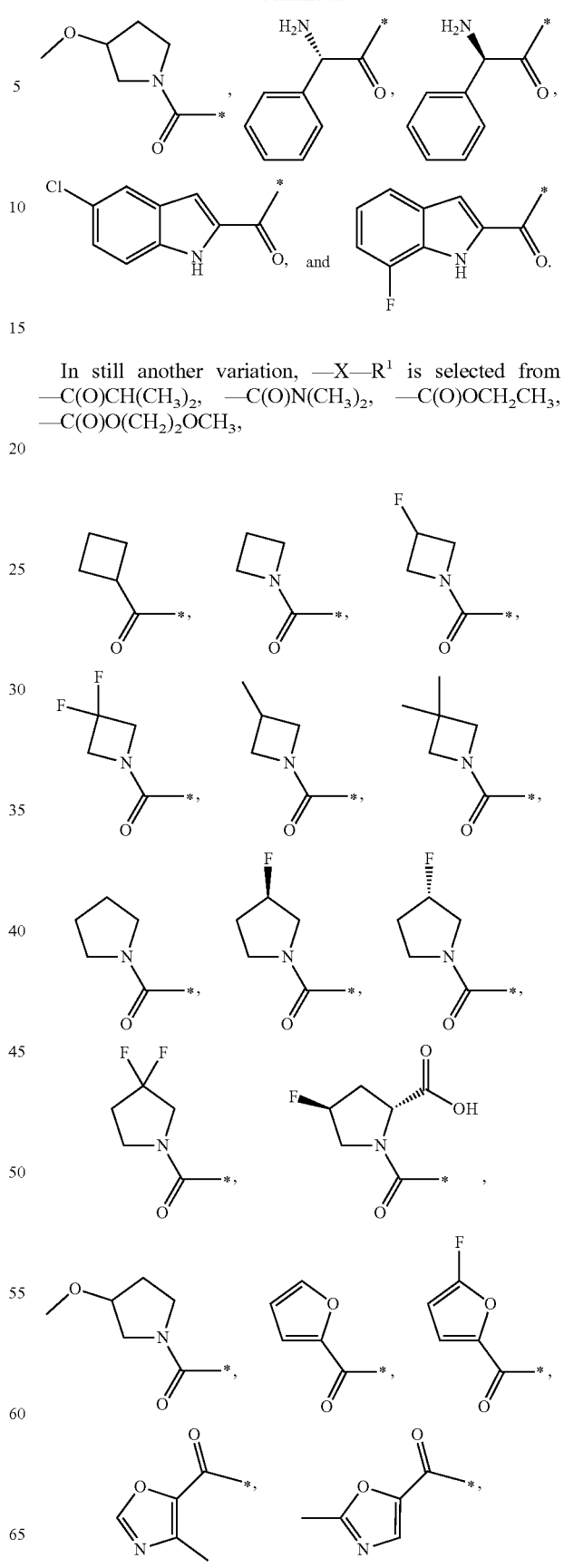
In still another variation, —X—R[1] is selected from —C(O)CH(CH$_3$)$_2$, —C(O)N(CH$_3$)$_2$, —C(O)OCH$_2$CH$_3$, —C(O)O(CH$_2$)$_2$OCH$_3$, -continued

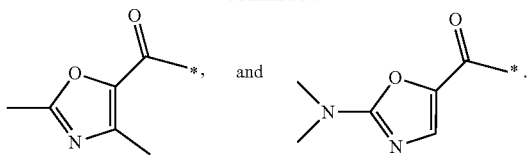

In a particular variation, —X—R¹ is

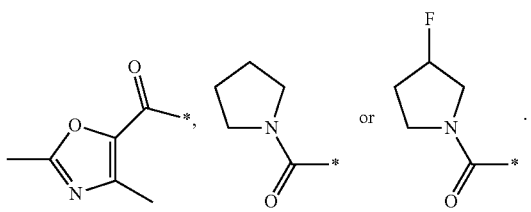

In another particular variation, —X—R¹ is

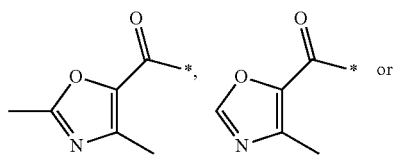

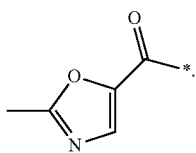

In still another particular variation, —X—R¹ is

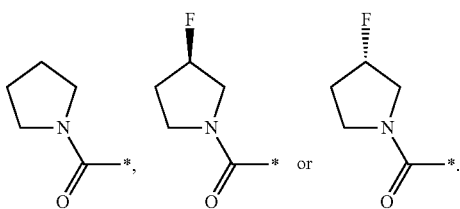

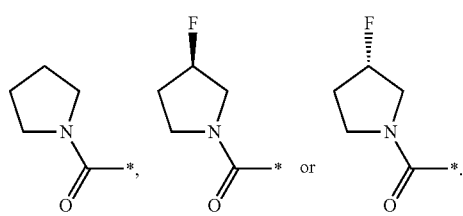

In still another particular variation, —X—R¹ is

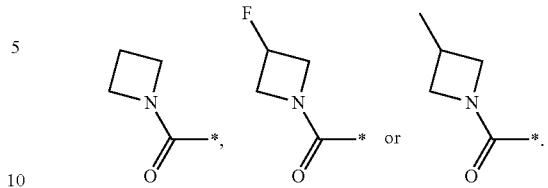

In still another embodiment of the above embodiments and variations of the compound of the invention, R³ is selected from hydrogen, halo, methyl, and trifluoromethyl. In one variation, R³ is halo, methyl, or trifluoromethyl. In another variation, R³ is methyl or trifluorormethyl. In yet another variation, R³ is hydrogen. In a particular variation, R³ is halo; preferably, chloro or fluoro.

In a further embodiment of the above embodiments and variations of the compounds of the invention, R⁰ is selected from hydrogen, hydroxyl, halo, $C_{1-4}$alkyl, $C_{1-4}$alkoxy, amino, $C_{1-4}$alkylamino, di$C_{1-4}$alkylamino, —NH(CH$_2$)$_{1-2}$-phenyl, —NR⁵C(O)R⁶, —Si(CH$_3$)$_3$, $C_{3-6}$cycloalkyl, $C_{5-6}$cycloalkenyl, $C_{4-6}$heterocycloalkyl, $C_{4-6}$heterocycloalkenyl, phenyl, and $C_{5-6}$heteroaryl, wherein the $C_{3-6}$cycloalkyl, $C_{5-6}$cycloalkenyl, $C_{4-6}$heterocycloalkyl, $C_{4-6}$heterocycloalkenyl, phenyl, or $C_{5-6}$heteroaryl of R⁰ is unsubstituted or substituted by 1 to 4 substituents independently selected from halo, $C_{1-4}$alkyl, —(CH$_2$)$_{1-4}$OH, halo$C_{1-4}$alkyl, —(CH$_2$)$_{1-4}$NR$^a$R$^b$, $C_{4-6}$heterocycloalkyl$C_{1-4}$alkyl, benzyl, $C_{1-4}$alkoxy, amino, $C_{1-4}$alkylamino, di$C_{1-4}$alkylamino, unsubstituted $C_6$heterocycloalkyl and $C_{1-4}$alkyl substituted $C_6$heterocycloalkyl, wherein R$^a$ and R$^b$ are each independently selected from hydrogen, $C_{1-4}$alkyl and $C_{3-6}$cycloalkyl;

R₅ is hydrogen or $C_{1-4}$alkyl; and

R₆ is selected from $C_{1-6}$alkyl, $C_{1-6}$alkoxy, $C_{3-6}$cycloalkyl, $C_{5-6}$heterocycloalkyl, and $C_{5-6}$heteroaryl, each of which is unsubstituted or substituted by 1 to 2 substituents independently selected from hydroxyl, $C_{1-6}$alkyl, $C_{1-4}$alkoxy, amino, and $C_{1-4}$alkylamino.

In one variation, of the above embodiment, R⁰ is selected from hydrogen, chloro, bromo, tert-butyl, isopropylamino, isopropoxycarbonylamino, methylethylamino, methylisopropylamino, dimethyamino, diethylamino, —Si(CH$_3$)$_3$, cyclopropyl, cyclopentenyl, azetidinyl, pyrrolidinyl, piperidinyl, piperazinyl, morpholinyl, 2,5-dihydro-1H-pyrrolyl, 1,2,5,6-tetrahydropyridinyl, azabicyclo[3.2.1]oct-3-en-3-yl, 3,6-dihydro-2H-pyranyl, pyrazolyl, phenyl, pyridinyl, and pyrazinyl; wherein the cyclopropyl, cyclopentenyl, azetidinyl, pyrrolidinyl, piperidinyl, azabicyclo[3.2.1]oct-3-en-3-yl, piperazinyl, morpholinyl, 2,5-dihydro-1H-pyrrolyl, 1,2,5,6-tetrahydropyridinyl, 3,6-dihydro-2H-pyranyl, pyrazolyl, phenyl, pyridinyl, or pyrazinyl is unsubstituted or substituted by 1 to 4 substituents independently selected from fluoro, chloro, $C_{1-4}$alkyl, trifluoromethyl, morpholinylethyl, benzyl, $C_{1-4}$alkoxy, piperazinyl, N-methylpiperazinyl, and morpholinyl.

In another variation of the above embodiment, R⁰ is selected from hydrogen, halo, nitro, hydroxyl, $C_{1-4}$alkoxy, amino, $C_{1-4}$alkylamino, —NH(CH$_2$)$_{1-2}$-phenyl, —NR⁵C(O)R⁶, —NR⁵S(O)$_2$R₈, oxazolidin-2-one, 1,2,4-triazol-5(4H)-one, pyrrolidin-2-one, phenyl and $C_{5-6}$heteroaryl; wherein the oxazolidin-2-one, 1,2,4-triazol-5(4H)-one, pyrrolidin-2-one, phenyl or $C_{5-6}$heteroaryl is unsubstituted or substituted with halo, $C_{1-4}$alkyl, $C_{1-4}$alkoxy, amino, $C_{1-4}$alkylamino, —(CH$_2$)$_{1-4}$OH, and —(CH$_2$)$_{1-4}$NR$^a$R$^b$, wherein R$^a$ and R$^b$ are each independently hydrogen, $C_{1-4}$alkyl or $C_{3-6}$cycloalkyl;

$R^5$ is hydrogen or $C_{1-4}$alkyl;

$R^6$ is selected from $C_{1-6}$alkyl, $C_{1-6}$alkoxyl, $C_{3-6}$cycloalkyl, $C_{5-6}$heterocycloalkyl, and $C_{5-6}$heteroaryl, each of which is unsubstituted or substituted with 1 to 2 substituents independently selected from hydroxyl, $C_{1-4}$alkoxy, amino, $C_{1-4}$alkylamino; and $R^8$ is $C_{1-4}$alkyl or $C_{1-4}$alkylamino.

In another variation of the above embodiments and variations, $R^0$ is selected from trifluoromethyl, di-fluoromethyl, and pyrrolidinyl.

In another variation of the above embodiment, $R^0$ is selected from hydrogen, fluoro, chloro, nitro, methyl, —NH$_2$, —NH(CH$_3$), —NH(CH$_2$CH$_3$), —N(CH$_3$)$_2$, —NHCH$_2$C(CH$_3$)$_2$NH$_2$, —NH(CH$_2$)$_{1-2}$-4-fluorophenyl, —NH-pyridin-3-yl, —NHCH$_2$-pyridin-4-yl, —NHCH$_{2-2}$-hydroxypyridin-3-yl, —NHCH$_2$-piperidin-4-yl, phenyl, thiophenyl, imidazolyl, oxazolidin-2-one, 1,2,4-triazol-5 (4H)-one, and pyrrolidin-2-one, wherein the oxazolidin-2-one, 1,2,4-triazol-5(4H)-one, and pyrrolidin-2-one are each unsubstituted or substituted by $C_{1-4}$alkyl, —(CH$_2$)$_{1-4}$OH, and —(CH$_2$)$_{1-4}$NR$^a$R$^b$, wherein R$^a$ and R$^b$ are each independently hydrogen, $C_{1-4}$alkyl or $C_{3-6}$cycloalkyl.

In yet another variation of the above embodiment, $R^0$ is —NR$^5$C(O)R$^6$, wherein $R^5$ is hydrogen or $C_{1-4}$alkyl;

$R^6$ is hydrogen, $C_{1-4}$alkyl, $C_{1-4}$alkoxy, amino, $C_{3-6}$cycloalkyloxy, $C_{3-6}$cycloalkyl, $C_{5-6}$heterocycloalkyl, and $C_{5-6}$heteroaryl, wherein
  the $C_{1-4}$alkyl, $C_{1-4}$alkoxy, amino and $C_{3-6}$cycloalkyloxy are each unsubstituted or substituted by 1-2 substituents independently selected from halo, hydroxyl, $C_{1-4}$alkyl, halo$C_{1-4}$alkyl, $C_{1-4}$alkoxy, —NH$_2$, $C_{1-4}$alkylamino, —NHC(O)OC(CH$_3$)$_3$, pyrrolidinyl, piperidinyl, morpholinyl, and pyridinyl, wherein the pyrrolidinyl, piperidinyl, morpholinyl, or pyridinyl are each unsubstituted or substituted by hydroxy, $C_{1-4}$alkyl, or —C(O)OC(CH$_3$)$_3$);
  the $C_{5-6}$heteroaryl is unsubstituted or substituted with 1-2 substituents independently selected from hydroxyl and $C_{1-4}$alkyl;
  the $C_{3-6}$cycloalkyl or $C_{4-6}$heterocycloalkyl, each of which is independently unsubstituted or substituted by 1-2 substituents independently selected from halo, cyano, hydroxy, methyl, trifluoromethyl, —CH$_2$OCH$_3$, —CH$_2$NHC(O)(O)C(CH$_3$)$_3$, —C(O)(O)C(CH$_3$)$_3$, and —C(O)NH$_2$.

In yet still another variation of the above embodiment, $R^0$ is —NHC(O)R$^6$, wherein R$^6$ is selected from hydrogen, methyl, ethyl propyl, isopropyl, butyl, isobutyl, tert-butyl, —(CH$_2$)NH$_2$, —(CH$_2$)$_2$NH$_2$, —(CH$_2$)$_3$NH$_2$, —CH$_2$C(CH$_3$)$_2$NH$_2$, —CH(CH$_3$)NH$_2$, —C(CH$_3$)$_2$NH$_2$, —CH$_2$N(CH$_3$)$_2$, —(CH$_2$)$_2$NHC(O)OC(CH$_3$)$_3$, —(CH$_2$)-piperidin-4-yl, —CH$_{2-2}$-hydroxypiperidin-3-yl, —(CH$_2$)-pyrrolidin-3-yl, —CH$_2$-(1-tert-butoxycarbonyl)pyrrolidin-3-yl, —(CH$_2$)$_{2-3}$-morpholinyl, —(CH$_2$)-pyridin-3-yl, —(CH$_2$)$_2$OH, —C(CH$_3$)$_2$CH$_2$OH, —CH(OH)CH$_2$OH, —(CH$_2$)$_2$OCH$_3$; —OCH$_3$, —OCH$_2$CH$_3$, —OCH$_2$CH$_2$CH$_3$, —OCH(CH$_3$)$_2$, —OCH(CH$_3$)(CH$_2$CH$_3$), 1-methylcycopropoxy, —O(CH$_2$)$_2$F, —OC(CH$_3$)$_2$NH$_2$, —OCH$_2$C(CH$_3$)$_2$NH$_2$, —O(CH$_2$)$_2$OCH$_3$, —O(CH$_2$)$_2$—NHC(O)OC(CH$_3$)$_3$, —OCH$_2$C(CH$_3$)$_2$—NHC(O)OC(CH$_3$)$_3$, —NH$_2$, —NH(CH$_3$), —NHCH(CH$_3$)$_2$, —N(CH$_3$)$_2$, and —N(CH$_3$)CH(CH$_3$)$_2$, and —NH-pyridin-3-yl.

In yet still another variation of the above embodiment, $R^0$ is —NHC(O)R$^6$, wherein R$^6$ is selected from thiazolyl, pyridinyl, cyclopropyl, cyclobutyl, azetidinyl, pyrrolidinyl, pyrrolidinyl, piperidinyl, and oxetanyl, each of which is independently unsubstituted or substituted with 1-2 substituents independently selected from fluoro, cyano, hydroxy, $C_{1-4}$alkyl, trifluoromethyl, —CH$_2$NHC(O)OC(CH$_3$)$_3$, —C(O)NH$_2$, —CH$_2$O(CH$_3$), and —C(O)OC(CH$_3$)$_3$.

In yet still another variation of the above embodiment, $R^0$ is —NHS(O)$_2$R$^8$, wherein R$^8$ is $C_{1-4}$ alkyl or $C_{1-4}$alkylamino.

In yet still another variation of the above embodiment, $R^0$ is —NHS(O)$_2$R$^8$, wherein R$^8$ is methyl, isopropyl, methylamino or dimethylamino.

In still another embodiment of the above embodiments and variations of the compounds of the invention, $L^3$ is a bond.

In yet another embodiment of the above embodiments and variations of the compounds of the invention, in one variation, -L$^3$R$^0$ is selected from chloro, bromo, nitro, —NHC(O)OCH(CH$_3$)$_2$, —N(CH$_2$CH$_3$)C(O)OCH(CH$_3$)$_2$, NHC(O)OCH$_3$, —NHC(O)N(CH$_3$)$_2$, phenyl, and thiophen-3-yl.

In another variation of the above embodiment, -L$^3$R$^0$ is selected from —NH—C(O)CH(CH$_3$)$_2$, —NH—C(O)-cyclopropyl, —NH—C(O)O-cyclopropyl, —NH—C(O)-cyclobutyl, wherein the cyclopropyl and cyclobutyl are each independently unsubstituted or substituted by a substituent independently selected from cyano, halo and $C_{1-4}$alkyl.

In another variation, -L$^3$R$^0$ is selected from halo, isopropyl, tert-butyl, trifluoromethyl, 2,2,2-trifluoroethyl, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH(CH$_3$)$_2$, Si(CH$_3$)$_3$, —NHC(O)OCH(CH$_3$)$_2$, —NHC(O)OCH$_2$CH$_3$, —NHC(O)OCH$_3$, nitro,

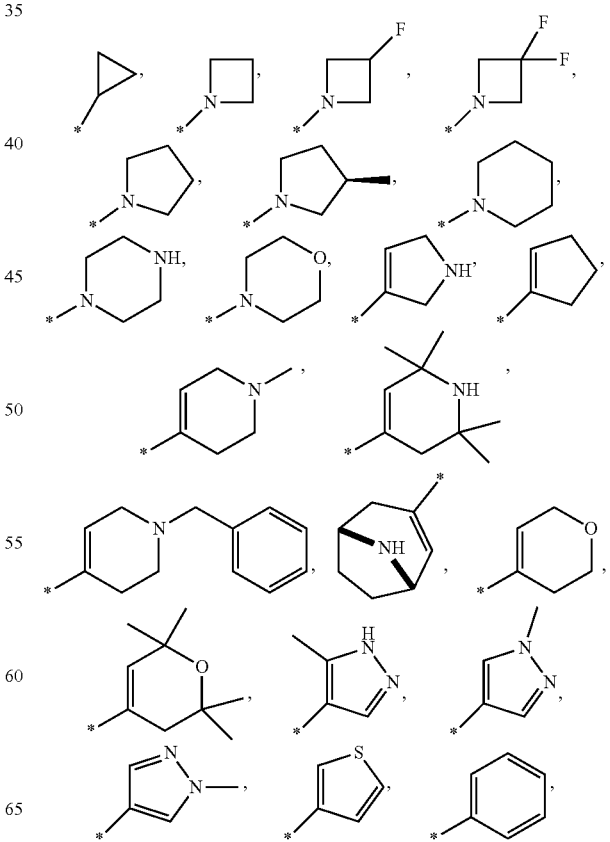

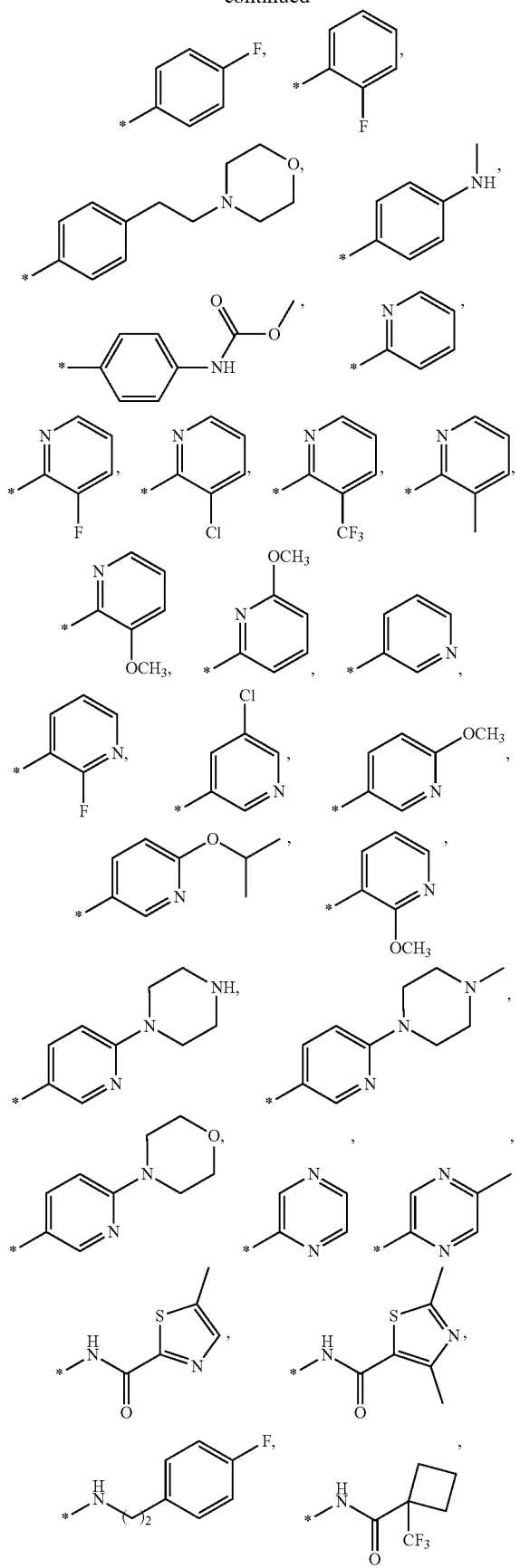
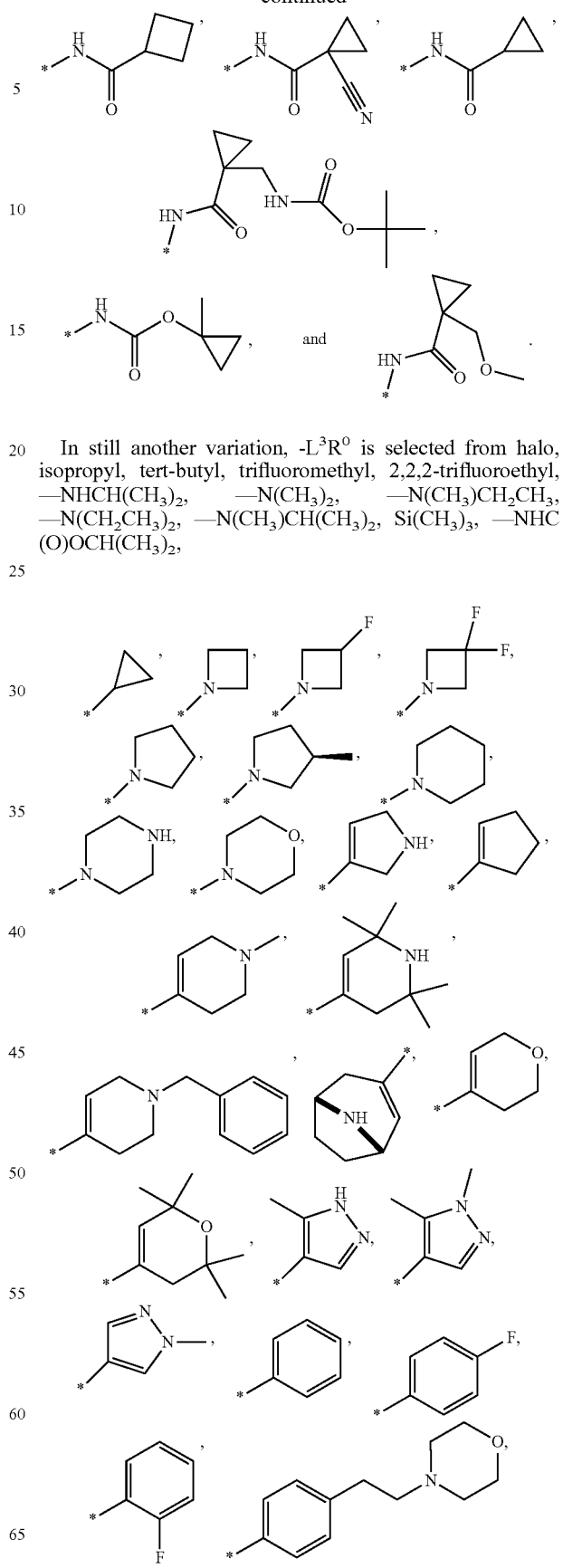
In still another variation, -L³R⁰ is selected from halo, isopropyl, tert-butyl, trifluoromethyl, 2,2,2-trifluoroethyl, —NHCH(CH₃)₂, —N(CH₃)₂, —N(CH₃)CH₂CH₃, —N(CH₂CH₃)₂, —N(CH₃)CH(CH₃)₂, Si(CH₃)₃, —NHC(O)OCH(CH₃)₂, -continued

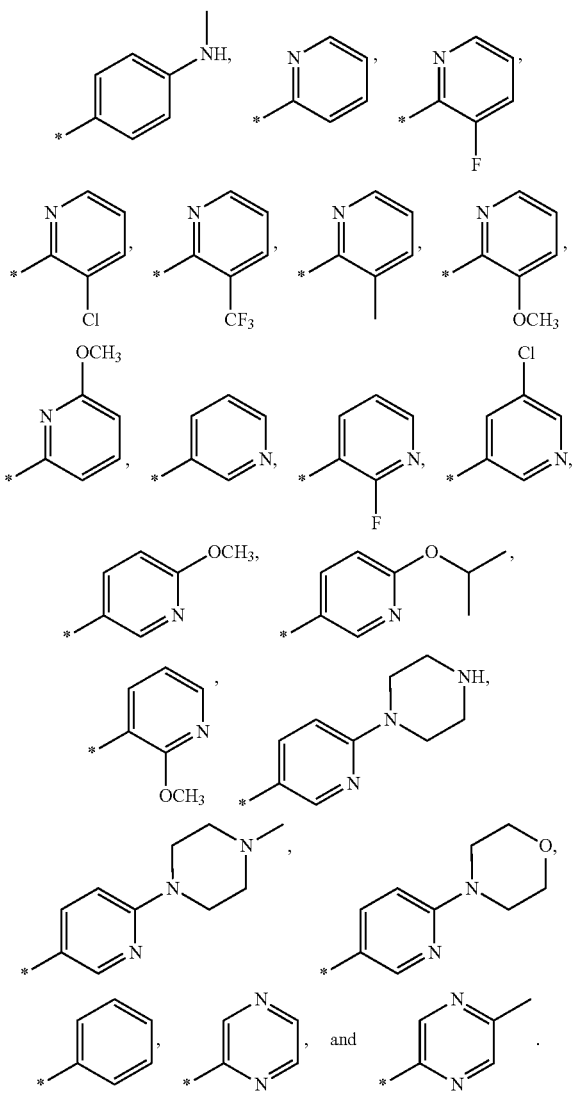

In yet still another variation, -L³R⁰ is isopropyl, tert-butyl, trifluoromethyl, 2,2,2-trifluoroethyl,

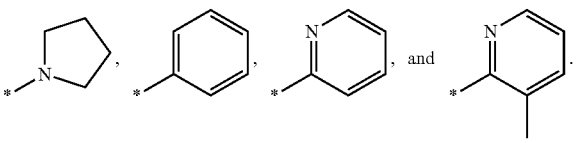

In yet another embodiment, -L³R⁰ is —NHC(O)OCH(CH₃)₂.

In a particular embodiment, the compound of the invention is represented by Formula Ia:

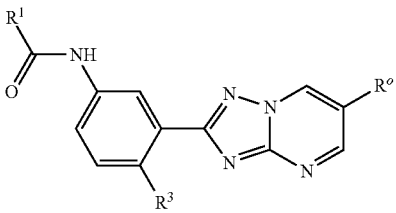

or a pharmaceutically acceptable salt, or stereoisomer thereof; wherein
R¹ is selected from $C_{1-4}$alkoxy, di-$C_{1-4}$alkylamino, $C_{3-6}$cycloalkyl, $C_{4-6}$heterocycloalkyl, and $C_{5-6}$heteroaryl, wherein the $C_{3-6}$cycloalkyl, $C_{4-6}$heterocycloalkyl, or $C_{5-6}$heteroaryl is unsubstituted or substituted by 1 to 2 substituents independently selected from halo, $C_{1-4}$alkyl, $C_{1-4}$alkoxy, di$C_{1-4}$alkylamino, and hydroxycarbonyl;
R³ is halo;
R⁰ is selected from hydrogen, halo, $C_{1-4}$alkyl, —NR$^{2a}$R$^{2b}$, —Si(CH₃)₃, $C_{3-6}$cycloalkyl, $C_{5-6}$cycloalkenyl, $C_{4-6}$heterocycloalkyl, $C_{5-6}$heterocycloalkenyl, phenyl, and $C_{5-6}$heteroaryl; wherein
R$^{2a}$ is hydrogen or $C_{1-4}$alkyl;
R$^{2b}$ is selected from hydrogen, $C_{1-4}$alkyl, and —C(O)OCH(CH₃)₂; and
the $C_{3-6}$cycloalkyl, $C_{5-6}$cycloalkenyl, $C_{4-6}$heterocycloalkyl, $C_{5-6}$heterocycloalkenyl, phenyl, or $C_{5-6}$heteroaryl of R⁰ is unsubstituted or substituted by 1 to 4 substituents independently selected from halo, $C_{1-4}$alkyl, halo$C_{1-4}$alkyl, $C_{4-6}$heterocycloalkyl $C_{1-4}$alkyl, benzyl, $C_{1-4}$alkoxy, unsubstituted $C_6$heterocycloalkyl, and $C_{1-4}$alkyl substituted $C_6$heterocycloalkyl.

In one variation of Formula Ia, R¹ is oxazolyl or pyrrolidinyl, wherein the oxazolyl or pyrrolidinyl is unsubstituted or substituted by 1 to 2 substituents independently selected from halo, $C_{1-4}$alkyl, $C_{1-4}$alkoxy, di$C_{1-4}$alkylamino, and hydroxycarbonyl; R³ is fluoro or chloro; and R⁰ is selected from $C_{1-4}$alkyl, pyrrolidinyl, phenyl and pyridinyl, wherein the pyrrolidinyl, phenyl or pyridinyl is unsubstituted or substituted by one substituent selected from halo, $C_{1-4}$alkyl, halo$C_{1-4}$alkyl, $C_{1-4}$alkoxy, unsubstituted $C_6$heterocycloalkyl, and $C_{1-4}$alkyl substituted $C_6$heterocycloalkyl.

The compounds of the invention include, but are not limited to, Compounds 1 to 97 listed in Table 4.

In another embodiment, Compounds of the invention include, but are not limited to, Compounds 1 to 80 listed in Table 4, namely: N-(4-fluoro-3-(6-phenyl-[1,2,4]triazolo[1,5-a]pyrimidin-2-yl)phenyl)-2,4-dimethyloxazole-5-carboxamide; N-(4-fluoro-3-(6-phenyl-[1,2,4]triazolo[1,5-a]pyrimidin-2-yl)phenyl)-2-methyloxazole-5-carboxamide; 2-(dimethylamino)-N-(4-fluoro-3-(6-phenyl-[1,2,4]triazolo[1,5-a]pyrimidin-2-yl)phenyl)oxazole-5-carboxamide; N-(4-fluoro-3-(6-phenyl-[1,2,4]triazolo[1,5-a]pyrimidin-2-yl)phenyl)cyclobutanecarboxamide; N-(4-fluoro-3-(6-phenyl-[1,2,4]triazolo[1,5-a]pyrimidin-2-yl)phenyl)pyrrolidine-1-carboxamide; (R)—N-(4-fluoro-3-(6-phenyl-[1,2,4]triazolo[1,5-a]pyrimidin-2-yl)phenyl)-3-methoxypyrrolidine-1-carboxamide; 3-(4-fluoro-3-(6-phenyl-[1,2,4]triazolo[1,5-a]pyrimidin-2-yl)phenyl)-1,1-dimethyl(deuterated) urea; N-(4-fluoro-3-(6-phenyl-[1,2,4]triazolo[1,5-a]pyrimidin-2-yl)phenyl)-3,3-dimethylazetidine-1-carboxamide; N-(4-fluoro-3-(6-phenyl-[1,2,4]triazolo[1,5-a]pyrimidin-2-yl)phenyl)azetidine-1-carboxamide; (R)-3-fluoro-N-(4-fluoro-3-(6-phenyl-[1,2,4]triazolo[1,5-a]pyrimidin-2-yl)phenyl)pyrrolidine-1-carboxamide; (2S,4R)-4-fluoro-1-((4-fluoro-3-(6-phenyl-[1,2,4]triazolo[1,5-a]pyrimidin-2-yl)phenyl)carbamoyl)pyrrolidine-2-carboxylic acid; 3-fluoro-N-(4-fluoro-3-(6-phenyl-[1,2,4]triazolo[1,5-a]pyrimidin-2-yl)phenyl)azetidine-1-carboxamide; N-(4-fluoro-3-(6-phenyl-[1,2,4]triazolo[1,5-a]pyrimidin-2-yl)phenyl)-3-methylazetidine-1-carboxamide; 3,3-difluoro-N-(4-fluoro-3-(6-phenyl-[1,2,4]triazolo[1,5-a]pyrimidin-2-yl)phenyl)azetidine-1-carboxamide; Isopropyl (4-fluoro-3-(6-phenyl-[1,2,4]triazolo[1,5-a]pyrimidin-2-yl)phenyl)carbamate; N-(4-chloro-3-(6-phenyl-[1,2,4]triazolo[1,5-a]pyrimidin-2-yl)phenyl)furan-2-carboxamide; N-(4-chloro-3-(6-phenyl-[1,2,4]triazolo[1,5-a]pyrimidin-2-yl)phenyl)pyrrolidine-1-carboxamide; N-(4-fluoro-3-(6-(pyridine-2-yl)-[1,2,4]triazolo[1,5-a]pyrimidin-2-yl)phenyl)-2,4-dimethyloxazole-5-carboxamide; N-(4-fluoro-3-(6-(pyridine-2-yl)-[1,2,4]triazolo[1,5-a]pyrimidin-2-yl)phenyl)-2-methyloxazole-5-carboxamide; N-(4-fluoro-3-(6-(pyridine-2-yl)-[1,2,4]triazolo[1,5-a]pyrimidin-2-yl)phenyl)azetidine-1-carboxamide; N-(3-(6-(tert-butyl)-[1,2,4]triazolo[1,5-a]pyrimidin-2-yl)-4-fluorophenyl)-2,4-dimethyloxazole-5-carboxamide; N-(3-(6-chloro-[1,2,4]triazolo[1,5-a]pyrimidin-2-yl)-4-fluorophenyl)-2,4-dimethyloxazole-5-carboxamide; N-(3-(6-chloro-[1,2,4]triazolo[1,5-a]pyrimidin-2-yl)-4-fluorophenyl)-2-methyloxazole-5-carboxamide; N-(3-(6-chloro-[1,2,4]triazolo[1,5-a]pyrimidin-2-yl)-4-fluorophenyl)pyrrolidine-1-carboxamide; N-(3-(6-chloro-[1,2,4]triazolo[1,5-a]pyrimidin-2-yl)-4-fluorophenyl)-3-fluoroazetidine-1-carboxamide; N-(3-(6-chloro-[1,2,4]triazolo[1,5-a]pyrimidin-2-yl)-4-fluorophenyl)-3,3-difluoroazetidine-1-carboxamide; (R)—N-(3-(6-chloro-[1,2,4]triazolo[1,5-a]pyrimidin-2-yl)-4-fluorophenyl)-3-methoxypyrrolidine-1-carboxamide; N-(3-(6-(3,6-dihydro-2H-pyran-4-yl)-[1,2,4]triazolo[1,5-a]pyrimidin-2-yl)-4-fluorophenyl)-2,4-dimethyloxazole-5-carboxamide; 3-(3-(6-(3,6-dihydro-2H-pyran-4-yl)-[1,2,4]triazolo[1,5-a]pyrimidin-2-yl)-4-fluorophenyl)-1,1-dimethylurea; N-(3-(6-(3,6-dihydro-2H-pyran-4-yl)-[1,2,4]triazolo[1,5-a]pyrimidin-2-yl)-4-fluorophenyl)-3-fluoroazetidine-1-carboxamide; N-(3-(6-(3,6-dihydro-2H-pyran-4-yl)-[1,2,4]triazolo[1,5-a]pyrimidin-2-yl)-4-fluorophenyl)azetidine-1-carboxamide; (R)—N-(3-(6-(3,6-dihydro-2H-pyran-4-yl)-[1,2,4]triazolo[1,5-a]pyrimidin-2-yl)-4-fluorophenyl)-3-fluoropyrrolidine-1-carboxamide; N-(3-(6-bromo-[1,2,4]triazolo[1,5-a]pyrimidin-2-yl)-4-chlorophenyl)furan-2-carboxamide; N-(3-(6-cyclopropyl-[1,2,4]triazolo[1,5-a]pyrimidin-2-yl)-4-fluorophenyl)-2,4-dimethyloxazole-5-carboxamide; N-(3-(6-(cyclopent-1-en-1-yl)-[1,2,4]triazolo[1,5-a]pyrimidin-2-yl)-4-fluorophenyl)-2,4-dimethyloxazole-5-carboxamide; N-(4-fluoro-3-(6-(2,2,6,6-tetramethyl-3,6-dihydro-2H-pyran-4-yl)-[1,2,4]triazolo[1,5-a]pyrimidin-2-yl)phenyl)-2,4-dimethyloxazole-5-carboxamide; N-(4-fluoro-3-(6-(1-methyl-1,2,5,6-tetrahydropyridin-3-yl)-[1,2,4]triazolo[1,5-a]pyrimidin-2-yl)phenyl)-2,4-dimethyloxazole-5-carboxamide; N-(3-(6-((1R,5S)-8-azabicyclo[3.2.1]oct-3-en-3-yl)-[1,2,4]triazolo[1,5-a]pyrimidin-2-yl)-4-fluorophenyl)-2,4-dimethyloxazole-5-carboxamide; N-(4-fluoro-3-(6-(2,2,6,6-tetramethyl-1,2,3,6-tetrahydropyridin-4-yl)-[1,2,4]triazolo[1,5-a]pyrimidin-2-yl)phenyl)-2,4-dimethyloxazole-5-carboxamide; N-(3-(6-(1-benzyl-1,2,3,6-tetrahydropyridin-4-yl)-[1,2,4]triazolo[1,5-a]pyrimidin-2-yl)-4-fluorophenyl)-2,4-dimethyloxazole-5-carboxamide; N-(4-fluoro-3-(6-(1-methyl-1,2,3,6-tetrahydropyridin-4-yl)-[1,2,4]triazolo[1,5-a]pyrimidin-2-yl)phenyl)-2,4-dimethyloxazole-5-carboxamide; N-(3-(6-(2,5-dihydro-1H-pyrrol-3-yl)-[1,2,4]triazolo[1,5-a]pyrimidin-2-yl)-4-fluorophenyl)-2,4-dimethyloxazole-5-carboxamide; N-(4-fluoro-3-(6-(4-(2-morpholinoethyl)phenyl)-[1,2,4]triazolo[1,5-a]pyrimidin-2-yl)phenyl)-2,4-dimethyloxazole-5-carboxamide; N-(4-fluoro-3-(6-(2-fluorophenyl)-[1,2,4]triazolo[1,5-a]pyrimidin-2-yl)phenyl)-2,4-dimethyloxazole-5-carboxamide; N-(4-fluoro-3-(6-(5-methyl-1H-pyrazol-4-yl)-[1,2,4]triazolo[1,5-a]pyrimidin-2-yl)phenyl)-2,4-dimethyloxazole-5-carboxamide; N-(4-fluoro-3-(6-(1-methyl-1H-pyrazol-5-yl)-[1,2,4]triazolo[1,5-a]pyrimidin-2-yl)phenyl)-2,4-dimethyloxazole-5-carboxamide; N-(4-fluoro-3-(6-(1-methyl-1H-pyrazol-3-yl)-[1,2,4]triazolo[1,5-a]pyrimidin-2-yl)phenyl)-2,4-dimethyloxazole-5-carboxamide; N-(4-fluoro-3-(6-(2-fluorophenyl)-[1,2,4]triazolo[1,5-a]pyrimidin-2-yl)phenyl)-2,4-dimethyloxazole-5-carboxamide; N-(4-fluoro-3-(6-(6-methoxypyridin-3-yl)-[1,2,4]triazolo[1,5-a]pyrimidin-2-yl)phenyl)-2,4-dimethyloxazole-5-carboxamide; N-(3-([1,2,4]triazolo[1,5-a]pyrimidin-2-yl)-4-fluorophenyl)-2,4-dimethyloxazole-5-carboxamide; N-(4-fluoro-3-(6-(pyridine-3-yl)-[1,2,4]triazolo[1,5-a]pyrimidin-2-yl)phenyl)-2,4-dimethyloxazole-5-carboxamide; N-(4-fluoro-3-(6-(6-methoxypyridin-3-yl)-[1,2,4]triazolo[1,5-a]pyrimidin-2-yl)phenyl)-2,4-dimethyloxazole-5-carboxamide; N-(4-fluoro-3-(6-(2-methoxypyridin-3-yl)-[1,2,4]triazolo[1,5-a]pyrimidin-2-yl)phenyl)-2,4-dimethyloxazole-5-carboxamide; N-(4-fluoro-3-(6-(6-(piperazin-1-yl) pyridine-3-yl)-[1,2,4]triazolo[1,5-a]pyrimidin-2-yl)phenyl)-2,4-dimethyloxazole-5-carboxamide; N-(4-fluoro-3-(6-(6-(4-methylpiperazin-1-yl) pyridine-3-yl)-[1,2,4]triazolo[1,5-a]pyrimidin-2-yl)phenyl)-2,4-dimethyloxazole-5-carboxamide; N-(4-fluoro-3-(6-(6-isopropoxypyridin-3-yl)-[1,2,4]triazolo[1,5-a]pyrimidin-2-yl)phenyl)-2,4-dimethyloxazole-5-carboxamide; N-(3-(6-(5-chloropyridin-3-yl)-[1,2,4]triazolo[1,5-a]pyrimidin-2-yl)-4-fluorophenyl)-2,4-dimethyloxazole-5-carboxamide; N-(4-fluoro-3-(6-(6-morpholinopyridin-3-yl)-[1,2,4]triazolo[1,5-a]pyrimidin-2-yl)phenyl)-2,4-dimethyloxazole-5-carboxamide; N-(4-fluoro-3-(6-(3-fluoropyridin-2-yl)-[1,2,4]triazolo[1,5-a]pyrimidin-2-yl)phenyl)-2,4-dimethyloxazole-5-carboxamide; N-(4-fluoro-3-(6-(3-(trifluoromethyl)pyridine-2-yl)-[1,2,4]triazolo[1,5-a]pyrimidin-2-yl)phenyl)-2,4-dimethyloxazole-5-carboxamide; N-(4-fluoro-3-(6-(3-methylpyridin-2-yl)-[1,2,4]triazolo[1,5-a]pyrimidin-2-yl)phenyl)-2,4-dimethyloxazole-5-carboxamide; N-(4-fluoro-3-(6-(3-methoxypyridin-2-yl)-[1,2,4]triazolo[1,5-a]pyrimidin-2-yl)phenyl)-2,4-dimethyloxazole-5-carboxamide; N-(4-fluoro-3-(6-(5-methylpyrazin-2-yl)-[1,2,4]triazolo[1,5-a]pyrimidin-2-yl)phenyl)-2,4-dimethyloxazole-5-carboxamide; N-(4-fluoro-3-(6-(pyrazin-2-yl)-[1,2,4]triazolo[1,5-a]pyrimidin-2-yl)phenyl)-2,4-dimethyloxazole-5-carboxamide; N-(3-(6-(3-chloropyridin-2-yl)-[1,2,4]triazolo[1,5-a]pyrimidin-2-yl)-4-fluorophenyl)-2,4-dimethyloxazole-5-carboxamide; N-(4-fluoro-3-(6-(trimethylsilyl)-[1,2,4]triazolo[1,5-a]pyrimidin-2-yl)phenyl)-2,4-dimethyloxazole-5-carboxamide; N-(4-fluoro-3-(6-(piperidin-1-yl)-[1,2,4]triazolo[1,5-a]pyrimidin-2-yl)phenyl)-2,4-dimethyloxazole-5-carboxamide; N-(4-fluoro-3-(6-morpholino-[1,2,4]triazolo[1,5-a]pyrimidin-2-yl)phenyl)-2,4-dimethyloxazole-5-carboxamide; N-(3-(6-(ethyl(methyl)amino)-[1,2,4]triazolo[1,5-a]pyrimidin-2-yl)-4-fluorophenyl)-2,4-dimethyloxazole-5-carboxamide; N-(3-(6-(azetidin-1-yl)-[1,2,4]triazolo[1,5-a]pyrimidin-2-yl)-4-fluorophenyl)-2,4-dimethyloxazole-5-carboxamide; N-(4- fluoro-3-(6-(3-fluoroazetidin-1-yl)-[1,2,4]triazolo[1,5-a]pyrimidin-2-yl)phenyl)-2,4-dimethyloxazole-5-carboxamide; N-(4-fluoro-3-(6-(isopropyl(methyl)amino)-[1,2,4]triazolo[1,5-a]pyrimidin-2-yl)phenyl)-2,4-dimethyloxazole-5-carboxamide; N-(3-(6-(dimethylamino)-[1,2,4]triazolo[1,5-a]pyrimidin-2-yl)-4-fluorophenyl)-2,4-dimethyloxazole-5-carboxamide; N-(3-(6-(diethylamino)-[1,2,4]triazolo[1,5-a]pyrimidin-2-yl)-4-fluorophenyl)-2,4-dimethyloxazole-5-carboxamide; N-(3-(6-(3,3-difluoroazetidin-1-yl)-[1,2,4]triazolo[1,5-a]pyrimidin-2-yl)-4-fluorophenyl)-2,4-dimethyloxazole-5-carboxamide; N-(4-fluoro-3-(6-(pyrrolidin-1-yl)-[1,2,4]triazolo[1,5-a]pyrimidin-2-yl)phenyl)-2,4-dimethyloxazole-5-carboxamide; (R)—N-(4-fluoro-3-(6-(3-fluoropyrrolidin-1-yl)-[1,2,4]triazolo[1,5-a]pyrimidin-2-yl)phenyl)-2,4-dimethyloxazole-5-carboxamide; N-(4-fluoro-3-(6-(piperazin-1-yl)-[1,2,4]triazolo[1,5-a]pyrimidin-2-yl)phenyl)-2,4-dimethyloxazole-5-carboxamide; N-(4-fluoro-3-(6-(isopropylamino)-[1,2,4]triazolo[1,5-a]pyrimidin-2-yl)phenyl)-2,4-dimethyloxazole-5-carboxamide; and Isopropyl (2-(5-(2,4-dimethyloxazole-5-carboxamido)-2-fluorophenyl)-[1,2,4]triazolo[1,5-a]pyrimidin-6-yl)carbamate.

In still another embodiment, the compounds of the invention include, but not limited to, Compounds 81 to 97 listed in Table 4, namely: N-(4-fluoro-3-(6-(pyridin-2-yl)-[1,2,4]triazolo[1,5-a]pyrimidin-2-yl)phenyl)-N,2,4-trimethyloxazole-5-carboxamide; N-(4-fluoro-3-(6-(3-methylpyridin-2-yl)-[1,2,4]triazolo[1,5-a]pyrimidin-2-yl)phenyl)-N,2,4-trimethyloxazole-5-carboxamide; N-(3-(6-(3-(difluoromethyl)pyridin-2-yl)-[1,2,4]triazolo[1,5-a]pyrimidin-2-yl)-4-fluorophenyl)-2,4-dimethyloxazole-5-carboxamide; N-(3-(6-(7-azabicyclo[2.2.1]hept-2-en-2-yl)-[1,2,4]triazolo[1,5-a]pyrimidin-2-yl)-4-fluorophenyl)-2,4-dimethyloxazole-5-carboxamide; 2,4-dimethyl-N-(4-(6-phenyl-[1,2,4]triazolo[1,5-a]pyrimidin-2-yl)pyridin-2-yl)oxazole-5-carboxamide; 2,4-dimethyl-N-(5-(6-phenyl-[1,2,4]triazolo[1,5-a]pyrimidin-2-yl)pyridin-3-yl)oxazole-5-carboxamide; 2,4-dimethyl-N-(2-(6-phenyl-[1,2,4]triazolo[1,5-a]pyrimidin-2-yl)pyridin-4-yl)oxazole-5-carboxamide; N-(2,4-difluoro-3-(6-phenyl-[1,2,4]triazolo[1,5-a]pyrimidin-2-yl)phenyl)-2,4-dimethyloxazole-5-carboxamide; 2,4-dimethyl-N-(6-(6-phenyl-[1,2,4]triazolo[1,5-a]pyrimidin-2-yl)pyridin-2-yl)oxazole-5-carboxamide; N-(4-fluoro-3-(6-(pyrrolidin-1-yl)-[1,2,4]triazolo[1,5-a]pyrimidin-2-yl)phenyl)-2,4-dimethyloxazole-5-carboxamide; N-(2,4-difluoro-5-(6-phenyl-[1,2,4]triazolo[1,5-a]pyrimidin-2-yl)phenyl)-2,4-dimethyloxazole-5-carboxamide; (R)-3-fluoro-N-(3-(6-phenyl-[1,2,4]triazolo[1,5-a]pyrimidin-2-yl)phenyl)pyrrolidine-1-carboxamide; (R)—N-(3-(6-chloro-[1,2,4]triazolo[1,5-a]pyrimidin-2-yl)-4-fluorophenyl)-3-fluoropyrrolidine-1-carboxamide; N-(4-fluoro-3-(6-isopropyl-[1,2,4]triazolo[1,5-a]pyrimidin-2-yl)phenyl)-2,4-dimethyloxazole-5-carboxamide; 2,4-dimethyl-N-(3-(6-phenyl-[1,2,4]triazolo[1,5-a]pyrimidin-2-yl)phenyl)oxazole-5-carboxamide; N-(3-(6-(3,6-dihydro-2H-pyran-4-yl)-[1,2,4]triazolo[1,5-a]pyrimidin-2-yl)phenyl)-2,4-dimethyloxazole-5-carboxamide; and (R)-3-fluoro-N-(3-(6-phenyl-[1,2,4]triazolo[1,5-a]pyrimidin-2-yl)phenyl)pyrrolidine-1-carboxamide.

It is noted that the compounds of the above embodiments of the present invention may be in the form of a pharmaceutically acceptable salt. It is further note that the compounds of the present invention may be a mixture of stereoisomers, or the compound may comprise a single stereoisomer.

Further compounds of the invention are detailed in the Examples, infra.

In another aspect, the present invention is directed to a pharmaceutical composition which includes as an active ingredient a compound according to any one of the above embodiments and variations in combination with a pharmaceutically acceptable carrier, diluent or excipient.

In another embodiment, the pharmaceutical composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In yet another embodiment, the pharmaceutical composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the present application is directed to a compound or a pharmaceutical composition according to any one of the above embodiments and variations for use in a therapeutic application.

In another aspect, the present application is directed to a compound or a pharmaceutical composition according to any one of the above embodiments and variations for use as a medicament.

In still another aspect, the present application is directed to a compound or a pharmaceutical composition according to any one of the above embodiments and variations for treating, preventing, inhibiting, ameliorating, or eradicating the pathology and/or symptomology of a parasitic disease, wherein parasitic disease is leishmaniasis, human African trypanosomiasis, or Chagas disease. The compound or composition for treating leishmaniasis, human African trypanosomiasis, or Chagas diseases may further include a second agent which may be other drugs that are known for treating said diseases. For treating leishmaniasis, the second agent includes, but is not limited to, meglumine antimoniate, stibogluconate, Amphotericin, Miltefosine and paromomycin. For treating human African trypanosomiasis, the second agent includes, but is not limited to, pentamidine, suramin, melarsoprol, and eflornithine. For treating Chagas disease, the second agent includes, but is not limited to, benznidazole, nifurtimox or Amphotericin b.

In yet another aspect, the present invention is directed to a method for treating, preventing, inhibiting, ameliorating, or eradicating the pathology and/or symptomology of a parasitic disease. The method involves administering to a subject in need thereof, a therapeutically effective amount of a compound or a pharmaceutical composition according to the above embodiments and variations.

In one embodiment of the above method for treating, preventing, inhibiting, ameliorating, or eradicating the pathology and/or symptomology of a parasitic disease, the compound of the invention is capable of inhibiting the proteolytic activity of the proteasome of the parasite causing the parasitic disease.

In another embodiment of the above method for treating, preventing, inhibiting, ameliorating, or eradicating the pathology and/or symptomology of a parasitic disease, the compound of the invention is capable of inhibiting the chymotrypsin-like proteolytic activity of the proteasomes of the parasite causing the parasitic disease.

In another embodiment of the method of the invention, the disease being treated is leishmaniasis, human African trypanosomiasis, or Chagas disease.

In still another embodiment of the method of the invention, the disease being treated is Leishmaniasis caused by the parasite *Leishmania donovani, Leishmania infantum, Leishmania braziliensis, Leishmania panamensis, Leishmania guayanensis, Leishmania amazonensis, Leishmania mexicana, Leishmania tropica*, or *Leishmania major*.

In still another embodiment of the method of the invention, the disease being treated is visceral Leishmaniasis caused by the parasite *Leishmania donovani*.

In still another embodiment of the method of the invention, the disease being treated is Human African Trypanosomiasis caused by *Trypanosoma brucei*, particularly, by the subspecies *T.b. gambiense* or *T.b. rhodesiense*.

In still another embodiment of the method of the invention, the disease being treated is Chagas disease, (also call American trypanosomiasis) caused by *Trypanosoma cruzi*.

In the above method of the invention, the compounds or pharmaceutical compositions may be administered prior to, simultaneously with, or after a second agent. The second agent can be other drugs that are known for treating leishmaniasis, human African trypanosomiasis, or Chagas diseases. In one particular variation for treating leishmaniasis, the second agent is selected from meglumine antimoniate, stibogluconate, Amphotericin, Miltefosine and paromomycin. In another variation, for treating human African trypanosomiasis, the second agent is selected from pentamidine, suramin, melarsoprol, and eflornithine. In another particular variation of the method, for treating Chagas disease, the second agent is selected from benznidazole, nifurtimox or Amphotericin b.

In another aspect, the invention is directed to a compound, salt, steroisomer, or pharmaceutical composition thereof, according to any one of the above embodiments or variation, for treating, preventing, inhibiting, ameliorating, or eradicating the pathology and/or symptomology of a disease caused by the parasite *Leishmania donovani, Leishmania infantum, Leishmania braziliensis, Leishmania panamensis, Leishmania guayanensis, Leishmania amazonensis, Leishmania mexicana, Leishmania tropica, Leishmania major, Trypanosoma cruzi*, or *Trypanosoma brucei*. In one embodiment, the disease is visceral Leishmaniasis caused by *Leishmania donovani*. In another embodiment, the disease is Human African Trypanosomiasis caused by *Trypanosoma brucei*. In yet another embodiment, the disease is Chagas disease caused by *Trypanosoma cruzi*.

In still another aspect, the present invention is directed to the use of the compound, or a salt, a stereoisomer, or a pharmaceutical composition thereof, according to the any one of the above embodiments or variations in the manufacture of a medicament for treating, preventing, inhibiting, ameliorating, or eradicating the pathology and/or symptomology of a disease caused by *Leishmania donovani, Leishmania infantum, Leishmania braziliensis, Leishmania panamensis, Leishmania guayanensis, Leishmania amazonensis, Leishmania mexicana, Leishmania tropica, Leishmania major, Trypanosoma cruzi*, or *Trypanosoma brucei*. In one embodiment, the medicament is for treating visceral Leishmaniasis caused by *Leishmania donovani*. In another embodiment, the medicament is for treating Human African Trypanosomiasis caused by *Trypanosoma brucei*. In yet another embodiment, the medicament is for treating Chagas disease caused by *Trypanosoma cruzi*.

The medicament, in addition to the compound of the invention, may further include a second agent. The second agent may be other drugs that are known for treating Leishmaniasis, Human African Trypanosomiasis, or Chagas diseases. In one particular variation of the medicament, for treating Leishmaniasis, the second agent is selected from meglumine antimoniate, stibogluconate, Amphotericin, Miltefosine and paromomycin. In another particular variation of the medicament, for treating Human African Trypanosomiasis, the second agent is selected from pentamidine, suramin, melarsoprol, and eflornithine. In yet another particular variation of the medicament, for treating Chagas disease, the second agent is selected from benznidazole, nifurtimox or Amphotericin b.

In a further aspect, the invention provide a method of treating, preventing, inhibiting, ameliorating, or eradicating the pathology and/or symptomology of a disease caused by a parasite, wherein the method comprising administering to a subject in need thereof a therapeutically effective amount of an agent capable of inhibiting the proteolytic activity of the proteasomes of the parasite, wherein the disease is selected from leishmaniasis, human African trypanosomiasis and Chagas disease.

In an embodiment of the method of the invention immediately above, the agent is capable of inhibiting the chymotrypsin-like proteolytic activity of the proteasomes.

In another embodiment of the embodiments of the method of the invention, the agent capable of inhibiting the chymotrypsin-like proteolytic activity of the proteasome of the parasite is a low molecular weight compound.

In another embodiment of the embodiments of the method of the invention, the low molecular weight compound is a compound of the present invention.

In another aspect, the invention is related to a kit which comprises a compound of any one of the above embodiments and variations, and optionally a second therapeutic agent. In one particular variation, the kit comprises the compound in a multiple dose form.

ENUMERATED EMBODIMENTS

Various enumerated embodiments of the invention are described herein. It will be recognized that features specified in each embodiment may be combined with other specified features to provide further embodiments of the present invention.

In a first embodiment, the invention provides a compound of Formula (A):

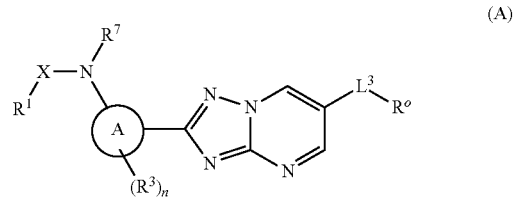

(A)

or a pharmaceutically acceptable salt, or stereoisomer thereof; wherein

Ring A is phenyl or pyridyl;

X is —C(O)— or —S(O)$_2$—;

R$^1$ is selected from nitro, C$_{1-4}$alkyl, C$_{1-6}$alkoxy, amino, C$_{1-6}$alkylamino, di-C$_{1-6}$alkylamino, —N(C$_2$H$_3$)$_2$, C$_{3-6}$cycloalkyl, C$_{4-6}$heterocycloalkyl, C$_{4-8}$heterocycloalkenyl, and C$_{5-9}$heteroaryl, wherein the C$_{1-6}$alkoxy, C$_{1-6}$alkylamino, C$_{3-6}$cycloalkyl, C$_{4-6}$heterocycloalkyl, C$_{4-8}$heterocycloalkenyl, or C$_{5-9}$heteroaryl of R$^1$ is unsubstituted or substituted by 1-2 substituents independently selected from halo, cyano, $C_{1-4}$alkyl, halo$C_{1-4}$alkyl, $C_{1-4}$alkoxy, amino, $C_{1-4}$alkylamino, di$C_{1-4}$alkylamino, and hydroxycarbonyl, and $C_{1-4}$alkylcarbonyl;

$R^3$ is selected from hydrogen, halo, cyano, $C_{1-4}$alkyl, and halo$C_{1-4}$alkyl, and n is 0, 1, or 2;

$R^7$ is selected from hydrogen or $C_{1-4}$alkyl;

$L^3$ is a bond, phenylene, or $C_{5-6}$heteroarylene;

$R^0$ is selected from hydrogen, hydroxyl, halo, nitro, —N=CHN(CH$_3$)$_2$, $C_{1-4}$alkyl, $C_{4-6}$heterocycloalkyl$C_{1-4}$alkyl, $C_{1-4}$alkoxy, —NR$^{2a}$R$^{2b}$, —NR$^5$C(O)R$^6$, —NR$^5$S(O)$_2$R$_8$, —Si(CH$_3$)$_3$, $C_{3-6}$cycloalkyl, $C_{5-6}$cycloalkenyl, $C_{4-6}$heterocycloalkyl, $C_{5-8}$heterocycloalkenyl, $C_{6-10}$aryl, and $C_{5-6}$heteroaryl; wherein
the $C_{1-4}$alkyl or $C_{1-4}$alkoxy of $R^0$ is unsubstituted or substituted by 1-2 substituents independently selected from $C_{1-4}$alkoxy, amino, phenyl and $C_{5-6}$heteroaryl; wherein the phenyl or $C_{5-6}$heteroaryl substituent of $R^0$ is unsubstituted or further substituted by halo or $C_{1-4}$alkyl;
the $C_{3-6}$cycloalkyl, $C_{5-6}$cycloalkenyl, $C_{4-6}$heterocycloalkyl, $C_{5-8}$heterocycloalkenyl, $C_{6-10}$aryl, and $C_{5-6}$heteroaryl of $R^0$ is unsubstituted or substituted by 1 to 4 substituents independently selected from halo, oxo, $C_{1-4}$alkyl, hydroxy$C_{1-4}$ alkyl, halo$C_{1-4}$alkyl, —(CH$_2$)$_{1-4}$NR$^a$R$^b$, $C_{4-6}$heterocycloalkyl$C_{1-4}$alkyl, benzyl, $C_{1-4}$alkoxy, amino, $C_{1-4}$alkylamino, di$C_{1-4}$alkylamino, unsubstituted $C_{4-6}$heterocycloalkyl and $C_{1-4}$ alkyl substituted $C_{4-6}$heterocycloalkyl, wherein $R^a$ and $R^b$ are each independently selected from hydrogen, $C_{1-4}$alkyl, and $C_{3-6}$cycloalkyl;

$R^{2a}$ is hydrogen or $C_{1-4}$alkyl;

$R^{2b}$ is selected from hydrogen, $C_{1-4}$alkyl and —C(O)OCH(CH$_3$)$_2$, wherein the $C_{1-4}$alkyl of $R^{2b}$ is unsubstituted or substituted by amino, $C_{4-6}$heterocycloalkyl, phenyl or $C_{5-6}$heteroaryl, wherein the $C_{4-6}$heterocycloalkyl, phenyl or $C_{5-6}$heteroaryl substituent of $R^{2b}$ is unsubstituted or substituted by hydroxyl, halo or $C_{1-4}$alkyl;

$R^5$ is hydrogen or $C_{1-4}$alkyl;

$R^6$ is selected from hydrogen, $C_{1-4}$alkyl, $C_{1-4}$alkoxy, $C_{3-6}$cycloalkyloxy, amino, $C_{3-6}$cycloalkyl, $C_{4-6}$heterocycloalkyl, and $C_{5-6}$heteroaryl, wherein
the $C_{1-4}$alkyl, $C_{1-4}$alkoxy, $C_{3-6}$cycloalkyloxy, or amino of $R^6$ is unsubstituted or substituted by 1 to 2 substituents independently selected from halo, hydroxyl, $C_{1-4}$alkyl, halo$C_{1-4}$alkyl, $C_{1-4}$alkoxy, —NR$^{9a}$R$^{9b}$, $C_{3-6}$cycloalkyl, $C_{5-6}$heterocycloalkyl, and $C_{5-6}$heteroaryl, wherein $R^{9a}$ is hydrogen or $C_{1-4}$alkyl, $R^{9b}$ is selected from hydrogen, $C_{1-4}$alkyl, $C_{1-4}$alkylcarbonyl and $C_{1-4}$alkoxycarbonyl, and the $C_{5-6}$heterocycloalkyl or $C_{5-6}$heteroaryl substituent of $R^6$ is unsubstituted or substituted by 1-2 substituents independently selected from hydroxyl, $C_{1-4}$alkyl and $C_{1-4}$alkoxycarbonyl,
the $C_{3-6}$cycloalkyl or $C_{4-6}$heterocycloalkyl of $R^6$ is unsubstituted or substituted by 1 to 2 substituents independently selected from halo, cyano, hydroxyl, $C_{1-4}$alkyl, halo$C_{1-4}$alkyl, $C_{1-4}$alkoxy$C_{1-4}$alkyl, $C_{1-4}$alkoxy, amino, $C_{1-4}$ alkylamino, di-$C_{1-4}$alkylamino, aminocarbonyl, $C_{1-4}$alkoxycarbonyl, and $C_{1-4}$alkoxycarbonylamino$C_{1-4}$alkyl, and
the $C_{5-6}$heteroaryl of $R^6$ is unsubstituted or substituted by 1-2 substituents independently selected from hydroxyl, $C_{1-4}$alkyl, $C_{1-4}$alkoxy, amino, $C_{1-4}$alkylamino, di-$C_{1-4}$alkylamino, and $C_{1-4}$alkoxycarbonyl; and $R^8$ is $C_{1-4}$alkyl or $C_{1-4}$alkylamino.

Embodiment 2

A compound according to Embodiment 1, or a pharmaceutically acceptable salt, or a stereoisomer thereof, wherom the compound is represented by Formula (I),

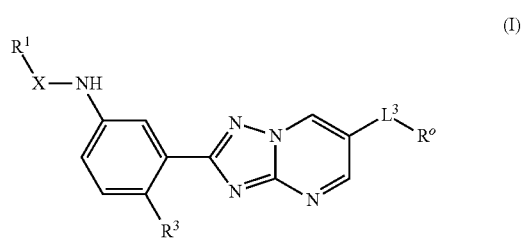

or a pharmaceutically acceptable salt, or a stereoisomer thereof; wherein

X is —C(O)— or —S(O)$_2$—;

$R^1$ is selected from nitro, $C_{1-4}$alkyl, $C_{1-4}$alkoxy, amino, $C_{1-6}$alkylamino, di-$C_{1-6}$alkylamino, —N(C$_2$H$_3$)$_2$, $C_{3-6}$cycloalkyl, $C_{4-6}$heterocycloalkyl, $C_{4-8}$heterocycloalkenyl, and $C_{5-9}$heteroaryl, wherein the $C_{1-6}$alkoxy, $C_{1-6}$alkylamino, $C_{3-6}$cycloalkyl, $C_{4-6}$heterocycloalkyl, $C_{4-8}$heterocycloalkenyl, or $C_{5-9}$heteroaryl of $R^1$ is unsubstituted or substituted by 1-2 substituents independently selected from halo, cyano, $C_{1-4}$alkyl, halo$C_{1-4}$alkyl, $C_{1-4}$alkoxy, amino, $C_{1-4}$alkylamino, di$C_{1-4}$alkylamino, and hydroxycarbonyl, and $C_{1-4}$alkylcarbonyl;

$R^3$ is selected from hydrogen, halo, cyano, $C_{1-4}$alkyl, and halo$C_{1-4}$alkyl;

$L^3$ is a bond, phenylene, or $C_{5-6}$heteroarylene;

$R^0$ is selected from hydrogen, hydroxyl, halo, nitro, —N=CHN(CH$_3$)$_2$, $C_{1-4}$alkyl, $C_{4-6}$heterocycloalkyl$C_{1-4}$alkyl, $C_{1-4}$alkoxy, —NR$^{2a}$R$^{2b}$, —NR$^5$C(O)R$^6$, —NR$^5$S(O)$_2$R$_8$, —Si(CH$_3$)$_3$, $C_{3-6}$cycloalkyl, $C_{5-6}$cycloalkenyl, $C_{4-6}$heterocycloalkyl, $C_{5-6}$heterocycloalkenyl, $C_{6-10}$aryl, and $C_{5-6}$heteroaryl; wherein
the $C_{1-4}$alkyl or $C_{1-4}$alkoxy of $R^0$ is unsubstituted or substituted by 1-2 substituents independently selected from $C_{1-4}$alkoxy, amino, phenyl and $C_{5-6}$heteroaryl; wherein the phenyl or $C_{5-6}$heteroaryl substituent of $R^0$ is unsubstituted or substituted by halo or $C_{1-4}$alkyl;
the $C_{3-6}$cycloalkyl, $C_{5-6}$cycloalkenyl, $C_{4-6}$heterocycloalkyl, $C_{5-6}$heterocycloalkenyl, $C_{6-10}$aryl, and $C_{5-6}$heteroaryl of $R^0$ is unsubstituted or substituted by 1 to 4 substituents independently selected from halo, oxo, $C_{1-4}$alkyl, hydroxy$C_{1-4}$ alkyl, halo$C_{1-4}$alkyl, —(CH$_2$)$_{1-4}$NR$^a$R$^b$, $C_{4-6}$heterocycloalkyl$C_{1-4}$alkyl, benzyl, $C_{1-4}$alkoxy, amino, $C_{1-4}$alkylamino, di$C_{1-4}$alkylamino, unsubstituted $C_{4-6}$heterocycloalkyl and $C_{1-4}$alkyl substituted $C_{4-6}$heterocycloalkyl, wherein $R^a$ and $R^b$ are each independently selected from hydrogen, $C_{1-4}$alkyl, and $C_{3-6}$cycloalkyl;

$R^{2a}$ is hydrogen or $C_{1-4}$alkyl;

$R^{2b}$ is selected from hydrogen, $C_{1-4}$alkyl and —C(O)OCH(CH$_3$)$_2$, wherein the $C_{1-4}$alkyl of $R^{2b}$ is unsubstituted or substituted by amino, $C_{4-6}$heterocycloalkyl, phenyl or $C_{5-6}$heteroaryl, wherein the $C_{4-6}$heterocycloalkyl, phenyl or $C_{5-6}$heteroaryl substituent of $R^{2b}$ is unsubstituted or substituted by hydroxyl, halo or $C_{1-4}$alkyl;

$R^5$ is hydrogen or $C_{1-4}$alkyl;

$R^6$ is selected from hydrogen, $C_{1-4}$alkyl, $C_{1-4}$alkoxy, $C_{3-6}$cycloalkyloxy, amino, $C_{3-6}$cycloalkyl, $C_{5-6}$heterocycloalkyl, and $C_{5-6}$heteroaryl, wherein the $C_{1-4}$alkyl, $C_{1-4}$alkoxy, $C_{3-6}$cycloalkyloxy, or amino of $R^6$ is unsubstituted or substituted by 1 to 2 substituents independently selected from halo, hydroxyl, $C_{1-4}$alkyl, halo$C_{1-4}$alkyl, $C_{1-4}$alkoxy, —$NR^{9a}R^{9b}$, $C_{3-6}$cycloalkyl, $C_{5-6}$heterocycloalkyl, and $C_{5-6}$heteroaryl, wherein $R^{9a}$ is hydrogen or $C_{1-4}$alkyl, $R^{9b}$ is selected from hydrogen, $C_{1-4}$alkyl, $C_{1-4}$alkylcarbonyl and $C_{1-4}$alkoxycarbonyl, and the $C_{5-6}$heterocycloalkyl or $C_{5-6}$heteroaryl substituent of $R^6$ is each unsubstituted or substituted by 1-2 substituents independently selected from hydroxyl, $C_{1-4}$alkyl and $C_{1-4}$alkoxycarbonyl, the $C_{3-6}$cycloalkyl or $C_{4-6}$heterocycloalkyl of $R^6$ is unsubstituted or substituted by 1 to 2 substituents independently selected from halo, cyano, hydroxyl, $C_{1-4}$alkyl, halo$C_{1-4}$alkyl, $C_{1-4}$alkoxyl$C_{1-4}$alkyl, $C_{1-4}$alkoxy, amino, $C_{1-4}$alkylamino, di-$C_{1-4}$alkylamino, aminocarbonyl, $C_{1-4}$alkoxycarbonyl, and $C_{1-4}$alkoxycarbonylamino$C_{1-4}$alkyl, and the $C_{5-6}$heteroaryl of $R^6$ is unsubstituted or substituted by 1 to 2 substituents independently selected from hydroxyl, $C_{1-4}$alkyl, $C_{1-4}$alkoxy, amino, $C_{1-4}$alkylamino, di-$C_{1-4}$alkylamino, and $C_{1-4}$alkoxycarbonyl; and $R^8$ is $C_{1-4}$alkyl or $C_{1-4}$alkylamino.

Embodiment 3

A compound according to Embodiment 1 or 2, or a pharmaceutically acceptable salt, or a stereoisomer thereof, wherein X is —C(O)—.

Embodiment 4

A compound according to any one of Embodiments 1 to 3 or a pharmaceutically acceptable salt, or stereoisomer thereof, wherein $R^1$ is selected from $C_{1-4}$alkyl, $C_{1-4}$alkoxy, amino, $C_{1-4}$alkylamino, di$C_{1-4}$alkylamino, —$N(C_2H_3)_2$, $C_{3-6}$cycloalkyl, $C_{4-6}$heterocycloalkyl, and $C_{5-6}$heteroaryl, wherein the $C_{1-6}$alkoxy or $C_{1-6}$alkylamino of $R^1$ is unsubstituted or substituted by 1 to 2 substituents independently selected from $C_{1-4}$alkyl and $C_{1-4}$alkoxy; and the $C_{3-6}$cycloalkyl, $C_{4-6}$heterocycloalkyl or $C_{5-6}$heteroaryl of $R^1$ is unsubstituted or substituted by 1 to 2 substituents independently selected from halo, cyano, $C_{1-4}$alkyl, halo$C_{1-4}$ alkyl, $C_{1-4}$alkoxy, amino, $C_{1-6}$alkylamino, di$C_{1-6}$alkylamino, and hydroxycarbonyl.

Embodiment 5

A compound according to any one of Embodiments 1 to 3 or a pharmaceutically acceptable salt, or a stereoisomer thereof, wherein $R^1$ is selected from $C_{1-4}$ alkoxy, di$C_{1-4}$alkylamino, —$N(C_2H_3)_2$, cyclobutyl, azetidinyl, pyrrolidinyl, furanyl and oxazolyl, wherein the cyclobutyl, azetidinyl, pyrrolidinyl, furanyl or oxazolyl is unsubstituted or substituted by 1 to 2 substituents independently selected from halo, $C_{1-4}$alkyl, $C_{1-4}$alkoxy, di$C_{1-4}$alkylamino, and hydroxycarbonyl.

Embodiment 6

A compound according to any one of Embodiments 1 to 5, or a pharmaceutically acceptable salt, or a stereoisomer thereof, wherein $R_3$ is halo.

Embodiment 7

A compound according to any one of Embodiments 1 to 6, or a pharmaceutically acceptable salt, or a stereoisomer thereof, wherein $L^3$ is a bond.

Embodiment 8

A compound according to any one of Embodiments 1 to 7, or a pharmaceutically acceptable salt, or a stereoisomer thereof, wherein $R^0$ is selected from hydrogen, hydroxyl, halo, $C_{1-4}$alkyl, $C_{1-4}$alkoxy, amino, $C_{1-4}$alkylamino, di$C_{1-4}$alkylamino, —$NH(CH_2)_{1-2}$-phenyl, —$NR^5C(O)R^6$, —$Si(CH_3)_3$, $C_{3-6}$cycloalkyl, $C_{5-6}$cycloalkenyl, $C_{4-6}$heterocycloalkyl, $C_{4-6}$heterocycloalkenyl, phenyl, and $C_{5-6}$heteroaryl, wherein the $C_{3-6}$cycloalkyl, $C_{5-6}$cycloalkenyl, $C_{4-6}$heterocycloalkyl, $C_{4-6}$heterocycloalkenyl, phenyl, or $C_{5-6}$heteroaryl of $R^0$ is unsubstituted or substituted by 1 to 4 substituents independently selected from halo, $C_{1-4}$alkyl, —$(CH_2)_{1-4}OH$, halo$C_{1-4}$alkyl, —$(CH_2)_{1-4}NR^aR^b$, $C_{4-6}$heterocycloalkyl$C_{1-4}$alkyl, benzyl, $C_{1-4}$alkoxy, amino, $C_{1-4}$alkylamino, di$C_{1-4}$alkylamino, unsubstituted $C_6$heterocycloalkyl and $C_{1-4}$alkyl substituted $C_6$heterocycloalkyl, wherein $R^a$ and $R^b$ are each independently selected from hydrogen, $C_{1-4}$alkyl and $C_{3-6}$cycloalkyl;

$R_5$ is hydrogen or $C_{1-4}$alkyl; and $R_6$ is selected from $C_{1-6}$alkyl, $C_{1-6}$alkoxy, $C_{3-6}$cycloalkyl, $C_{5-6}$heterocycloalkyl, and $C_{5-6}$heteroaryl, each of which is unsubstituted or substituted by 1 to 2 substituents independently selected from hydroxyl, $C_{1-6}$alkyl, $C_{1-4}$alkoxy, amino, and $C_{1-4}$alkylamino.

Embodiment 9

A compound according to any one of Embodiments 1 to 7, or a pharmaceutically acceptable salt, or a stereoisomer thereof, wherein $R^0$ is selected from hydrogen, chloro, bromo, tert-butyl, isopropylamino, isopropoxycarbonylamino, methylethylamino, methylisopropylamino, dimethyamino, diethylamino, —$Si(CH_3)_3$, cyclopropyl, cyclopentenyl, azetidinyl, pyrrolidinyl, piperidinyl, piperazinyl, morpholinyl, 2,5-dihydro-1H-pyrrolyl, 1,2,5,6-tetrahydropyridinyl, azabicyclo[3.2.1]oct-3-en-3-yl, 3,6-dihydro-2H-pyranyl, pyrazolyl, phenyl, pyridinyl, and pyrazinyl; wherein the cyclopropyl, cyclopentenyl, azetidinyl, pyrrolidinyl, piperidinyl, azabicyclo[3.2.1]oct-3-en-3-yl, piperazinyl, morpholinyl, 2,5-dihydro-1H-pyrrolyl, 1,2,5,6-tetrahydropyridinyl, 3,6-dihydro-2H-pyranyl, pyrazolyl, phenyl, pyridinyl, or pyrazinyl is unsubstituted or substituted by 1 to 4 substituents independently selected from fluoro, chloro, $C_{1-4}$alkyl, trifluoromethyl, morpholinylethyl, benzyl, $C_{1-4}$alkoxy, piperazinyl, N-methylpiperazinyl, and morpholinyl.

Embodiment 10

A compound according to Embodiment 1 or 2, wherein the compound is represented by Formula Ia:

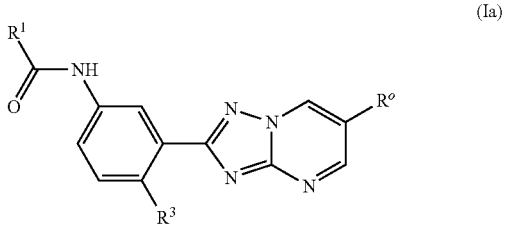

(Ia)

or a pharmaceutically acceptable salt, or a stereoisomer thereof; wherein
- $R^1$ is selected from $C_{1-4}$alkoxy, di-$C_{1-4}$alkylamino, $C_{3-6}$cycloalkyl, $C_{4-6}$heterocycloalkyl, and $C_{5-6}$heteroaryl, wherein the $C_{3-6}$cycloalkyl, $C_{4-6}$heterocycloalkyl, or $C_{5-6}$heteroaryl is unsubstituted or substituted by 1 to 2 substituents independently selected from halo, $C_{1-4}$alkyl, $C_{1-4}$alkoxy, di$C_{1-4}$alkylamino, and hydroxycarbonyl;
- $R^3$ is halo;
- $R^0$ is selected from hydrogen, halo, $C_{1-4}$alkyl, —$NR^{2a}R^{2b}$, —$Si(CH_3)_3$, $C_{3-6}$cycloalkyl, $C_{5-6}$cycloalkenyl, $C_{4-6}$heterocycloalkyl, $C_{5-6}$heterocycloalkenyl, phenyl, and $C_{5-6}$heteroaryl; wherein
- $R^{2a}$ is hydrogen or $C_{1-4}$alkyl;
- $R^{2b}$ is selected from hydrogen, $C_{1-4}$alkyl, and —C(O)OCH(CH$_3$)$_2$; and
- the $C_{3-6}$cycloalkyl, $C_{5-6}$cycloalkenyl, $C_{4-6}$heterocycloalkyl, $C_{5-6}$heterocycloalkenyl, phenyl, or $C_{5-6}$heteroaryl of $R^0$ is unsubstituted or substituted by 1 to 4 substituents independently selected from halo, $C_{1-4}$alkyl, halo$C_{1-4}$alkyl, $C_{4-6}$heterocycloalkyl $C_{1-4}$alkyl, benzyl, $C_{1-4}$alkoxy, unsubstituted $C_6$heterocycloalkyl, and $C_{1-4}$alkyl substituted $C_6$heterocycloalkyl.

Embodiment 11

A compound of according to Embodiment 10, or a pharmaceutically acceptable salt, or a stereoisomer thereof, wherein
- $R^1$ is oxazolyl or pyrrolidinyl, wherein the oxazolyl or pyrrolidinyl is unsubstituted or substituted by 1 to 2 substituents independently selected from halo, $C_{1-4}$alkyl, $C_{1-4}$alkoxy, di$C_{1-4}$alkylamino, and hydroxycarbonyl;
- $R^3$ is fluoro or chloro;
- $R^0$ is selected from $C_{1-4}$alkyl, pyrrolidinyl, phenyl and pyridinyl, wherein the pyrrolidinyl, phenyl or pyridinyl is unsubstituted or substituted by one substituent selected from halo, $C_{1-4}$alkyl, halo$C_{1-4}$alkyl, $C_{1-4}$alkoxy, unsubstituted $C_6$heterocycloalkyl, and $C_{1-4}$alkyl substituted $C_6$heterocycloalkyl.

Embodiment 12

A compound or a pharmaceutically acceptable salt, or a stereoisomer thereof, according to Embodiment 1, selected from Compounds 1 to 97 listed in Table 1.

Embodiment 13

A compound or a pharmaceutically acceptable salt, or a stereoisomer thereof, according to Embodiment 2, selected from Compounds 1 to 80 listed in Table 4.

Embodiment 14

A pharmaceutical composition comprising a compound according to any one of Embodiments 1 to 13 as an active ingredient and at least one excipient.

Embodiment 15

A method for treating, preventing, inhibiting, ameliorating, or eradicating the pathology and/or symptomology of a disease caused by a parasite, comprising administering to a subject in need thereof a therapeutically effective amount of a compound according to any one of Embodiments 1 to 13 or a composition according to Embodiment 14, wherein the parasitic disease is selected from Leishmaniasis, Human African Trypanosomiasis, and Chagas disease.

Embodiment 16

The method according to Embodiment 15, wherein the compound is capable of inhibiting the proteolytic activity of the proteasomes of said parasite.

Embodiment 17

The method according to Embodiment 15, wherein the compound is capable of inhibiting the chymotrypsin-like proteolytic activity of the proteasomes of said parasite.

Embodiment 18

The method according to any one of Embodiments 15 to 17, wherein the parasitic disease is leishmaniasis.

Embodiment 19

The method according to Embodiment 18, further comprising administering a second agent selected from stibogluconate, meglumine antimoniate, Amphotericin, Miltefosine and paromomycin.

Embodiment 20

The method according to any one of Embodiments 15 to 17, wherein the parasitic disease is Human African Trypanosomiasis.

Embodiment 21

The method according to Embodiment 20, further comprising administering a second agent selected from pentamidine, suramin, melarsoprol, eflornithine, and nifurtimox.

Embodiment 22

The method according to any one of Embodiments 15 to 17, wherein the parasitic disease is Chagas disease.

Embodiment 23

The method according to Embodiment 22, further comprising administering a second agent selected from benznidazole, nifurtimox and Amphotericin.

Embodiment 24

A compound, or a salt, tautomer or stereoisomer thereof, according to any one of Embodiments 1 to 13 or a pharmaceutical composition according to Embodiment 14 for treating, preventing, inhibiting, ameliorating, or eradicating the pathology and/or symptomology of a parasitic disease, wherein the disease is selected from Leishmaniasis, Human African Trypanosomiasis and Chagas disease, and wherein the compound is optionally used in combination with a second agent.

Embodiment 25

The compound or composition according to Embodiment 24, the compound is capable of inhibiting the proteolytic activity of the proteasomes of said parasite.

Embodiment 26

The compound or composition according to Embodiment 24, wherein the compound is capable of inhibiting the chymotrypsin-like proteolytic activity of the proteasomes of said parasite.

Embodiment 27

The compound or composition of any one of Embodiments 24 to 26, wherein the parasitic disease is Leishmaniasis, wherein the second agent is selected from stibogluconate, meglumine antimoniate, Amphotericin, Miltefosine and paromomycin.

Embodiment 28

The compound or composition of any one of Embodiments 24 to 26, wherein the parasitic disease is Human African Trypanosomiasis, wherein the second agent is selected from pentamidine, suramin, melarsoprol, eflornithine, and nifurtimox.

Embodiment 29

The compound or composition of any one of Embodiments 24 to 26, wherein the parasitic disease is Chagas disease, wherein the second agent is selected from benznidazole, nifurtimox and Amphotericin.

Embodiment 30

Use of a compound according to any one of Embodiments 1 to 13 for the manufacture of a medicament for treating, preventing, inhibiting, ameliorating, or eradicating the pathology and/or symptomology of a parasitic disease, wherein the disease is selected from Leishmaniasis, Human African Trypanosomiasis and Chagas disease.

Embodiment 31

A method for treating, preventing, inhibiting, ameliorating, or eradicating the pathology and/or symptomology of a disease caused by a parasite, comprising administering to a subject in need thereof a therapeutically effective amount of an agent capable of inhibiting the activity of the proteasomes of the parasite, wherein the disease is selected from leishmaniasis, human African trypanosomiasis and Chagas disease.

Embodiment 32

The method according to Embodiment 31, wherein the agent is capable of inhibiting the chymotrypsin-like proteolytic activity of the proteasomes.

Embodiment 33

The method according to Embodiment 31 or 32, wherein the agent is a low molecular weight compound.

Embodiment 34

The method according to Embodiment 33, wherein the low molecular weight compound is a compound of any one of Embodiments 1 to 13.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S.

Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Plasdmodium or (ii) associated with Plasdmodium activity, or (iii) characterized by activity (normal or abnormal) of Plasdmodium; or (2) reduce or inhibit the activity of Plasdmodium; or (3) reduce or inhibit the growth of Plasdmodium. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Plasdmodium; or at least partially reducing or inhibiting the growth of Plasdmodium.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process. An inhibitor of proteasome activity refers to an agent which is capable of decreasing the chymotrypsin-like proteolytic activity of the proteasome to at least 10%, 20%, 30%, 50%, 60%, 70%, 80% or at least 90% of an untreated control.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

GENERAL PROCESSES FOR PREPARING COMPOUNDS OF THE INVENTION

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "*Protective Groups in Organic Synthesis*", John Wiley and Sons, 1991.

Typically, the compounds of formula (I) can be prepared according to Schemes 1 to 8 provided infra., where the variables: n, X, $L^3$, $R^0$, $R^1$, $R^{2a}$, $R^{2b}$, $R^3$, $R^5$, $R^6$, $R^7$, $R^8$, $R^a$, $R^b$, $R^{9a}$, $R^{9b}$, and others are as defined in the Summary of the Invention. The following reaction schemes are given to be illustrative, not limiting, descriptions of the synthesis of compounds of the invention. Detailed descriptions of the synthesis of compounds of the Invention are given in the Examples, infra.

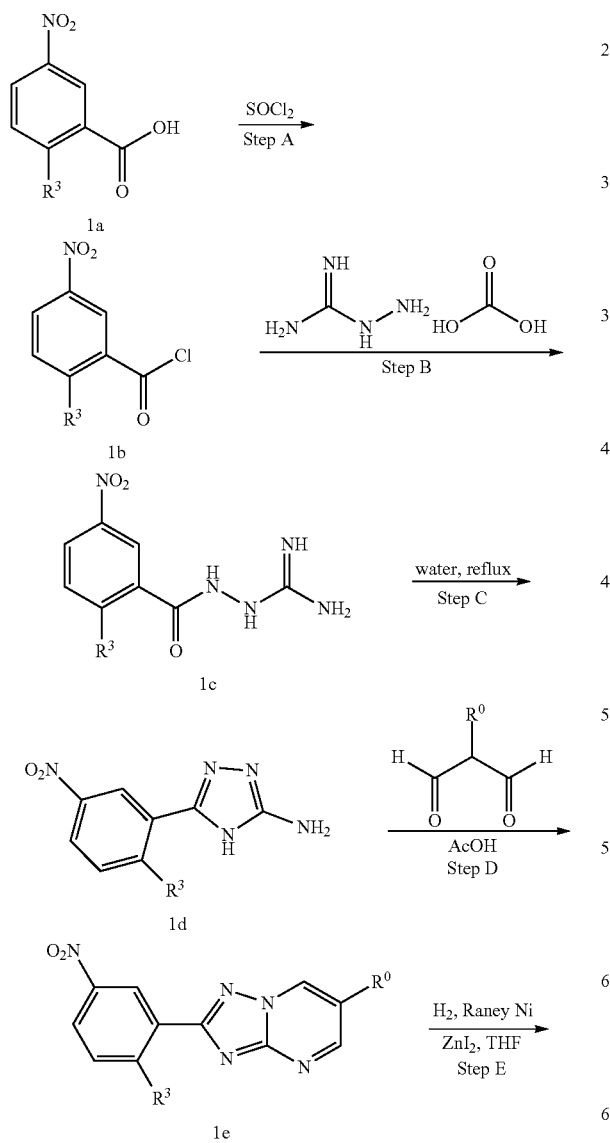

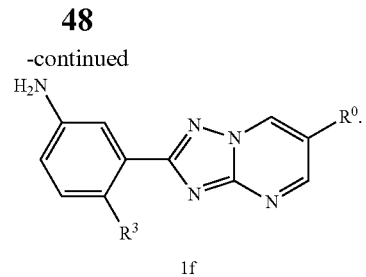

Scheme 2. Preparation of triazolopyridine compounds where W is halo.

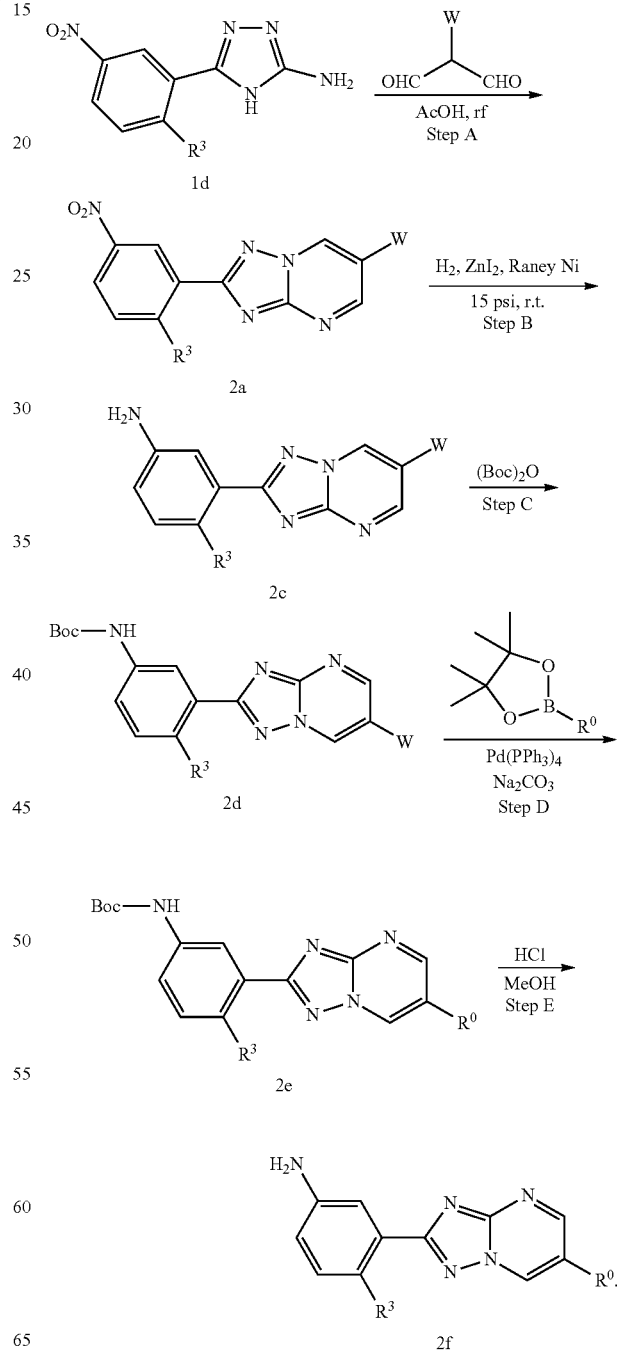

Scheme 3. Coupling of —C(O)—R¹ where R¹ is C₅₋₆heteroaryl or C₃₋₆cycloalkyl to the phenyl-triazolopyrimidine
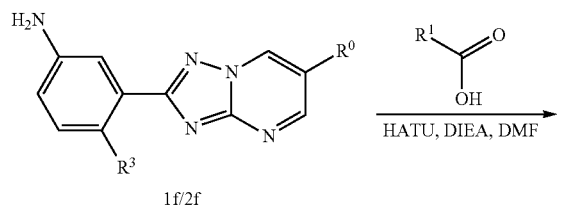
1f/2f
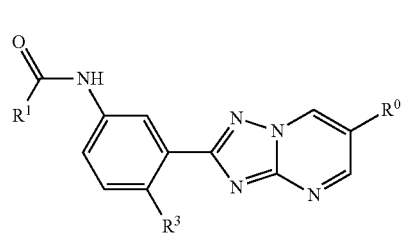
Scheme 4. Coupling of —C(O)R¹ where R¹ is C₅₋₆heteroaryl to the phenyl-triazolopyrimidine
1F/2F
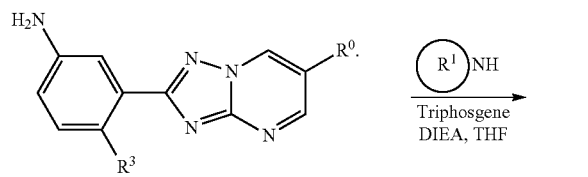
Scheme 5.
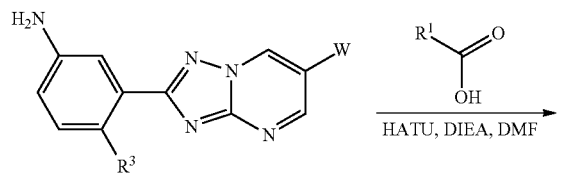
2c
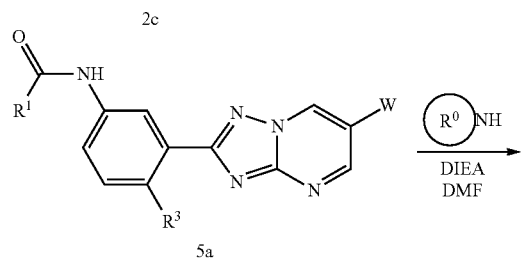
5a
-continued
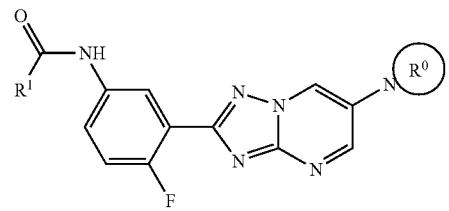
Scheme 6.
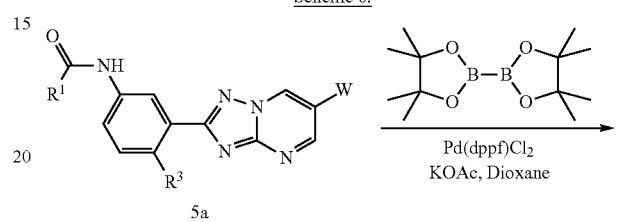
5a
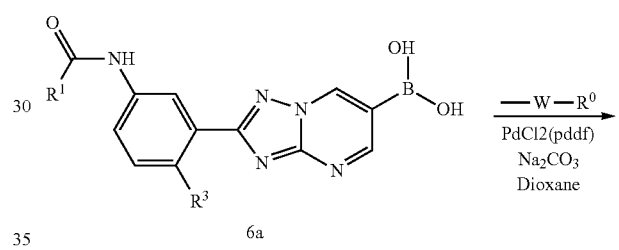
6a
Scheme 7. Alternative route for the preparation of triazolopyrimidine compounds.
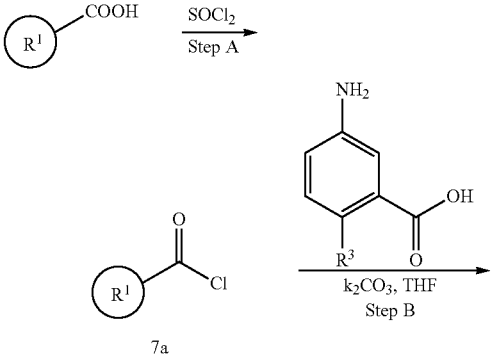
7a -continued

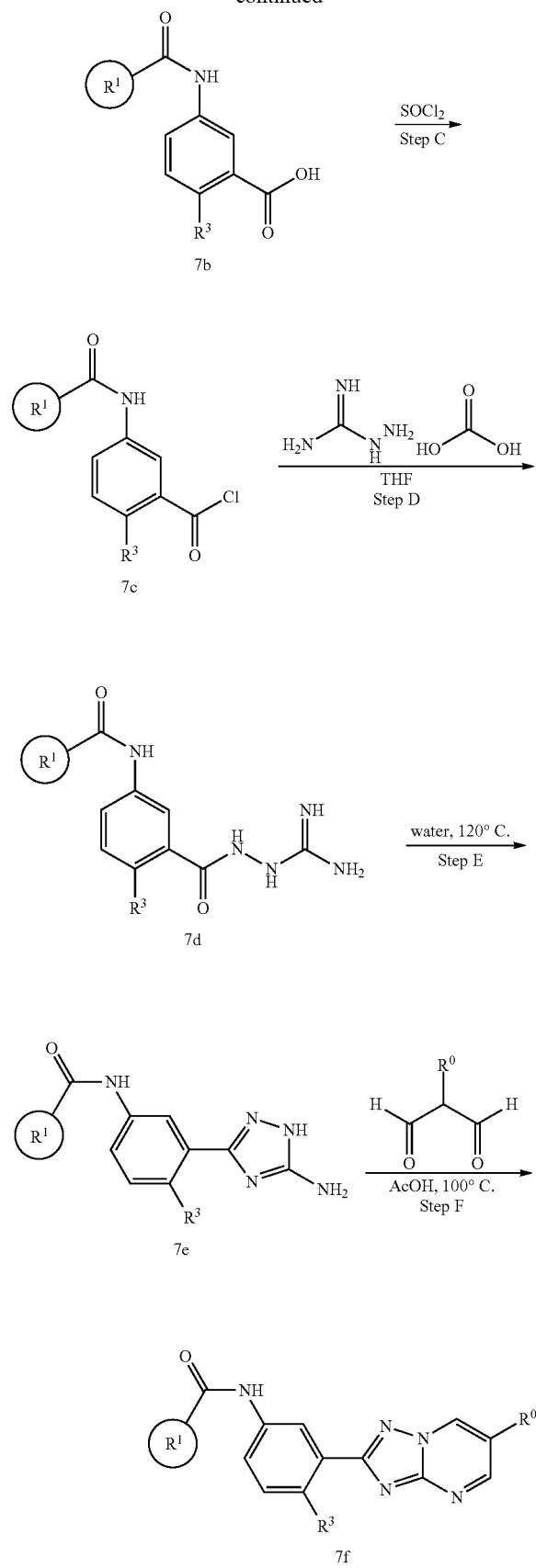

Scheme 8.

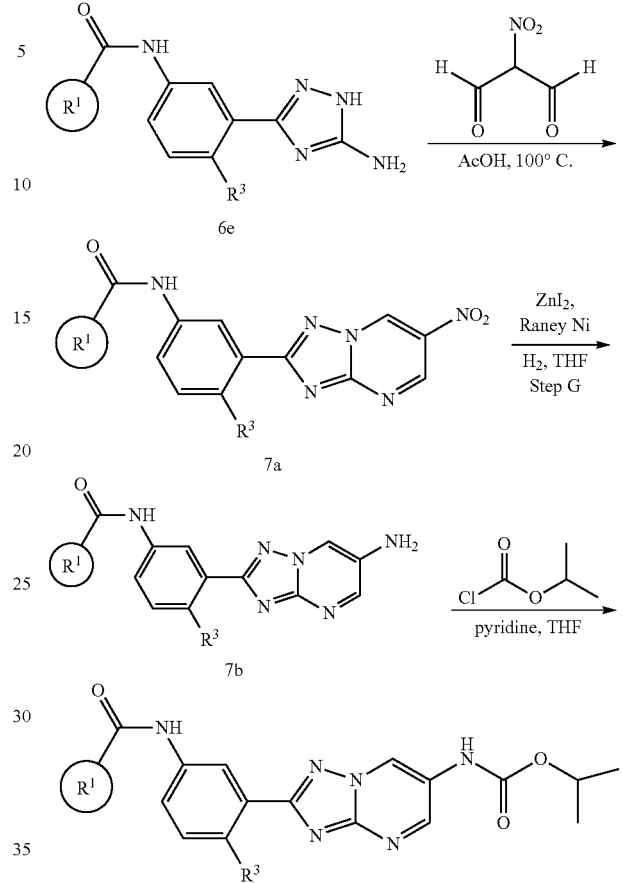

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

Pharmacology and Indications

Compounds of the invention are useful in the treatment and/or prevention of infections such as Leishmaniasis, Human African Trypanosomiasis, or Chagas disease.

Leishmaniasis is a disease caused by protozoan parasites that belong to the genus *Leishmania*, typically caused by *Leishmania donovani. Leishmania infantum, Leishmania braziliensis, Leishmania panamensis, Leishmania guayanensis, Leishmania amazonensis, Leishmania mexicana, Leishmania tropica*, or *Leishmania major*, and more typically caused by *Leishmania donovani*. These parasites are typically transmitted by the bite of an infected female sandfly from *Phlebotomus* or *Lutzomyia* genus.

Leishmaniasis is mostly a disease of the developing world, and is rarely known in the developed world outside a small number of cases, mostly in instances where troops are stationed away from their home countries. Leishmaniasis can be transmitted in many tropical and subtropical countries, and is found in parts of about 88 countries. Approximately 350 million people live in these areas. The settings in which leishmaniasis is found range from rainforests in Central and South America to deserts in West Asia and the Middle East. It affects as many as 12 million people worldwide, with 1.5-2 million new cases each year.[19] The visceral form of leishmaniasis has an estimated incidence of 500,000 new cases and 60,000 deaths each year. More than 90 percent of the world's cases of visceral leishmaniasis are in India, Bangladesh, Nepal, Sudan, and Brazil. Kabul is estimated as the largest center of cutaneous leishmaniasis in the world, with approximately 67,500 cases as of 2004.

There are four main forms of Leishmaniasis. Cutaneous leishmaniasis is the most common form of leishmaniasis. Visceral leishmaniasis, also called kala-azar, is the most serious form in which the parasites migrate to the vital organs. Visceral leishmaniasis is caused by the parasite *Leishmania donovani*, and is potentially fatal if untreated.

Currently, no vaccines are in routine use. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects. Amphotericin (AmBisome) is now the treatment of choice. Miltefosine (Impavido), and paromomycin are the other treatment alternatives. These drugs are known to produce a definitive cure in >90% of patients. Amphotericin (AmBisome) is expansive and has to be given intravenously; it is not affordable to most patients affected. Paromomycin, although affordable, requires intramuscular injections for 3 weeks; compliance is a major issue. Miltefosine is an oral drug and has shown to be more effective and better tolerated than other drugs. However, there are problems associated with the use of miltefosine that arise from its teratogenicity and pharmacokinetics. Miltefosine was shown to be much slower eliminated from the body and was still detectable five months after the end of treatment. The presence of subtherapeutic miltefosine concentrations in the blood beyond five months after treatment might contribute to the selection of resistant parasites and, moreover, the measures for preventing the teratogenic risks of miltefosine must be reconsidered. This led to some reluctance to taking Miltefosine by affected populations.

The Drugs for Neglected Diseases Initiative is actively facilitating the search for novel therapeutics. Our invention meets that need.

Human African trypanosomiasis (HAT), also known as African sleeping sickness, is a vector-borne parasitic disease caused by the protozoa *Trypanosoma brucei*. There are two subspecies that infect humans, *T.b. gambiense* and *T.b. rhodesiense*, with the former accounting for over 95% of reported cases and the latter accounting for the remaining reported cases. The parasites are transmitted to humans by tsetse fly (*Glossina* genus) bites which have acquired their infection from human beings or from animals harboring the human pathogenic parasites.

The disease has been recorded as occurring in 36 countries, all in subtropical and equatorial Africa. It is endemic in southeast Uganda and western Kenya. In 1995, the WHO estimated that 300,000 people were afflicted with the disease. In its 2001 report, the WHO set the figure of people at risk of infection at 60 million, of which only 4 to 5 million had access to any kind of medical monitoring. In 2006, the WHO estimated that about 70,000 people could have the disease, and many cases are believed to go unreported. About 48,000 people died of sleeping sickness in 2008. Public health efforts in prevention and the eradication of the tsetse fly population have proven to be successful in controlling the spread of the disease; under 10,000 new cases were reported in 2009 according to WHO figures, which represents a huge decrease from the estimated 300,000 new cases in 1998.

African trypanosomiasis symptoms occur in two stages. In the first stage, known as the haemolymphatic phase, the trypanosomes multiply in subcutaneous tissues, blood and lymph. The haemolymphatic phase is characterized by bouts of fever, headaches, joint pains and itching. In the second stage, the neurological phase, the parasites cross the blood-brain barrier to infect the central nervous system. It is in this stage when more obvious signs and symptoms of the disease appear: changes of behaviour, confusion, sensory disturbances and poor coordination. Disturbance of the sleep cycle, which gives the disease its name, is an important feature of the second stage of the disease. Without treatment, the disease is invariably fatal, with progressive mental deterioration leading to coma, systemic organ failure, and death.

Four drugs are registered for the treatment of sleeping sickness. The protocol depends on the stage of the disease. The current standard treatment for first-stage disease is intravenous or intramuscular pentamidine (for *T.b. gambiense*), or intravenous suramin (for *T.b. rhodesiense*). The current standard treatment for second-stage disease is: Intravenous melarsoprol, or interavenous melarsoprol in combination with oral nifurtimox, intravenous eflornithine only or eflornithine in combination with nifurtimox. All of the drugs have undesirable or sometime serious side effects. For example, 3-10% of patients those injected with Melarsoprol (Arsobal), an organoarsenical, developed reactive encephalopathy (convulsions, progressive coma, or psychotic reactions), and 10-70% of such cases result in death. There remains a need for new therapy.

Chagas disease, also called American trypanosomiasis, is a tropical parasitic disease caused by the flagellate protozoan *Trypanosoma cruzi*. *T. cruzi* is commonly transmitted to humans and other mammals by the blood-sucking "kissing bugs" of the subfamily Triatominae (family Reduviidae).

Chagas disease is contracted primarily in the Americas. It is endemic in twenty one Cental and Latin American countries; particularly in poor, rural areas of Mexico, Central America, and South America. Large-scale population movements from rural to urban areas of Latin America and to other regions of the world have increased the geographic distribution of Chagas disease, and cases have been noted in many countries, particularly in Europe. Rarely, the disease has been found in the Southern part of the United States.

Each year, an estimated 10 to 15 million people across the world are infected with Chagas disease, most of whom do not know they are infected. Every year, 14,000 people die as a consequence of the disease. In Central and South America, Chagas kills more people than any other parasite-borne disease, including malaria. By applying published seroprevalence figures to immigrant populations, CDC estimates that more than 300,000 persons with *Trypanosoma cruzi* infection live in the United States. Most people with Chagas disease in the United States acquired their infections in endemic countries.

Chagas disease has an acute and a chronic phase. If untreated, infection is lifelong.

Acute Chagas disease occurs immediately after infection, may last up to a few weeks or months, and parasites may be found in the circulating blood. Infection may be mild or asymptomatic. There may be fever or swelling around the site of inoculation (where the parasite entered into the skin or mucous membrane). Rarely, acute infection may result in severe inflammation of the heart muscle or the brain and lining around the brain. The initial acute phase is responsive to antiparasitic treatments, with 60-90% cure rates.

Following the acute phase, most infected people enter into a prolonged asymptomatic form of disease (called "chronic indeterminate") during which few or no parasites are found in the blood. During this time, most people are unaware of their infection. Many people may remain asymptomatic for life and never develop Chagas-related symptoms. However, an estimated 20-30% of infected people will develop debilitating and sometimes life-threatening medical problems over the course of their lives.

The symptoms of Chagas disease vary over the course of an infection. In the early, acute stage, symptoms are mild and usually produce no more than local swelling at the site of infection. The initial acute phase is responsive to antiparasitic treatments, with 60-90% cure rates. After 4-8 weeks, individuals with active infections enter the chronic phase of Chagas disease that is asymptomatic for 60-80% of chronically infected individuals through their lifetime.

There is no vaccine against Chagas disease. Treatment for Chagas disease focuses on killing the parasite and managing signs and symptoms.

During the acute phase of Chagas disease, the drugs currently available for treatment are benznidazole and nifurtimox. Once Chagas disease reaches the chronic phase, medications aren't effective for curing the disease. Instead, treatment depends on the specific signs and symptoms. However, problems with these current therapies include their diverse side effects, the length of treatment, and the requirement for medical supervision during treatment. Resistance to the two frontline drugs has already occurred. The antifungal agent Amphotericin b has been proposed as a second-line drug, but this drug is costly and relatively toxic.

In accordance with the foregoing, the present invention further provides a method for preventing or treating Leishmaniasis, Chaga disease or Human African Trypanosomiasis in a subject in need of such treatment, which method comprises administering to said subject a therapeutically effective amount of a compound selected from Formula I or a pharmaceutically acceptable salt thereof. The required dosage will vary depending on the mode of administration, the particular condition to be treated and the effect desired.

In one embodiment of the method of the invention, the disease being treated is Leishmaniasis caused by the parasites *Leishmania donovani, Leishmania infantum, Leishmania braziliensis, Leishmania panamensis, Leishmania guayanensis, Leishmania amazonensis, Leishmania mexicana, Leishmania tropica, Leishmania major*. In one variation of the above embodiment, the disease being treated is Visceral leishmaniasis, caused by the parasite *Leishmania donovani*.

In another embodiment of the method of the invention, the disease being treated is Human African Trypanosomiasis caused by a protozoa belonging to the species *Trypanosoma brucei*.

In one embodiment, the protozoa is *Trypanosoma brucei gambiense*. In another embodiment, the protozoa is *Trypanosoma brucei rhodesiense*.

In yet another embodiment of the method of the invention, the disease being treated is Chagas disease (also call American Trypanosomiasis) caused by protozoa *Trypanosoma cruzi*.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). In one embodiment, the compound of the invention is administered with the known treatment drugs. For example, for the treatment of Leishmaniasis, compound of the invention may be used in combination with stibogluconate, meglumine antimoniate, Amphotericin, Miltefosine and paromomycin. For the treatment of Human African Trypanosomiasis, the compound of the invention may be used in combination with pentamidine, suramin, melarsoprol, eflornithine, and nifurtimox. For the treatment of Chagas disease, the compound of the invention may be used in combination with benznidazole, nifurtimox and Amphotericin.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) optionally co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

BIOLOGICAL ASSAYS

Assay for Growth Inhibition of *Leishmania donovani* Axenic Amastigote

*Leishmania donovani* axenic amastigote parasites are grown at 37° C., 5% $CO_2$ in media made of RPMI 1640, 4 mM L-glutamine, 20% heat inactivated FBS, 100 units/ml of penicillin and 100 µg/ml of streptomycin, 23 µM Folic Acid, 100 µM Adenosine, 22 mM D-glucose, 25 mM MES. The pH of media is adjusted to 5.5 at 37° C. using HCl. 20 µL of media is first dispensed into 384 well plates and 100 nL of the compounds of invention in DMSO are added to the plate wells. At the same time control compounds and DMSO are added to plates to serve as the positive and negative controls, respectively. 40 µL of parasite culture (9600 parasites) are then added to the plate wells. The plates are then placed into incubators. After 2 day incubation, 20 µL of Cell TiterGlo (Promega) is added to the plate wells. The luminescence signal of each well is measured using the Envision reader (Perkin Elmer). The percentage inhibition of 50%, $EC_{50}$, is calculated for each of the compounds.

Compounds of the invention have an $EC_{50}$ of 25 µM or less, typically less than 1 µm, and about half of the compounds have an $EC_{50}$ below 0.1 µM. Selected compounds of the invention can significantly delay the proliferation of *L. donovani*. The inhibitory efficacy of the compounds of the invention against *L. donovani* axenic amastigotes in vitro is provided in Table I.

Assay for the Inhibition of Parasitemia of *Leishmania* Parasites (*L. donovani*) in Mouse Macrophages The activity of a compound according to the present invention for inhibition of parasitemai can be assessed by the parasite proliferation assay. The assay measures the increase in the parasite number in the assayed plate well using a DNA intercalating dye, SYBR Green I® dye (IN-VITROGEN) to stain *Leishmania* cell nuclei. It is understood that the assays illustrate the invention without in any way limiting the scope of the invention.

*L. donovani* HU3 strain is propagated by infecting BALB/c mice through tail vein injection with $10^7$ *Leishmania* parasites. Infected mice are allowed to develop infection during 9-11 weeks post-infection. During this time, the parasites accumulate in the infected mouse spleens to large numbers, and the infected mice serve as the source of parasites for the in vitro measurement of compound efficacies. To assay a compound for anti-leishmanial activity, peritoneal macrophages isolated from non-infected BALB/c mice are seeded into 384-well plates at density $2 \times 10^4$ macrophages per well in 25 mL of medium (RPMI1640, 10% fetal serum albumin, 10 mM HEPES, 1 mM sodium pyruvate, 1% Pen/Strep). Subsequently, the seeded plates are placed into an incubator set to maintain 37° C. temperature and atmosphere with 5% $CO_2$. The next day, *Leishmania* parasites are isolated from the spleens of mice infected for 9-11 weeks and $4 \times 10^5$ isolated parasites in 10 mL of the above media are added to each plate well. Plates are then returned into incubators and infection is allowed to proceed for 24 hours. After the infection of macrophages is completed, 5 mL of compounds of the invention in the above medium, which also contains 5% DMSO, are added to plate wells containing infected macrophages. At the same time control compounds (miltefosine and amphotericin B) and DMSO are added to plates to serve as the positive and negative controls, respectively. After the compound addition, the plates are returned into incubator and cells infected with parasites are cultured for 5 days. At the end of cultivation, 40 mL of 8% paraformaldehyde is added to plate wells and incubated for 15 min at room temperature. Following the incubation, the paraformaldehyde from plate wells is aspirated, and 40 mL of PBS containing 0.2% Triton X-100 is added to wells. After 15 min incubation, the solution is aspirated from wells again, and replaced with SybrGreen Dye solution in PBS (1:125,000 dilution). Infected cells are imaged with Evotec Opera high-content microscope, and the number of parasites in well is determined by counting parasite nuclei visualized by staining with SybrGreen dye. The percentage inhibition of 50%, $EC_{50}$, is calculated for each compound.

Compounds of the invention have an $EC_{50}$ of ranging from greater less than 50 µM to less than 0.1 µM. Typically, the compounds analyzed have an $EC_{50}$ of less than 0.1 µm. Selected compounds have EC50 less than 50 nM. The data shows the compounds of the invention can significantly delay the proliferation of *L. donovani*.

The inhibitory efficacy of the compounds of the invention against proliferation of *L. donovani* in mouse peritoneal macrophages is provided in Table I.

Assay for Growth Inhibition of Kinetoplastid Parasite *Trypanosoma cruzi*.

Compounds of the invention can be assayed to measure their capacity to inhibit proliferation of kinetoplastid parasite *Trypanosoma cruzi*. The screening procedure is for identifying compounds with inhibitor activity against *Trypanosoma cruzi* amastigotes cultured in 3T3 fibroblast cells. The assay is done using the mammalian stage (amastigotes) of *T. cruzi* that replicates in the intracellular space of host cells. The host cells are initially infected with the culture-derived trypomastigotes that rapidly invade and then divide as amastigotes. The protocol uses the Tulahuen strain of *T. cruzi* that has been engineered to express the *E. coli* beta-galactosidase gene (Lac-Z) (Antimicr. Agents Chemoth. 40:2592, 1996). This allows for a colorimetric readout by using the substrate CPRG and an absorbance plate reader.

3T3 fibroblast cells are re-suspended in RPMI-1640 medium without phenol red medium supplemented with 10% FBS (heat inactivated), 100 µg/ml penicillin, and 100 µg/ml streptomycin. Forty µL of suspension (1,000 cells) is dispensed into 384-well plates and incubated overnight at 37° C. temperature and in atmosphere containing 5% $CO_2$. The following day, 100 nL of compounds of the invention in DMSO are added to plate wells containing 3T3 cells. At the same time control compounds (benznidazole and nifurtimox) and DMSO are added to plates to serve as the positive and negative controls, respectively. After that, 10 µL of media containing 10,000 *T. cruzi* trypomastigotes are added to each plate well and plates are placed back into incubators. After 6 day incubation, 10 µL of reagent solution (0.6 mM CPRG, 0.6% NP-40 in PBS) is added to plates and incubated at room temperature for 2 hours. Absorbance is then measured on SpectraMax Gemini fluorimeter to determine relative number of *T. cruzi* cells present in each plate well. The percentage inhibition of 50%, $EC_{50}$, is calculated for each compound.

Compounds of the invention have an $EC_{50}$ of ranging from >10 µM to less than 0.01 µM. Typically, the compounds analyzed have an $EC_{50}$ of <1 µm, and greater than 30% of the compounds have an $EC_{50}$ of <0.1 µm. Selected compounds have EC50 less than 50 nM. For example, Compound 1, N-(4-fluoro-3-(6-phenyl-[1,2,4]triazolo[1,5-a]pyrimidin-2-yl)phenyl)-2,4-dimethyloxazole-5-carboxamide, has an EC50 of 18 nM; Compound 61, N-(4-fluoro-3-(6-(3-methylpyridin-2-yl)-[1,2,4]triazolo[1,5-a]pyrimidin-2-yl)phenyl)-2,4-dimethyloxazole-5-carboxamide, has an EC50 of 16 nM; and Compound 76, N-(4-fluoro-3-(6-(pyrrolidin-1-yl)-[1,2,4]triazolo[1,5-a]pyrimidin-2-yl)phenyl)-2,4-dimethyloxazole-5-carboxamide, has an EC50 of 43 nM. The data shows selected compounds of the invention can significantly delay the proliferation of *T. Cruzi*. The inhibitory efficacy of the compounds of the invention against proliferation of *T. cruzi* is reported in Table I below.

Assay for Growth Inhibition *Trypanosoma brucei Brucei* Growth Inhibition

The proliferation is quantified by the addition of Cell Titer Glo (Promega®) a luminescent cell viability assay that measures the number of viable cells in culture based on the quantification of cellular ATP amount, which is an indicator of metabolically active cells.

*Trypanosoma brucei brucei* (Lister 427) strain was grown in Hirumi 9 (HMI-9) media supplemented with 10% v/v fetal bovine serum (FBS) and 10% v/v serum plus. For measurement of cell proliferation inhibition, test compounds were three fold serially diluted in duplicates to 384-well white plates, resulting in 10 dilutions for each compound. A volume of 40 µl of *T. b. brucei* culture (10,000 parasites/ml) was added to each well, and the assay plates were incubated at 37° C. for 2 days in a $CO_2$ incubator. Growth inhibition was monitored by measuring ATP levels, which, is used as a surrogate marker for growth. Relative luminescence units were measured using Tecan M1000 after 30 min of adding 40 µl of cell titre glo (CTG). $IC_{50}$ values were determined by analyzing the data using HELIOS software. $IC_{50}$ is defined as the lowest concentration of the compound that inhibited 50% growth of the *T. b. brucei* wild type strain compared to untreated controls.

Compounds of the invention have an $EC_{50}$ ranged from >10 µM to 0.01 µM, typically less than 1 µM, and more typically less than 500 nM. Selected compounds exhibited $EC_{50}$ of less than 100 nM. The data supports that compounds of the invention can significantly delay the proliferation of *T. brucei*.

The inhibitory efficacy of the compounds of the invention against the proliferation of *T. brucei brucei* is provided in Table I, infra.

TABLE 1

Inhibitory efficacy of seleced compounds of the invention aganist proliferation of *L. donovani*, *T cruzi* or *T. brucei*

| Compound No. | L. donovani amastigotes EC50 (µM) | L. donavani Macrophage EC50 (µM) | T cruzi growth inhibition EC50 (µM) | T. b. brucei growth Inhibition EC50 (µM) |
|---|---|---|---|---|
| 1 | 0.026 | 0.0708 | 0.0175 | 0.0191 |
| 2 | 0.0268 | 0.0653 | 0.0173 | 0.0525 |
| 3 | 4.14 | 16.73 | 3.83 | 3.103 |
| 4 | 0.583 | 1.456 | 0.365 | 0.353 |
| 5 | 0.0449 | 0.0879 | 0.0121 | 0.0105 |
| 6 | 0.1057 | 0.2682 | 0.1584 | 0.465 |
| 7 | 0.1354 | 0.682 | 0.0654 | 0.0556 |
| 8 | 0.308 | 0.618 | 0.399 | 0.345 |
| 9 | 0.0341 | 0.089 | 0.0155 | 0.0145 |
| 10 | 0.0245 | 0.0342 | 0.0157 | 0.0051 |
| 11 | 2.347 | 4.51 | 1.364 | 1.014 |
| 12 | 0.0316 | 0.0802 | 0.0191 | 0.0179 |
| 13 | 0.0705 | 0.0997 | 0.0126 | 0.018 |
| 14 | 0.0337 | 0.0633 | 0.0331 | 0.0226 |
| 15 | 0.2112 | 0.569 | 0.0917 | 0.1616 |
| 16 | 0.381 | 0.371 | n.d. | n.d. |
| 17 | 0.0783 | 0.1134 | n.d. | n.d. |
| 18 | 0.0341 | 0.0661 | 0.0547 | 0.1542 |
| 19 | 0.0088 | 0.0222 | 0.0378 | 0.0382 |
| 20 | 0.0076 | 0.0305 | 0.0175 | 0.0039 |
| 21 | 0.0717 | 0.0802 | 0.0193 | 0.0549 |
| 22 | 0.566 | 7.56 | 1.401 | 0.455 |
| 23 | 11.32 | >50 | >17.9 | 32.07 |
| 24 | 0.2888 | 2.154 | 0.93 | 0.1635 |
| 25 | 0.321 | 1.761 | 1.216 | 0.472 |
| 26 | 0.543 | 2.919 | 2.291 | 0.349 |
| 27 | 2.995 | 23.66 | 11.34 | 8.8 |
| 28 | 0.0707 | 0.1938 | 0.0637 | 0.0536 |
| 29 | 0.2389 | 0.707 | 0.427 | 0.098 |
| 30 | 0.0537 | 0.2428 | 0.498 | 0.0214 |
| 31 | 0.0315 | 0.1225 | 0.1589 | 0.0132 |
| 32 | 0.0503 | 0.1777 | 0.2027 | 0.0172 |
| 33 | 2.816 | 5.39 | n.d. | n.d. |
| 34 | 0.058 | >2.538 | 0.038 | 0.0525 |
| 35 | 0.0835 | 0.0864 | 0.0515 | n.d. |
| 36 | 0.2462 | 0.371 | 0.454 | n.d. |
| 37 | 10.73 | 0.402 | 0.423 | 0.1602 |

TABLE 1-continued

Inhibitory efficacy of seleced compounds of the invention aganist proliferation of L. donovani, T cruzi or T. brucei

| Compound No. | L. donovani amastigotes EC50 (μM) | L. donavani Macrophage EC50 (μM) | T cruzi growth inhibition EC50 (μM) | T. b. brucei growth Inhibition EC50 (μM) |
|---|---|---|---|---|
| 38 | >25 | 24.75 | 10.23 | 4.76 |
| 39 | 18.3 | 5.5 | 3.82 | 1.522 |
| 40 | 1.038 | 0.1613 | 0.1382 | 0.064 |
| 41 | 15.32 | 0.842 | 1.143 | 0.362 |
| 42 | 4.08 | 8.62 | 5.52 | n.d. |
| 43 | 0.2788 | 0.0634 | 0.0449 | 0.1257 |
| 44 | 0.0317 | 0.0689 | 0.0209 | 0.0318 |
| 45 | 0.878 | 8.26 | 4.49 | n.d. |
| 46 | 0.2418 | 0.62 | 0.2365 | 0.1433 |
| 47 | 0.1325 | 0.1495 | 0.1481 | 0.1767 |
| 48 | 0.1787 | 0.1728 | 0.1441 | 0.1556 |
| 49 | 0.0971 | 0.2203 | 0.2656 | 0.461 |
| 50 | 0.862 | 4.7 | 1.718 | 0.944 |
| 51 | 0.1336 | 0.2929 | 0.1771 | 0.1578 |
| 52 | 0.2296 | 0.414 | 0.1328 | 0.2107 |
| 53 | 0.1201 | 0.1803 | 0.132 | 0.1014 |
| 54 | 1.212 | 5.77 | 1.254 | 0.2557 |
| 55 | 1.825 | 3.45 | 0.157 | 0.2445 |
| 56 | 0.171 | 0.253 | 0.0583 | 0.1558 |
| 57 | 0.1375 | 0.2096 | 0.0772 | 0.1161 |
| 58 | 0.2554 | 0.776 | 0.1573 | 0.236 |
| 59 | 0.0394 | 0.0651 | 0.0116 | 0.0652 |
| 60 | 0.0235 | 0.0483 | 0.0155 | 0.0524 |
| 61 | 0.0243 | 0.0645 | 0.0164 | 0.0526 |
| 62 | 0.0174 | 0.0359 | 0.0391 | 0.0538 |
| 63 | 0.1545 | 0.4 | 0.409 | 0.357 |
| 64 | 0.1095 | 0.43 | 0.173 | 0.453 |
| 65 | 0.014 | 0.0277 | 0.017 | 0.024 |
| 66 | 0.0993 | 0.3037 | 0.1209 | 0.1175 |
| 67 | 0.0215 | 0.0518 | 0.0184 | 0.0177 |
| 68 | 0.1541 | 0.426 | 0.2332 | 0.0657 |
| 69 | 0.1265 | 0.35 | 0.1394 | 0.0687 |
| 70 | 0.1515 | 0.339 | 0.1463 | 0.1569 |
| 71 | 0.1002 | 0.2524 | 0.2411 | 0.0875 |
| 72 | 0.1648 | 0.2741 | 0.1597 | 0.1088 |
| 73 | 0.1477 | 0.1184 | 0.1366 | 0.1491 |
| 74 | 0.672 | 1.645 | 0.531 | 0.3128 |
| 75 | 0.634 | 3.037 | 1.138 | 0.627 |
| 76 | 0.0647 | 0.0547 | 0.043 | 0.0129 |
| 77 | 0.0898 | 0.2894 | 0.1498 | 0.0395 |
| 78 | >25 | 23.48 | >10.69 | 1.582 |
| 79 | 0.0898 | 0.2897 | n.d. | n.d. |
| 80 | 0.1691 | 0.392 | 1.205 | 0.1386 |
| 81 | 5.944 | 18.537 | 7.539 | n.d. |
| 82 | >25 | >50 | n.d. | n.d. |
| 83 | 0.025 | 0.075 | 0.023 | n.d. |
| 84 | 18.09 | 10.97 | 4.01 | n.d. |
| 85 | 3.39 | 18.67 | n.d. | n.d. |
| 86 | >11.9 | 4.96 | n.d. | n.d. |
| 87 | 1.315 | 7.34 | n.d. | n.d. |
| 88 | >22.37 | >35.36 | n.d. | n.d. |
| 89 | 8.35 | 12.04 | n.d. | 9.32 |
| 90 | 0.068 | 0.044 | 0.022 | 0.036 |
| 91 | 0.173 | 2.95 | 0.142 | n.d. |
| 92 | 0.03 | 0.062 | 0.015 | 0.017 |
| 93 | 0.179 | 0.597 | 0.461 | 0.098 |
| 94 | 0.077 | 0.211 | 0.045 | 0.069 |
| 95 | 0.079 | 0.17 | 0.05 | n.d. |
| 96 | 0.067 | 0.198 | 0.097 | n.d. |
| 97 | 0.043 | 0.161 | 0.417 | 0.058 | n.d. means not determined.

Target Identification

To identify the mechanism whereby compounds of the invention inhibit growth of kinetoplastid parasites, a population of drug-resistant *T. cruzi* epimastigotes was selected through a long-term parasite culture in the presence of the compounds of the invention. As tolerance for compounds of invention gradually increased over time, the selection pressure was periodically escalated by raising the inhibitor concentration. In the course of nine months, the $EC_{50}$ of the *T. cruzi* culture shifted >250-fold from 0.07 μM to >25 μM.

The mutations associated with parasite resistance to compounds of inventions were identified through whole genome sequencing of resistant parasites and found to be located in the beta 4 subunit of *Trypanosoma cruzi* proteasome. Altogether, two different mutations (F24L and 129M) that are positioned in a region of beta 4 subunit that is distinct from the predicted protease active sites (FIG. 1).

Effect of Compounds of the Invention on Proteolytic Activities of Proteasomes

Proteasomes are proteolytic enzymes that were previously characterized in great detail and were found to harbor three different proteolytic activities—chymotrypsin-like, trypsin-like and caspase-like activity. The effect of the compounds of invention on all three proteolytic activities were evaluated on proteasomes from wild type *T. cruzi*, two resistant strains of *T. cruzi* (F24L and 129M), *Leishmania tarentolae* and human in biochemical assays. The test compounds were N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound 61), N-(4-fluoro-3-(6-isopropylimidazo[1,2-a]pyrimidin-2-yl)phenyl)-2,4-dimethyloxazole-5-carboxamide (Compound 412 of WO 2014/151784), and N-(4-fluoro-3-(6-(2,2,2-trifluoroethyl)imidazo[1,2-a]pyrimidin-2-yl)phenyl)-2,4-dimethyloxazole-5-carboxamide (Compound 575 of WO 2014/151784).

The result shows the compounds all potently inhibited chymotrypsin-like activity of both *Trypanosoma cruzi* and *Leishmania tarentolae* proteasomes, and did not have any effect on trypsin-like and caspase-like activities (Table 2). This result is in a good agreement with the observation that the resistance-conferring mutants are in proximity to the active site of beta 5 subunit, which is known to harbor chymotrypsin-like activity of proteasome. When comparing to the result on growth inhibition of the indicated parasites by the tested compounds, the result also strongly indicates that inhibition of chymotrypsin-like activity of parasitic proteasome is responsible for observed growth inhibition of live parasites.

In contrast, the result shows that chymotrypsin-like activity of proteasomes from the two *Trypanosoma cruzi* strains harboring beta 4 subunit resistance mutations-(F24L or 129M) was fully refractory to inhibition by the tested compounds up to 25 μM concentration (Table 2). Thus, the mutations that confer resistance to compounds of inventions in intact cells in growth assays also confer resistance to isolated mutated proteasome in biochemical assays. Such correlation is again a strong indication that compounds of the invention inhibit growth of parasite cells through inhibition of parasite proteasome.

Further, for inhibition of the two human proteasomes—constitutive and immunoproteasome, none of evaluated compounds showed any inhibition of either human proteasome activity up to 25 μM concentration. The result demonstrates that the tested compounds are selective in inhibiting parasitic proteasome over human proteasomes.

TABLE 2

Inhibition of chymotrypsin-like activity of indicated proteasomes and\parasites by the tested compounds.

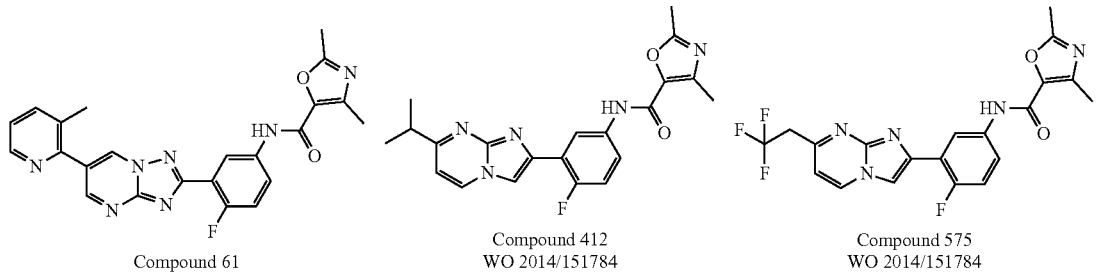

| | Compound 61 | Compound 412 WO 2014/151784 | Compound 575 WO 2014/151784 |
|---|---|---|---|
| **Wild type *T. cruzi*** | | | |
| chymotrypsin IC$_{50}$ [µM] | 0.026 | 0.052 | 0.022 |
| amastigote EC$_{50}$ [µM] | 0.016 | 0.048 | 0.029 |
| epimastigote EC$_{50}$ [µM] | 0.32 | 0.44 | 0.28 |
| ***T. cruzi* with F24L mutation in beta 4 subunit of proteasome** | | | |
| chymotrypsin IC$_{50}$ [µM] | >25 | >25 | >25 |
| epimastigote EC$_{50}$ [µM] | >25 | >25 | >25 |
| ***T. cruzi* with I29M mutation in beta 4 subunit of proteasome** | | | |
| chymotrypsin IC$_{50}$ [µM] | >25 | >25 | >25 |
| epimastigote EC$_{50}$ [µM] | >25 | >25 | >25 |
| **Wild type *Leishmania*** | | | |
| chymotrypsin IC$_{50}$ [µM] (*L. tarentolae*) | 0.035 | 0.040 | 0.024 |
| amastigote EC$_{50}$ [µM] (*L. donovani*) | 0.037 | 0.040 | 0.031 |
| ***H. sapiens* proteasome** | | | |
| chymotrypsin IC$_{50}$ [µM] (constitutive) | >25 | >25 | >25 |

TABLE 2-continued

Inhibition of chymotrypsin-like activity of indicated proteasomes and\parasites by the tested compounds.

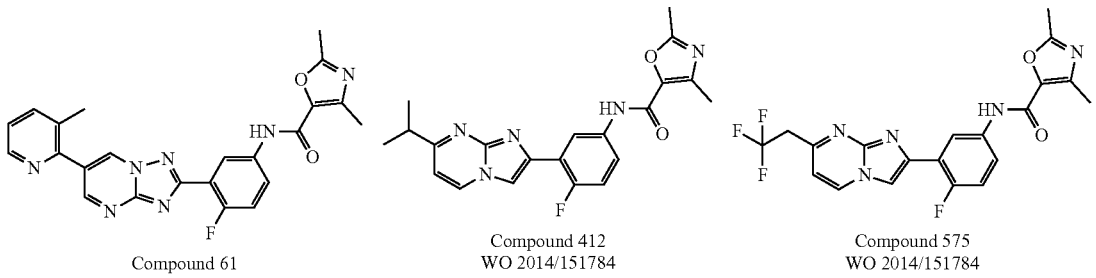

| | Compound 61 | Compound 412<br>WO 2014/151784 | Compound 575<br>WO 2014/151784 |
|---|---|---|---|
| chymotrypsin EC$_{50}$ [µM] (immunoproteasome) | >25 | >25 | >25 |

Effect of Proteasome Inhibition on Cellular Protein Turnover

Trypomastigotes were first labeled for 2 hours with $^{35}$S methionine, which indiscriminately incorporates into newly synthesized proteins. Subsequently, the Trypomastigotes were washed amd resuspended in a growth medium containing excess of non-radioactive methionine to prevent any further incorporation of the 35S methionine into the newly synthesized proteins. The labeled trypomastigotes were incubated in the presence of DMSO, N-(4-fluoro-3-(6-(pyridin-2-yl)imidazo[1,2-a]pyrimidin-2-yl)phenyl)-2,4-dimethyloxazole-5-carboxamide (Compound 18) or bortezomib, a prototypical proteasome inhibitor for up to 48 hours. Total cellular labeled proteins were analyzed by PAGE at 0, 24 and 48 hours.

During this incubation period, radioactively labeled proteins were gradually degraded through the action of proteasome; a general decrease in the amount of radioactive proteins present in labeled trypomastigotes was observed in the DMSO control (FIG. 2—DMSO). When labeled trypomastigotes were incubated in the presence of 10 µM bortezomib or 2 µM of Compound 18, degradation of labeled proteins was blocked or dramatically slowed down (FIG. 2). This result suggests that Compound 18 inhibits *Trypanosoma cruzi* proteasome not only in a biochemical assay, but also in the context of live *Trypanosoma cruzi* trypomastigotes.

Effect of Proteasome Inhibition on Growth of Wild Type *T. cruzi* Epimastigotes

*T. cruzi* epimastigotes were cultured in the presence of various concentrations of Compound 18, bortezomib and MG132 (another prototypical proteasome inhibitor), and parasites were quantified after 7 days of compound treatment. The effective concentrations of inhibitors that effected killing of 50% of parasites (EC$_{50}$) were calculated and listed in Table 3.

The data shown that all three compounds inhibits growth of wild type *T. cruzi* epimastigotes, and potently by the prototypical proteasome inhibitors. As bortezomib and MG132 are structurally distinct from Compound 18 and from each other, the growth inhibition data strongly suggest that inhibition of parasitic proteasome irrespective of a particular mode of inhibitor interaction with parasitic proteasome will result in *T. cruzi* killing. By extension, any inhibitor of chymotrypsin-like activity of *T. cruzi* proteasome would then be expected to effect *T. cruzi* killing and be used for Chagas disease drug discovery.

TABLE 3

Inhibition of growth of wild type *T. cruzi* epimastigotes by Compound 18, bortezomib and MG132.

| | Compound 18 | Bortezomib | MG132 |
|---|---|---|---|
| *T. cruzi* epimastigote EC$_{50}$ [µM] | 1.8 | 0.19 | 0.56 |

EXAMPLES

The present invention is further exemplified, but not to be limited, by the following examples and intermediates that illustrate the preparation of compounds of the invention. It is understood that if there appears to be a discrepancy between the name and structure of a particular compound, the structure is to be considered correct as the compound names were generated from the structures.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Method for Analysis:

Method 1:

The system consists of:

LEAP PAL Autosampler

Waters Acquity Binary Sovent Manager (UPB)

Waters Acquity PDA Detector (UPD)

Waters Acquity ELS Detector (UPE)

Waters ZQ mass spectrometer

Waters MassLynx Software

The system flows at 1 mL/min with each sample being screened through a 1.7 um 2.1×30 mm Waters Acquity BEH C18 column. Mobile phase A is Water+0.05% formic acid and mobile phase B is Acetonitrile+0.05% formic acid.

| Time (min) | Flow rate (mL/min) | % B |
|---|---|---|
| 0 | 1 | 5 |
| 0.1 | 1 | 5 |
| 1.5 | 1 | 95 |
| 1.6 | 1 | 95 |
| 1.7 | 1 | 100 |
| 1.9 | 1 | 5 |
| 2.25 | 1 | 5 |

The DAD acquires data between 214 nm and 400 nm at 2.5 Hz; 214 nm and 254 nm are extracted during data processing. The ZQ acquires typically between 180 amu and 800 amu. If the sample mass lies outside of the 180 amu range another MS method that scans over a broader range will be used.

Method 2:

Quantitative QC analysis is conducted on the "Pacer"LC/MS/CLND system, which consists of:

Waters Acquity Sampler Manager

Waters Acquity Binary pump

Waters Acquity Photodiode Array Detector (PDA)

Antek 8060-R Chemiluminescent Nitrogen Detector (CLND)

Waters 3100 Mass Detector

Leap Technologies HTC PAL autosampler

UPLC Pump Method:

| Time (min) | Flow rate (mL/min) | % B |
|---|---|---|
| 0 | 1 | 2 |
| 1 | 1 | 2 |
| 3.5 | 1 | 95 |
| 4 | 1 | 95 |
| 4.25 | 1 | 2 |
| 5 | 1 | 2 |

Mobile Phases:

A. 95% H2O/5% MeOH/IPA (75/25)+0.05% formic acid

B. MeOH/IPA (75/25)+0.035% formic acid

Column: Thermo Syncronis 2.1×30 mm, 1.7 u particle C18

MS Method"Scan range is 150-1000 amu

UV Scan: 200-400 nm

Synthesis of Intermediates

Intermediate 1: 4-fluoro-3-(6-phenyl-[1,2,4]triazolo[1,5-a]pyrimidin-2-yl)aniline (I-1)

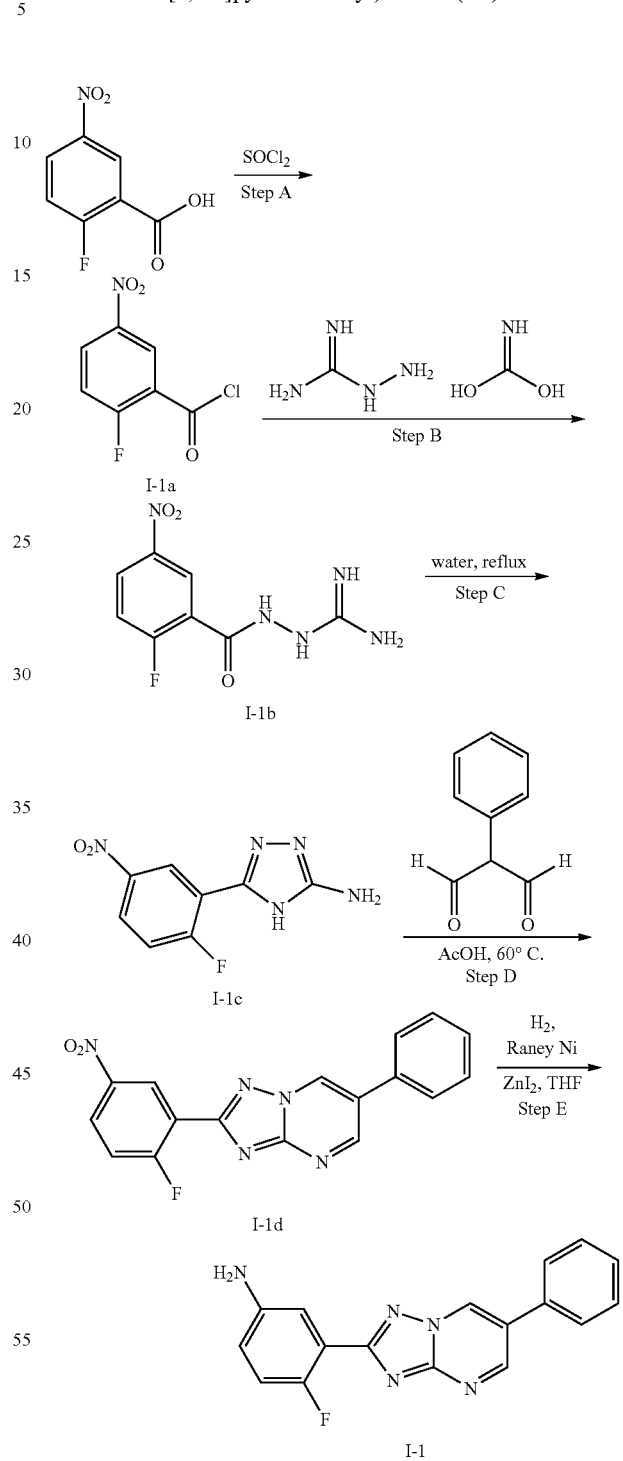

Step A:

A solution of 2-fluoro-5-nitrobenzoic acid (50 g, 270 mmol) in thionyl chloride (100 mL) was heated to 80° C. and stirred for 4 hours. The mixture was allowed to cool down to room temperature and the solvent removed to give compound I-1a (54 g, 98% yield).

Step B:

To a solution of aminoguanidine carbonate (36.2 g, 266 mmol) in dry toluene (300 mL) cooled to 0° C. was added compound I-1a (54 g, 0.266 mol) over 30 minutes. The mixture was stirred at room temperature for 12 hours. The formed precipitate was removed by filtration, and the residue was treated with H$_2$O (400 mL) and made alkaline with sodium carbonate. The solid was collected and recrystallized from water to obtain compound I-1b (62 g, 97% yield). M/Z 241.1 (M+1)

Step C:

A solution of compound I-1b (62 g, 0.257 mol) in H$_2$O (800 mL) was stirred for 8 hours at 100° C. After cooling, the solid obtained was filtered, and the cake was washed with H$_2$O (100 mL), THF (100 mL), and dried to give I-1c (34 g, 51% yield). $^1$H NMR (400 MHz, DMSO) 12.42 (s, 1H), 8.74 (dd, J=6.27, 3.01, 1H), 8.26 (dt, J=8.97, 3.42, 1H), 7.57 (t, J=9.54, 1H), 6.29 (s, 2H).

Step D:

To a solution of compound I-1c (0.5 g, 2.24 mmol) in AcOH (5 mL) was added 2-phenylmalonaldehyde (0.39 g, 2.7 mmol) at room temperature. The mixture was heated to 100° C. and stirred for 4 hours. The mixture was allowed to cool to room temperature, water (10 mL) was added, filtered, and the filter cake was washed with THF, and dried under vacuum to give compound I-1d (0.36 g, 48% yield). $^1$H NMR (400 MHz, DMSO) 9.93 (d, J=2.4, 1H), 9.38 (d, J=2.8, 1H), 8.90 (s, 1H), 7.93 (d, J=7.78, 2H), 7.69 (d, J=8.53, 1H), 7.61-7.50 (m, 2H), 7.31 (t, J=7.40, 1H), 6.88 (s, 1H).

Step E:

To a solution of compound I-1d (2.5 g, 7.4 mmol) in THF (200 mL) was added ZnI$_2$ (1.2 g, 3.7 mmol) and Raney Nickel (3.5 g). This mixture was stirred at room temperature for 4 hour under H$_2$ at 50 psi, then the mixture was filtrated and washed with MeOH (20 mL) to give compound I-1 (2.0 g, 87% yield). $^1$H NMR (400 MHz, DMSO) 9.81 (d, J=2.4, 1H), 9.27 (d, J=2.8, 1H, 7.90 (d, J=7.6, 2H), 7.58-7.53 (m, 2H), 7.45-7.50 (m, 2H), 7.09-7.05 (m, 1H), 6.74-6.70 (m, 1H), 5.22 (s, 2H). M/Z 306.1 (M+1)

Intermediate 2: 4-fluoro-3-(6-(pyridin-2-yl)-[1,2,4]triazolo[1,5-a]pyrimidin-2-yl)aniline (I-2)

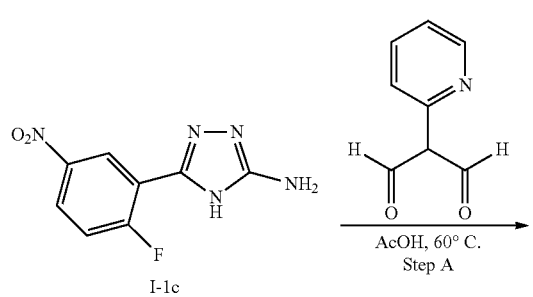

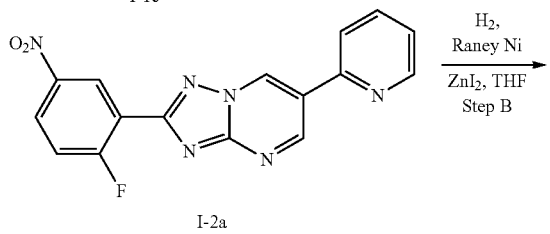

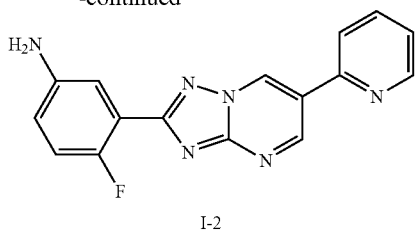

I-2

Step A:

To a solution of compound I-1c (1 g, 4.48 mmol) in AcOH (20 mL) was added 2-(pyridin-2-yl)malonaldehyde (0.8 g, 5.376 mmol) at room temperature. The mixture was heated to 100° C. and stirred for 4 hours. The mixture was allowed to cool to room temperature before adding water (50 mL), filtered, and the filter cake was washed with saturate sodium bicarbonate solution (100 mL), H$_2$O (100 mL), and THF (100 mL) and dried under vacuum to give compound I-2a (0.9 g, 60% yield). $^1$H NMR (400 MHz, DMSO) 10.13 (d, J=2.01, 1H), 9.68 (d, J=2.01, 1H), 9.09-9.02 (m, 1H), 8.77 (d, J=4.27, 1H), 8.28-8.19 (m, 1H), 8.15-7.96 (m, 2H), 7.77 (t, J=9.54, 1H), 7.56-7.43 (m, 1H).

Step B:

To a solution of compound I-2a (0.15 g, 0.443 mmol) in THF (5 mL) was added Raney Nickel (0.2 g) and ZnI$_2$ (71 mg) at room temperature. The mixture was stirred under H$_2$ (50 psi) at 25° C. for 2.5 hours. The mixture was diluted with MeOH (10 mL) and filtered. The solvent were removed and the crude product was washed with MeOH (5 mL×2) and dried under vacuum to give compound I-2 (90 mg, 66% yield). $^1$H NMR (400 MHz, DMSO) 10.01-10.06 (m, 1H), 9.62-9.58 (m, 1H), 8.73-8.78 (m, 1H), 8.24-8.20 (m, 1H), 8-02-7.96 (m, 1H), 7.57-7.47 (m, 2H), 7.08-7.05 (m, 1H), 6.76-6.70 (m, 1H), 5.24 (s, 2H) M/Z 307.01 (M+1).

Intermediate 3: 3-(6-(tert-butyl)-[1,2,4]triazolo[1,5-a]pyrimidin-2-yl)-4-fluoroaniline (I-3)

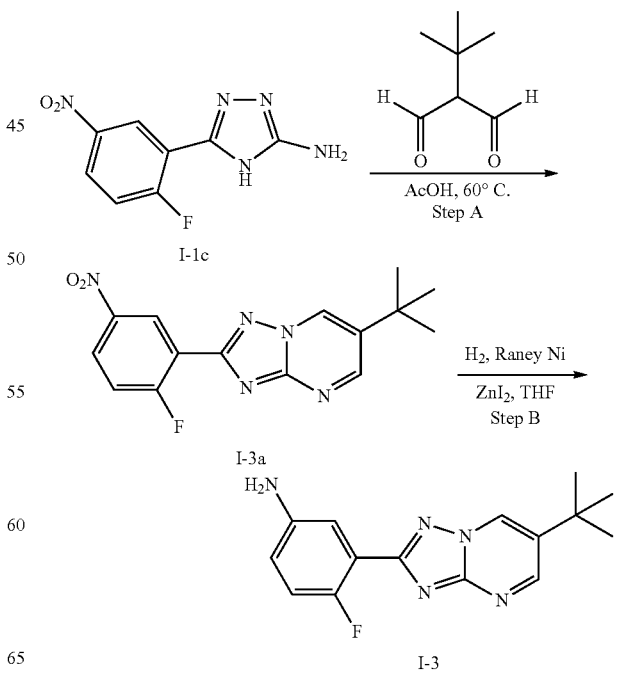

Step A:

To a solution of compound I-1c (0.5 g, 2.24 mmol) in AcOH (10 mL) was added 2-(tert-butyl)malonaldehyde (0.286 g, 2.24 mmol) at room temperature. The mixture was heated to 120° C., and stirred for 3 hours. The mixture was allowed to cool to room temperature before adding water (20 mL), filtered, and the filter cake was washed with MeOH (5 mL), dried under vacuum to give compound I-3a (0.7 g, crude). M/Z 316.1 (M+1)

Step B:

To a solution of compound I-3a (0.3 g, 0.96 mmol) in THF (30 mL) was added $ZnI_2$ (123 mg, 0.39 mmol) and Raney Nickel (300 mg). This mixture was stirred at room temperature under 15 psi of $H_2$ for 8 hours, then the solid was filtrated and concentrated to give compound I-3 (0.27 g, crude). $^1$H NMR (400 MHz, DMSO): 9.28 (s, 1H), 9.08 (s, 1H), 7.41-7.39 (m, 1H), 7.03 (t, J=9.2, 1H), 6.71-6.68 (m, 1H), 5.20 (s, 2H), 1.41 (s, 9H). M/Z 286.2 (M+1).

Intermediate 4: 3-(6-bromo-[1,2,4]triazolo[1,5-a]pyrimidin-2-yl)-4-fluoroaniline (I-4)

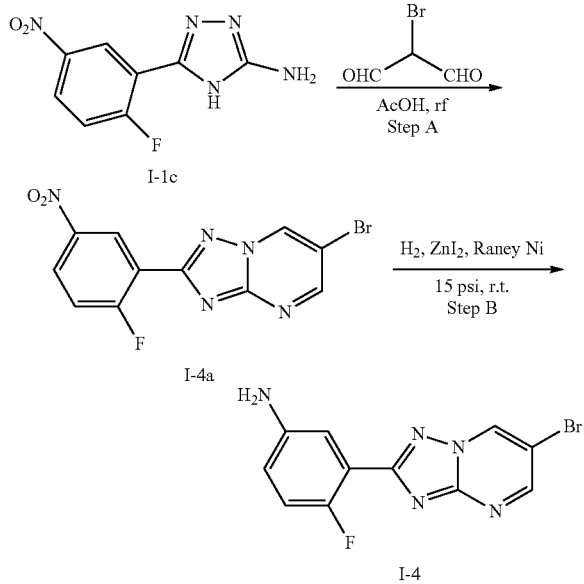

Step A:

To a solution of compound I-1c (10 g, 44.8 mmol) in AcOH (50 mL) was added 2-bromomalonaldehyde (8.12 g, 53.8 mmol) at room temperature. The mixture was heated to 100° C. and stirred for 4 hours. The mixture was allowed to cool to room temperature before adding water (100 mL), filtered, and the filter cake was washed with THF, dried under vacuum to give compound I-4a (6.5 g, 43% yield). $^1$H NMR (400 MHz, DMSO) 10.04 (s, 1H), 9.08 (s, 1H), 8.96-9.04 (m, 1H), 8.47 (dt, J=9.03, 3.39, 1H), 7.76 (t, J=9.54, 1H).

Step B:

To a solution of compound I-4a (6 g, 17.7 mmol) in THF (150 mL) was added Raney Nickel (7 g) and $ZnI_2$ (2.26 g, 7.1 mmol), the suspension was degassed under vacuum and the mixture was stirred under $H_2$ (50 psi) at 25° C. for 2 hours. The mixture was filtered and the solvents removed to give the crude product. The crude product was washed with MeOH (50 mL×2) and dried under vacuum to give compound I-4 (4.2 g, 77% yield). $^1$H NMR (400 MHz, DMSO): 9.93 (d, J=2.26, 1H), 8.98 (d, J=2.0, 1H), 7.39-7.45 (m, 1H), 6.99-7.10 (m, 1H), 6.67-6.76 (m, 1H), 5.76 (s, 1H), 5.25 (brs, 2H).

Intermediate 5: 3-(6-chloro-[1,2,4]triazolo[1,5-a]pyrimidin-2-yl)-4-fluoroaniline (I-5)

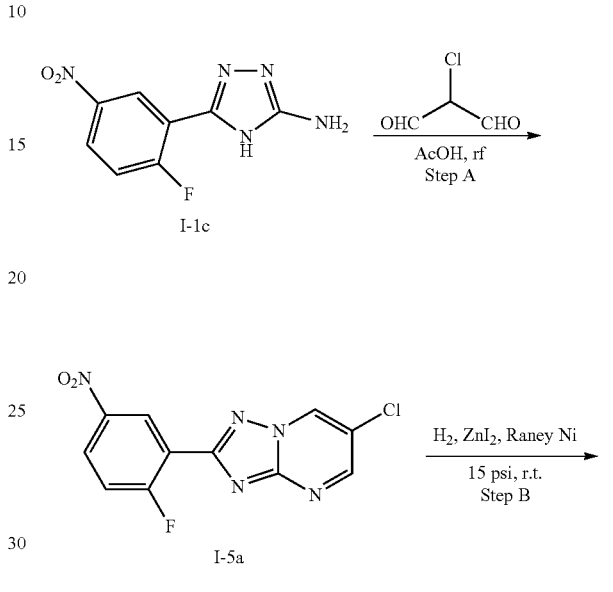

Step A:

To a solution of compound I-1c (2 g, 8.97 mmol) in AcOH (20 mL) was added 2-chloromalonaldehyde (1.46 g, 9.86 mmol) at room temperature. The mixture was heated to 120° C., and stirred for 3 hours. The mixture was allowed to cool to room temperature before adding water (100 mL), filtered, and the filter cake was washed with MeOH (20 mL), dried under vacuum to give compound I-5a (2.3 g, 87.7% yield). $^1$H NMR (400 MHz, DMSO) 9.99 (s, 1H), 9.05 (d, J=1.76, 1H), 8.99 (dd, J=5.77, 2.51, 1H), 8.39-8.54 (m, 1H), 7.75 (t, J=9.54, 1H).

Step B:

To a solution of compound I-5a (2 g, 6.83 mmol) in THF (150 mL) was added Raney Nickel (4 g) and $ZnI_2$ (0.8 g, 2.7 mmol), The suspension was degassed and sparged with $H_2$ several times. The mixture was stirred under $H_2$ at 25° C. for 2 hours. The mixture was filtered, the solvent removed, and the crude product was washed with MeOH (50 mL×2) and dried under vacuum to give compound I-5 (1 g, 55% yield) $^1$H NMR (400 MHz, DMSO) 9.88 (d, J=1.76, 1H), 8.96 (d, J=2.01, 1H), 7.49-7.37 (m, 1H), 7.05 (t, J=9.79, 1H), 6.80-6.65 (m, 1H), 5.23 (brs, 2H). M/Z 264.1 (M+1).

Intermediate 6: 3-(6-(3,6-dihydro-2H-pyran-4-yl)-[1,2,4]triazolo[1,5-a]pyrimidin-2-yl)-4-fluoroaniline (I-6)

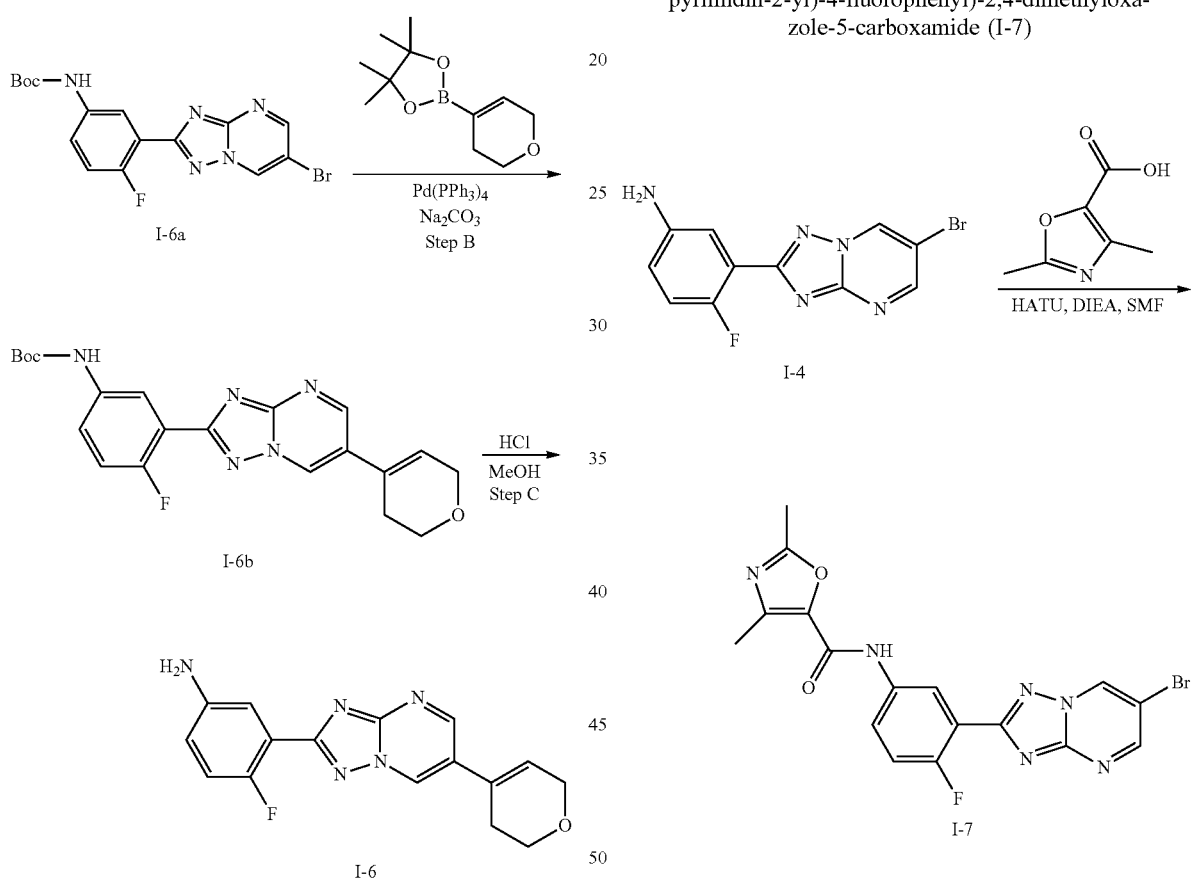

Step A:

A solution of compound I-4 (3.0 g, 10 mmol) in (Boc)₂O (20 mL) was heated to 100° C. for 12 hours. The mixture was then filtrated and washed with PE (40 mL) to give compound I-6a (2.5 g, crude) which was used directly in the next step.

Step B:

To a solution of compound I-6a (2.5 g, 8.1 mmol) in dioxane (150 mL) and water (15 mL) was added 2-(3,6-dihydro-2H-pyran-4-yl)-4,4,5,5-tetramethyl-1,3,2-dioxaborolane (2.0 g, 9.72 mmol), tetrakis(triphenylphosphine)palladium (936 mg, 0.81 mmol) and sodium carbonate (1.72 g, 16.2 mmol). The mixture was degassed and heated to 100° C. for 12 hours under nitrogen. Water (100 mL) was then added and the mixture was extracted with Ethyl Acetate/ THF (150 mL/200 mL). The organic layer was concentrated and washed with MeOH (50 mL) to give compound I-6b (1.0 g, 30% yield).

Step C:

To a solution of compound I-6b (1.0 g, 2.4 mmol) in MeOH (20 mL) was added HCl/MeOH (10 mL). This mixture was stirred at room temperature for 4 hours. Then the solvent was removed to provide compound I-6 (0.8 g, 93% yield). ¹H NMR (400 MHz, DMSO) 9.44 (d, J=2.01, 1H), 9.16 (d, J=2.26, 1H), 7.43 (dd, J=6.02, 2.76, 1H), 7.05 (dd, J=10.54, 9.03, 1H), 6.75-6.71 (m, 1H), 6.64 (brs, 1H), 5.23 (brs, 2H), 4.28 (d, J=2.01, 2H), 3.87 (t, J=5.40, 2H), 1.36 (s, 2H).

Intermediate 7: N-(3-(6-bromo-[1,2,4]triazolo[1,5-a]pyrimidin-2-yl)-4-fluorophenyl)-2,4-dimethyloxazole-5-carboxamide (I-7)

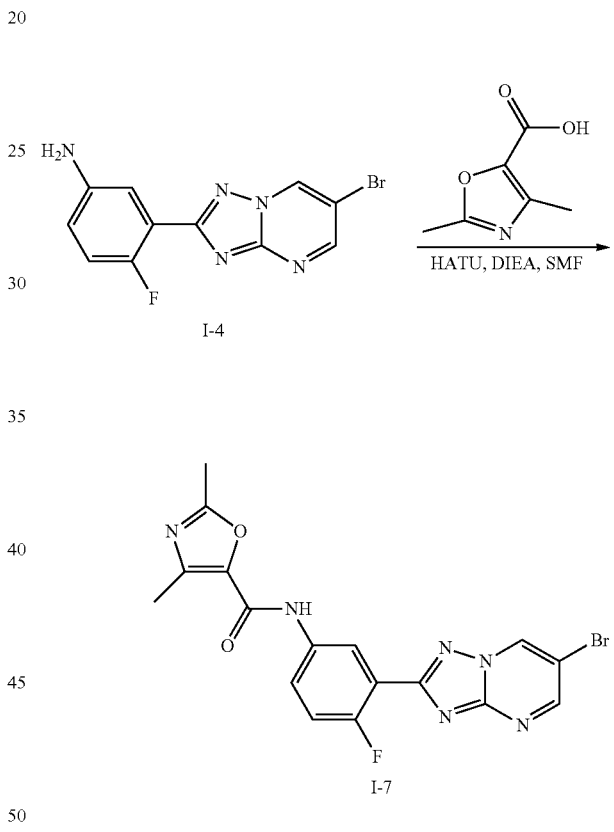

To a solution of 2,4-dimethyloxazole-5-carboxylic acid (1.92 g, 13.6 mmol) in DMF (50 mL) was added HATU (6.2 g, 16.32 mmol) and DIEA (3.5 g, 27.2 mmol) at room temperature. The mixture was stirred for 30 mins, and the compound I-4 (4.2 g, 13.6 mmol) was added. The mixture was stirred for 3 hours, water (100 mL) was added. The mixture was filtered, the filter cake was washed with H₂O (50 mL×2), THF (50 mL×2) and dried to give I-7 (3.1 g, 53%). ¹H NMR (400 MHz, DMSO) 10.41 (s, 1H), 9.97 (s, 1H), 9.02 (brs, 1H), 8.75 (s, 1H), 7.93 (s, 1H), 7.40 (t, J=9.66, 1H), 2.50 (s, 3H), 2.39 (s, 3H).

Intermediate 8: N-(4-fluoro-3-(6-(4,4,5,5-tetramethyl-1,3,2-dioxaborolan-2-yl)-[1,2,4]triazolo[1,5-a]pyrimidin-2-yl)phenyl)-2,4-dimethyloxazole-5-carboxamide (I-8)

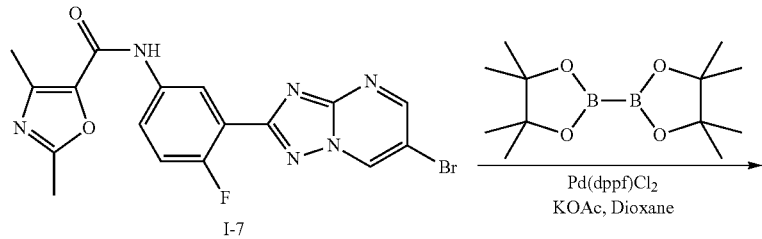

To a solution of compound I-7 (3.0 g, 7.0 mmol) in dioxane (60 mL) was added 4,4,4',4',5,5,5',5'-octamethyl-2,2'-bi(1,3,2-dioxaborolane) (7.1 g, 28 mmol), Pd(dppf)Cl$_2$ (0.5 g, 0.7 mmol) and KOAc (2.0 g, 21 mmol) under nitrogen. This mixture was heated to 100° C. for 16 hours. The solvent was concentrated and triturated with MTBE to give compound I-8 (0.67 g, 24% yield). $^1$H NMR (400 MHz, DMSO) 10.41 (s, 1H), 9.48-9.45 (m, 1H), 9.09-9.08 (m, 1H), 8.73-8.71 (m, 1H), 7.96-7.92 (m, 1H), 7.43-7.38 (m, 1H), 2.51 (s, 3H), 2.40 (s, 3H). M/Z 397.1 (M−82+1).

Intermediate 9: N-(3-(6-amino-[1,2,4]triazolo[1,5-a]pyrimidin-2-yl)-4-fluorophenyl)-2,4-dimethyloxazole-5-carboxamide (I-9)

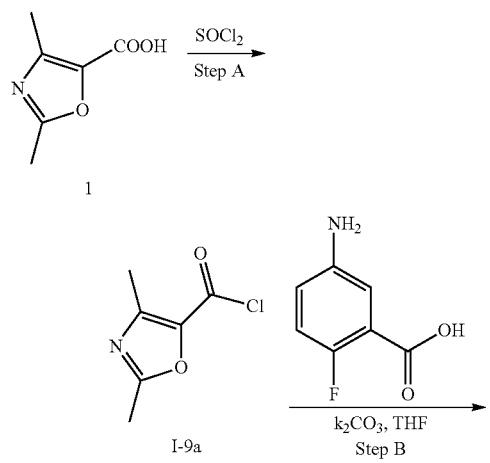

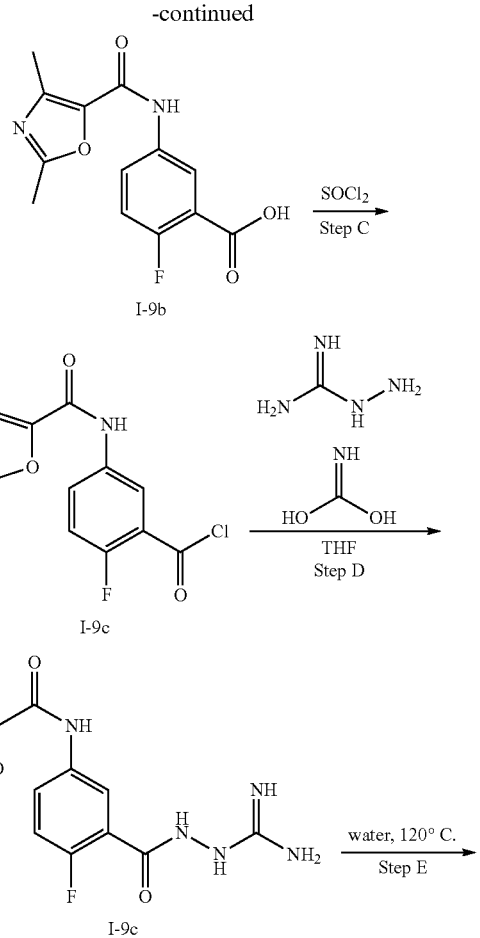

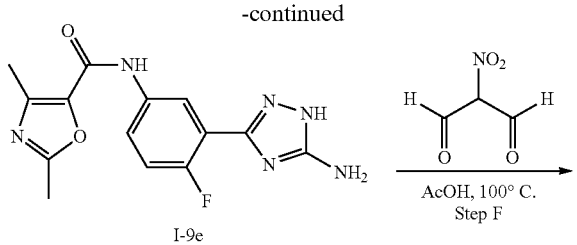

I-9e

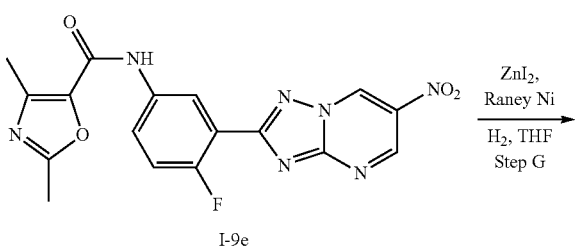

I-9e

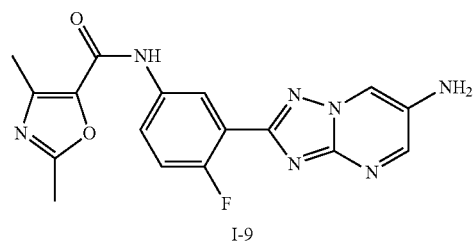

I-9

Step A:

A mixture of 2,4-dimethyloxazole-5-carboxylic acid (10 g, 71 mmol) in thionyl chloride (100 mL) was stirred at 80° C. for 4 hours. The reaction mixture was concentrated under vacuo, and the residue I-9a was used directly in the next step.

Step B:

A mixture of compound I-9a (71 mmol), potassium carbonate (18 g, 129 mmol) and 5-amino-2-fluorobenzoic acid (10 g, 64.5 mmol) in THF (200 mL) was stirred at room temperature under nitrogen overnight. The reaction mixture was concentrated under vacuo, acidified with 2 N HCl to pH=6, and Ethyl Acetate (100 mL) was added. The reaction mixture was stirred at room temperature for 30 min, and filtered. The solid was washed with water (3×100 mL) and acetone (3×20 mL). The solid was dried under vacuo to give compound I-9b (10 g, 50% yield) as a gray solid. $^1$H NMR (400 MHz, DMSO) 13.31 (s, 1H), 10.34 (s, 1H), 8.34 (dd, J=6.53, 2.76, 1H), 7.89-8.02 (m, 1H), 7.29 (dd, J=10.16, 9.16, 1H), 2.46-2.50 (m, 3H), 2.38 (s, 3H).

Step C:

The solution of compound I-9b (11 g, 39.6 mmol) in thionyl chloride (200 mL) was heated at reflux for 2 hours. The thionyl chloride was removed under vacuo, additional thionyl chloride (150 mL) was added, and this mixture was stirred at reflux for another 6 hours. The reaction mixture was concentrated and dried under vacuo, and the residue was used for the next step directly.

Step D:

The mixture of compound I-9c (39.6 mmol) and hydrazinecarboximidamide carbonate (16 g, 119 mmol) in THF (150 mL) was stirred at room temperature for 48 hours. The reaction mixture was concentrated under vacuo. The residue was triturated with 1N NaOH solution (200 mL) for 30 minutes. The solid was collected by filtration, washed with water (3×50 mL), ethyl acetate (2×50 mL), acetone (20 mL) and dried under vacuo to give compound I-9d (4 g, 31% yield) as a gray solid. $^1$H NMR (400 MHz, DMSO) 10.13 (s, 1H), 7.99 (dd, J=6.53, 2.51, 1H), 7.60-7.77 (m, 1H), 7.07 (t, J=9.54, 1H), 6.71 (brs, 3H), 2.49 (s, 3H), 2.38 (s, 3H).

Step E:

The mixture of compound I-9d (4 g, 3.65 mmol) in water (60 mL) was stirred under reflux for 24 hours. The reaction mixture was cooled down, and filtered. The solid was washed with water (3×10 mL), ethanol (20 mL), and dried under vacuo to give compound I-9e (3 g, 90% yield) as a gray solid. $^1$H NMR (400 MHz, DMSO) 12.21 (s, 1H), 10.26 (s, 1H), 8.43 (d, J=4.27, 1H), 7.68 (d, J=3.76, 1H), 7.22 (t, J=8.91, 1H), 6.12 (brs, 2H), 2.43 (s, 3H), 2.38 (s, 3H). M/Z 317.1 (M+1).

Step F:

The mixture of compound I-9e (1.5 g, 4.9 mmol) and nitromalonaldehyde (0.9 g, 5.9 mmol) in AcOH (30 mL) was stirred at 100° C. for 3 hours. The reaction mixture was cooled down, diluted with water (100 mL) and filtered. The solid was washed with saturated sodium bicarbonate solution (20 mL), water (20 mL) and triturated with MeOH (10 mL) to give compound I-9f (1.2 g, crude). $^1$H NMR (400 MHz, DMSO) 10.73 (s, 1H), 10.47 (s, 1H), 9.64 (d, J=2.51, 1H), 8.83 (dd, J=6.40, 2.64, 1H), 7.98 (brs, 1H), 7.46 (t, J=9.79, 1H), 2.51 (s, 3H), 2.44 (s, 3H). M/Z 398.3 (M+1).

Step G:

The reaction mixture of I-9f (1.1 g, 2.9 mmol), ZnI$_2$ (0.4 g, 1 mmol) and Raney Nickel (2 g) in THF (100 mL) was stirred under a balloon of hydrogen for 5 hours. The reaction mixture was filtered, and the cake was washed with 50% MeOH/THF (3×100 mL). The filtrate was concentrated under vacuo, and the residue was purified by HPLC to give compound I-11 (250 mg, 30% yield) as a brown solid. $^1$H NMR (400 MHz, DMSO) 10.36 (s, 1H), 8.63 (dd, J=6.52, 2.51, 1H), 8.55 (s, 1H), 8.45 (s, 1H), 7.87 (dt, J=8.47, 3.54, 1H), 7.35 (t, J=9.79, 1H), 5.60 (s, 2H), 2.46-2.50 (s, 3H), 2.40 (s, 3H). M/Z 368.0 (M+1).

Intermediate 10: N-(3-(5-amino-1H-1,2,4-triazol-3-yl)-4-chlorophenyl)furan-2-carboxamide (I-10)

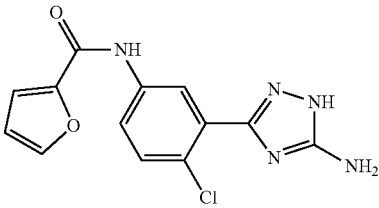

I-10

The intermediate I-10 was prepared following the same route as the intermediate I-9e using furan-2-carboxylic acid and 5-amino-2-chlorobenzoic acid as starting materials.

Synthesis of Products

Example 1: Synthesis of N-(4-fluoro-3-(6-phenyl-[1,2,4]triazolo[1,5-a]pyrimidin-2-yl)phenyl)-2,4-dimethyloxazole-5-carboxamide (Compound 1)

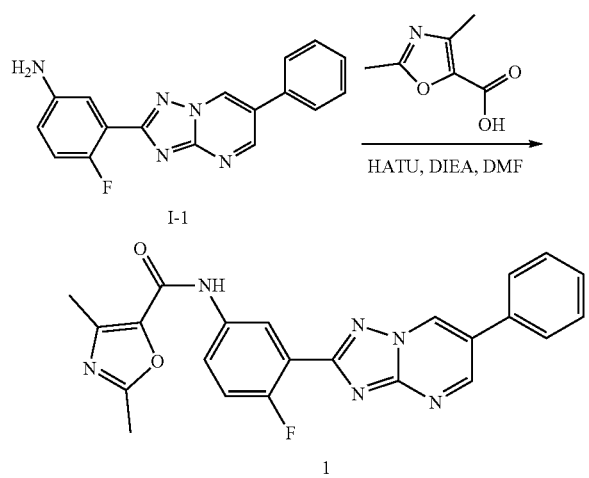

To a solution of 2,4-dimethyloxazole-5-carboxylic acid (0.56 g, 3.9 mmol) in DMF (30 mL) was added DIEA (0.85 g, 6.66 mmol) and HATU (1.5 g, 3.9 mmol). This mixture was stirred at room temperature for 30 minutes, then compound I-1 (1.0 g, 3.28 mmol) was added. The mixture was then stirred at room temperature for 4 hours, diluted with water (50 mL) and extracted with THF/Ethyl Acetate (100 mL/50 mL), the organic layer was dried over sodium sulfate and concentrated to give the crude product. It was purified by HPLC to give product 1 (0.91 g, yield, 65%) as a white solid. $^1$H NMR (400 MHz, MeOD) 9.49 (d, J=2.4, 1H), 9.22 (d, J=2.4, 1H), 8.51 (dd, J=6.4, 2.8, 1H), 7.90 (ddd, J=8.9, 4.2, 2.8, 1H), 7.86-7.76 (m, 2H), 7.63-7.55 (m, 2H), 7.54-7.45 (m, 1H), 7.32 (dd, J=10.4, 9.0, 1H), 2.56 (s, 3H), 2.47 (s, 3H). M/Z=429.2 (M+1). RT=1.83 min, Method 1.

Compounds 2, 3 and 4 were synthesized according to the protocol described above using 2-methyloxazole-5-carboxylic acid, 2-(dimethylamino)oxazole-5-carboxylic acid and cyclobutyl carboxylic acid respectively.

Example 2: Synthesis of N-(4-fluoro-3-(6-phenyl-[1,2,4]triazolo[1,5-a]pyrimidin-2-yl)phenyl)azetidine-1-carboxamide (Compound 9)

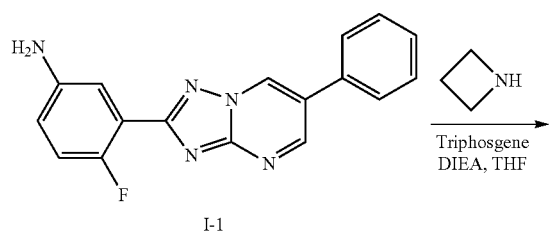

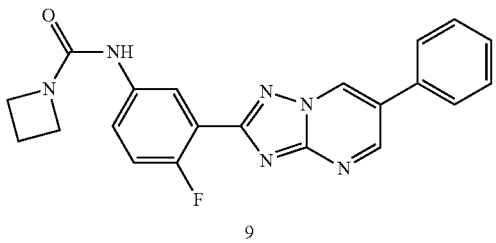

To a solution of triphosgene (6.4 mg, 0.022 mmol) in THF (0.3 mL) was slowly added the intermediate I-1 (20 mg, 0.066 mmol) in THF (1.5 ml) at −5° C.-0° C. The reaction was stirred at room temperature for 5 minutes then a solution of azetidine hydrochloride (7.2 mg, 0.13 mmol) and DIEA (34 μl, 0.20 mmol) in THF (1 ml) was added in one portion. The reaction mixture was then stirred for 30 minutes at RT. The reaction mixture was purified by HPLC to afford compound 9 as a white solid. $^1$H NMR (400 MHz, MeOD) 9.47 (d, J=2.3, 1H), 9.21 (d, J=2.4, 1H), 8.22 (dd, J=6.4, 2.8, 1H), 7.85-7.76 (m, 2H), 7.73-7.62 (m, 1H), 7.61-7.46 (m, 4H), 7.26-7.11 (m, 1H), 4.11 (q, J=8.8, 8.2, 4H), 2.33 (p, J=7.6, 2H). M/Z 389.4 (M+1).

Compounds 5, 6, 7, 8, 10, 11, 12, 13 and 14 were synthesized according to the protocol described above using the corresponding amines.

Example 3: Synthesis of Isopropyl (4-fluoro-3-(6-phenyl-[1,2,4]triazolo[1,5-a]pyrimidin-2-yl)phenyl) carbamate (Compound 15)

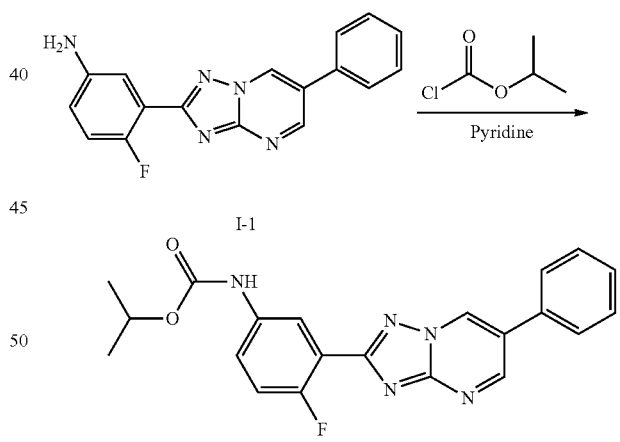

To a solution of 4-fluoro-3-(6-phenyl-[1,2,4]triazolo[1,5-a]pyrimidin-2-yl)aniline (20 mg, 0.066 mmol) in pyridine (2 mL) was added isopropyl chloroformate (25 mg, 0.2 mmol). The reaction was stirred at room temperature for 16 hours. The reaction mixture was purified by HPLC to afford product 15 as a white solid. $^1$H NMR (400 MHz, MeOD) 9.50 (d, J=2.4, 1H), 9.23 (d, J=2.4, 1H), 8.25 (dd, J=6.2, 2.8, 1H), 7.82 (dd, J=7.3, 1.8, 2H), 7.72-7.64 (m, 1H), 7.64-7.46 (m, 3H), 7.25 (dd, J=10.4, 8.9, 1H), 5.04-4.96 (m, 1H), 1.33 (d, J=6.2, 6H). M/Z 392.4 (M+1).

Example 4: Synthesis of N-(4-chloro-3-(6-phenyl-[1,2,4]triazolo[1,5-a]pyrimidin-2-yl)phenyl)furan-2-carboxamide (Compound 16)

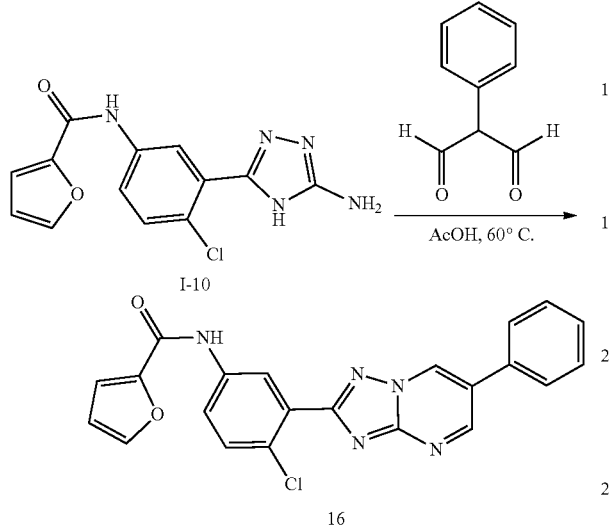

Intermediate I-10 (50 mg, 0.165 mmol) was dissolved in acetic acid and 2-phenylmalonaldehyde was added. The reaction mixture was stirred for 2 hours at 60° C. The mixture was concentrated and purified by HPLC. $^1$H NMR (400 MHz, DMSO) 10.48 (s, 1H), 9.81 (d, J=2.4, 1H), 9.27 (d, J=2.4, 1H), 8.54 (d, J=2.7, 1H), 7.96-7.89 (m, 2H), 7.89-7.81 (m, 2H), 7.56 (t, J=10.4, 1H), 7.53 (s, 2H), 7.46-7.37 (m, 1H), 7.34 (d, J=3.5, 1H), 6.66 (dd, J=1.7, 3.5, 1H). M/Z=416.0 (M+1).

Compound 33 was prepared according to the same protocol as compound 16 using bromomalonaldehyde as starting material.

Example 5: Synthesis of N-(4-chloro-3-(6-phenyl-[1,2,4]triazolo[1,5-a]pyrimidin-2-yl)phenyl)pyrrolidine-1-carboxamide (Compound 17)

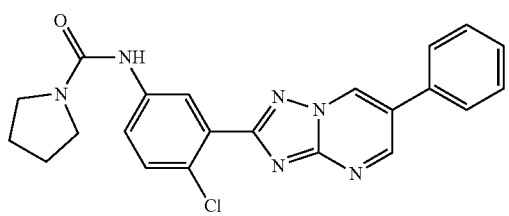

Compound 17 was prepared following the same route as compound 9 using 2-chloro-5-nitrobenzoic acid as starting material and pyrolidine for the urea formation.

$^1$H NMR (400 MHz, DMSO) 9.78 (d, J=2.5, 1H), 9.25 (d, J=2.4, 1H), 8.45 (s, 1H), 8.29 (d, J=2.7, 1H), 7.90-7.79 (m, 2H), 7.72 (dd, J=2.7, 8.8, 1H), 7.56-7.46 (m, 2H), 7.47-7.37 (m, 2H), 3.32 (t, J=6.7, 4H), 1.79 (t, J=6.6, 4H). M/Z=419.1 (M+1).

Example 6: Synthesis of N-(4-fluoro-3-(6-(pyridin-2-yl)-[1,2,4]triazolo[1,5-a]pyrimidin-2-yl)phenyl)-2,4-dimethyloxazole-5-carboxamide (Compound 18)

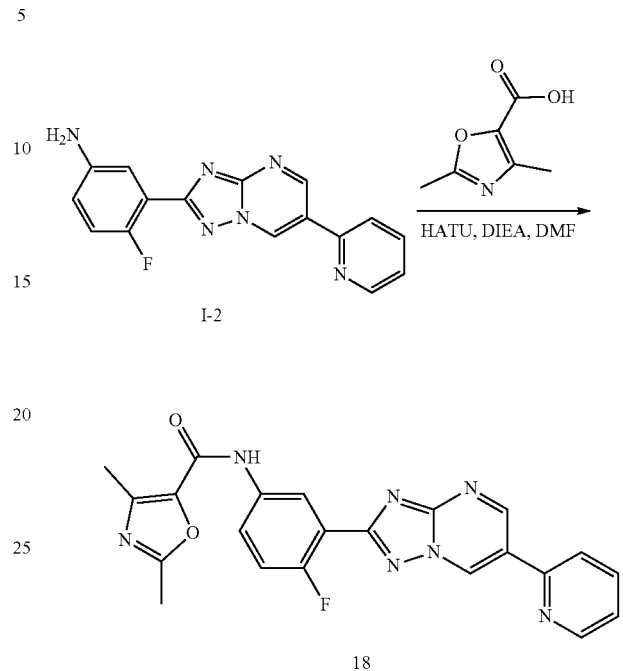

To a solution of 2,4-dimethyloxazole-5-carboxylic acid (40.6 mg, 0.28 mmol) in DMF (5 mL) was added HATU (118.6 mg, 0.31 mmol) and DIEA (72.4 mg, 0.56 mmol) at room temperature. The mixture was stirred for 30 min, the intermediate I-2 (80 mg, 0.26 mmol) was added at room temperature. The mixture was stirred for 3 hours, water (10 mL) was added, the mixture was filtered, and the filter cake was washed with H$_2$O (2×5 mL), THF (2×5 mL) and purified by HPLC to give product 18 (33 mg, 31% yield). $^1$H NMR (400 M, MeOD) 9.84 (d, J=2.4, 1H), 9.61 (d, J=2.3, 1H), 8.76 (dt, J=4.8, 1.4, 1H), 8.54 (dd, J=6.4, 2.7, 1H), 8.12 (dt, J=8.0, 1.1, 1H), 8.00 (td, J=7.8, 1.8, 1H), 7.93 (ddd, J=8.9, 4.1, 2.7, 1H), 7.49 (ddd, J=7.5, 4.9, 1.0, 1H), 7.34 (dd, J=10.4, 9.0, 1H), 2.57 (s, 3H), 2.48 (s, 3H). M/Z=430.13 (M+1).

Compound 19 was prepared using the same protocol as described above using 2-methyloxazole-5-carboxylic acid as starting material.

Example 7: Synthesis of N-(4-fluoro-3-(6-(pyridin-2-yl)-[1,2,4]triazolo[1,5-a]pyrimidin-2-yl)phenyl)azetidine-1-carboxamide (Compound 20)

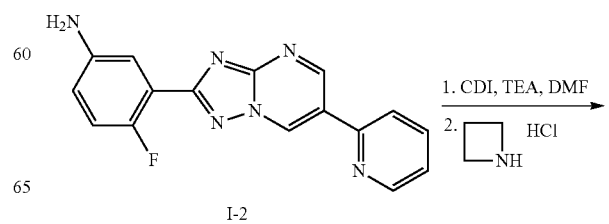

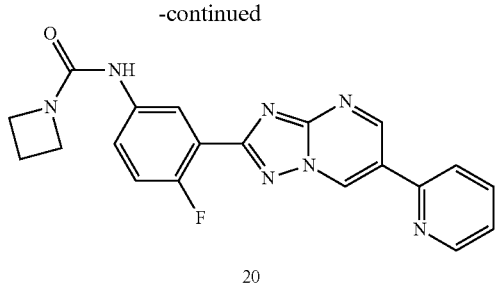

20

To a solution of CDI (84 mg, 0.52 mmol) and TEA (105 mg, 1.04 mmol) in anhydrous DMF (1 mL) was added compound I-2 (100 mg, 0.26 mmol) portion wise at 0° C. This reaction mixture was stirred at this temperature for one hour, then warmed up to room temperature. Azetidine (49 mg, 0.52 mmol) was added an hour later. The resulting reaction mixture was stirred at room temperature for another hour and the residue was purified by HPLC to give product 20 (18 mg, 18% yield) as a yellow solid. $^1$H NMR (400 MHz, DMSO) 10.08 (s, 1H), 9.64 (s, 1H), 8.78 (d, J=4.27, 1H), 8.67 (s, 1H), 8.44 (dd, J=6.53, 2.76, 1H), 8.24 (d, J=8.03, 1H), 8.02 (td, J=7.78, 1.51, 1H), 7.75-7.83 (m, 1H), 7.51 (dd, J=7.15, 5.14, 1H), 7.28-7.33 (m, 1H), 3.99 (t, J=7.53, 4H), 2.17-2.25 (m, 2H). M/Z 389.9 (M+1).

Example 8: Synthesis of N-(3-(6-(tert-butyl)-[1,2,4]triazolo[1,5-a]pyrimidin-2-yl)-4-fluorophenyl)-2,4-dimethyloxazole-5-carboxamide (Compound 21)

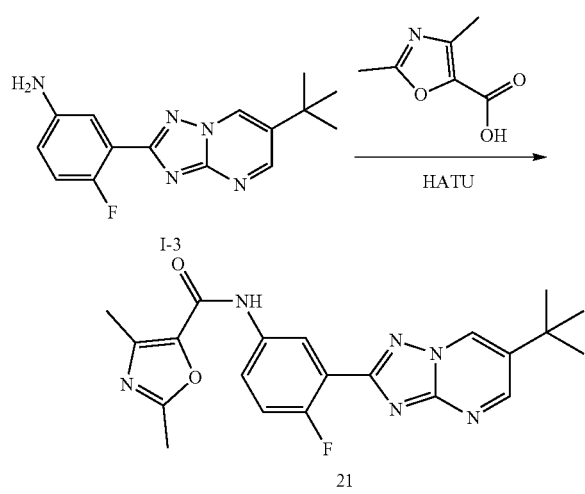

21

To a solution of 2,4-dimethyloxazole-5-carboxylic acid (64 mg, 0.46 mmol) in DMF (1 mL) was added DIEA (90 mg, 0.70 mmol) and HATU (172 mg, 0.46 mmol). This mixture was stirred at room temperature for 30 minutes, then compound I-3 (100 mg, 0.35 mmol) was added. This mixture was stirred at room temperature for 4 hour, then water (10 mL) was added and extracted with Ethyl Acetate/THF (30 mL/60 mL). The organic layer was concentrated and purified by HPLC to give product 21 (28 mg, 20% yield). $^1$H NMR (400 MHz, DMSO) 10.40 (s, 1H), 9.34 (d, J=2.51, 1H), 9.13 (d, J=2.51, 1H), 8.76 (dd, J=6.53, 2.76, 1H), 7.87-7.91 (m, 1H), 7.37-7.42 (m, 1H), 2.51 (s, 3H), 2.41 (s, 3H), 1.43 (s, 9H). M/Z=409.7 (M+1).

Example 9: Synthesis of N-(3-(6-chloro-[1,2,4]triazolo[1,5-a]pyrimidin-2-yl)-4-fluorophenyl)-2,4-dimethyloxazole-5-carboxamide (Compound 22)

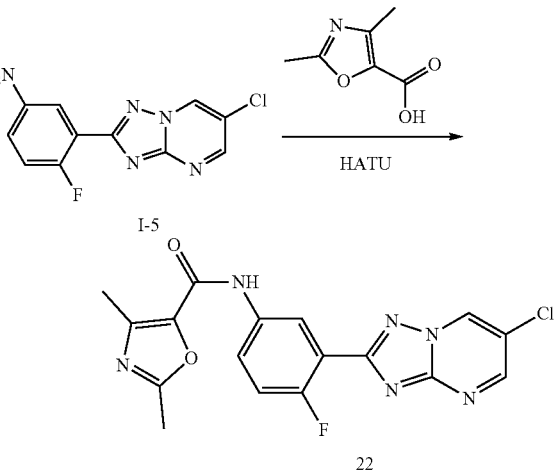

22

To a solution of 2,4-dimethyloxazole-5-carboxylic acid (47 mg, 0.334 mmol) in DMF (5 mL) was added DIEA (78.4 mg, 0.608 mmol) and HATU (127 mg, 0.334 mmol). This mixture was stirred at room temperature for 30 minutes, then compound I-5 (80 mg, 0.304 mmol) was added. This mixture was stirred at room temperature for 4 hours, then water (30 mL) was added and extracted with Ethyl Acetate/THF (100 mL/50 mL). The organic layer was concentrated and purified by HPLC to give compound 22 (31 mg, 26% yield). $^1$H NMR (400 MHz, DMSO) 10.41 (s, 1H), 9.92 (s, 1H), 9.00 (s, 1H), 8.74 (dd, J=6.53, 2.76, 1H), 7.88-7.97 (m, 1H), 7.40 (t, J=9.79, 1H), 2.5 (s, 3H), 2.39 (s, 3H). M/Z=387.0 (M+1).

Compound 23 was prepared using the same protocol as described above using 2-methyloxazole-5-carboxylic acid as starting material.

Example 10: Synthesis of N-(3-(6-chloro-[1,2,4]triazolo[1,5-a]pyrimidin-2-yl)-4-fluorophenyl)pyrrolidine-1-carboxamide (Compound 24)

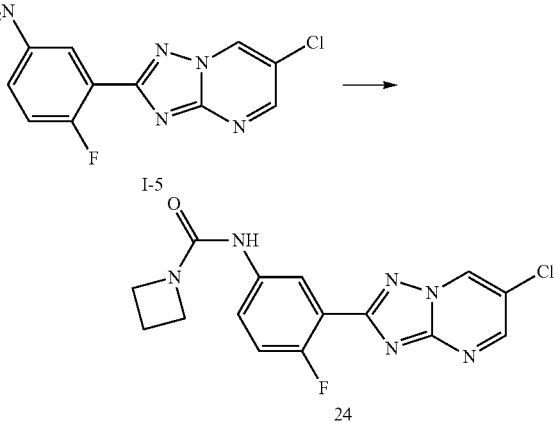

24

Compound 24 was prepared using the protocol described for compound 9 using compound I-5 as intermediate. ¹H NMR (400 MHz, MeOD) 9.50 (d, J=2.4, 1H), 8.91 (d, J=2.4, 1H), 8.22 (dd, J=6.3, 2.8, 1H), 7.67 (dt, J=8.6, 3.6, 1H), 7.21 (dd, J=10.3, 9.0, 1H), 4.11 (t, J=7.6, 4H), 2.33 (p, J=7.6, 2H). M/Z=347.0 (M+1).

Compounds 25, 26 and 27 were prepared following the same protocol using 3-fluoroazetidine, 3,3-difluoroazetidine and (R)-3-methoxypyrrolidine respectively in place of the azetidine.

Example 11: Synthesis of N-(3-(6-(3,6-dihydro-2H-pyran-4-yl)-[1,2,4]triazolo[1,5-a]pyrimidin-2-yl)-4-fluorophenyl)-2,4-dimethyloxazole-5-carboxamide (Compound 28)

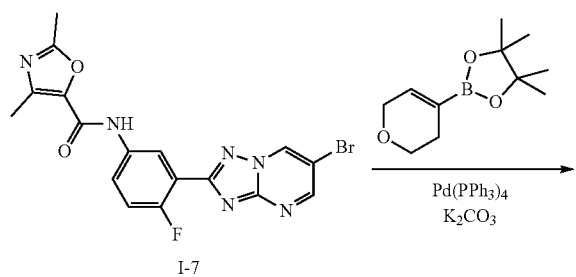

Example 12: Synthesis of 3-(3-(6-(3,6-dihydro-2H-pyran-4-yl)-[1,2,4]triazolo[1,5-a]pyrimidin-2-yl)-4-fluorophenyl)-1,1-dimethylurea (Compound 29)

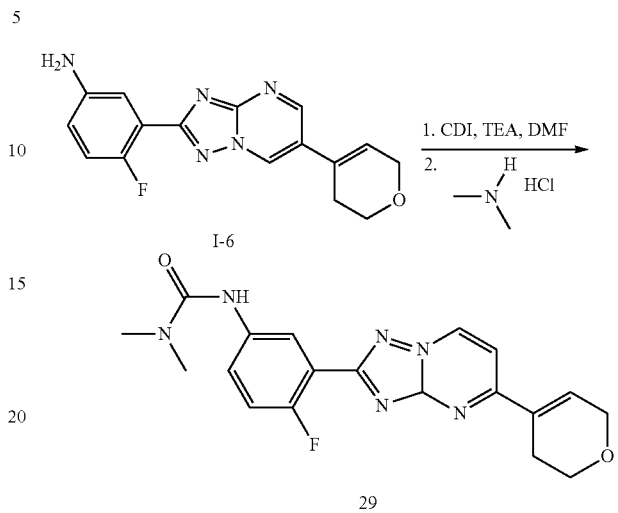

To a solution of CDI (83 mg, 0.52 mmol) and TEA (104 mg, 1.0 mmol) in anhydrous DMF (1 mL) was added compound I-6 (80 mg, 0.26 mmol) portion wise at 0° C. This reaction mixture was stirred at this temperature for an hour, then warmed up to room temperature. Dimethylamine hydrochloride (43 mg, 0.52 mmol) was added an hour later. The result reaction mixture was stirred at room temperature for another hour. The mixture was purified by HPLC to give product 29 (22 mg, 22% yield) as a white solid. ¹H NMR (400 MHz, DMSO) 9.45 (brs, 1H), 9.17 (brs, 1H), 8.39-8.55 (m, 2H), 7.69 (brs, 1H), 7.27 (brs, 1H), 6.64 (brs, 1H), 4.28 (brs, 2H), 3.87 (brs, 2H), 2.95 (brs, 6H), 2.39 (s, 2H). M/Z 383.1 (M+1).

Compounds 30, 31 and 32 were prepared following the same protocol using 3-fluoroazetidine, azetidine and (R)-3-fluoropyrrolidine respectively in place of the dimethylamine.

Example 13: Synthesis of N-(3-(6-cyclopropyl-[1,2,4]triazolo[1,5-a]pyrimidin-2-yl)-4-fluorophenyl)-2,4-dimethyloxazole-5-carboxamide (Compound 34)

To a solution of compound I-7 (150 mg, 0.348 mmol) and 2-(3,6-dihydro-2H-pyran-4-yl)-4,4,5,5-tetramethyl-1,3,2-dioxaborolane (87.7 mg, 0.417 mmol) in DMF (5 mL) and H₂O (0.5 mL) was added tetrakis(triphenylphosphine) palladium (80 mg, 0.0696 mmol) and potassium carbonate (96 mg, 0.696 mmol) at room temperature under N₂. This mixture was heated to 100° C. for 4 hours, cooled down, and extracted with THF (50 mL) and Ethyl Acetate (50 mL). The combined organic layers were dried over sodium sulfate, and concentrated. The residue was purified by HPLC to give compound 28 (30 mg, 22% yield). ¹H NMR (400 MHz, DMSO) 10.41 (s, 1H), 9.48 (d, J=2.01, 1H), 9.20 (d, J=2.51, 1H), 8.73-8.83 (m, 1H), 7.90 (d, J=8.4, 1H), 7.34-7.47 (m, 1H), 6.66 (brs, 1H), 4.29 (d, J=2.51, 2H), 3.87 (t, J=5.52, 2H), 2.56 (brs, 2H), 2.47-2.49 (m, 3H), 2.40 (s, 3H). M/Z 435.1 (M+1).

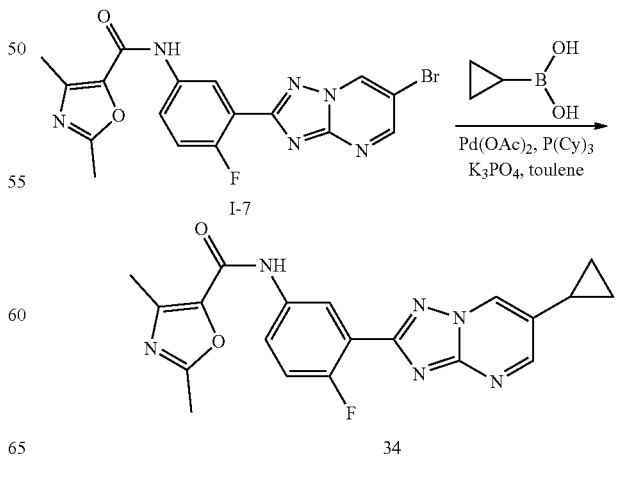

To a solution of intermediate I-7 (300 mg, 0.698 mmol) in toluene (15 mL) and water (1 mL) was added cyclopropylboronic acid (120 mg, 1.4 mmol), Pd(OAc)$_2$ (15.6 mg, 0.0698 mmol), P(Cy)$_3$ (40 mg, 0.14 mmol), and K$_3$PO$_4$ (297 mg, 1.4 mmol) at room temperature. The mixture was heated to 120° C., and stirred for 4 hours. The mixture was allowed to cool down to room temperature; diluted with water (20 mL), and extracted with Ethyl Acetate (50 ml) and THF (50 ml). The combined organic layers were washed with brine (50 mL), dried over Na$_2$SO$_4$, and concentrated. The residue was purified by HPLC to give compound 34 (81.1 mg, 32% yield). $^1$H NMR (400 MHz, DMSO) 10.39 (s, 1H), 9.26 (d, J=2.26, 1H), 8.82 (d, J=2.26, 1H), 8.73 (dd, J=6.78, 2.76, 1H), 7.85-7.93 (m, 1H), 7.34-7.43 (m, 1H), 2.50 (s, 3H), 2.40 (s, 3H), 2.07-2.17 (m, 1H), 1.01-1.11 (m, 2H), 0.86-0.99 (m, 2H). M/Z=393.1 (M+1).

Example 13: Synthesis of N-(4-fluoro-3-(6-(2,2,6,6-tetramethyl-1,2,3,6-tetrahydropyridin-4-yl)-[1,2,4]triazolo[1,5-a]pyrimidin-2-yl)phenyl)-2,4-dimethyloxazole-5-carboxamide (Compound 39)

To a degassed solution of 2,2,6,6-tetramethyl-4-(4,4,5,5-tetramethyl-1,3,2-dioxaborolan-2-yl)-1,2,3,6-tetrahydropyridine (29.4 mg, 0.111 mmol), potassium phosphate (59.2 mg, 0.279 mmol) and compound I-7 (40 mg, 0.093 mmol) in THF:H$_2$O (4:1) was added SilicaCat®DPP-Pd (37 mg, 0.0093 mmol). The vial was sealed and heated in a microwave oven at 150° C. for 45 minutes. The reaction mixture was filtered through Celite, concentrated and purified by HPLC to provide compound 39 as a white solid. $^1$H NMR (400 MHz, DMSO) 10.36 (s, 1H), 9.36 (d, J=2.5, 1H), 9.10 (d, J=2.4, 1H), 8.70 (dd, J=2.7, 6.7, 1H), 7.82 (dd, J=2.5, 8.9, 1H), 7.38-7.29 (m, 1H), 6.43 (s, 1H), 2.50 (s, 3H), 2.33 (s, 3H), 2.20 (s, 2H), 1.15 (s, 6H), 1.08 (s, 6H).

Compounds 35, 36, 37, 38, 40, 41 and 42 were prepared following the same protocol as described above using the appropriate boronic ester.

Example 14: Synthesis of N-(4-fluoro-3-(6-(4-(2-morpholinoethyl)phenyl)-[1,2,4]triazolo[1,5-a]pyrimidin-2-yl)phenyl)-2,4-dimethyloxazole-5-carboxamide (Compound 43)

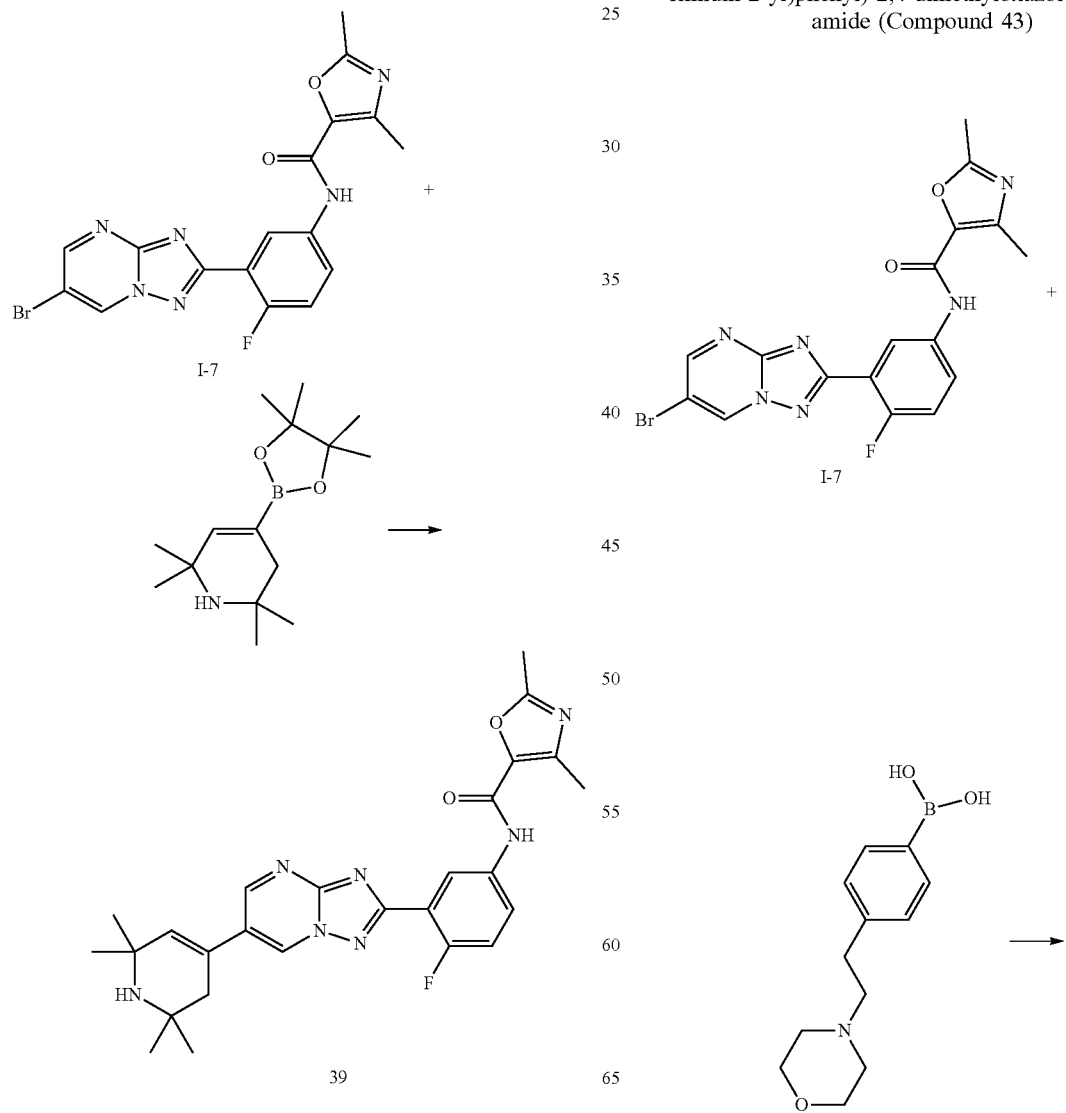

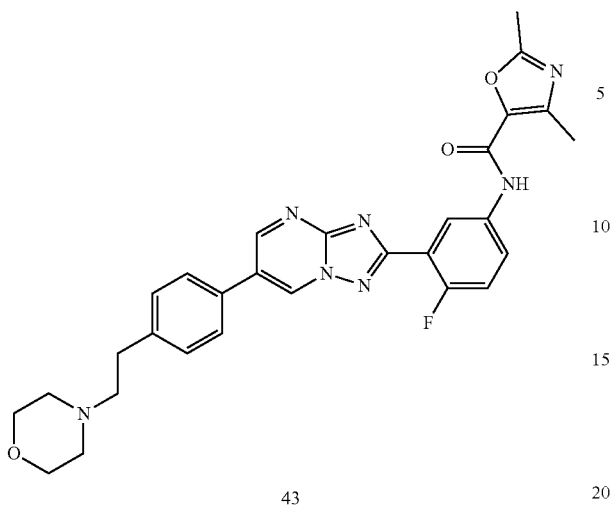

43

In a vial, compound I-7 (100 mg, 0.232 mmol), 4-(2-morpholinoethyl)phenylboronic acid (60.0 mg, 0.255 mmol), sodium carbonate (73.7 mg, 0.696 mmol), and PdCl2(dppf) (9.47 mg, 0.012 mmol) were taken up in dioxane (3 mL) and water (0.200 mL). The resulting suspension was sparged with argon, and subsequently heated to 100° C. The crude material was evaporated on silica gel and purified by flash column chromatography to give the product 43 as an off-white solid. $^1$H NMR (400 MHz, DMSO) 10.43 (s, 1H), 9.84 (d, J=2.4, 1H), 9.31 (d, J=2.4, 1H), 8.81 (dd, J=6.6, 2.7, 1H), 7.92 (ddd, J=9.0, 4.2, 2.8, 1H), 7.86-7.78 (m, 2H), 7.43 (dd, J=8.6, 2.0, 2H), 3.58 (t, J=4.6, 4H), 2.82 (dd, J=8.8, 6.5, 2H), 2.56 (dd, J=9.0, 6.5, 2H), 2.51 (s, 3H), 2.44 (t, J=4.4, 4H), 2.41 (s, 3H). M/Z=542.2 (M+1).

Example 15: Synthesis of N-(4-fluoro-3-(6-(2-fluorophenyl)-[1,2,4]triazolo[1,5-a]pyrimidin-2-yl)phenyl)-2,4-dimethyloxazole-5-carboxamide (Compound 44)

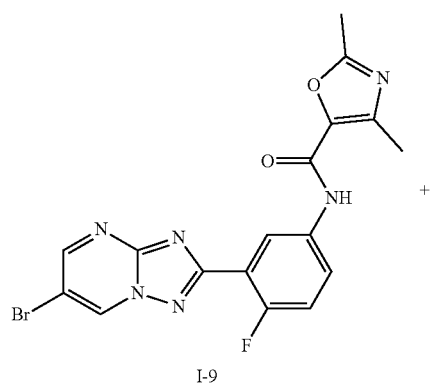

I-9

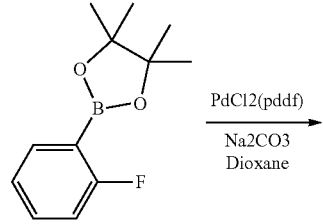

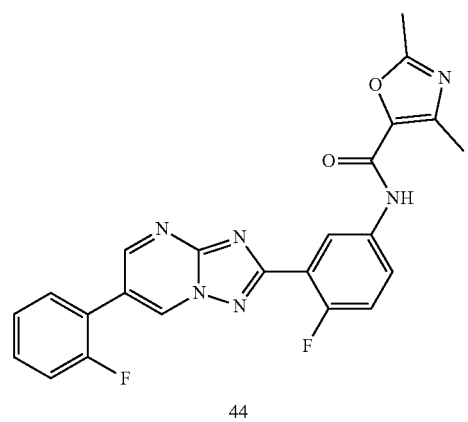

44

To a solution of compound I-7 (20 mg, 0.046 mmol) and 2-(2-fluorophenyl)-4,4,5,5-tetramethyl-1,3,2-dioxaborolane (10.3 mg, 0.046 mmol) in 1,4-dioxane (2 mL) was added 1N sodium carbonate (0.23 ml, 0.23 mmol) and [1,1'-Bis(diphenylphosphino)ferrocene]dichloropalladium(II), complex with dichloromethane (1.9 mg, 0.0023 mmol) at room temperature. The reaction was purged with N$_2$ for 1 min and stirred at 80° C. for 16 hours. The reaction mixture was filtered and was purified by HPLC to give product 44 as a white solid. $^1$H NMR (400 MHz, MeOD) 9.49 (d, J=2.4 Hz, 1H), 9.15 (t, J=2.0 Hz, 1H), 8.54 (dt, J=6.0, 2.9 Hz, 1H), 7.92 (ddd, J=8.9, 4.2, 2.7 Hz, 1H), 7.75 (td, J=7.8, 1.7 Hz, 1H), 7.56 (tdd, J=7.4, 5.0, 1.6 Hz, 1H), 7.46-7.26 (m, 3H), 2.56 (s, 3H), 2.48 (s, 3H). M/Z 447.4 (M+1).

Compounds 44, 45, 46 and 47 were prepared following the same protocol as described above using the appropriate boronic ester.

Example 16: Synthesis of N-(4-fluoro-3-(6-(2-fluorophenyl)-[1,2,4]triazolo[1,5-a]pyrimidin-2-yl)phenyl)-2,4-dimethyloxazole-5-carboxamide (Compound 48)

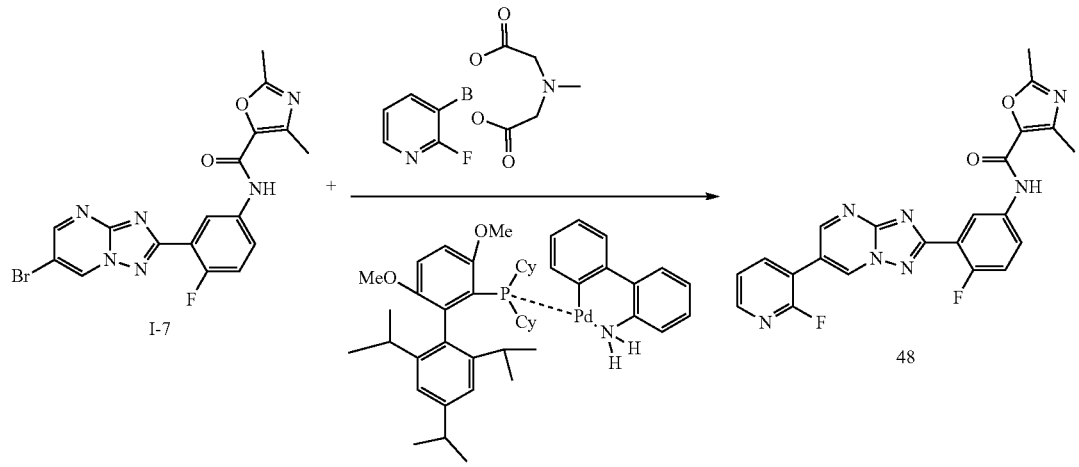

Under ambient atmosphere, to a 15 mL vial equipped with a stir bar was added compound I-7 (0.1 g, 0.23 mmol), 2-fluoropyridin-3-yl MIDA boronate (0.088 g, 0.35 mmol), $K_2CO_3$ (0.16 g, 1.16 mmol) and $Cu(OAc)_2$ (0.023 g, 0.116 mmol) in 8 mL of DMF. The mixture was degased with a stream of nitrogen. Subsequently, Buchwald pre-catalyst (9.8 mg, 0.012 mmol) was added.

The reaction mixture was stirred at 100° C. for 4 h. The mixture was cooled to room temperature and then was transferred to a 60 mL separatory funnel and was diluted with aq NaOH (1.0 M, 10 mL). The mixture was extracted with EtOAc (3×10 mL). The combined organics were dried over $MgSO_4$, filtered and concentrated in vacuo. The crude residue purified by HPLC to provide product 48 as a solid after evaporation of solvent. M/Z=448.0 (M+1). RT=0.83 min, Method 1

Compounds 49 to 58 were prepared following the same protocol as described above using the appropriate boronate. Compound 50 was obtained as a side product of those reactions

Example 17: Synthesis of N-(4-fluoro-3-(6-(3-methylpyridin-2-yl)-[1,2,4]triazolo[1,5-a]pyrimidin-2-yl)phenyl)-2,4-dimethyloxazole-5-carboxamide (Compound 61)

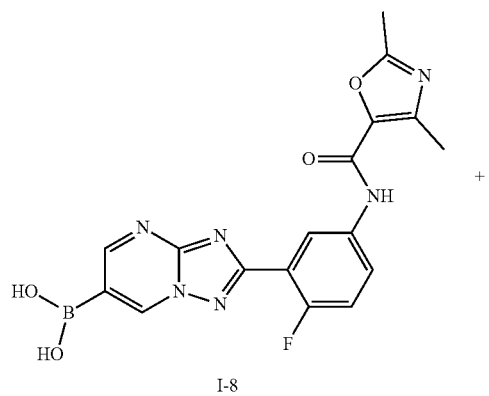

To a solution of compound I-8 (100 mg, 0.21 mmol) and 2-bromo-3-methylpyridine (54 mg, 0.31 mmol) in 1,4-dioxane (10 mL) was added 1N sodium carbonate (1.1 ml, 1.1 mmol) and [1,1'-Bis(diphenylphosphino)ferrocene] dichloropalladium(II), complex with dichloromethane (8.5 mg, 0.011 mmol) at room temperature. The reaction was purged with $N_2$ for 1 minute and stirred at 80° C. for 16 hours. The reaction mixture was diluted with ethyl acetate and washed with saturated $NaHCO_3$ and brine. The organic layer was dried over magnesium sulfate, filtered and reduced to dryness. The crude product was purified by HPLC to afford compound 61 (36 mg) as a white solid. $^1$H NMR (400 MHz, MeOD) 9.57 (d, J=2.4 Hz, 1H), 9.14 (d, J=2.3 Hz, 1H), 8.67 (dd, J=5.1, 1.6, 1H), 8.58 (dd, J=6.4, 2.7, 1H), 8.09 (dd, J=7.8, 1.6 Hz, 1H), 7.91 (ddd, J=8.9, 4.3, 2.8, 1H), 7.63 (dd, J=7.9, 5.1, 1H), 7.34 (dd, J=10.4, 9.0 Hz, 1H), 2.56 (s, 6H), 2.48 (s, 3H). M/Z 444.4 (M+1).

Compounds 59 to 65 were prepared following the same protocol as described above using the appropriate bromide.

Example 18: Synthesis of N-(4-fluoro-3-(6-(trimethylsilyl)-[1,2,4]triazolo[1,5-a]pyrimidin-2-yl)phenyl)-2,4-dimethyloxazole-5-carboxamide (Compound 66)

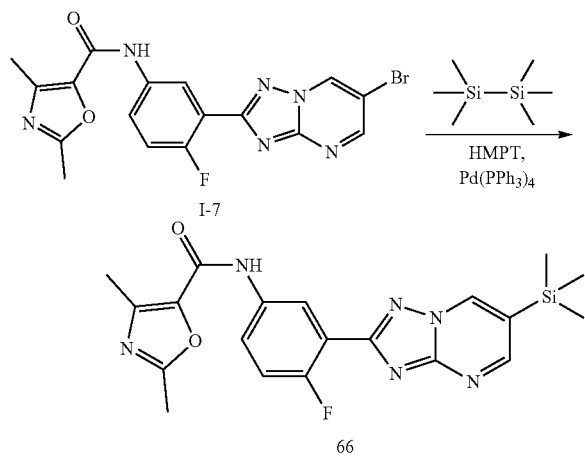

A mixture of I-7 (180 mg, 0.42 mmol), 1,1,1,2,2,2-hexamethyldisilane (180 mg, 1.25 mmol) and tetrakis(triphenylphosphine)palladium (25 mg, 0.021 mmol) in HMPT (1 mL) was stirred at 120° C. under nitrogen for 24 hours. The reaction mixture was cooled down, diluted with water (20 mL) and extracted with 50% Ethyl Acetate/THF (2×20 mL). The combined organic layers were washed with brine (20 ml), dried with sodium sulfate, and concentrated. The residue was purified by HPLC to give product 66 (50 mg, 30% yield) as a white solid. $^1$H NMR (400 MHz, DMSO) 10.39 (s, 1H), 9.42 (s, 1H), 8.95 (s, 1H), 8.77 (dd, J=6.65, 2.63, 1H), 7.83-7.96 (m, 1H), 7.40 (t, J=9.79, 1H), 2.48-2.50 (m, 3H), 2.40 (s, 3H), 0.41 (s, 9H). M/Z=425.1 (M+1).

Example 19: Synthesis of N-(4-fluoro-3-(6-(piperidin-1-yl)-[1,2,4]triazolo[1,5-a]pyrimidin-2-yl)phenyl)-2,4-dimethyloxazole-5-carboxamide (Compound 67)

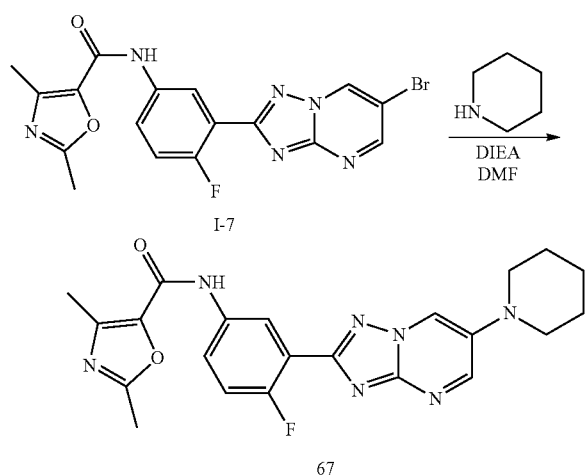

To a solution of compound I-7 (50 mg, 0.116 mmol) in DMF (1 ml), was added DIEA (0.405 mL, 2.31 mmol) and piperidine (1 mL). The mixture was stirred at 80° C. overnight. The solvents were evaporated under reduced pressure and the residue was purified by HPLC. 1H NMR (400 MHz, MeOD) 8.91 (d, J=2.9, 1H), 8.59 (d, J=2.9, 1H), 8.41 (dd, J=2.8, 6.4, 1H), 7.87 (ddd, J=2.8, 4.2, 8.9, 1H), 7.29 (dd, J=9.0, 10.4, 1H), 3.28-3.19 (m, 4H), 2.56 (s, 3H), 2.47 (s, 3H), 1.81 (dt, J=5.7, 11.2, 4H), 1.73-1.60 (m, 2H).

Compounds 67 to 78 were prepared according to the same protocol described above using the appropriate amine. Hydrochloric salts of the amines (20 eq) were used for the preparation of compounds 71, 73, 75 and 77. N-Boc-piperazine was used for the preparation of compound 78 (The Boc protecting group was removed after HPLC by treatment with a solution of TFA/DCM (1:4) for 2 hours at room temperature and subsequent evaporation of solvents).

Example 20: Synthesis of N-(4-fluoro-3-(6-(isopropylamino)-[1,2,4]triazolo[1,5-a]pyrimidin-2-yl)phenyl)-2,4-dimethyloxazole-5-carboxamide (Compound 79)

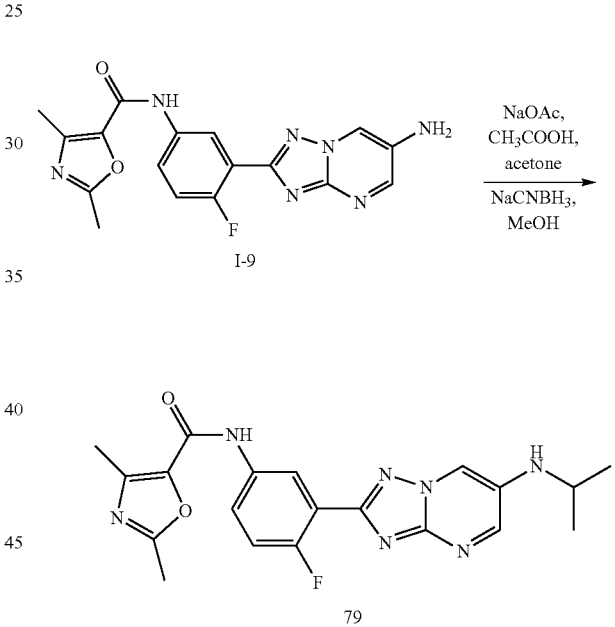

To a solution of compound I-9 (100 mg, 0.273 mmol) in MeOH (5 mL) was added acetone (79 mg, 1.365 mmol), acetic acid (33 mg, 0.546 mmol), and sodium acetate (23 mg, 0.273 mmol) at room temperature. After 30 minutes, the sodium cyanoborohydride (34 mg, 0.546 mmol) was added, and the reaction mixture was stirred at room temperature for 3 days, the mixture was concentrated and purified by HPLC to give product 79 (30 mg, 27% yield). $^1$H NMR (400 MHz, DMSO) 10.18-10.52 (m, 1H), 8.62-8.73 (m, 1H), 8.54 (d, J=2.76, 1H), 8.50 (s, 1H), 7.79-7.90 (m, 1H), 7.29-7.43 (m, 1H), 6.09 (s, 1H), 3.57 (d, J=7.28, 1H), 2.44 (s, 3H), 2.40 (s, 3H), 1.19 (d, J=6.27, 6H). M/Z 410.1 (M+1).

Example 21: Synthesis of Isopropyl (2-(5-(2,4-dimethyloxazole-5-carboxamido)-2-fluorophenyl)-[1,2,4]triazolo[1,5-a]pyrimidin-6-yl)carbamate (Compound 80)

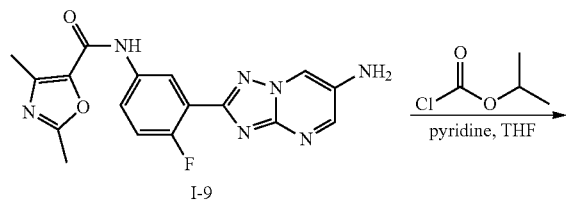

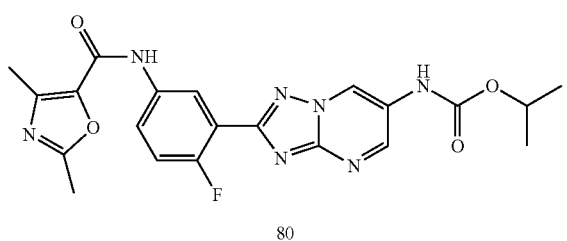

To a solution of compound I-9 (45 mg, 0.273 mmol) in THF (2 mL) was added pyridine (29 mg, 0.368 mmol) at room temperature. After 5 minutes, isopropyl chloroformate (22 mg, 0.184 mmol) was added, and the reaction mixture was stirred at room temperature for 20 minutes until the reaction was complete. The mixture was diluted with water (5 mL) and filtered. The solid was washed with MeOH (2×5 mL) and purified by HPLC to give compound 80 (17 mg, 31% yield). $^1$H NMR (400 MHz, DMSO) 10.66-10.13 (m, 2H), 9.41 (s, 1H), 8.86 (s, 1H), 8.69 (dd, J=6.53, 2.26, 1H), 7.99-7.84-7 (m, 1H), 7.30-7.45 (m, 1H), 5.05-4.90 (m, 1H), 2.50-2.45 (s, 3H), 2.40 (s, 3H), 1.30 (d, J=6.02, 6H). M/Z 454.2 (M+1).

Example 22: Synthesis of N-(4-fluoro-3-(6-(pyridin-2-yl)-[1,2,4]triazolo[1,5-a]pyrimidin-2-yl)phenyl)-N,2,4-trimethyloxazole-5-carboxamide (Compound 81)

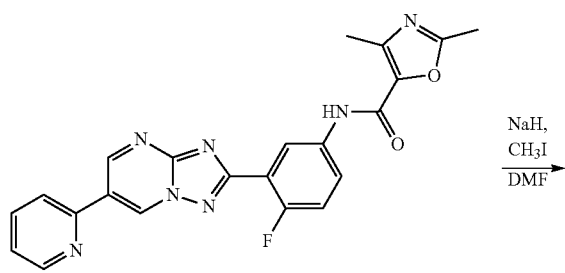

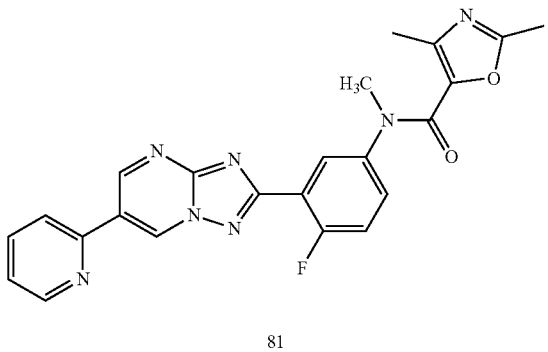

To a solution of compound 18 (200 mg, 0.466 mmol) in DMF (5 mL) was added sodium hydride 60% dispersion in mineral oil (37 mg, 0.932 mmol) and methyl iodide (132 mg, 0.932 mmol). The mixture was stirred overnight at room temperature under a nitrogen atmosphere. The precipitate was filtered out and the crude solid was recrystallized from acetonitrile to give compound 81 (103 mg, 47% yield). $^1$H NMR (400 MHz, DMSO) 10.03 (d, J=2.4, 1H), 9.57 (d, J=2.4, 1H), 8.70 (ddd, J=4.8, 1.8, 0.9, 1H), 8.17 (dt, J=8.1, 1.0, 1H), 8.03 (dd, J=6.5, 2.5, 1H), 7.94 (td, J=7.8, 1.8, 1H), 7.50-7.34 (m, 3H), 3.34 (s, 3H), 2.13 (s, 3H), 2.03 (s, 3H). $^{19}$F NMR (376 MHz, DMSO) −112.83. M/Z 444.2 (M+1).

Example 23: Synthesis of N-(4-fluoro-3-(6-(3-methylpyridin-2-yl)-[1,2,4]triazolo[1,5-a]pyrimidin-2-yl)phenyl)-N,2,4-trimethyloxazole-5-carboxamide (Compound 82)

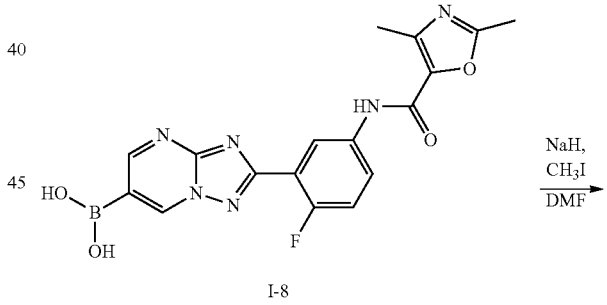

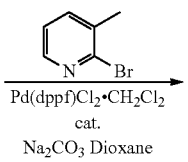

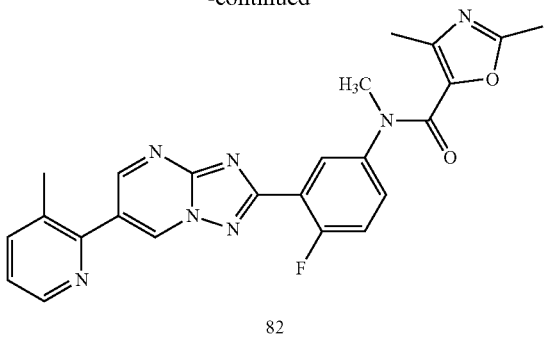

82

Compound 82a was prepared by N-methylation of intermediate I-8 following the same protocol as described for the methylation of compound 18 (Example 22). ¹H NMR (400 MHz, MeOD) 9.31 (m, 1H), 9.08 (t, J=1.7, 1H), 8.09 (ddd, J=6.2, 2.7, 1.4, 1H), 7.51-7.41 (m, 1H), 7.37 (ddd, J=10.0, 9.0, 1.5, 1H), 3.48 (s, 3H), 2.31 (d, J=0.9, 3H), 2.11 (s, 3H). M/Z 411.1 (M+1).

Compound 82 was prepared following the protocol described in Example 17 using compound 82a as starting material. ¹H NMR (400 MHz, MeOD) 9.39 (d, J=2.3, 1H), 9.04 (d, J=2.3, 1H), 8.48 (d, J=4.0, 1H), 8.02 (dd, J=2.8, 6.3, 1H), 7.78 (d, J=7.8, 1H), 7.44-7.32 (m, 2H), 7.32-7.21 (m, 1H), 3.39 (s, 3H), 2.42 (s, 3H), 2.21 (s, 3H), 2.02 (s, 3H). ¹⁹F NMR (376 MHz, MeOD) −113.76. M/Z 458.2 (M+1).

Example 24: Synthesis of N-(3-(6-(3-(difluoromethyl)pyridin-2-yl)-[1,2,4]triazolo[1,5-a]pyrimidin-2-yl)-4-fluorophenyl)-2,4-dimethyloxazole-5-carboxamide (Compound 83)

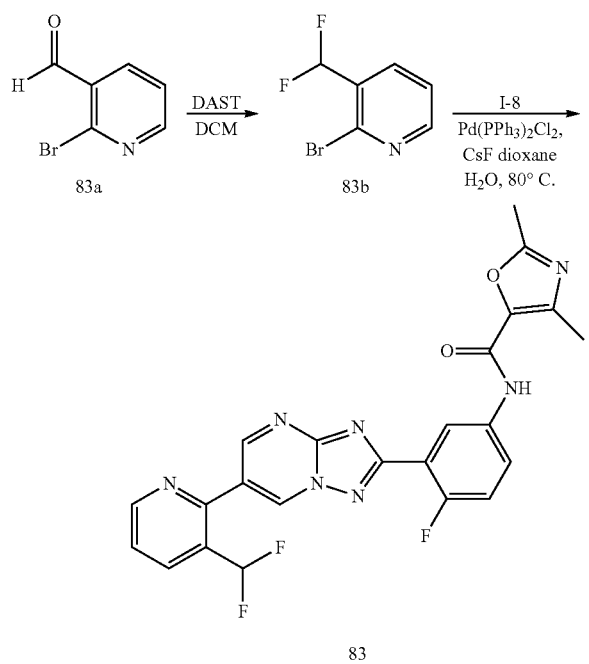

To a solution of 2-bromonicotinaldehyde 83a (25.0 g, 134 mmol) in DCM (200 mL) was added DAST (31.20 g, 201 mmol) dropwise at 0° C. over a period of 30 minutes under N₂, during which the temperature was maintained below 0° C. The reaction mixture was warmed up to room temperature and stirred for 12 hours. LCMS showed the starting material was consumed completely. The reaction was quenched by slow addition of a saturated solution of NaHCO₃ (200 mL), and then extracted with DCM (250 mL×3). The combined organic phase was washed with brine (100 mL×2), dried over anhydrous Na₂SO₄, filtered and concentrated in vacuo. The residue was purified by flash column chromatography (EtOAc:PE=1:50) to give the compound 83b (9.00 g, 33.5% yield) as a yellow oil. ¹H NMR (400 MHz, CDCl₃) 8.52 (d, J=4.52, 1H), 7.99 (d, J=7.53, 1H), 7.44 (dd, J=7.78, 4.77, 1H), 6.75-7.07 (t, 1H). M/Z 232 (M+23).

To a mixture of intermediate I-8 (13.00 g, 27.18 mmol) and compound 83a (11.31 g, 54.36 mmol) in dioxane (100 mL) and water (25 mL) was added CsF (12.30 g, 81.46 mol), Pd(PPh₃)₂Cl₂ (950 mg, 1.36 mmol) in one portion at 10° C. under N₂. The mixture was then heated to 80° C. and stirred for 6 hours. LCMS showed the reaction was complete. The resulting mixture was dissolved in THF (1 L) and filtered through a pad of silica gel. The filter cake was washed with THF (100 mL×4). The combined filtrates were evaporated on silica gel and purified by flash column chromatography (EtOAc:PE=6:1) and recrystallized from MeOH (30 mL) to afford compound 83 (2.1 g, 15% yield) as a yellow solid. ¹H NMR (400 MHz, DMSO) 10.46 (s, 1H), 9.60 (d, J=2.26, 1H), 9.08 (d, J=2.26, 1H), 8.96 (d, J=4.52, 1H), 8.81 (dd, J=6.53, 2.51, 1H), 8.31 (d, J=7.78, 1H), 7.92-8.00 (m, 1H), 7.72-7.80 (dd, 1H), 7.14-7.49 (m, 2H), 2.48-2.50 (m, 3H), 2.41 (s, 3H). ¹⁹F NMR (376 MHz, DMSO) −116.48, −108.99. M/Z 480.0 (M+1).

Example 25: Synthesis of N-(3-(6-(7-azabicyclo [2.2.1]hept-2-en-2-yl)-[1,2,4]triazolo[1,5-a]pyrimidin-2-yl)-4-fluorophenyl)-2,4-dimethyloxazole-5-carboxamide (Compound 84)

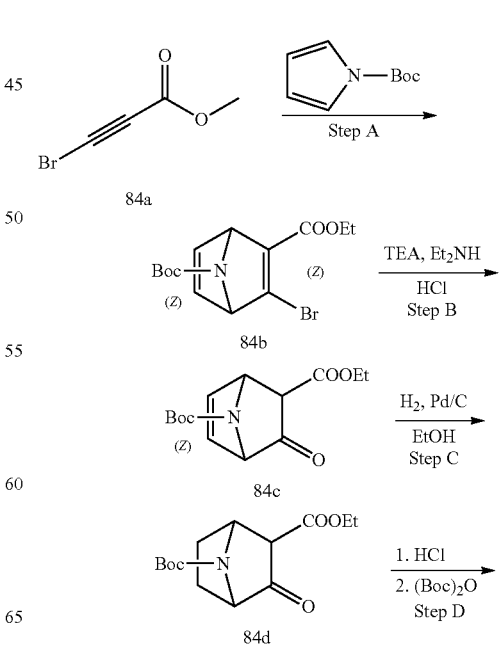

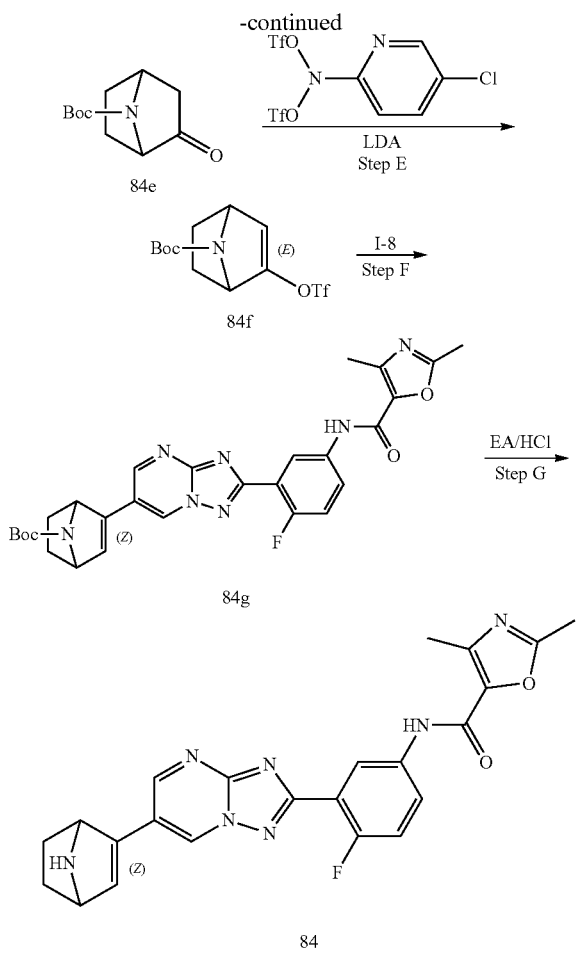

Step A:

A mixture of compound 84a (10 g, 56.5 mmol) and tert-butyl 1H-pyrrole-1-carboxylate (50 mL) was stirred at 110° C. for 12 hours. The reaction mixture was cooled down to room temperature and purified by column chromatography (EtOAc/PE) to give compound 84b (7 g, yield, 37% yield). $^1$H NMR (400 MHz, CDCl$_3$) 7.13 (brs, 2H), 5.48 (brs, 1H), 5.13 (brs, 1H), 4.15-4.37 (m, 2H), 1.41 (s, 9H), 1.32 (t, J=7.15, 3H).

Step B:

To a mixture of compound 84b (5.50 g, 15.98 mmol, 1.00 eq.) and TEA (8.09 g, 79.90 mmol, 5.00 eq.) in CH$_3$CN (50 mL) was added Et$_2$NH (1.65 mL, 17.58 mmol, 1.1 eq.) dropwise at room temperature, under N$_2$. The mixture was stirred at room temperature for 5 hours. HCl (25 mL, 10%) was then added dropwise, and the resulting mixture was stirred at room temperature overnight. The mixture was quenched with water (100 mL) and extracted with EtOAc (100 mL×2). The combined organic phase was washed with saturated brine (200 mL×2), dried with anhydrous Na$_2$SO$_4$, filtered and concentrated under vacuum. The residue was purified by silica gel (PE/EtOAc) to afford compound 84c (3.00 g, 8.53 mmol, 53% yield) as a yellow oil. $^1$H NMR (400 MHz, CDCl$_3$) 6.98 (d, J=4.02, 1H), 6.38 (brs, 1H), 5.12 (brs, 1H), 4.72 (brs, 1H), 4.10-4.30 (m, 2H), 3.38 (d, J=3.2, 1H), 1.47 (s, 9H), 1.30 (t, J=7.15, 3H).

Step C:

To a solution of compound 84c (3.33 g, 10.66 mmol, 1.00 eq.) in EtOH (30 mL) was added Pd/C (10%, 0.3 g) under N$_2$. The suspension was degassed under vacuum and purged with H$_2$ several times. The mixture was stirred under H$_2$ (15 psi) at 25° C. for 16 hours. TLC monitoring (PE:EtOAc=5:1) showed that the starting material was completely consumed. The reaction mixture was filtered and the filtrate was concentrated to give compound 84d (3.00 g, 9.53 mmol, 89.4% yield) as a yellow oil. $^1$H NMR (400 MHz, CDCl$_3$) 4.69-4.91 (m, 1H), 4.28-4.45 (m, 1H), 4.09-4.28 (m, 2H), 2.97 (s, 1H), 2.04 (ddd, J=12.61, 8.60, 3.89, 2H), 1.62-1.93 (m, 2H), 1.39-1.52 (m, 9H), 1.22-1.35 (m, 3H).

Step D:

A mixture of compound 84d (2.80 g, 9.88 mmol, 1.00 eq.) in 10% HCl (5 mL) was stirred at 10° C. for 6 hours, and concentrated under reduced pressure at 60° C. The residue was diluted with DCM (50 mL), and TEA (5 g, 49.4 mmol) and (Boc)$_2$O (3.23 g, 14.82 mmol) were added. The reaction mixture was stirred overnight at room temperature, then quenched with water and extracted with DCM (50 mL×3). The combined organic phase was washed with saturated brine (50 mL×2), dried with anhydrous Na$_2$SO$_4$, filtered and concentrated under vacuum. The residue was purified by silica gel chromatography (PE/EtOAc) to afford compound 84e (1.50 g, 7.10 mmol, 71.8% yield) as a yellow oil. $^1$H NMR (400 MHz, CDCl$_3$) 4.56 (brs, 1H), 4.25 (d, J=4.77, 1H), 2.47 (dd, J=17.44, 5.40, 1H), 1.90-2.09 (m, 3H), 1.53-1.71 (m, 2H), 1.45 (s, 9H).

Step E:

To a mixture of compound 84e (211 mg, 998 μmol, 1.00 eq.) in THF (10 mL) was added LDA (160.48 mg, 1.50 mmol, 1.50 eq.) dropwise at −78° C. under N$_2$. The resulting mixture was stirred at −78° C. for 3 hours, then N-(5-chloropyridin-2-yl)-O-(((trifluoromethyl)sulfonyl)-N-(((trifluoromethyl)sulfonyl)oxy) (784.39 mg, 2.00 mmol, 2.00 eq.) was added in one portion and the mixture was stirred at −78° C. for 3 hours. The reaction mixture was slowly warmed up to room temperature and stirred for 2 days, quenched with a saturated NH$_4$Cl solution (20 mL) and extracted with EtOAc (20 mL×2). The combined organic layers were washed with brine (20 mL), dried and concentrated. The residue was purified by TLC (PE/EtOAc: 10/1) to afford compound 84f (100 mg, 279.8 μmol, 28% yield) as a yellow oil. $^1$H NMR (400 MHz, CDCl$_3$) 5.96 (brs, 1H), 4.76 (brs, 1H), 4.68 (d, J=2.51, 1H), 1.94-2.11 (m, 2H), 1.28-1.55 (m, 11H).

Step F:

A mixture of intermediate I-8 (200 mg, 418.16 μmol, 1.00 eq.), compound 84f (100 mg, 292 μmol, 0.70 eq.) and Pd(PPh$_3$)$_4$ (24.16 mg, 20.91 μmol, 0.05 eq.), DME (10 mL) and saturated Na$_2$CO$_3$ solution (3 mL) was degassed and then heated to 80° C. overnight under N$_2$. LCMS showed that the starting material was completely consumed. The reaction mixture was poured into H$_2$O (20 mL). The mixture was extracted with EtOAc (3×50 mL). The organic phase was washed with saturated brine (20 mL), dried over anhydrous MgSO$_4$, concentrated under vacuum to give a residue, which was purified by column chromatography (100% EtOAc) to afford the compound 84g (60 mg, 21% yield). M/Z 546.3 (M+1).

Step G:

A mixture of compound 84g (6 mg, 1 mmol) in 4N HCl (10 mL) was stirred at room temperature for 6 hours, concentrated under vacuum and purified by HPLC (CH$_3$CN/NH$_4$OH) to give compound 84 (1.5 mg: 30% yield). $^1$H NMR (400 MHz, MeOD) 9.31 (d, J=2.01, 1H), 9.12 (d, J=2.26, 1H), 8.50 (dd, J=6.52, 2.76, 1H), 7.84-7.96 (m, 1H), 7.26-7.38 (m, 1H), 6.96 (d, J=1.76, 1H), 4.72 (d, J=2.76, 1H), 4.36 (brs, 1H), 2.56 (s, 3H), 2.47 (s, 3H), 1.92-2.03 (m, 2H), 1.23-1.45 (m, 3H). M/Z 446.4 (M+1).

Example 26: Synthesis of 2,4-dimethyl-N-(4-(6-phenyl-[1,2,4]triazolo[1,5-a]pyrimidin-2-yl)pyridin-2-yl)oxazole-5-carboxamide (Compound 85)

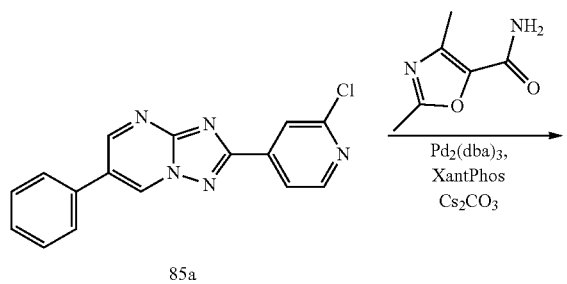

85a

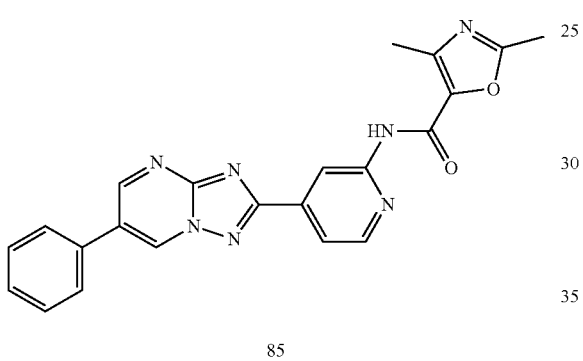

85

Compound 85a was prepared in a similar fashion as intermediate I-1d using 2-chloroisonicotinic acid as starting material. ¹H NMR (400 MHz, DMSO) 9.89 (d, J=2.26, 1H), 9.38 (d, J=2.51, 1H), 8.67 (d, J=5.52, 1H), 8.14-8.22 (m, 2H), 7.93 (d, J=7.28, 2H), 7.58 (m, J=7.78, 3H). M/Z 308 (M+1).

A solution of 2,4-dimethyloxazole-5-carboxamide (52 mg, 0.371 mmol), Pd₂(dba)₃ (17 mg, 0.019 mmol), Xant-Phos (21 mg, 0.037 mmol), Cs₂CO₃ (120 mg, 0.37 mmol) and compound 85a (57 mg, 0.185 mmol) in dioxane (2 mL) was stirred at 150° C. for 30 minutes (MW, 100 W). The mixture was concentrated and the resulting residue was dissolved in THF (50 mL). The organic layer was filtered through a pad of silica gel and the pad was washed with THF (10 mL×2) The combined filtrates were concentrated. The crude product was purified by column chromatography followed by HPLC purification to give the compound 85 (4 mg, 6% yield) as a yellow solid. ¹H NMR (400 MHz, DMSO) 9.91 (d, J=2.26, 1H), 9.37 (d, J=2.26, 1H), 9.04 (s, 1H), 8.60 (d, J=5.02, 1H), 7.90-7.97 (t, 2H), 7.59 (t, J=7.40, 2H), 7.50-7.54 (m, 1H), 7.39 (brs, 1H), 7.29-7.35 (m, 1H), 2.46-2.48 (m, 3H), 2.44 (s, 3H). M/Z 412.2 (M+1).

Example 26: Synthesis of 2,4-dimethyl-N-(4-(6-phenyl-[1,2,4]triazolo[1,5-a]pyrimidin-2-yl)pyridin-2-yl)oxazole-5-carboxamide (Compound 86)

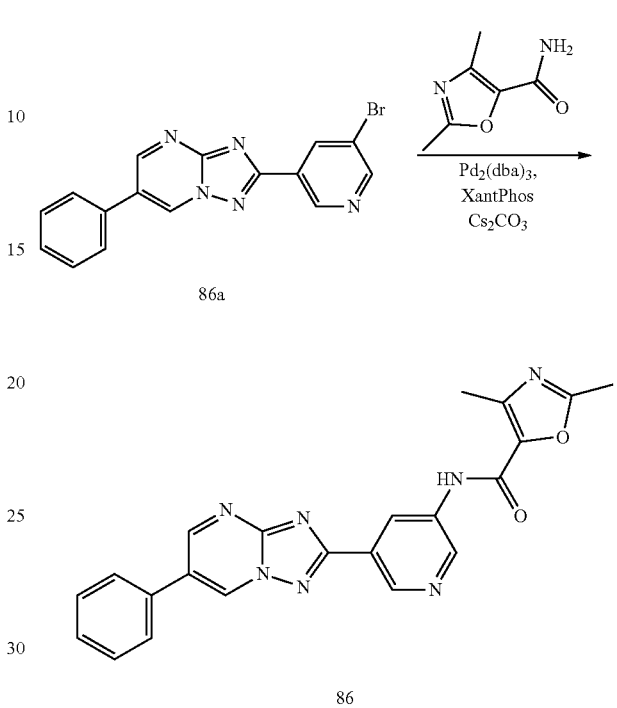

86a

86

Compound 86a was prepared in a similar fashion as intermediate I-1d using 5-bromonicotinic acid as starting material. ¹H NMR (400 MHz, DMSO) 9.36 (d, J=4.52, 1H), 9.24 (s, 2H), 9.15 (s, 1H), 8.42 (s, 1H), 7.83 (d, J=7.53, 2H), 7.43 (t, J=7.53, 2H), 7.26-7.34 (m, 1H).

Compound 86 was prepared from compound 86a following the same protocol as described for compound 85 (Example 25). ¹H NMR (400 MHz, DMSO) 10.66 (brs, 1H), 9.87 (d, J=2.51, 1H), 9.33 (d, J=2.26, 1H), 9.15 (brs, 1H), 9.10 (brs, 1H), 9.03 (brs, 1H), 7.92 (d, J=7.53, 2H), 7.59 (t, J=7.53, 2H), 7.52 (d, J=7.28, 1H), 2.46-2.48 (m, 3H), 2.44 (s, 3H). M/Z 412.2 (M+1).

Example 27: Synthesis of 2,4-dimethyl-N-(2-(6-phenyl-[1,2,4]triazolo[1,5-a]pyrimidin-2-yl)pyridin-4-yl)oxazole-5-carboxamide (Compound 87)

4-chloropicolinic acid

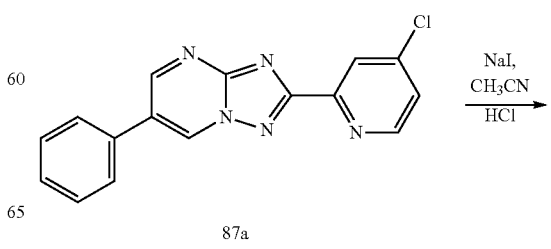

87a

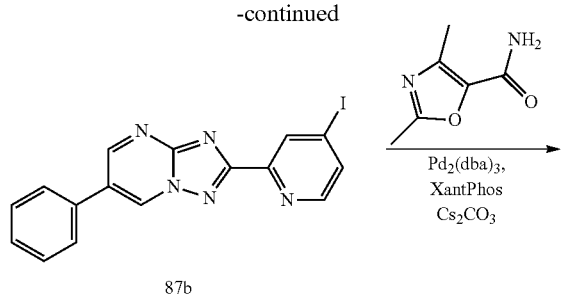

87b

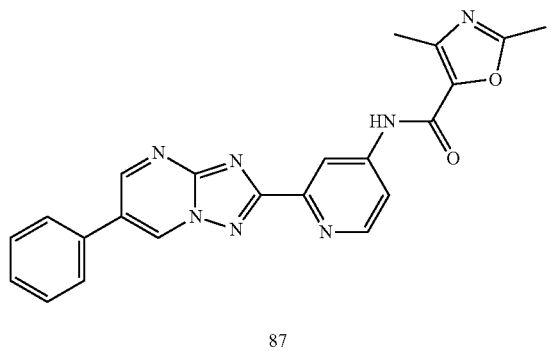

87

Compound 87a was prepared in a similar fashion as intermediate I-1d using 4-chloropicolinic acid as starting material. A mixture of compound 87a (200 mg, 0.65 mmol) was dissolved in THF (15 mL) and concentrated HCl (5 mL) to give a clear solution. This solution was concentrated under vacuum, and to this residue was added CH$_3$CN (10 mL) and NaI (487 mg, 0.525 mmol). The mixture was heated to 100° C. and stirred for 2 hours. The reaction mixture was cooled to room temperature and extracted with EtOAc (50 mL×2). The combined organic layer was washed with a solution of Na$_2$S$_2$O$_3$ (50 mL), brine (20 mL), dried over Na$_2$SO$_4$ and concentrated to give compound 87b (70 mg, 35% yield). M/Z 400.1 (M+1).

Compound 87 was prepared from compound 87b following the same protocol as described for compound 85 (Example 25). $^1$H NMR (400 MHz, DMSO) 10.75 (s, 1H), 9.28 (d, J=2.0, 1H), 9.31 (s, 1H), 8.91 (s, 1H), 8.64 (d, J=5.6, 1H), 7.90-7.92 (m, 3H), 7.50-7.60 (m, 3H), 3.6 (s, 3H), 3.02 (s, 3H). M/Z 412.3 (M+1).

Example 28: Synthesis of N-(2,4-difluoro-3-(6-phenyl-[1,2,4]triazolo[1,5-a]pyrimidin-2-yl)phenyl)-2,4-dimethyloxazole-5-carboxamide (Compound 88)

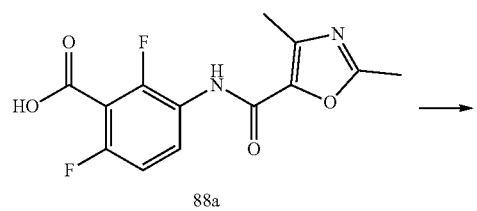

88a

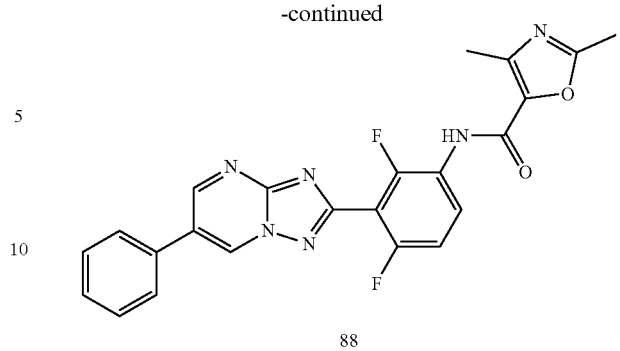

88

Compound 88a was prepared in a similar fashion as intermediate I-9b using 3-amino-2,6-difluorobenzoic acid as starting material. $^1$H NMR (400 MHz, DMSO) 10.08 (s, 1H), 7.53-7.81 (m, 1H), 7.10-7.33 (m, 1H), 2.49 (s, 3H), 2.35 (s, 3H).

Compound 88 was prepared in a similar fashion as intermediate I-1d using compound 88a as starting material. $^1$H NMR (400 MHz, DMSO) 10.14 (s, 1H), 9.89 (d, J=2.51, 1H), 9.36 (d, J=2.51, 1H), 7.93 (d, J=7.28, 2H), 7.76 (t, J=8.66, 1H), 7.48-7.62 (m, 3H), 7.38 (t, J=8.91, 1H), 2.51 (s, 3H), 2.38 (s, 3H). M/Z 447.2 (M+1).

Compound 91 was prepared in the same fashion as compound 88 using 5-amino-2,4-difluorobenzoic acid as starting material. $^1$H NMR (400 MHz, DMSO) 10.16 (s, 1H), 9.88 (s, 1H), 9.33 (s, 1H), 8.50 (t, J=8.0, 1H), 7.92 (d, J=4.0, 2H), 7.51-7.65 (m, 4H), 2.39 (s, 3H), 2.40 (s, 3H). M/Z 447.2 (M+1).

Example 29: Synthesis of 2,4-dimethyl-N-(6-(6-phenyl-[1,2,4]triazolo[1,5-a]pyrimidin-2-yl)pyridin-2-yl)oxazole-5-carboxamide (Compound 89)

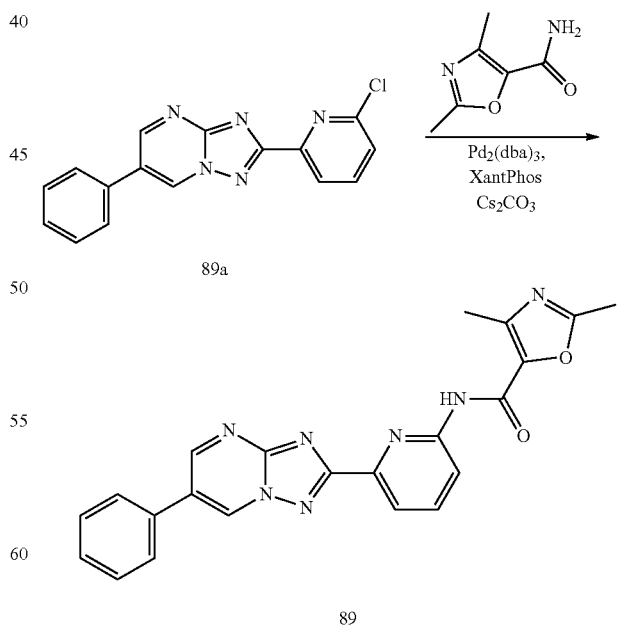

89a

89

Compound 89a was prepared in a similar fashion as intermediate I-1d using 6-chloropicolinic acid as starting material. $^1$H NMR (400 MHz, DMSO) 9.86 (d, J=2.26, 1H), 9.35 (d, J=2.26, 1H), 8.33 (d, J=7.53, 1H), 8.11 (t, J=7.78, 1H), 7.92 (d, J=7.28, 2H), 7.72 (d, J=7.78, 1H), 7.57-7.61 (m, 2H), 7.53 (d, J=7.28, 1H).

Compound 89 was prepared from compound 89a following the same protocol as described for compound 85 (Example 25). ¹H NMR (400 MHz, DMSO) 10.27 (s, 1H), 9.79 (d, J=2.26, 1H), 9.33 (d, J=2.01, 1H), 8.26 (d, J=7.78, 1H), 8.04-8.14 (m, 2H), 7.91 (d, J=7.53, 2H), 7.55-7.64 (m, 2H), 7.53 (d, J=7.28, 1H), 2.41 (s, 3H), 2.34 (brs, 3H). M/Z 412.4 (M+1).

Example 30: Synthesis of N-(4-fluoro-3-(6-(pyrrolidin-1-yl)-[1,2,4]triazolo[1,5-a]pyrimidin-2-yl)phenyl)-2,4-dimethyloxazole-5-carboxamide (Compound 90)

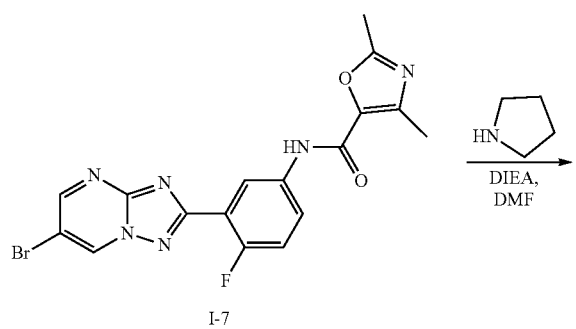

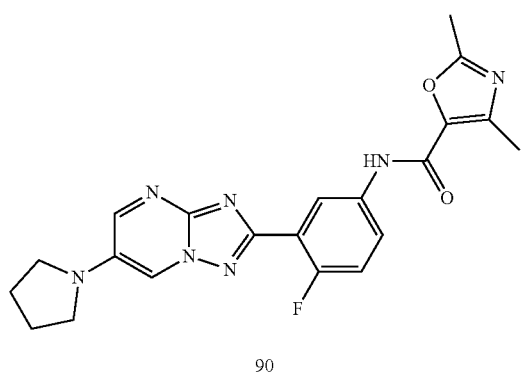

To a solution of intermediate I-7 (6 g, 13.9 mmol) in DMF (100 mL) was added pyrrolidine (5.93 g, 13.9 mmol) and DIEA (21.57 g, 166.8 mmol) at room temperature, the reaction mixture was heated to 90° C. and stirred for 12 hours. The mixture was allowed to cool down to room temperature before water (500 mL) was added, and filtered. The filter cake was purified by silica gel column (DCM: MeOH=10:1 to 8:1), recrystallized with MeOH/DCM (1:1, 50 mL), and dried under vacuum to give compound 90 (1.12 g, 19% yield) as a brown solid. ¹H NMR (400 MHz, DMSO) 8.53 (d, J=2.01, 1H), 8.21 (d, J=3.26, 1H), 8.08-8.16 (m, 1H), 8.03 (d, J=6.02, 2H), 7.18-7.25 (m, 1H), 3.36 (brs, 4H), 2.53 (s, 3H), 2.51 (s, 3H), 2.03-2.26 (m, 4H). M/Z 422.1 (M+1).

Example 31: Synthesis of (R)-3-fluoro-N-(3-(6-phenyl-[1,2,4]triazolo[1,5-a]pyrimidin-2-yl)phenyl)pyrrolidine-1-carboxamide (Compound 92)

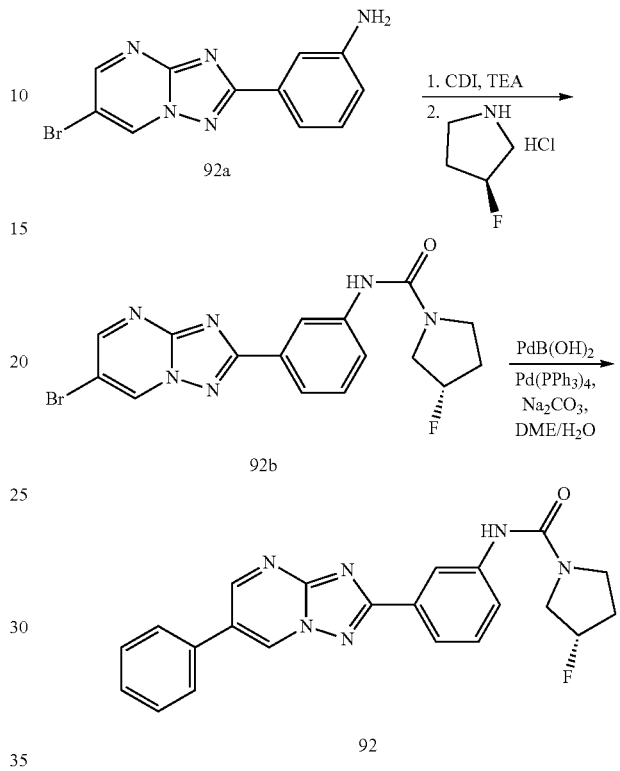

Compound 92a was prepared in the same fashion as intermediate I-1 using 3-nitrobenzoic acid as starting material. ¹H NMR (400 MHz, DMSO) 9.79-9.91 (m, 1H), 8.85-9.02 (m, 1H), 7.43-7.58 (m, 1H), 7.31-7.42 (m, 1H), 7.11-7.26 (m, 1H), 6.63-6.82 (m, 1H), 5.10-5.52 (m, 2H). M/Z 290.0 (M+1).

Compound 92b was prepared using the same protocol as described in Example 7 using (R)-3-fluoropyrrolidine hydrochloride as reagent. M/Z 405.0 (M+1), 407.0 (M+3).

A mixture of compound 92b (120 mg, 0.3 mmol), phenylboronic acid (73 mg, 0.6 mmol), sodium carbonate (72 mg, 0.6 mmol), and tetrakis(triphenylphosphine)palladium (17 mg, 0.0015 mmol) in DME (5 mL), H₂O (0.5 mL) was stirred at 90° C. for 6 hours. The reaction mixture was cooled and quenched with water (10 mL) and extracted with 50% EtOAc/THF (30 mL). The organic layer was dried, concentrated, and the residue was purified by HPLC (NH₄OH/CH₃CN) to give compound 92 (30 mg, 25% yield). ¹H NMR (400 MHz, DMSO) 9.77 (s, 1H), 9.26 (s, 1H), 8.52 (d, J=14.31, 2H), 7.89 (d, J=7.28, 2H), 7.83 (d, J=7.78, 1H), 7.74 (dd, J=8.16, 1.13, 1H), 7.53-7.60 (m, 2H), 7.38-7.53 (m, 2H), 5.26-5.52 (m, 1H), 3.61-3.84 (m, 2H), 3.42-3.60 (m, 2H), 2.00-2.28 (m, 2H). M/Z 403.1 (M+1).

Compound 93 was prepared from intermediate I-5 using the same protocol as described in Example 7 to prepare compound 20.

Example 32: Synthesis of N-(4-fluoro-3-(6-isopropyl-[1,2,4]triazolo[1,5-a]pyrimidin-2-yl)phenyl)-2,4-dimethyloxazole-5-carboxamide (Compound 94)

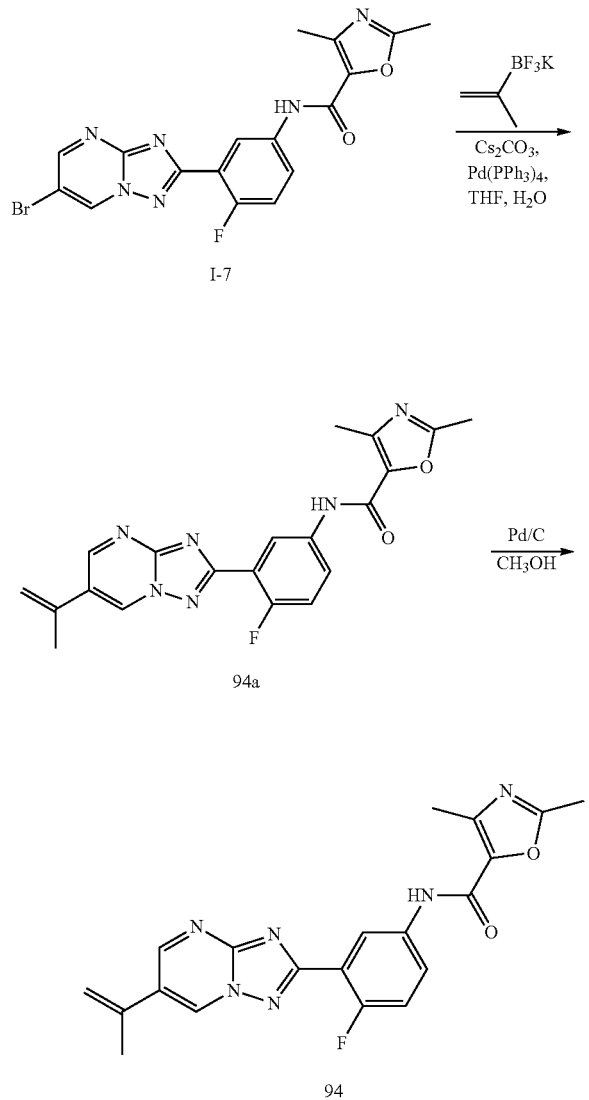

A mixture of intermediate I-7 (400 mg, 0.93 mmol), cesium carbonate (604 mg, 1.86 mmol), potassium trifluoro(prop-1-en-2-yl)borate (310 mg, 1.86 mmol) and Bis(triphenylphosphine) palladium(II) dichloride (32.6 mg, 0.05 mmol) in THF (15 mL) and H$_2$O (1.5 mL) was stirred at 80° C. under N$_2$ for 18 hours. The reaction mixture was cooled down, quenched with brine (20 mL), and extracted with 50% EtOAc/THF (20 mL×3). The combined organic layers were washed, dried and concentrated. The residue was triturated with MeOH (10 mL) to give compound 94a (200 mg, 65% yield) as a gray solid. $^1$H NMR (400 MHz, DMSO) 10.41 (s, 1H), 9.55 (s, 1H), 9.24 (s, 1H), 8.79 (dd, J=6.65, 2.63, 1H), 7.80-8.02 (m, 1H), 7.41 (t, J=9.79, 1H), 5.83 (s, 1H), 5.36 (s, 1H), 2.51 (s, 3H), 2.41 (s, 3H), 2.22 (s, 3H). M/Z 392.1 (M+1).

A mixture of compound 94a (100 mg, 0.25 mmol) and Pd/C (10 mg) in MeOH (10 mL) was stirred under an atmosphere of H$_2$ for 6 hours. The reaction mixture was filtered, and the filtrate was concentrated. The residue was purified by HPLC (basic condition) to give compound 94 (30 mg, 30% yield) as a white solid. $^1$H NMR (400 MHz, DMSO) 10.41 (s, 1H), 9.38 (s, 1H), 8.96 (s, 1H), 8.75 (dd, J=6.65, 2.64, 1H), 7.83-8.00 (m, 1H), 7.40 (t, J=9.79, 1H), 3.20-3.10 (m, 1H), 2.51 (s, 3H), 2.41 (s, 3H), 1.35 (d, J=6.78, 6H). M/Z 395.1 (M+1).

Example 33: Synthesis of 2,4-dimethyl-N-(3-(6-phenyl-[1,2,4]triazolo[1,5-a]pyrimidin-2-yl)phenyl)oxazole-5-carboxamide (Compound 95)

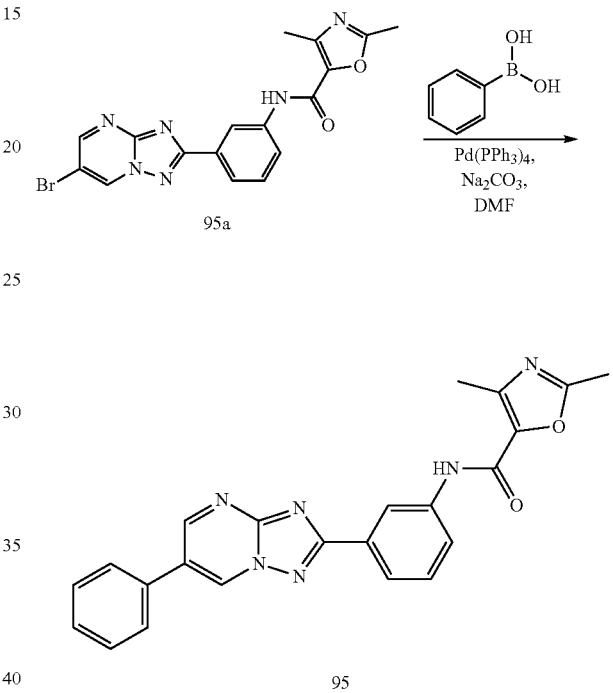

Compound 95a was prepared from compound 92a following the protocol described for the preparation of intermediate I-7.

To a solution of compound 95a (150 mg, 0.237 mol) in DMF (3 mL) was added sodium carbonate (77 mg, 0.711 mmol) and phenylboronic acid (53 mg, 0.43 mol), the reaction mixture was stirred at room temperature for 5 min under N$_2$ atmosphere, then Pd(PPh$_3$)$_4$ (21 mg, 0.018 mmol) was added and the mixture was stirred at 110° C. for 5 hours. The mixture was filtered through a celite pad and the filtrate was concentrated in vacuo. The resultant residue was triturated with EtOAc, and the mixture was concentrated and purified by HPLC to give compound 95 (50 mg, 34% yield). $^1$H NMR (400 MHz, DMSO) 10.27-10.49 (m, 1H), 9.78 (s, 1H), 9.17-9.39 (m, 1H), 8.76-8.96 (m, 1H), 7.90 (d, J=7.03, 4H), 7.40-7.70 (m, 4H), 2.51 (s, 3H), 2.41 (s, 3H). M/Z 411.0 (M+1).

Compound 96 was prepared following the protocol described above using (3,6-dihydro-2H-pyran-4-yl)boronic acid as reagent.

Compound 97 was prepared from intermediate I-6 using the protocol described in Example 12 using 3,3-difluoroazetidine hydrochloride as reagent.

The exemplified compounds of the invention and their physical characterization data are identified in Table 4.

TABLE 4

Exemplified Compounds of the Invention

| NO | Structure | ¹HNMR and/or mass and/or (retention time (mins) |
|---|---|---|
| 1 | 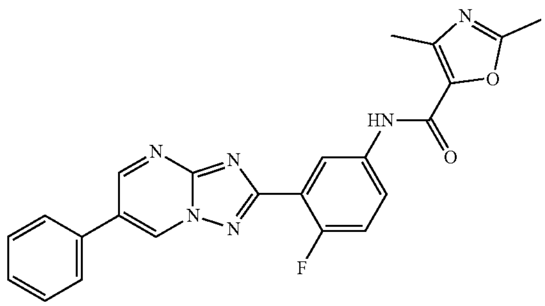 [SMILES: Cc1nc(C)c(C(=O)Nc2ccc(F)c(-c3nc4ncc(-c5ccccc5)cn4n3)c2)o1] | ¹H NMR (400 MHz, MeOD) 9.49 (d, J = 2.4, 1H), 9.22 (d, J = 2.4, 1H), 8.51 (dd, J = 6.4, 2.8, 1H), 7.90 (ddd, J = 8.9, 4.2, 2.8, 1H), 7.86-7.76 (m, 2H), 7.63-7.55 (m, 2H), 7.54-7.45 (m, 1H), 7.32 (dd, J = 10.4, 9.0, 1H), 2.56 (s, 3H), 2.47 (s, 3H). M/Z = 429.2 (M + 1). RT = 1.83 min, Method 1 |
| 2 | 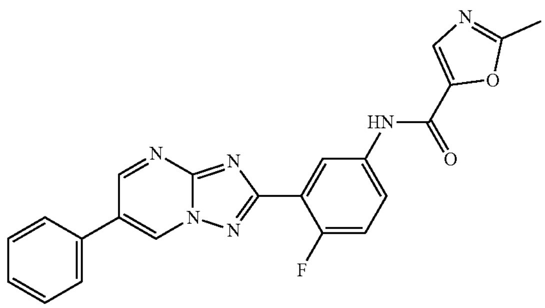 | ¹H NMR (400 MHz, MeOD) 9.52 (d, J = 2.4, 1H), 9.25 (d, J = 2.4, 1H), 8.54 (dd, J = 6.3, 2.8, 1H), 7.96 (ddd, J = 8.8, 7.6, 4.7, 1H), 7.88-7.75 (m, 3H), 7.65-7.45 (m, 3H), 7.41-7.22 (m, 1H), 2.61 (s, 3H). M/Z = 415.2 (M + 1). RT = 1.65 min, Method 1 |
| 3 | 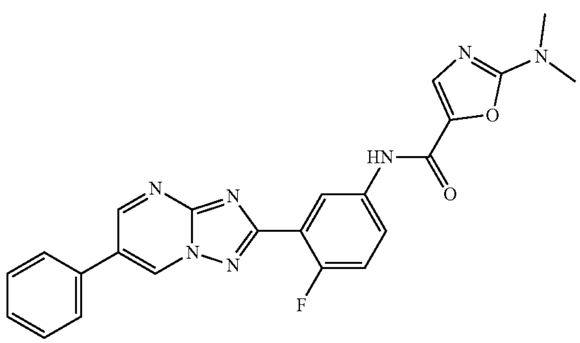 [SMILES: CN(C)c1ncc(C(=O)Nc2ccc(F)c(-c3nc4ncc(-c5ccccc5)cn4n3)c2)o1] | ¹H NMR (400 MHz, MeOD) 9.49 (d, J = 2.3, 1H), 9.23 (d, J = 2.4, 1H), 8.47 (dd, J = 6.2, 2.7, 1H), 7.92 (ddd, J = 8.9, 4.1, 2.8, 1H), 7.82 (dd, J = 7.2, 1.7, 2H), 7.75 (s, 1H), 7.65-7.44 (m, 3H), 7.32 (dd, J = 10.4, 9.0, 1H), 3.23 (s, 6H). M/Z = 444.0 (M + 1). RT = 0.93 min, Method 1 |
| 4 | 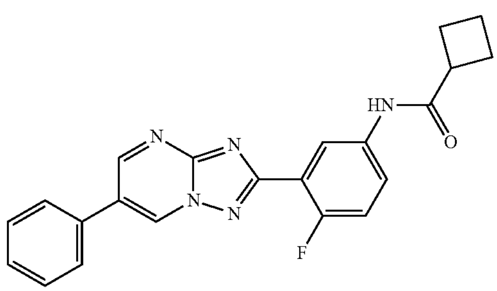 [SMILES: O=C(Nc1ccc(F)c(-c2nc3ncc(-c4ccccc4)cn3n2)c1)C1CCC1] | ¹H NMR (400 MHz, MeOD) 9.50 (d, J = 2.4, 1H), 9.23 (d, J = 2.5, 1H), 8.38 (dd, J = 6.5, 2.8, 1H), 7.96-7.72 (m, 3H), 7.64-7.45 (m, 3H), 7.27 (dd, J = 10.4, 8.9, 1H), 2.39 (dq, J = 11.5, 9.2, 2H), 2.29-2.17 (m, 2H), 2.08 (dq, J = 11.3, 8.8, 1H), 1.98-1.84 (m, 1H). M/Z = 388.1 (M + 1). RT = 1.08 min Method 1 |
| 5 | 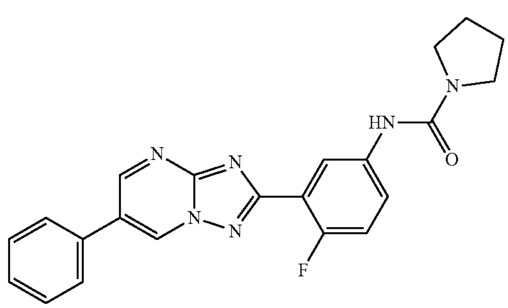 [SMILES: O=C(Nc1ccc(F)c(-c2nc3ncc(-c4ccccc4)cn3n2)c1)N1CCCC1] | ¹H NMR (400 MHz, DMSO) 9.78 (d, J = 2.5, 1H), 9.23 (d, J = 2.5, 1H), 8.40 (dd, J = 2.8, 6.6, 1H), 8.35 (s, 1H), 7.88-7.80 (m, 2H), 7.75-7.65 (m, 1H), 7.50 (t, J = 7.4, 2H), 7.43 (t, J = 7.3, 1H), 7.22 (dd, J = 9.0, 10.6, 1H), 3.33 (t, J = 6.7, 4H), 1.80 (t, J = 6.6, 4H). M/Z = 403.1 (M + 1). RT = 2.95 min, Method 2 |

TABLE 4-continued

Exemplified Compounds of the Invention

| NO | Structure | ¹HNMR and/or mass and/or (retention time (mins) |
|---|---|---|
| 6 | 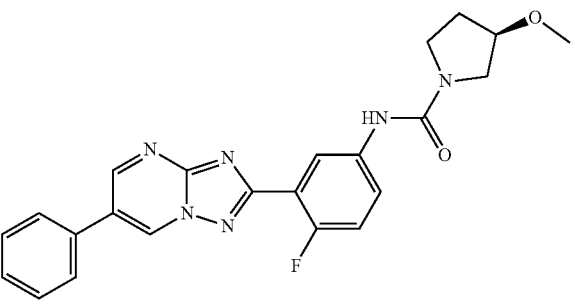 [SMILES: CO[C@@H]1CCN(C(=O)Nc2ccc(F)c(-c3nc4ncc(-c5ccccc5)cn4n3)c2)C1] | ¹H NMR (400 MHz, MeOD) 9.49 (d, J = 2.4, 1H), 9.23 (d, J = 2.4, 1H), 8.23 (dd, J = 6.3, 2.8, 1H), 7.82 (dd, J = 7.3, 1.9, 2H), 7.67 (ddd, J = 9.1, 4.2, 2.8, 1H), 7.62-7.46 (m, 3H), 7.24 (dd, J = 10.4, 9.0, 1H), 4.08 (dq, J = 4.8, 2.5, 1H), 3.65-3.47 (m, 4H), 3.38 (s, 3H), 2.20-2.00 (m, 2H). M/Z = 433.0 (M + 1). RT = 0.89 min, Method 1 |
| 7 | 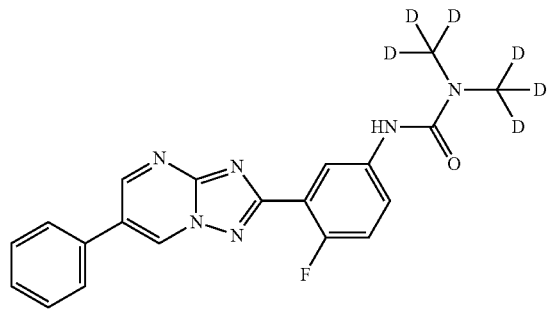 [SMILES: [2H]C([2H])([2H])N(C(=O)Nc1ccc(F)c(-c2nc3ncc(-c4ccccc4)cn3n2)c1)C([2H])([2H])[2H]] | ¹H NMR (400 MHz, DMSO) 9.86 (d, J = 2.4, 1H), 9.31 (d, J = 2.5, 1H), 8.58 (s, 1H), 8.44 (dd, J = 6.7, 2.8, 1H), 8.32-8.23 (m, 1H), 7.95-7.87 (m, 2H), 7.73 (ddd, J = 9.0, 4.2, 2.8, 2H), 7.64-7.18 (m, 2H), M/Z = 383.1 (M + 1). RT = 0.87 min, Method 1 |
| 8 | 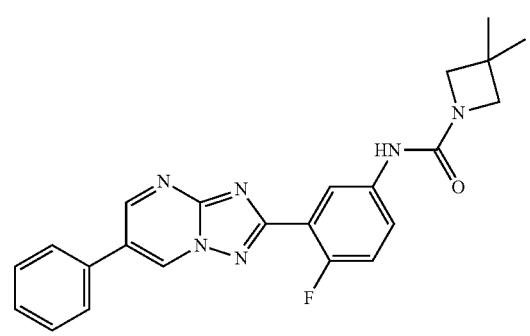 [SMILES: CC1(C)CN(C(=O)Nc2ccc(F)c(-c3nc4ncc(-c5ccccc5)cn4n3)c2)C1] | ¹H NMR (400 MHz, MeOD) 9.48 (t, J = 1.8, 1H), 9.32-9.03 (m, 1H), 8.23 (dd, J = 6.3, 2.8, 1H), 7.81 (dd, J = 7.8, 1.6, 2H), 7.69 (ddd, J = 9.1, 4.2, 2.9, 1H), 7.61-7.45 (m, 3H), 7.22 (dd, J = 10.4, 9.0, 1H), 3.78 (s, 4H), 1.33 (s, 6H). M/Z = 417.1 (M + 1). RT = 0.95 min, Method 1 |
| 9 | 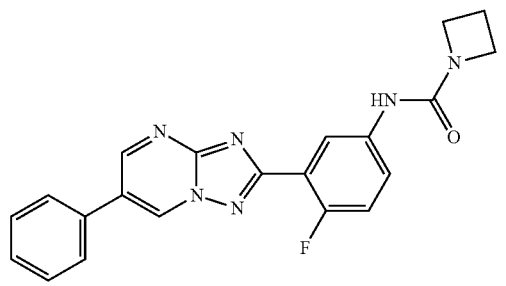 [SMILES: O=C(Nc1ccc(F)c(-c2nc3ncc(-c4ccccc4)cn3n2)c1)N1CCC1] | ¹H NMR (400 MHz, MeOD) 9.47 (d, J = 2.3, 1H), 9.21 (d, J = 2.4, 1H), 8.22 (dd, J = 6.4, 2.8, 1H), 7.85-7.76 (m, 2H), 7.73-7.62 (m, 1H), 7.61-7.46 (m, 3H), 7.26-7.11 (m, 1H), 4.11 (q, J = 8.8, 8.2, 4H), 2.33 (p, J = 7.6, 2H). M/Z = 389.0 (M + 1). RT = 2.88 min, Method 2 |

TABLE 4-continued
Exemplified Compounds of the Invention
| NO | Structure | ¹HNMR and/or mass and/or (retention time (mins)) |
|---|---|---|
| 10 | 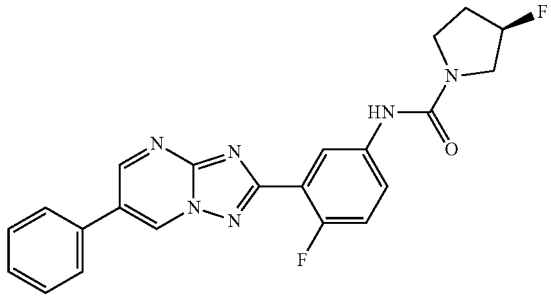 [SMILES: O=C(Nc1ccc(F)c(-c2nc3ncc(-c4ccccc4)cn3n2)c1)N1CC[C@@H](F)C1] | M/Z = 421.0 (M + 1). RT = 0.90 min, Method 1 |
| 11 | 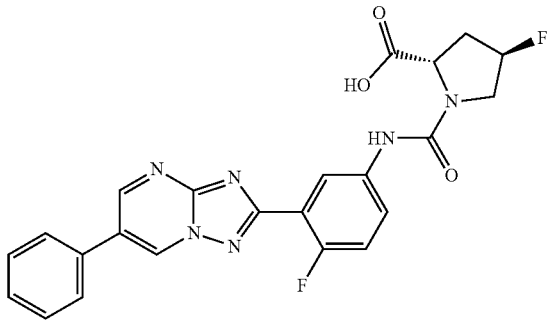 [SMILES: O=C(O)[C@@H]1C[C@@H](F)CN1C(=O)Nc1ccc(F)c(-c2nc3ncc(-c4ccccc4)cn3n2)c1] | M/Z = 465.3 (M + 1). RT = 2.81 min, Method 2 |
| 12 | 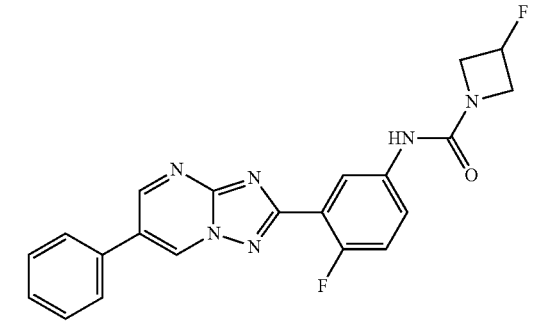 [SMILES: O=C(Nc1ccc(F)c(-c2nc3ncc(-c4ccccc4)cn3n2)c1)N1CC(F)C1] | M/Z = 407.2 (M + 1). RT = 2.89 min, Method 2 |
| 13 | 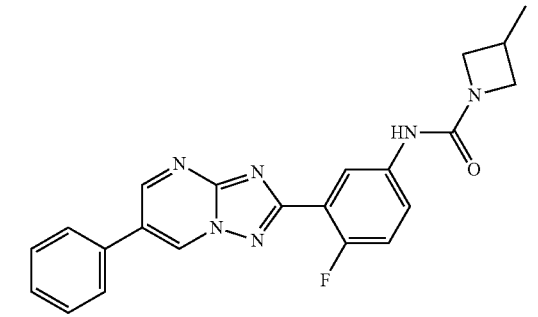 [SMILES: CC1CN(C(=O)Nc2ccc(F)c(-c3nc4ncc(-c5ccccc5)cn4n3)c2)C1] | ¹H NMR (400 MHz, MeOD) 9.48 (d, J = 2.4, 1H), 9.22 (d, J = 2.5, 1H), 8.22 (dd, J = 6.4, 2.8, 1H), 7.88-7.76 (m, 2H), 7.68 (ddd, J = 8.9, 4.2, 2.8, 1H), 7.61-7.44 (m, 3H), 7.22 (dd, J = 10.4, 9.0, 1H), 4.21 (t, J = 8.2, 2H), 3.65 (dd, J = 8.2, 5.4, 2H), 2.85-2.62 (m, 1H), 1.30 (d, J = 6.9, 3H). M/Z = 403.2 (M + 1). RT = 1.72 min, Method 1 |

TABLE 4-continued

Exemplified Compounds of the Invention

| NO | Structure | ¹HNMR and/or mass and/or (retention time (mins) |
|---|---|---|
| 14 | 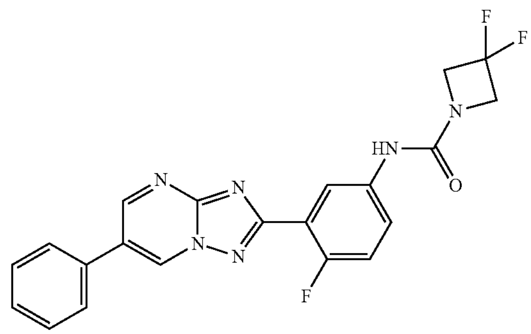 [SMILES: O=C(Nc1ccc(F)c(-c2nc3ncc(-c4ccccc4)cn3n2)c1)N1CC(F)(F)C1] | M/Z = 425.0 (M + 1). RT = 3.04 min, Method 2 |
| 15 | 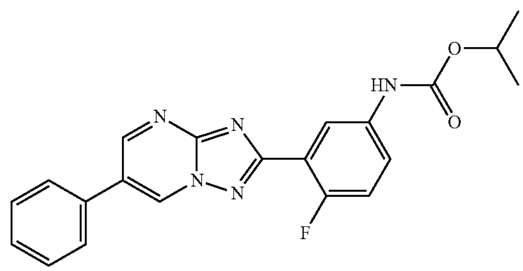 [SMILES: CC(C)OC(=O)Nc1ccc(F)c(-c2nc3ncc(-c4ccccc4)cn3n2)c1] | ¹H NMR (400 MHz, MeOD) 9.50 (d, J = 2.4, 1H), 9.23 (d, J = 2.4, 1H), 8.25 (dd, J = 6.2, 2.8, 1H), 7.82 (dd, J = 7.3, 1.8, 2H), 7.72-7.64 (m, 1H), 7.64-7.46 (m, 3H), 7.25 (dd, J = 10.4, 8.9, 1H), 5.04-4.96 (m, 1H), 1.33 (d, J = 6.2, 6H). M/Z = 392.1 (M + 1). RT = 3.25 min, Method 2 |
| 16 | 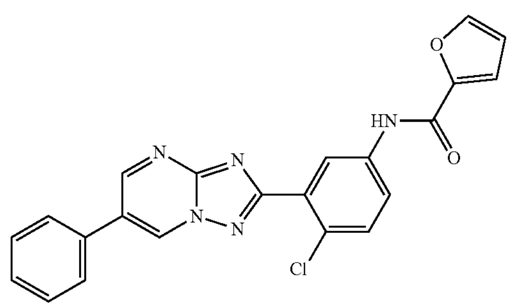 [SMILES: O=C(Nc1ccc(Cl)c(-c2nc3ncc(-c4ccccc4)cn3n2)c1)c1ccco1] | ¹H NMR (400 MHz, DMSO) 10.48 (s, 1H), 9.81 (d, J = 2.4, 1H), 9.27 (d, J = 2.4, 1H), 8.54 (d, J = 2.7, 1H), 7.96-7.89 (m, 2H), 7.89-7.81 (m, 2H), 7.56 (t, J = 10.4, 1H), 7.53 (s, 2H), 7.46-7.37 (m, 1H), 7.34 (d, J = 3.5, 1H), 6.66 (dd, J = 1.7, 3.5, 1H). M/Z = 416.1 (M + 1). RT = 3.12 min, Method 2 |
| 17 | 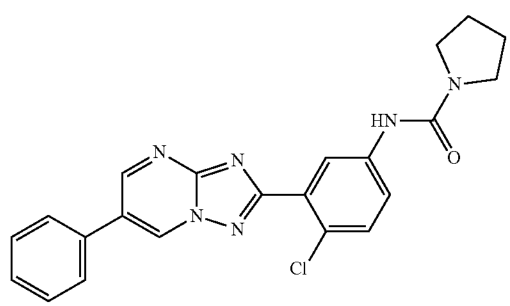 [SMILES: O=C(Nc1ccc(Cl)c(-c2nc3ncc(-c4ccccc4)cn3n2)c1)N1CCCC1] | ¹H NMR (400 MHz, DMSO) 9.78 (d, J = 2.5, 1H), 9.25 (d, J = 2.4, 1H), 8.45 (s, 1H), 8.29 (d, J = 2.7, 1H), 7.90-7.79 (m, 2H), 7.72 (dd, J = 2.7, 8.8, 1H), 7.56-7.46 (m, 2H), 7.47-7.37 (m, 2H), 3.32 (t, J = 6.7, 4H), 1.79 (t, J = 6.6, 4H). M/Z = 419.1 (M + 1). RT = 3.06 min, Method 2 |
| 18 | 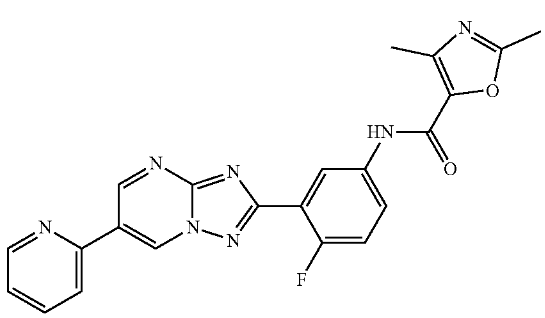 [SMILES: Cc1nc(C)c(C(=O)Nc2ccc(F)c(-c3nc4ncc(-c5ccccn5)cn4n3)c2)o1] | ¹H NMR (400 MHz, MeOD) 9.84 (d, J = 2.4, 1H), 9.61 (d, J = 2.3, 1H), 8.76 (dt, J = 4.8, 1.4, 1H), 8.54 (dd, J = 6.4, 2.7, 1H), 8.12 (dt, J = 8.0, 1.1, 1H), 8.00 (td, J = 7.8, 1.8, 1H), 7.93 (ddd, J = 8.9, 4.1, 2.7, 1H), 7.49 (ddd, J = 7.5, 4.9, 1.0, 1H), 7.34 (dd, J = 10.4, 9.0, 1H), 2.57 (s, 3H), 2.48 (s, 3H). M/Z = 430.0 (M + 1). RT = 0.83 min, Method 1 |

TABLE 4-continued

Exemplified Compounds of the Invention

| NO | Structure | ¹HNMR and/or mass and/or (retention time (mins) |
|----|-----------|------------------------------------------------|
| 19 | 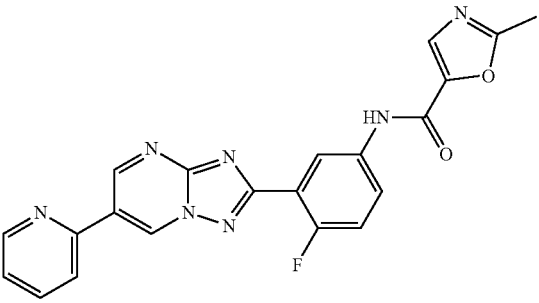 [SMILES: Cc1ncc(C(=O)Nc2ccc(F)c(-c3nc4ncc(-c5ccccn5)cn4n3)c2)o1] | ¹H NMR (400 MHz, DMSO) 10.58 (s, 1H), 10.09 (s, 1H), 8.77 (d, J = 4.4, 2H), 8.68 (m, 1H), 8.24 (d, J = 8, 1H), 7.9-8.01 (m, 2H), 7.9 (s, 1H), 7.45-7.5 (m, 2H), 2.55 (s, 3H). M/Z = 416.3 (M + 1). RT = 0.78 min, Method 1 |
| 20 | 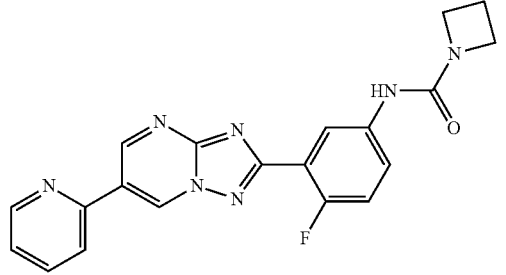 [SMILES: O=C(Nc1ccc(F)c(-c2nc3ncc(-c4ccccn4)cn3n2)c1)N1CCC1] | ¹H NMR (400 MHz, DMSO) 10.08 (s, 1H), 9.64 (s, 1H), 8.78 (d, J = 4.27, 1H), 8.67 (s, 1 H), 8.44 (dd, J = 6.53, 2.76, 1H), 8.24 (d, J = 8.03, 1H), 8.02 (td, J = 7.78, 1.51, 1H), 7.75-7.83 (m, 1H), 7.51 (dd, J = 7.15, 5.14, 1H), 7.28-7.33 (m, 1H), 3.99 (t, J = 7.53, 4H), 2.17-2.25 (m, 2H). M/Z = 390.0 (M + 1). RT = 0.71 min, Method 1 |
| 21 | 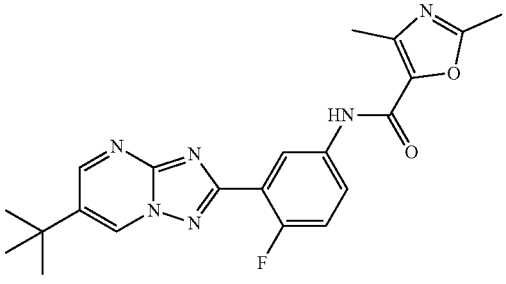 | ¹H NMR (400MHz, DMSO) 10.40 (s, 1H), 9.34 (d, J = 2.51, 1H), 9.13 (d, J = 2.51, 1H), 8.76 (dd, J = 6.53, 2.76, 1H), 7.87-7.91 (m, 1H), 7.37-7.42 (m, 1H), 2.51 (s, 3H), 2.41 (s, 3H), 1.43 (s, 9H). M/Z = 409.1 (M + 1). RT = 3.39 min, Method 2 |
| 22 | 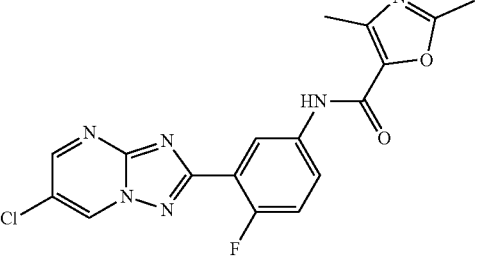 | ¹H NMR (400 MHz, DMSO) 10.41 (s, 1H), 9.92 (s, 1H), 9.00 (s, 1H), 8.74 (dd, J = 6.53, 2.76, 1H), 7.88-7.97 (m, 1H), 7.40 (t, J = 9.79, 1H), 2.5 (s, 3H), 2.39 (s, 3H). M/Z = 386.9 (M + 1). RT = 0.80 min, Method 1 |
| 23 | 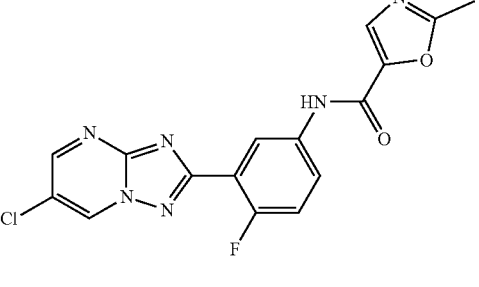 | ¹H NMR (400 MHz, DMSO) 10.58 (s, 1H), 9.94 (s, 1H), 9.00 (s, 1H), 8.65 (d, J = 4.02, 1H), 7.97 (d, J = 8.78, 1H), 7.89 (s, 1H), 7.41-7.47 (m, 1H), 2.54 (s, 3H). M/Z = 373.0 (M + 1). RT = 0.74 min, Method 1 |

TABLE 4-continued

Exemplified Compounds of the Invention

| NO | Structure | ¹HNMR and/or mass and/or (retention time (mins)) |
|---|---|---|
| 24 | 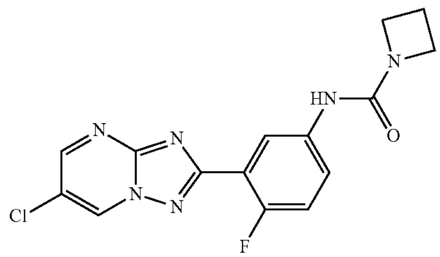 [SMILES: O=C(Nc1ccc(F)c(-c2nc3ncc(Cl)cn3n2)c1)N1CCC1] | ¹H NMR (400 MHz, MeOD) 9.50 (d, J = 2.4, 1H), 8.91 (d, J = 2.4, 1H), 8.22 (dd, J = 6.3, 2.8, 1H), 7.67 (dt, J = 8.6, 3.6, 1H), 7.21 (dd, J = 10.3, 9.0, 1H), 4.11 (t, J = 7.6, 4H), 2.33 (p, J = 7.6, 2H). M/Z = 347.0 (M + 1). RT = 0.72 min, Method 1 |
| 25 | 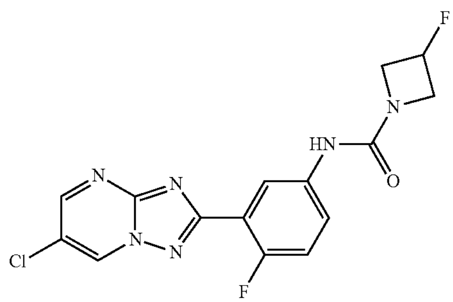 [SMILES: O=C(Nc1ccc(F)c(-c2nc3ncc(Cl)cn3n2)c1)N1CC(F)C1] | ¹H NMR (400 MHz, MeOD) 9.50 (d, J = 2.4, 1H), 8.91 (d, J = 2.5, 1H), 8.23 (dd, J = 6.3, 2.8, 1H), 7.68 (ddd, J = 9.0, 4.2, 2.8, 1H), 7.23 (dd, J = 10.4, 9.0, 1H), 5.46-5.23 (m, 1H), 4.39 (dddd, J = 20.9, 10.4, 6.1, 1.3, 2H), 4.14 (dddd, J = 24.3, 10.2, 3.1, 1.4, 2H). M/Z = 365.0 (M + 1). RT = 0.73 min, Method 1 |
| 26 | 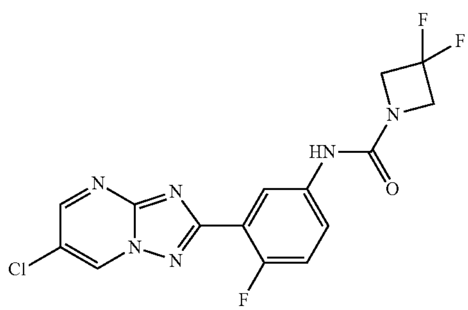 [SMILES: O=C(Nc1ccc(F)c(-c2nc3ncc(Cl)cn3n2)c1)N1CC(F)(F)C1] | ¹H NMR (400 MHz, MeOD) 9.51 (d, J = 2.4, 1H), 8.92 (d, J = 2.4, 1H), 8.25 (dd, J = 6.4, 2.8, 1H), 7.70 (ddd, J = 8.8, 4.2, 2.8, 1H), 7.24 (dd, J = 10.4, 9.0, 1H), 4.43 (t, J = 12.3, 4H). M/Z = 382.9 (M + 1). RT = 0.80 min, Method 1 |
| 27 | 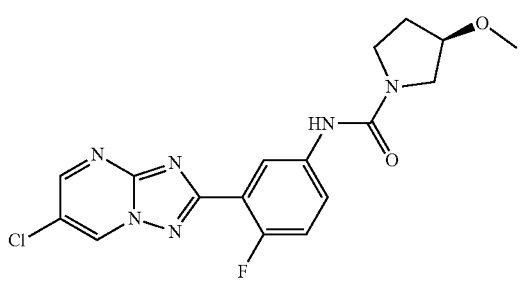 [SMILES: CO[C@@H]1CCN(C(=O)Nc2ccc(F)c(-c3nc4ncc(Cl)cn4n3)c2)C1] | ¹H NMR (400 MHz, MeOD) 9.50 (d, J = 2.4, 1H), 8.91 (d, J = 2.4, 1H), 8.22 (dd, J = 6.2, 2.8, 1H), 7.66 (ddd, J = 8.9, 4.3, 2.8, 1H), 7.23 (dd, J = 10.5, 9.0, 1H), 4.08 (dp, J = 4.6, 2.1, 1H), 3.65-3.47 (m, 4H), 3.38 (s, 3H), 2.20-2.00 (m, 2H). M/Z = 390.9 (M + 1). RT = 0.73 min, Method 1 |
| 28 | 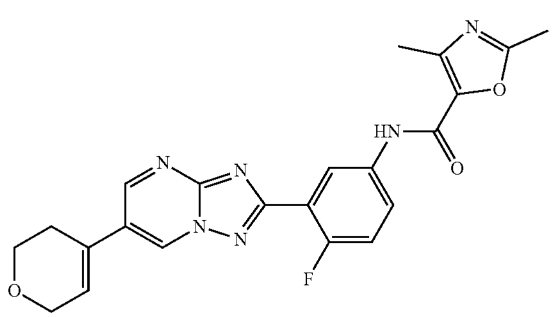 [SMILES: Cc1nc(C)c(C(=O)Nc2ccc(F)c(-c3nc4ncc(C5=CCOCC5)cn4n3)c2)o1] | ¹H NMR (400 MHz, DMSO) 10.41 (s, 1H), 9.48 (d, J = 2.01, 1H), 9.20 (d, J = 2.51, 1H), 8.73-8.83 (m, 1H), 7.90 (d, J = 8.4, 1H), 7.34-7.47 (m, 1H), 6.66 (brs, 1H), 4.29 (d, J = 2.51, 2H), 3.87 (t, J = 5.52, 2H), 2.56 (brs, 2H), 2.47-2.49 (m, 3H), 2.40 (s, 3H). M/Z = 435.1 (M + 1). RT = 2.73 min, Method 2 |

TABLE 4-continued

Exemplified Compounds of the Invention

| NO | Structure | ¹HNMR and/or mass and/or (retention time (mins)) |
|---|---|---|
| 29 | 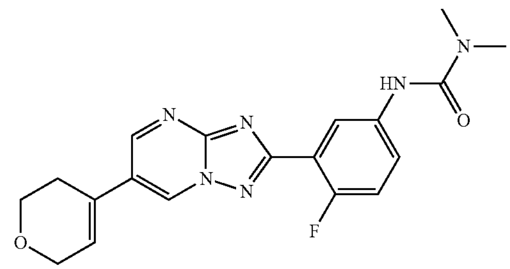 [SMILES: CN(C)C(=O)Nc1ccc(F)c(-c2nc3ncc(C4=CCOCC4)cn3n2)c1] | ¹H NMR (400 MHz, DMSO) 9.45 (brs, 1H), 9.17 (brs, 1H), 8.55 (brs, 1H), 8.40 (brs, 1H), 7.69 (brs, 1H), 7.27 (brs, 1H), 6.64 (brs, 1H), 4.28 (brs, 2H), 3.87 (brs, 2H), 2.95 (brs, 6H), 2.39 (s, 2H). M/Z = 383.0 (M + 1). RT = 0.70 min, Method 1 |
| 30 | 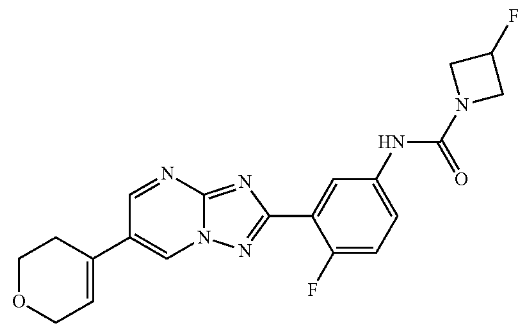 [SMILES: O=C(Nc1ccc(F)c(-c2nc3ncc(C4=CCOCC4)cn3n2)c1)N1CC(F)C1] | ¹H NMR (400 MHz, DMSO) 9.45 (brs, 1H), 9.18 (brs, 1H), 8.89 (brs, 1H), 8.40 (brs, 1H), 7.73 (brs, 1H), 7.30 (brs, 1H), 6.65 (brs, 1H), 5.33-5.48 (m, 1H), 4.29 (brs, 4H), 3.87-4.01 (m, 4H), 2.28 (s, 2H). M/Z = 413.0 (M + 1). RT = 0.74 min, Method 1 |
| 31 | 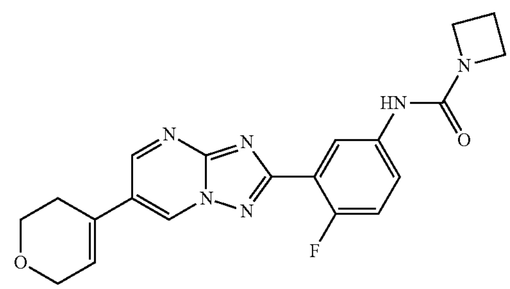 [SMILES: O=C(Nc1ccc(F)c(-c2nc3ncc(C4=CCOCC4)cn3n2)c1)N1CCC1] | ¹H NMR (400 MHz, DMSO) 9.46 (brs, 1H), 9.18 (brs, 1 H), 8.64 (brs, 1H), 8.41 (brs, 1H), 7.75 (brs, 1H), 7.28 (brs, 1H), 6.65 (brs, 1H), 4.29 (brs, 2H), 3.87-3.98 (m, 6H), 2.35 (brs, 2H), 2.20 (brs, 2H). M/Z = 395.0 (M + 1). RT = 0.72 min, Method 1 |
| 32 | 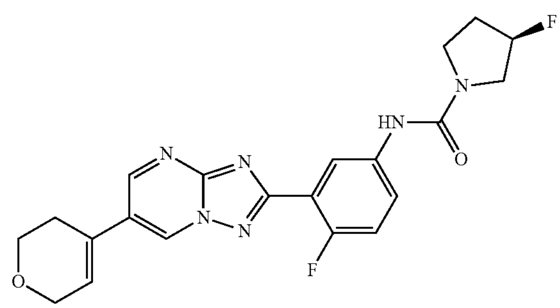 [SMILES: O=C(Nc1ccc(F)c(-c2nc3ncc(C4=CCOCC4)cn3n2)c1)N1CC[C@@H](F)C1] | ¹H NMR (400 MHz, DMSO) 9.45 (brs, 1H), 9.18 (brs, 1H), 8.55 (brs, 1H), 8.43 (brs, 1H), 7.74 (brs, 1H), 7.29 (t, J = 9.41, 1H), 6.65 (brs, 1H), 5.31-5.45 (m, 1H), 4.29 (brs, 2H), 3.67-3.87 (m, 6H), 2.52 (brs, 2H), 2.08-2.21 (m, 2H). M/Z = 427.0 (M + 1). RT = 0.75 min, Method 1 |
| 33 | 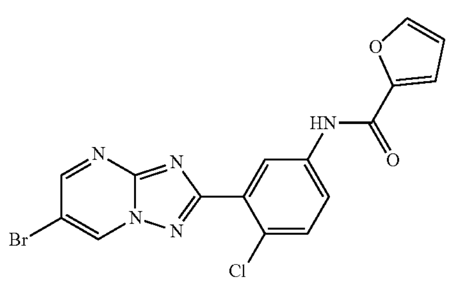 [SMILES: O=C(Nc1ccc(Cl)c(-c2nc3ncc(Br)cn3n2)c1)c1ccco1] | NMR (400 MHz, DMSO) 10.47 (s, 1H), 9.93 (d, J = 2.4, 1H), 8.98 (d, J = 2.4, 1H), 8.50 (d, J = 2.7, 1H), 7.91 (dd, J = 2.6, 8.8, 2H), 7.56 (d, J = 8.8, 1H), 7.33 (d, J = 3.5, 1H), 6.66 (dd, J = 1.7, 3.5, 1H), M/Z = 417.7 (M + 1). RT = 2.84 min, Method 2 |

TABLE 4-continued

Exemplified Compounds of the Invention

| NO | Structure | ¹HNMR and/or mass and/or (retention time (mins)) |
|---|---|---|
| 34 | 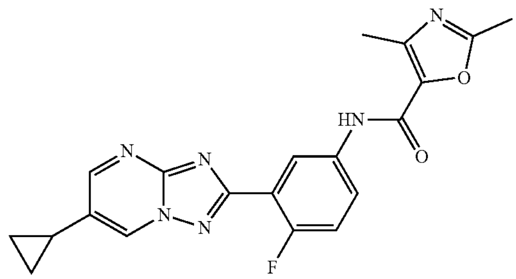 [SMILES: Cc1nc(C)c(C(=O)Nc2ccc(F)c(-c3nc4ncc(C5CC5)cn4n3)c2)o1] | ¹H NMR (400 MHz, DMSO) 10.39 (s, 1H), 9.26 (d, J = 2.26, 1H), 8.82 (d, J = 2.26, 1H), 8.73 (dd, J = 6.78, 2.76, 1H), 7.85-7.93 (m, 1H), 7.34-7.43 (m, 1H), 2.50 (s, 3H), 2.40 (s, 3H), 2.07-2.17 (m, 1H), 1.01-1.11 (m, 2H), 0.86-0.99 (m, 2H). M/Z = 393.1 (M + 1). RT = 3.22 min, Method 2 |
| 35 | 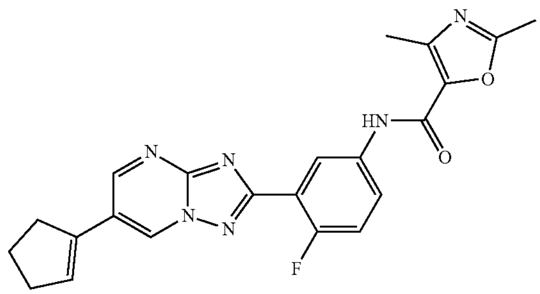 [SMILES: Cc1nc(C)c(C(=O)Nc2ccc(F)c(-c3nc4ncc(C5=CCCC5)cn4n3)c2)o1] | M/Z = 419.0 (M + 1). RT = 1.00 min, Method 1 |
| 36 | 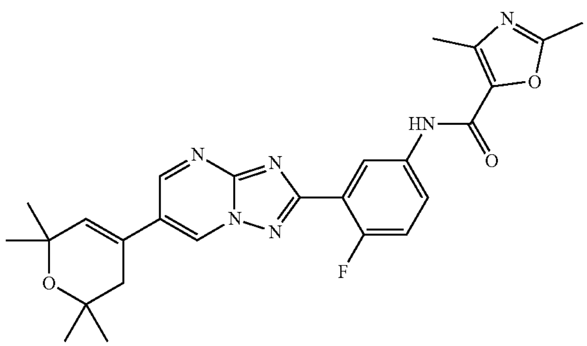 | M/Z = 491.2 (M + 1). RT = 1.03 min, Method 1 |
| 37 | 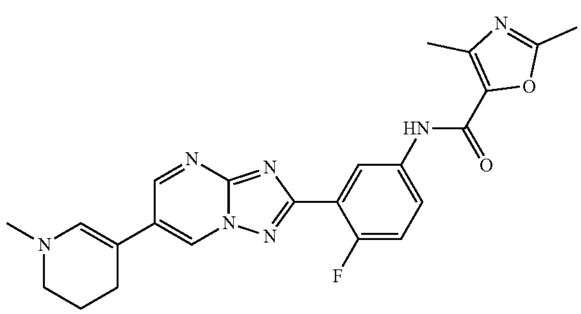 | M/Z = 448.3 (M + 1). RT = 1.24 min, Method 1 |
| 38 | 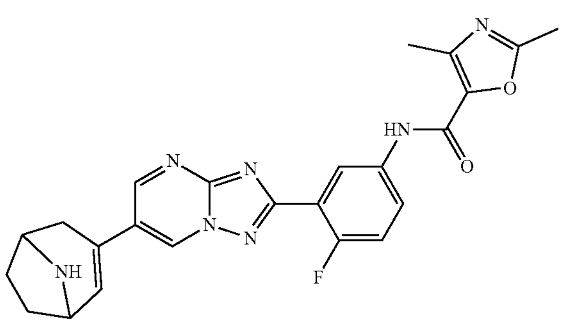 [SMILES: Cc1nc(C)c(C(=O)Nc2ccc(F)c(-c3nc4ncc(C5=CC6CCC(C5)N6)cn4n3)c2)o1] | M/Z = 460.1 (M + 1). RT = 0.56 min, Method 1 |

TABLE 4-continued

Exemplified Compounds of the Invention

| NO | Structure | ¹HNMR and/or mass and/or (retention time (mins)) |
|---|---|---|
| 39 | 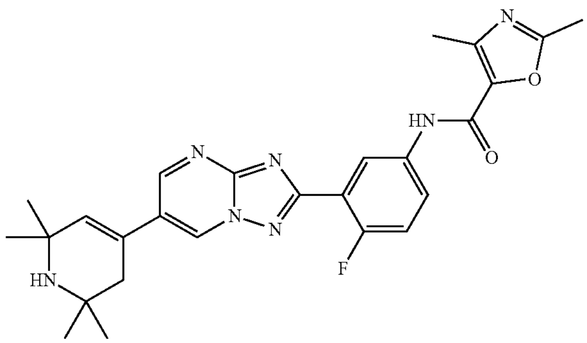 | ¹H NMR (400 MHz, DMSO) 10.36 (s, 1H), 9.36 (d, J = 2.5, 1H), 9.10 (d, J = 2.4, 1H), 8.70 (dd, J = 2.7, 6.7, 1H), 7.82 (dd, J = 2.5, 8.9, 1H), 7.38-7.29 (m, 1H), 6.43 (s, 1H), 2.50 (s, 3H), 2.33 (s, 3H), 2.20 (s, 2H), 1.15 (s, 6H), 1.08 (s, 6H). M/Z = 490.1 (M + 1). RT = 0.63 min, Method 1 |
| 40 | 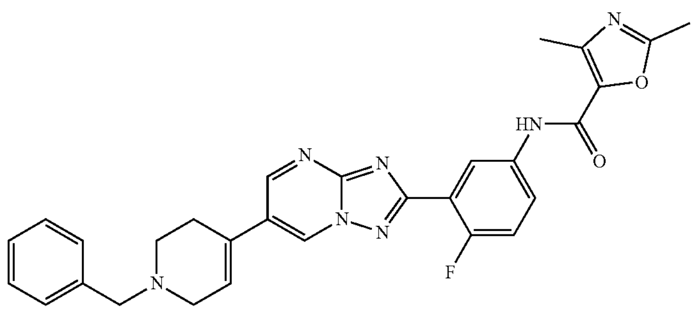 [SMILES: Cc1nc(C)c(C(=O)Nc2ccc(F)c(-c3nc4ncc(C5=CCN(Cc6ccccc6)CC5)cn4n3)c2)o1] | M/Z = 524.1(M + 1). RT = 0.67 min, Method 1 |
| 41 | 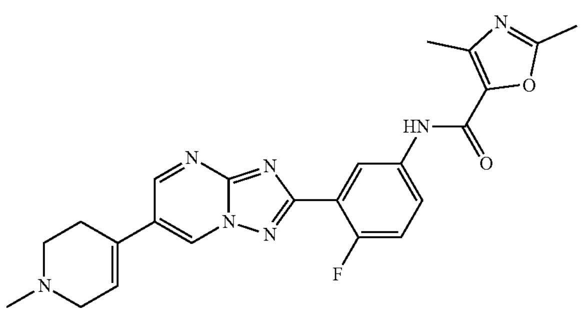 | M/Z = 448.1 (M + 1). RT = 0.56 min, Method 1 |
| 42 | 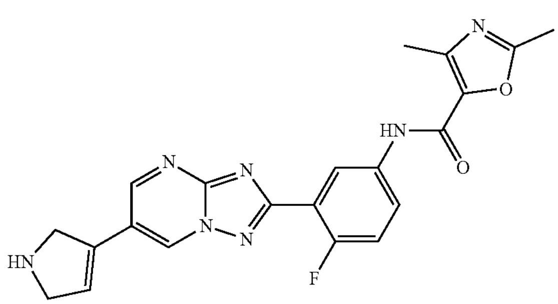 [SMILES: Cc1nc(C)c(C(=O)Nc2ccc(F)c(-c3nc4ncc(C5=CCNC5)cn4n3)c2)o1] | M/Z = 420.0 (M + 1). RT = 0.71 min, Method 1 |

TABLE 4-continued

Exemplified Compounds of the Invention

| NO | Structure | ¹HNMR and/or mass and/or (retention time (mins)) |
|---|---|---|
| 43 | 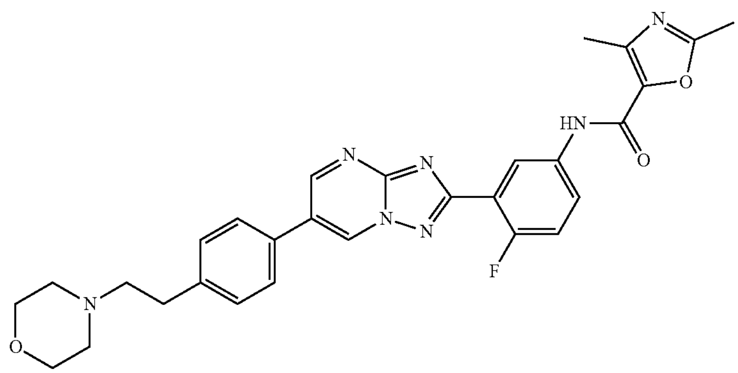 [SMILES: Cc1nc(C)c(C(=O)Nc2ccc(F)c(-c3nc4ncc(-c5ccc(CCN6CCOCC6)cc5)cn4n3)c2)o1] | ¹H NMR (400 MHz, DMSO) 10.43 (s, 1H), 9.84 (d, J = 2.4, 1H), 9.31 (d, J = 2.4, 1H), 8.81 (dd, J = 6.6, 2.7, 1H), 7.92 (ddd, J = 9.0, 4.2, 2.8, 1H), 7.86-7.78 (m, 2H), 7.43 (dd, J = 8.6, 2.0, 2H), 3.58 (t, J = 4.6, 4H), 2.82 (dd, J = 8.8, 6.5, 2H), 2.56 (dd, J = 9.0, 6.5, 2H), 2.51 (s, 3H), 2.44 (t, J = 4.4, 4H), 2.41 (s, 3H). M/Z = 542.2 (M + 1). RT = 0.64 min, Method 1 |
| 44 | 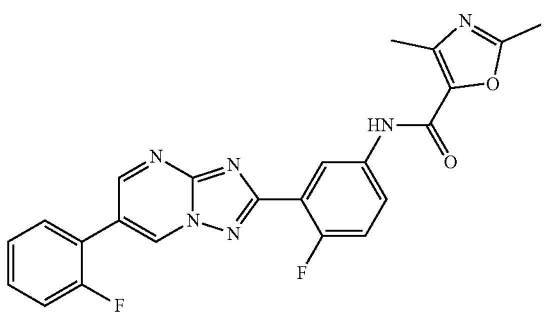 [SMILES: Cc1nc(C)c(C(=O)Nc2ccc(F)c(-c3nc4ncc(-c5ccccc5F)cn4n3)c2)o1] | ¹H NMR (400 MHz, MeOD) 9.49 (d, J = 2.4, 1H), 9.15 (t, J = 2.0, 1H), 8.54 (dt, J = 6.0, 2.9, 1H), 7.92 (ddd, J = 8.9, 4.2, 2.7, 1H), 7.75 (td, J = 7.8, 1.7, 1H), 7.56 (tdd, J = 7.4, 5.0, 1.6, 1H), 7.46-7.26 (m, 3H), 2.56 (s, 3H), 2.48 (s, 3H). M/Z = 447.3 (M + 1). RT = 3.08 min, Method 2 |
| 45 | 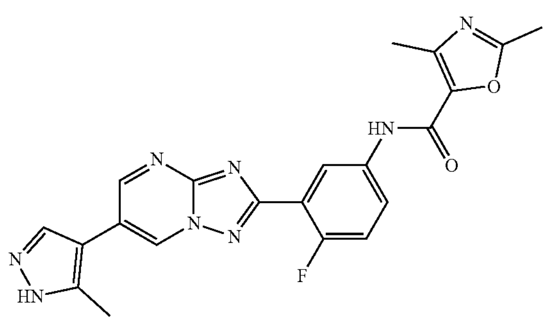 [SMILES: Cc1nc(C)c(C(=O)Nc2ccc(F)c(-c3nc4ncc(-c5cn[nH]c5C)cn4n3)c2)o1] | M/Z = 433.0 (M + 1). RT = 0.83 min, Method 1 |
| 46 | 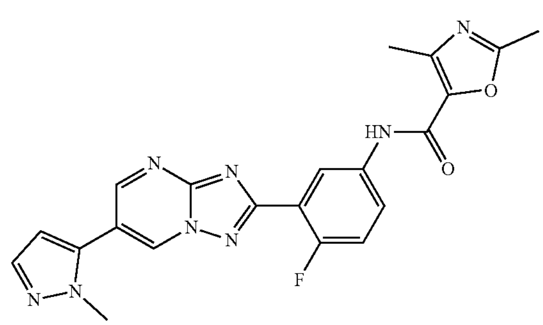 [SMILES: Cc1nc(C)c(C(=O)Nc2ccc(F)c(-c3nc4ncc(-c5ccnn5C)cn4n3)c2)o1] | ¹H NMR (400 MHz, MeOD) 9.52 (d, J = 2.3, 1H), 9.06 (d, J = 2.3, 1H), 8.56 (dd, J = 6.4, 2.8, 1H), 7.91 (ddd, J = 9.0, 4.2, 2.8, 1H), 7.34 (dd, J = 10.3, 9.0, 1H), 6.69 (d, J = 2.0, 1H), 5.50 (s, 1H), 4.02 (s, 3H), 2.56 (s, 3H), 2.48 (s, 3H). M/Z = 433.0 (M + 1). RT = 0.84 min, Method 1 |

TABLE 4-continued

Exemplified Compounds of the Invention

| NO | Structure | ¹HNMR and/or mass and/or (retention time (mins) |
|---|---|---|
| 47 | 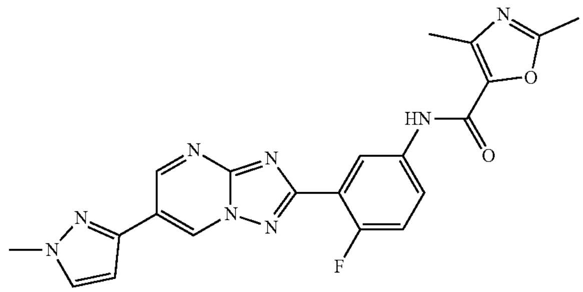 | ¹H NMR (400 MHz, MeOD) δ 9.55 (d, J = 2.3, 1H), 9.38 (d, J = 2.4, 1H), 8.51 (dt, J = 5.9, 2.9, 1H), 7.92 (ddd, J = 8.9, 4.3, 2.8, 1H), 7.74 (d, J = 2.4, 1H), 7.33 (dd, J = 10.3, 9.0, 1H), 6.88 (d, J = 2.4, 1H), 4.01 (s, 3H), 2.56 (s, 3H), 2.48 (s, 3H). M/Z = 433.2 (M + 1). RT = 1.55 min, Method 1 |
| 48 | 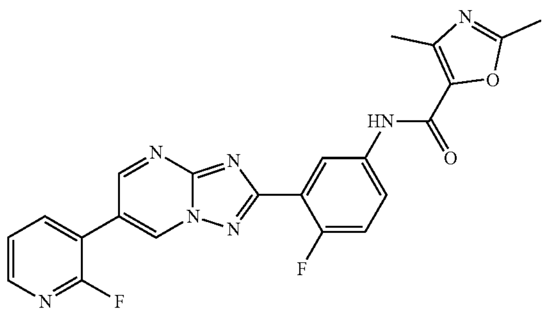 [SMILES: Cc1nc(C)c(C(=O)Nc2ccc(F)c(-c3nc4ncc(-c5cccnc5F)cn4n3)c2)o1] | M/Z = 448.0 (M + 1). RT = 0.83 min, Method 1 |
| 49 | 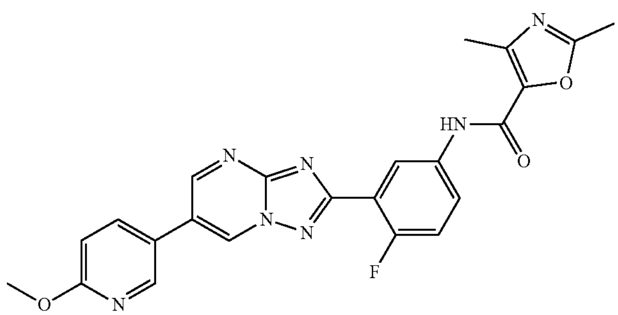 | M/Z = 460.3 (M + 1). RT = 1.59 min, Method 1 |
| 50 | 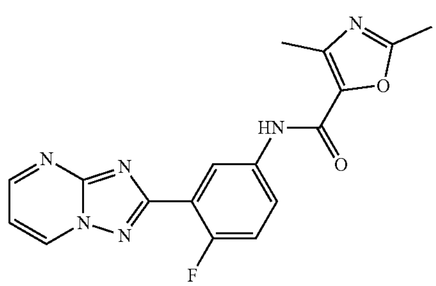 [SMILES: Cc1nc(C)c(C(=O)Nc2ccc(F)c(-c3nc4ncccn4n3)c2)o1] | ¹H NMR (400 MHz, MeOD) 9.82 (q, J = 2.2, 1H), 8.75 (d, J = 4.6, 1H), 8.11 (d, J = 7.9, 1H), 7.99 (td, J = 7.8, 1.5, 1H), 7.48 (dd, J = 7.5, 4.8, 1H), 7.32 (ddd, J = 10.4, 9.0, 2.0, 1H), 2.55 (s, 3H), 2.47 (s, 3H). M/Z = 353.1 (M + 1). RT = 0.69 min, Method 1 |
| 51 | 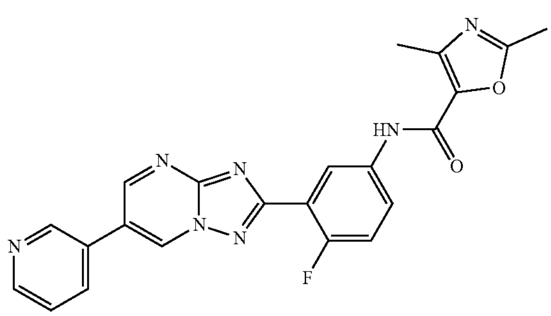 [SMILES: Cc1nc(C)c(C(=O)Nc2ccc(F)c(-c3nc4ncc(-c5cccnc5)cn4n3)c2)o1] | ¹H NMR (400 MHz, MeOD) 9.73 (q, J = 2.4, 1H), 9.44-9.12 (m, 2H), 8.99-8.64 (m, 2H), 8.55 (dt, J = 5.7, 2.5, 1H), 8.01 (h, J = 4.5, 3.8, 1H), 7.94-7.86 (m, 1H), 7.85-7.75 (m, 1H), 7.31 (t, J = 9.6, 1H), 2.56 (s, 3H), 2.48 (s, 3H). M/Z = 430.0 (M + 1). RT = 0.70 min, Method 1 |

TABLE 4-continued

Exemplified Compounds of the Invention

| NO | Structure | ¹HNMR and/or mass and/or (retention time (mins)) |
|---|---|---|
| 52 | 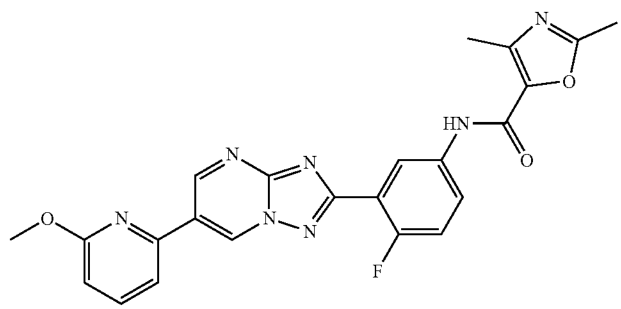 | ¹H NMR (400 MHz, DMSO) 10.44 (s, 1H), 10.10 (d, J = 2.3, 1H), 9.67 (d, J = 2.4, 1H), 8.83 (dd, J = 6.7, 2.8, 1H), 8.02-7.70 (m, 3H), 7.59-7.25 (m, 2H), 4.04 (s, 3H), 2.56 (s, 3H), 2.48 (s, 3H). M/Z = 460.0 (M + 1). RT = 0.98 min, Method 1 |
| 53 | 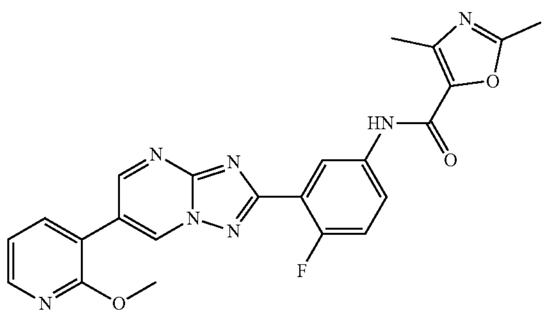 [SMILES: COc1ncccc1-c1cnc2nc(-c3cc(NC(=O)c4oc(C)nc4C)ccc3F)nn2c1] | ¹H NMR (400 MHz, DMSO) 10.44 (s, 1H), 9.73 (d, J = 2.4, 1H), 9.19 (d, J = 2.4, 1H), 8.81 (dd, J = 6.6, 2.8, 1H), 8.31 (dd, J = 5.0, 1.8, 1H), 8.08 (dd, J = 7.4, 1.9, 1H), 7.94 (ddd, J = 8.9, 6.7, 3.3, 1H), 7.54-7.28 (m, 1H), 7.22 (dd, J = 7.4, 5.0, 1H), 3.94 (s, 3H), 2.41 (s, 3H), 2.38 (s, 3H). M/Z = 460.0 (M + 1). RT = 0.86 min, Method 1 |
| 54 | 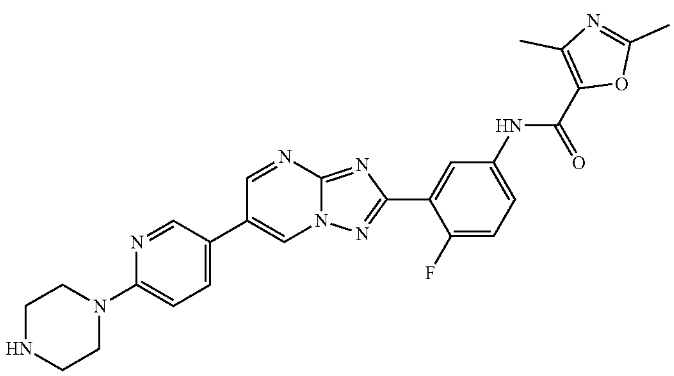 [SMILES: Cc1nc(C)c(C(=O)Nc2ccc(F)c(-c3nc4ncc(-c5ccc(N6CCNCC6)nc5)cn4n3)c2)o1] | ¹H NMR (400 MHz, DMSO) 10.44 (s, 1H), 9.85 (d, J = 2.4, 1H), 9.49 (dd, J = 6.7, 1.9, 1H), 9.31 (d, J = 2.5, 1H), 9.11-8.57 (m, 1H), 8.18 (dd, J = 9.1, 2.6, 1H), 7.90 (ddd, J = 9.1, 4.3, 2.6, 1H), 7.55-7.28 (m, 1H), 7.13 (d, J = 8.9, 1H), 3.83 (s, 4H), 3.23 (m, 4H), 2.50 (s, 3H). 2.40 (s, 3H). M/Z = 514.1 (M + 1). RT = 0.58 min, Method 1 |
| 55 | 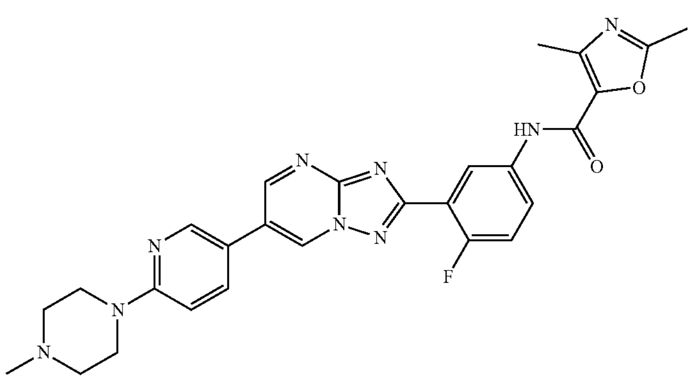 | M/Z = 528.4 (M + 1). RT = 2.15 min, Method 2 |

TABLE 4-continued

Exemplified Compounds of the Invention

| NO | Structure | ¹HNMR and/or mass and/or (retention time (mins)) |
|---|---|---|
| 56 | 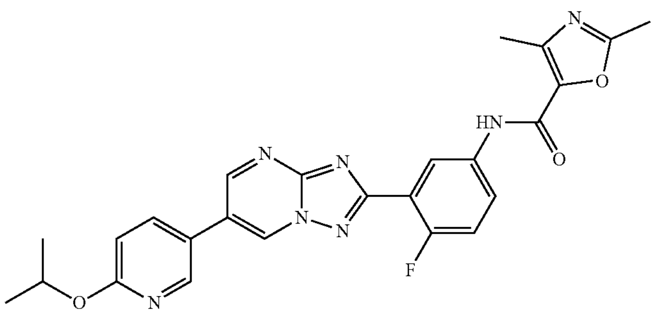 [SMILES: Cc1nc(C)c(C(=O)Nc2ccc(F)c(-c3nc4ncc(-c5ccc(OC(C)C)nc5)cn4n3)c2)o1] | M/Z = 488.3 (M + 1). RT = 3.20 min, Method 2 |
| 57 | 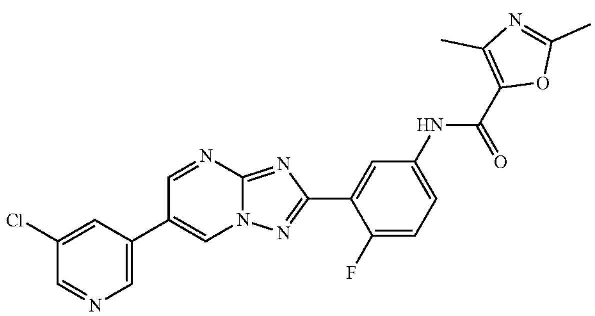 [SMILES: Cc1nc(C)c(C(=O)Nc2ccc(F)c(-c3nc4ncc(-c5cncc(Cl)c5)cn4n3)c2)o1] | M/Z = 464.2 (M + 1). RT = 2.86 min, Method 2 |
| 58 | 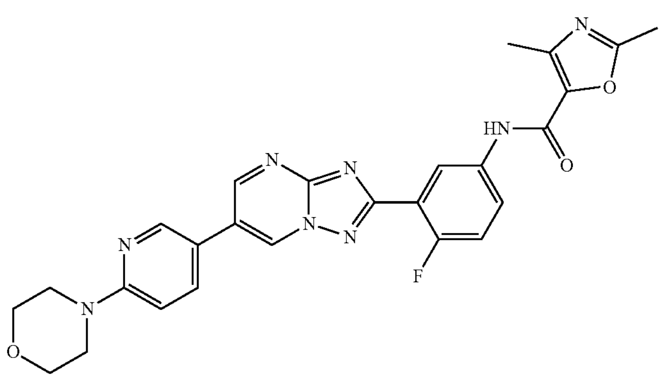 [SMILES: Cc1nc(C)c(C(=O)Nc2ccc(F)c(-c3nc4ncc(-c5ccc(N6CCOCC6)nc5)cn4n3)c2)o1] | M/Z = 515.3 (M + 1). RT = 2.77 min, Method 2 |
| 59 | 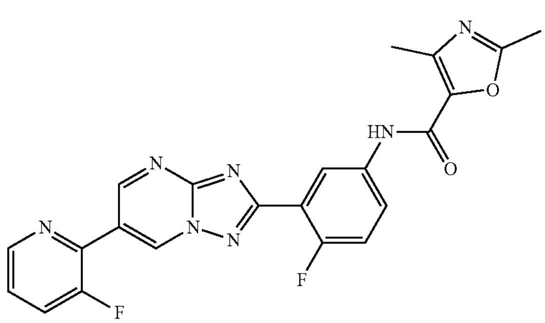 | ¹H NMR (400 MHz, MeOD) 9.84-9.75 (m, 1H), 9.63-9.52 (m, 1H), 8.66-8.62 (m, 1H), 8.57-8.48 (m, 1H), 7.95-7.76 (m, 2H), 7.62-7.52 (m, 1H), 7.37-7.27 (m, 1H), 2.57 (s, 3H), 2.48 (s, 3H). M/Z = 448.0 (M + 1). RT = 0.86 min, Method 1 |

TABLE 4-continued

Exemplified Compounds of the Invention

| NO | Structure | ¹HNMR and/or mass and/or (retention time (mins)) |
|---|---|---|
| 60 | 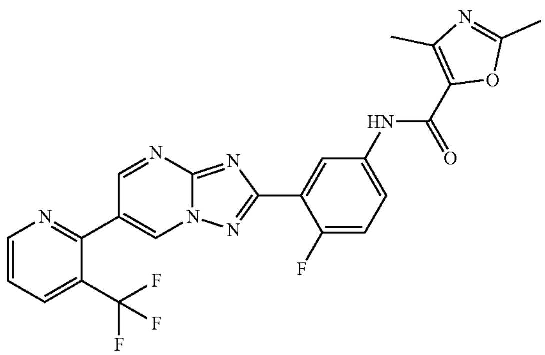 [SMILES: Cc1nc(C)c(C(=O)Nc2ccc(F)c(-c3nc4ncc(-c5ncccc5C(F)(F)F)cn4n3)c2)o1] | ¹H NMR (400 MHz, MeOD) 9.50 (d, J = 2.3, 1H), 9.08 (d, J = 2.3, 1H), 9.00 (dd, J = 5.0, 1.6, 1H), 8.56 (dd, J = 6.4, 2.7, 1H), 8.41 (dd, J = 7.9, 1.6, 1H), 7.93 (ddd, J = 8.8, 4.2, 2.8, 1H), 7.78 (dd, J = 8.1, 4.9, 1H), 7.35 (dd, J = 10.4, 9.0, 1H), 2.56 (s, 3H), 2.48 (s, 3H). M/Z = 498.1 (M + 1). RT = 0.92 min, Method 1 |
| 61 | 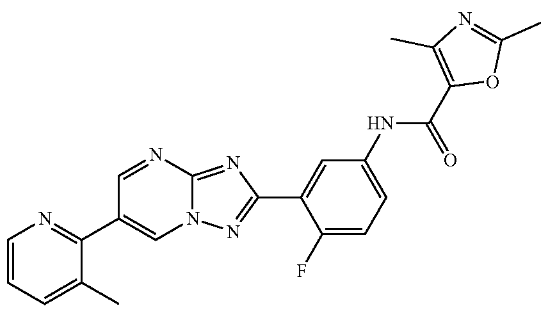 [SMILES: Cc1nc(C)c(C(=O)Nc2ccc(F)c(-c3nc4ncc(-c5ncccc5C)cn4n3)c2)o1] | ¹H NMR (400 MHz, MeOD) 9.57 (d, J = 2.4, 1H), 9.14 (d, J = 2.3, 1H), 8.67 (dd, J = 5.1, 1.6, 1H), 8.58 (dd, J = 6.4, 2.7, 1H), 8.09 (dd, J = 7.8, 1.6, 1H), 7.91 (ddd, J = 8.9, 4.3, 2.8, 1H), 7.63 (dd, J = 7.9, 5.1, 1H), 7.34 (dd, J = 10.4, 9.0, 1H), 2.56 (s, 6H), 2.48 (s, 3H). M/Z = 444.0 (M + 1). RT = 0.83 min, Method 1 |
| 62 | 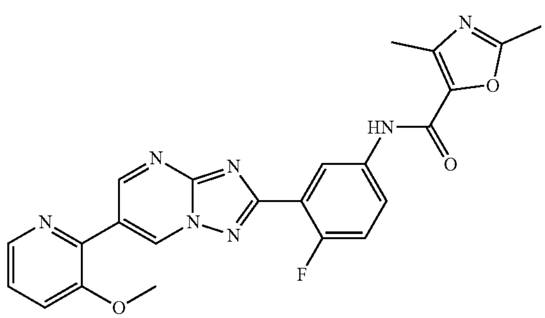 [SMILES: COc1cccnc1-c1cnc2nc(-c3cc(NC(=O)c4oc(C)nc4C)ccc3F)nn2c1] | ¹H NMR (400 MHz, MeOD) 9.82 (d, J = 2.3, 1H), 9.61 (d, J = 2.3, 1H), 8.54 (dd, J = 6.4, 2.7, 1H), 8.36 (dd, J = 4.6, 1.2, 1H), 7.92 (ddd, J = 9.0, 4.2, 2.8, 1H), 7.69 (dd, J = 8.5, 1.0, 1H), 7.50 (dd, J = 8.5, 4.7, 1H), 7.34 (dd, J = 10.3, 9.1, 1H), 4.06 (s, 3H), 2.57 (s, 3H), 2.48 (s, 3H). M/Z = 460.1 (M + 1). RT = 0.88 min, Method 1 |
| 63 | 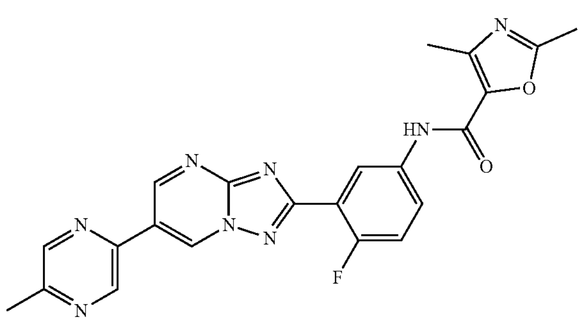 | ¹H NMR (400 MHz, MeOD) 9.93 (d, J = 2.3, 1H), 9.63 (d, J = 2.3, 1H), 9.22 (d, J = 1.5, 1H), 8.71 (s, 1H), 8.56 (dd, J = 6.3, 2.8, 1H), 7.93 (s, 1H), 7.44-7.19 (m, 1H), 2.66 (s, 3H), 2.56 (d, J = 4.1, 3H), 2.48 (d, J = 4.5, 3H). M/Z = 445.3 (M + 1). RT = 2.80 min, Method 2 |

TABLE 4-continued

Exemplified Compounds of the Invention

| NO | Structure | ¹HNMR and/or mass and/or (retention time (mins)) |
|---|---|---|
| 64 | 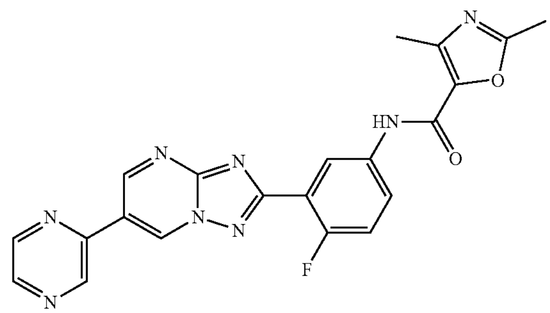 [SMILES: Cc1nc(C)c(C(=O)Nc2ccc(F)c(-c3nc4ncc(-c5cnccn5)cn4n3)c2)o1] | ¹H NMR (400 MHz, MeOD) 9.98 (d, J = 2.4, 1H), 9.66 (d, J = 2.3, 1H), 9.37 (d, J = 1.5, 1H), 8.81 (t, J = 2.0, 1H), 8.69 (d, J = 2.6, 1H), 8.07-7.80 (m, 1H), 8.62-8.44 (m, 1H), 7.45-7.15 (m, 1H), 2.56 (d, J = 4.2, 3H), 2.48 (d, J = 3.9, 3H). M/Z = 431.0 (M + 1). RT = 0.76 min, Method 1 |
| 65 | 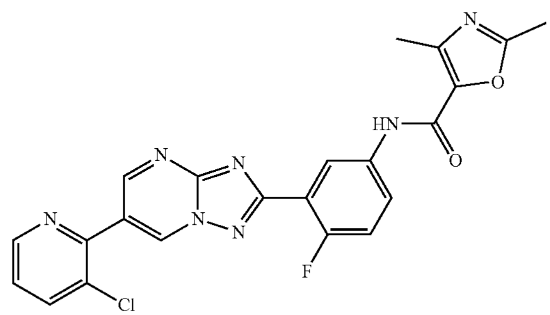 | ¹H NMR (400 MHz, MeOD) 9.71 (d, J = 2.3, 1H), 9.33 (d, J = 2.3, 1H), 8.72 (dd, J = 4.7, 1.4, 1H), 8.56 (dd, J = 6.4, 2.7, 1H), 8.11 (dd, J = 8.2, 1.4, 1H), 7.93 (ddd, J = 8.9, 4.3, 2.8, 1H), 7.54 (dd, J = 8.2, 4.6, 1H), 7.34 (dd, J = 10.3, 8.9, 1H), 2.56 (s, 3H), 2.48 (s, 3H). M/Z = 464.0 (M + 1). RT = 0.89 min, Method 1 |
| 66 | 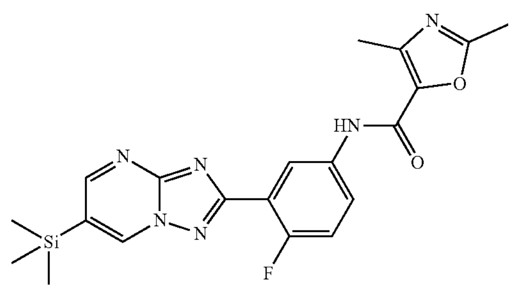 | ¹H NMR (400 MHz, DMSO) 10.39 (s, 1H), 9.42 (s, 1H), 8.95 (s, 1H), 8.77 (dd, J = 6.65, 2.63, 1H), 7.96-7.83 (m, 1H), 7.40 (t, J = 9.79, 1H), 2.50-2.48 (m, 3H), 2.40 (s, 3 H), 0.41 (s, 9H). M/Z = 425.3 (M + 1). RT = 3.20 min, Method 2 |
| 67 | 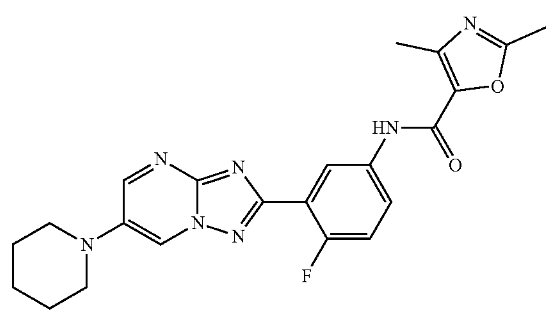 [SMILES: Cc1nc(C)c(C(=O)Nc2ccc(F)c(-c3nc4ncc(N5CCCCC5)cn4n3)c2)o1] | ¹H NMR (400 MHz, MeOD) 8.91 (d, J = 2.9, 1H), 8.59 (d, J = 2.9, 1H), 8.41 (dd, J = 2.8, 6.4, 1H), 7.87 (ddd, J = 2.8, 4.2, 8.9, 1H), 7.29 (dd, J = 9.0, 10.4, 1H), 3.28-3.19 (m, 4H), 2.56 (s, 3H), 2.47 (s, 3H), 1.81 (dt, J = 5.7, 11.2, 4H), 1.73-1.60 (m, 2H). M/Z = 436.4 (M + 1). RT = 3.04 min, Method 2 |
| 68 | 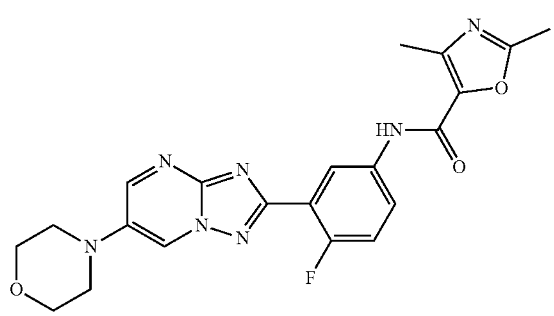 [SMILES: Cc1nc(C)c(C(=O)Nc2ccc(F)c(-c3nc4ncc(N5CCOCC5)cn4n3)c2)o1] | ¹H NMR (400 MHz, DMSO) 10.41 (s, 1H), 9.03 (d, J = 2.8, 1H), 8.95 (d, J = 2.9, 1H), 8.73 (dd, J = 6.6, 2.8, 1H), 7.87 (ddd, J = 8.9, 4.1, 2.7, 1H), 7.37 (dd, J = 10.5, 9.0, 1H), 3.79 (dd, J = 5.9, 3.5, 4H), 3.26-3.17 (m, 4H), 2.51 (s, 3H), 2.40 (s, 3H). M/Z = 438.0 (M + 1). RT = 2.70 min, Method 2 |

TABLE 4-continued

Exemplified Compounds of the Invention

| NO | Structure | ¹HNMR and/or mass and/or (retention time (mins) |
|---|---|---|
| 69 | 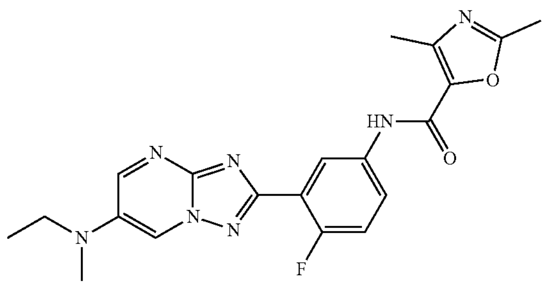 [SMILES: CCN(C)c1cnc2nc(-c3cc(NC(=O)c4oc(C)nc4C)ccc3F)nn2c1] | ¹H NMR (600 MHz, MeOD) 8.69 (d, J = 3.0, 1H), 8.28 (dd, J = 5.3, 8.0, 2H), 7.74 (d, J = 9.0, 1H), 7.16 (t, J = 9.7, 1H), 3.43 (q, J = 7.1, 2H), 2.89 (s, 3H), 2.43 (s, 3H), 2.35 (s, 3H), 1.10 (t, J = 7.1, 3H). M/Z = 410.1 (M + 1). RT = 0.85 min, Method 1 |
| 70 | 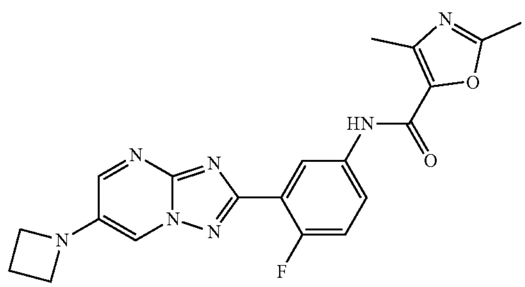 [SMILES: Cc1nc(C)c(C(=O)Nc2ccc(F)c(-c3nc4ncc(N5CCC5)cn4n3)c2)o1] | ¹H NMR (400 MHz, MeOD) 8.33 (d, J = 2.9, 1H), 8.28 (dd, J = 2.8, 6.4, 1H), 8.17 (d, J = 2.9, 1H), 7.75 (s, 1H), 7.22-7.13 (m, 1H), 3.95 (t, J = 7.3, 4H), 2.44 (s, 3H), 2.43-2.36 (m, 2H), 2.36 (s, 3H). M/Z = 408.1 (M + 1). RT = 0.80 min, Method 1 |
| 71 | 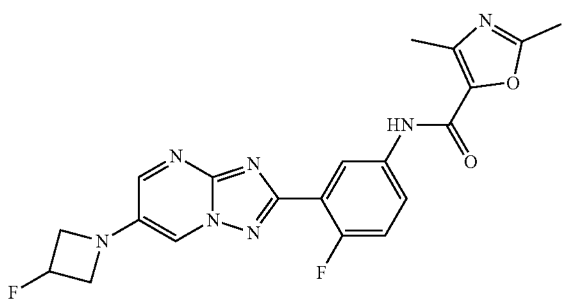 [SMILES: Cc1nc(C)c(C(=O)Nc2ccc(F)c(-c3nc4ncc(N5CC(F)C5)cn4n3)c2)o1] | ¹H NMR (400 MHz, MeOD) 8.40 (d, J = 2.9, 1H), 8.38-8.26 (m, 2H), 7.80-7.71 (m, 1H), 7.22-7.15 (m, 1H), 5.53-5.27 (m, 1H), 4.38-3.90 (m, 4H), 2.45 (s, 3H), 2.36 (s, 3H). M/Z = 426.3 (M + 1). RT = 2.68 min, Method 2 |
| 72 | 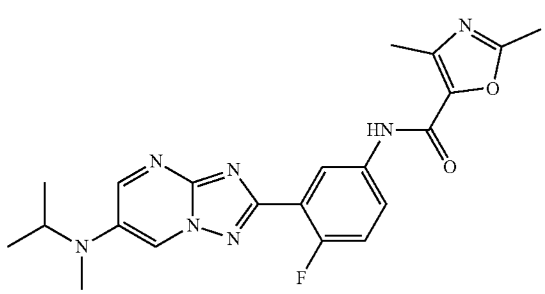 | M/Z = 424.0 (M + 1). RT = 0.91 min, Method 1 |
| 73 | 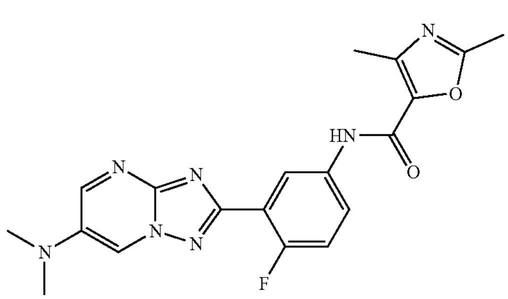 | ¹H NMR (600 MHz, MeOD) 8.82 (d, J = 3.0, 1H), 8.42 (d, J = 3.0, 1H), 8.39 (dd, J = 2.8, 6.4, 1H), 7.88-7.83 (m, 1H), 7.31-7.25 (m, 1H), 3.06 (s, 6H), 2.55 (s, 3H), 2.46 (s, 3H). M/Z = 396.1 (M + 1). RT = 0.78 min, Method 1 |

TABLE 4-continued

Exemplified Compounds of the Invention

| NO | Structure | ¹HNMR and/or mass and/or (retention time (mins)) |
|---|---|---|
| 74 | 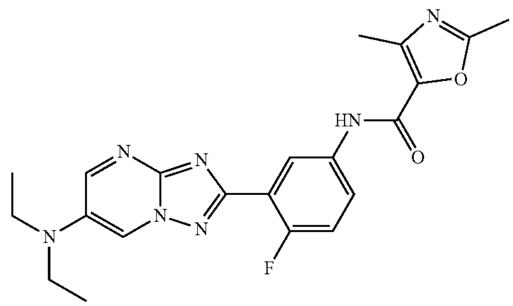 [SMILES: CCN(CC)c1cnc2nc(-c3cc(NC(=O)c4oc(C)nc4C)ccc3F)nn2c1] | M/Z = 424.1 M + 1). RT = 0.91 min, Method 1 |
| 75 | 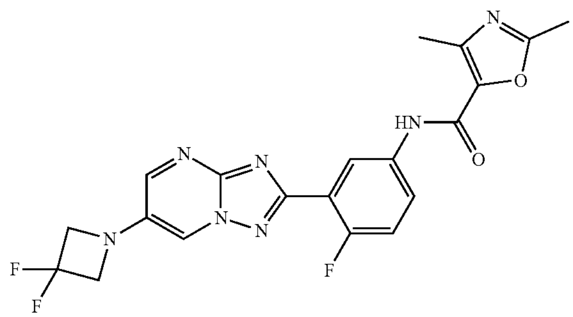 [SMILES: Cc1nc(C)c(C(=O)Nc2ccc(F)c(-c3nc4ncc(N5CC(F)(F)C5)cn4n3)c2)o1] | NMR (400 MHz, MeOD) 8.47 (s, 1H), 8.34-8.30 (m, 1H), 8.30 (s, 1H), 7.87-7.78 (m, 1H), 7.24-7.11 (m, 1H), 6.16 (d, J = 5.6, 1H), 4.95 (t, J = 11.7, 3H), 4.37 (t, J = 11.8, 1H), 2.45 (s, 3H), 2.37 (s, 3H). M/Z = 444.0 (M + 1). RT = 0.86 min, Method 1 |
| 76 | 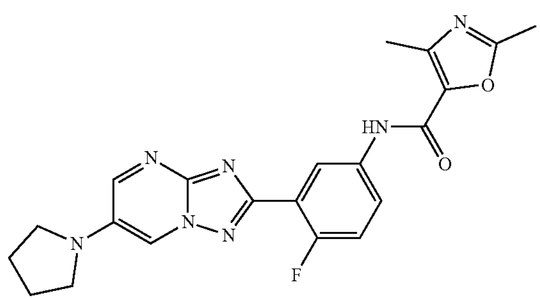 [SMILES: Cc1nc(C)c(C(=O)Nc2ccc(F)c(-c3nc4ncc(N5CCCC5)cn4n3)c2)o1] | NMR (400 MHz, MeOD) 8.57 (d, J = 2.9, 1H), 8.30 (dd, J = 2.7, 6.4, 1H), 8.22 (d, J = 2.9, 1H), 7.82-7.71 (m, 1H), 7.19 (dd, J = 9.1, 10.3, 1H), 3.32 (t, J = 6.5, 4H), 2.45 (s, 3H), 2.37 (s, 3H), 2.02 (dd, J = 5.0, 8.1, 4H). M/Z = 422.1 (M + 1). RT = 0.89 min, Method 1 |
| 77 | 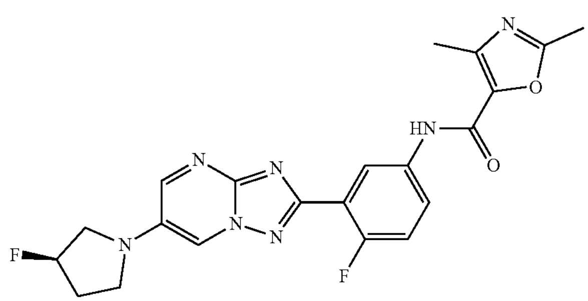 [SMILES: Cc1nc(C)c(C(=O)Nc2ccc(F)c(-c3nc4ncc(N5CC[C@@H](F)C5)cn4n3)c2)o1] | NMR (400 MHz, MeOD) 8.60 (d, J = 3.0, 1H), 8.36-8.24 (m, 2H), 7.77 (ddd, J = 2.8, 4.2, 8.9, 1H), 7.19 (dd, J = 9.1, 10.3, 1H), 5.37 (d, J = 53.3, 1H), 3.75-3.40 (m, 4H), 2.45 (s, 3H), 2.37 (s, 3H), 2.34-2.06 (m, 2H). M/Z = 440.0 (M + 1). RT = 0.82 min, Method 1 |
| 78 | 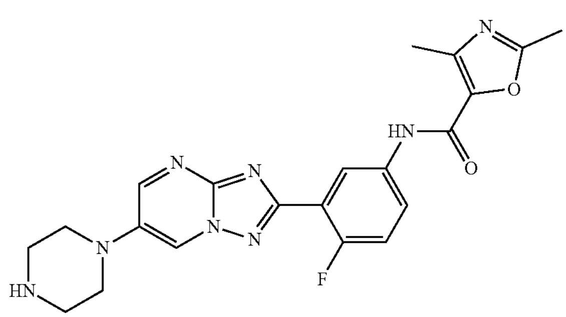 [SMILES: Cc1nc(C)c(C(=O)Nc2ccc(F)c(-c3nc4ncc(N5CCNCC5)cn4n3)c2)o1] | NMR (400 MHz, MeOD) 8.84 (d, J = 2.8, 1H), 8.55 (s, 1H), 8.32 (dd, J = 2.7, 6.4, 1H), 7.77 (dd, J = 3.8, 8.0, 1H), 7.19 (t, J = 9.7, 1H), 3.16-3.08 (m, 4H), 3.00-2.89 (m, 4H), 2.45 (s, 3H), 2.37 (s, 3H). M/Z = 437.1 (M + 1). RT = 0.56 min, Method 1 |

TABLE 4-continued

Exemplified Compounds of the Invention

| NO | Structure | ¹HNMR and/or mass and/or (retention time (mins)) |
|---|---|---|
| 79 | 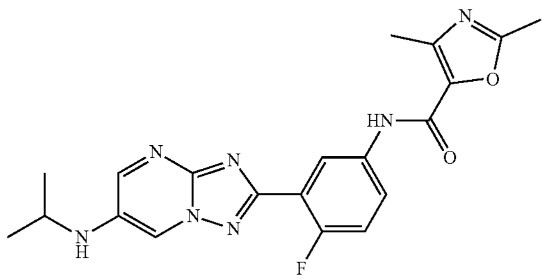 [SMILES: Cc1nc(C)c(C(=O)Nc2ccc(F)c(-c3nc4ncc(NC(C)C)cn4n3)c2)o1] | ¹H NMR (400 MHz, DMSO) 10.18-10.52 (m, 1H), 8.62-8.73 (m, 1H), 8.54 (d, J = 2.76, 1H), 8.50 (s, 1H), 7.79-7.90 (m, 1H), 7.29-7.43 (m, 1H), 6.09 (s, 1H), 3.57 (d, J = 7.28, 1H), 2.44 (s, 3H), 2.40 (s, 3H), 1.19 (d, J = 6.27, 6H). M/Z = 410.1 (M + 1). RT = 0.86 min, Method 1 |
| 80 | 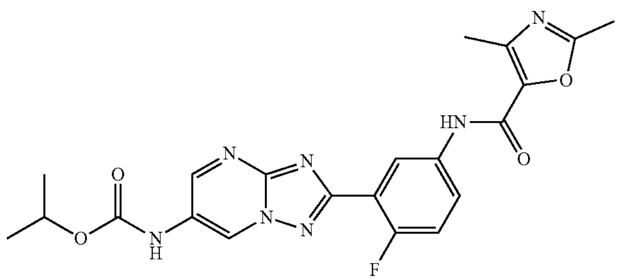 [SMILES: Cc1nc(C)c(C(=O)Nc2ccc(F)c(-c3nc4ncc(NC(=O)OC(C)C)cn4n3)c2)o1] | ¹H NMR (400 MHz, DMSO) 10.13-10.66 (m, 2H), 9.41 (s, 1H), 8.86 (s, 1H), 8.69 (dd, J = 6.53, 2.26, 1H), 7.84-7.99 (m, 1H), 7.30-7.45 (m, 1H), 4.90-5.05 (m, 1H), 2.45-2.50 (s, 3H), 2.40 (s, 3H), 1.30 (d, J = 6.02, 6H). M/Z = 454.0 (M + 1). RT = 0.87 min, Method 1 |
| 81 | 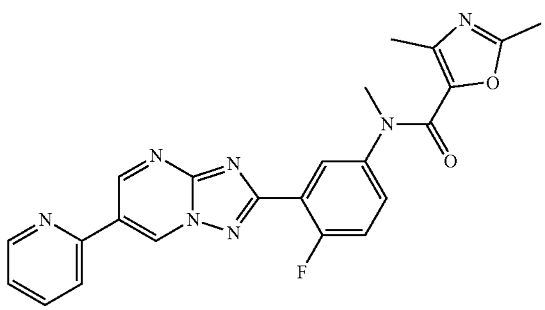 [SMILES: Cc1nc(C)c(C(=O)N(C)c2ccc(F)c(-c3nc4ncc(-c5ccccn5)cn4n3)c2)o1] | ¹H NMR (400 MHz, DMSO) 10.03 (d, J = 2.4, 1H), 9.57 (d, J = 2.4, 1H), 8.70 (ddd, J = 4.8, 1.8, 0.9, 1H), 8.17 (dt, J = 8.1, 1.0, 1H), 8.03 (dd, J = 6.5, 2.5, 1H), 7.94 (td, J = 7.8, 1.8, 1H), 7.50-7.34 (m, 3H), 3.34 (s, 3H), 2.13 (s, 3H), 2.03 (s, 3H). ¹⁹F NMR (376 MHz, DMSO) −112.83. M/Z 444.3 (M + 1). RT = 2.72 min, Method 2 |
| 82 | 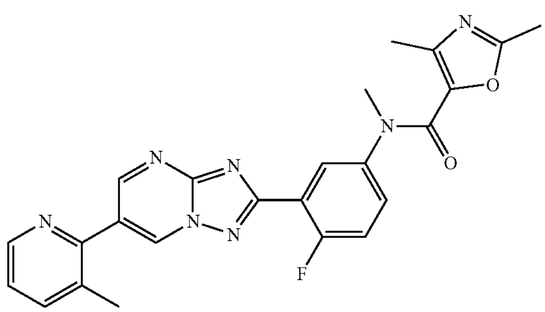 [SMILES: Cc1nc(C)c(C(=O)N(C)c2ccc(F)c(-c3nc4ncc(-c5ncccc5C)cn4n3)c2)o1] | ¹H NMR (400 MHz, MeOD) 9.39 (d, J = 2.3, 1H), 9.04 (d, J = 2.3, 1H), 8.48 (d, J = 4.0, 1H), 8.02 (dd, J = 2.8, 6.3, 1H), 7.78 (d, J = 7.8, 1H), 7.44-7.32 (m, 2H), 7.32-7.21 (m, 1H), 3.39 (s, 3H), 2.42 (s, 3H), 2.21 (s, 3H), 2.02 (s, 3H). ¹⁹F NMR (376 MHz, MeOD) −113.76. M/Z 458.3 (M + 1). RT = 0.81 min, Method 1 |
| 83 | 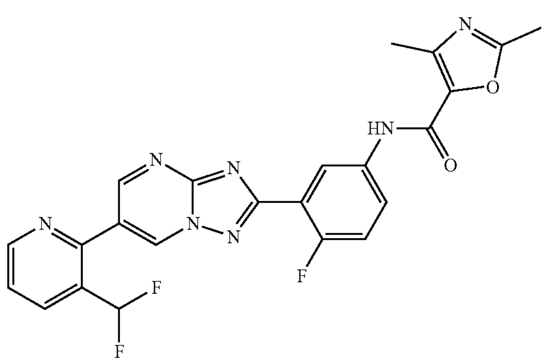 [SMILES: Cc1nc(C)c(C(=O)Nc2ccc(F)c(-c3nc4ncc(-c5ncccc5C(F)F)cn4n3)c2)o1] | ¹H NMR (400 MHz, DMSO) 10.46 (s, 1H), 9.60 (d, J = 2.26, 1H), 9.08 (d, J = 2.26, 1H), 8.96 (d, J = 4.52, 1H), 8.81 (dd, J = 6.53, 2.51, 1H), 8.31 (d, J = 7.78, 1H), 7.92-8.00 (m, 1H), 7.72-7.80 (dd, 1H), 7.14-7.49 (m, 2H), 2.48-2.50 (m, 3H), 2.41 (s, 3H). ¹⁹F NMR (400 MHz, DMSO) −116.48, −108.99. M/Z 480.0 (M + 1). RT = 0.88 min, Method 1 |

TABLE 4-continued

Exemplified Compounds of the Invention

| NO | Structure | ¹HNMR and/or mass and/or (retention time (mins) |
|---|---|---|
| 84 | 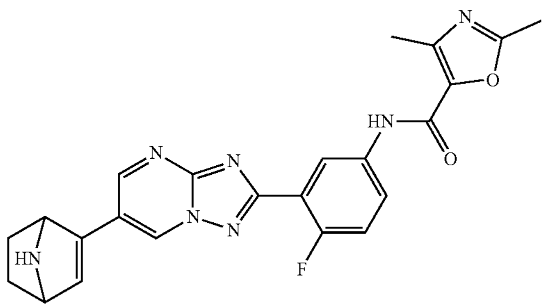 [SMILES: Cc1nc(C)c(C(=O)Nc2ccc(F)c(-c3nc4ncc(C5=CC6CCC5N6)cn4n3)c2)o1] | ¹H NMR (400 MHz, MeOD) 9.31 (d, J = 2.01, 1H), 9.12 (d, J = 2.26, 1H), 8.50 (dd, J = 6.52, 2.76, 1H), 7.84-7.96 (m, 1H), 7.26-7.38 (m, 2H), 6.96 (d, J = 1.76, 2H), 4.72 (d, J = 2.76, 1H), 4.36 (brs, 1H), 2.56 (s, 3H), 2.47 (s, 3H), 1.92-2.03 (m, 2H), 1.23-1.45 (m, 3H). M/Z 446.4 (M + 1). RT = 0.58 min, Method 1 |
| 85 | 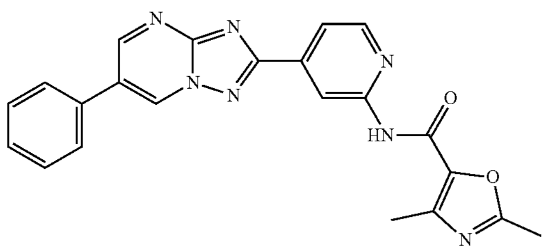 [SMILES: Cc1nc(C)c(C(=O)Nc2cc(-c3nc4ncc(-c5ccccc5)cn4n3)ccn2)o1] | ¹H NMR (400 MHz, DMSO) 9.91 (d, J = 2.26, 1H), 9.37 (d, J = 2.26, 1H), 9.04 (s, 1 H), 8.60 (d, J = 5.02, 1H), 7.90-7.97 (t, 2H), 7.59 (t, J = 7.40, 2H), 7.50-7.54 (m, 1H), 7.39 (brs, 1H) , 7.29-7.35 (m, 1H), 2.46-2.48 (m, 3H), 2.44 (s, 3H). M/Z 412.2 (M + 1). RT = 0.96 min, Method 1 |
| 86 | 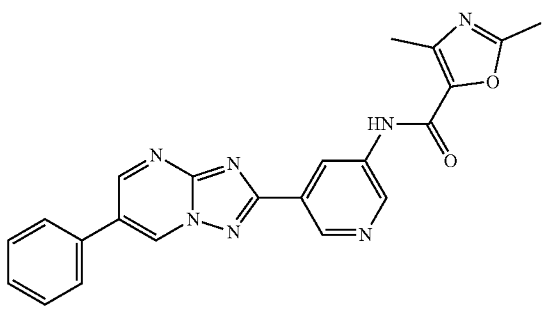 [SMILES: Cc1nc(C)c(C(=O)Nc2cncc(-c3nc4ncc(-c5ccccc5)cn4n3)c2)o1] | ¹H NMR (400 MHz, DMSO) 10.66 (brs, 1H), 9.87 (d, J = 2.51, 1H), 9.33 (d, J = 2.26, 1H), 9.15 (brs, 1H), 9.10 (brs, 1H), 9.03 (brs, 1H), 7.92 (d, J = 7.53, 2H), 7.59 (t, J = 7.53, 2H), 7.52 (d, J = 7.28, 1H), 2.46-2.48 (m, 3H), 2.44 (s, 3H). M/Z 412.2 (M + 1). RT = 0.87 min, Method 1 |
| 87 | 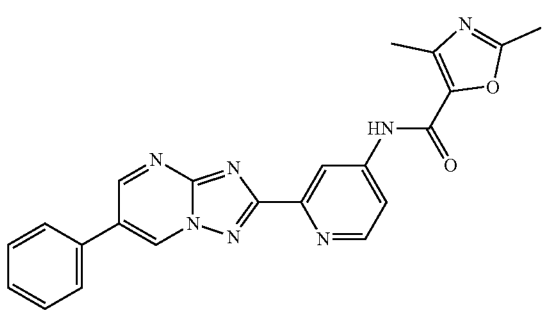 [SMILES: Cc1nc(C)c(C(=O)Nc2ccnc(-c3nc4ncc(-c5ccccc5)cn4n3)c2)o1] | ¹H NMR (400 MHz, DMSO) 10.75 (s, 1H), 9.28 (d, J = 2, 1H), 9.31 (s, 1H), 8.91 (s, 1H), 8.64 (d, J = 5 .6 , 1H), 7.90-7.92 (m, 3H), 7.50-7.60 (m, 3H), 3.6 (s, 3H), 3.02 (s, 3H). M/Z 412.3 (M + 1). RT = 0.81 min, Method 1 |
| 88 | 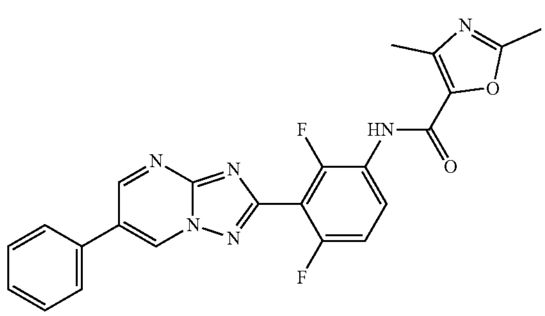 [SMILES: Cc1nc(C)c(C(=O)Nc2ccc(F)c(-c3nc4ncc(-c5ccccc5)cn4n3)c2F)o1] | ¹H NMR (400 MHz, DMSO) 10.14 (s., 1H), 9.89 (d, J = 2.51, 1H), 9.36 (d, J = 2.51, 1H), 7.93 (d, J = 7.28, 2H), 7.76 (t, J = 8.66, 1H), 7.48-7.62 (m, 3H), 7.38 (t, J = 8.91, 1H), 2.51 (s, 3H), 2.38 (s, 3H). M/Z 447.2 (M + 1). RT = 0.94 min, Method 1 |

TABLE 4-continued

Exemplified Compounds of the Invention

| NO | Structure | ¹HNMR and/or mass and/or (retention time (mins)) |
|---|---|---|
| 89 | 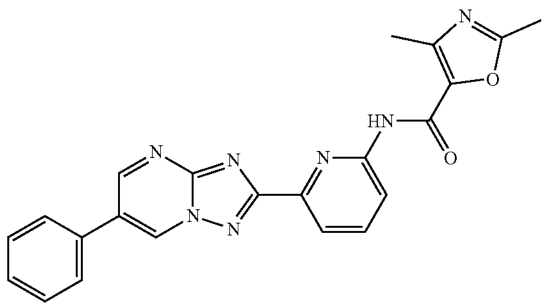 [SMILES: Cc1nc(C)c(C(=O)Nc2cccc(-c3nc4ncc(-c5ccccc5)cn4n3)n2)o1] | ¹H NMR (400 MHz, DMSO) 2.34 (br s, 3H), 2.41 (s, 3H), 7.53 (d, J = 7.28, 1H), 7.55-7.64 (m, 2H), 7.91 (d, J = 7.53, 2H), 8.04-8.14 (m, 2H), 8.26 (d, J = 7.78, 1H), 9.33 (d, J = 2.01, 1H), 9.79 (d, J = 2.26, 1H), 10.27 (s, 1H). M/Z 412.4 (M + 1). RT = 0.93 min, Method 1 |
| 90 | 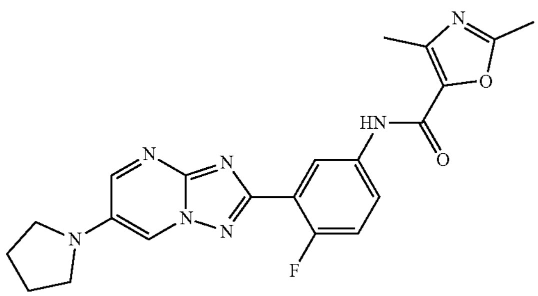 [SMILES: Cc1nc(C)c(C(=O)Nc2ccc(F)c(-c3nc4ncc(N5CCCC5)cn4n3)c2)o1] | ¹H NMR (400 MHz, DMSO) 8.53 (d, J = 2.01, 1H), 8.21 (d, J = 3.26, 1H), 8.08-8.16 (m, 1H), 8.03 (d, J = 6.02, 2H), 7.18-7.25 (m, 1H), 3.36 (br. s, 4H), 2.52 (d, J = 5.02, 6H), 2.03-2.26 (m, 4H). M/Z 422.1 (M + 1). RT = 0.89 min, Method 1 |
| 91 | 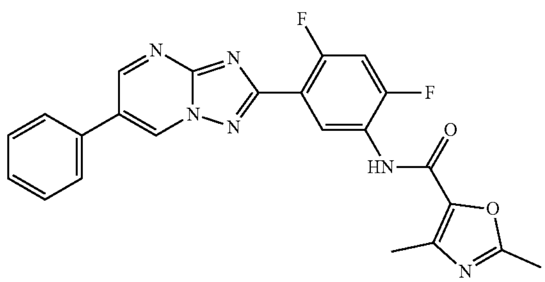 [SMILES: Cc1nc(C)c(C(=O)Nc2cc(-c3nc4ncc(-c5ccccc5)cn4n3)c(F)cc2F)o1] | ¹H NMR (400 MHz, DMSO) 10.16 (s, 1H), 9.88 (s, 1H), 9.33 (s, 1H), 8.50 (t, J = 8.0, 1H), 7.92 (d, J = 4.0, 2H), 7.51-7.65 (m, 4H), 2.39 (s, 3H), 2.40 (s, 3H). M/Z 447.2 (M + 1). RT = 0.97 min, Method 1 |
| 92 | 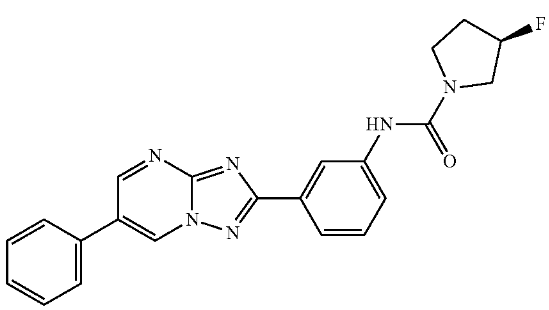 [SMILES: O=C(Nc1cccc(-c2nc3ncc(-c4ccccc4)cn3n2)c1)N1CC[C@@H](F)C1] | ¹H NMR (400 MHz, DMSO) 9.77 (s, 1H), 9.26 (s, 1H), 8.52 (d, J = 14.31, 2H), 7.89 (d, J = 7.28, 2H), 7.83 (d, J = 7.78, 1H), 7.74 (dd, J = 8.16, 1.13, 1H), 7.53-7.60 (m, 2H), 7.38-7.53 (m, 2H), 5.26-5.52 (m, 1H), 3.61-3.84 (m, 2H), 3.42-3.60 (m, 2H), 2.00-2.28 (m, 2H). M/Z 403.1 (M + 1). RT = 0.94 min, Method 1 |
| 93 | 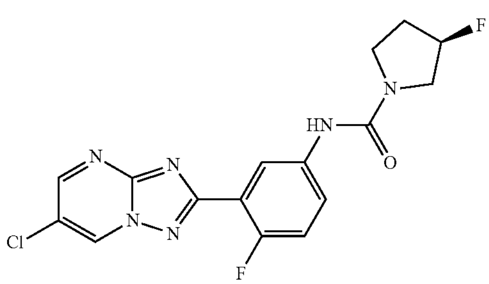 [SMILES: O=C(Nc1ccc(F)c(-c2nc3ncc(Cl)cn3n2)c1)N1CC[C@@H](F)C1] | ¹H NMR (400 MHz, DMSO) 9.92 (d, J = 2.4, 1H), 8.99 (d, J = 2.4, 1H), 8.42 (dd, J = 6, 2.4, 1H, 7.77 (dd. J = 5.2, 3.2, 1H), 7.30 (dt, J = 10.4, 9.2, 1H), 5.44 (d, J = 53.2, 1H), 3.75-3.65 (m, 2H), 3.56-3.45 (m, 2H), 2.20-2.15 (m, 2H). M/Z 379.2 (M + 1). RT = 2.61 min, Method 2 |

TABLE 4-continued

Exemplified Compounds of the Invention

| NO | Structure | ¹HNMR and/or mass and/or (retention time (mins) |
|---|---|---|
| 94 | 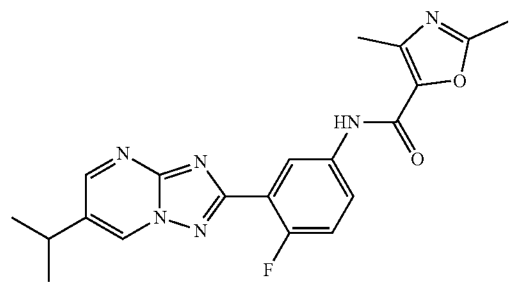 [SMILES: Cc1nc(C)c(C(=O)Nc2ccc(F)c(-c3nc4ncc(C(C)C)cn4n3)c2)o1] | ¹H NMR (400 MHz, DMSO) 10.41 (s, 1H), 9.38 (s, 1H), 8.96 (s, 1H), 8.75 (dd, J = 6.65, 2.64, 1H), 7.83-8.00 (m, 1H), 7.40 (t, J = 9.79, 1H), 3.20-3.10 (m, 1H), 2.51 (s, 3H), 2.41 (s, 3H), 1.35 (d, J = 6.78, 6H). M/Z 395.1 (M + 1). RT = 0.89 min, Method 1 |
| 95 | 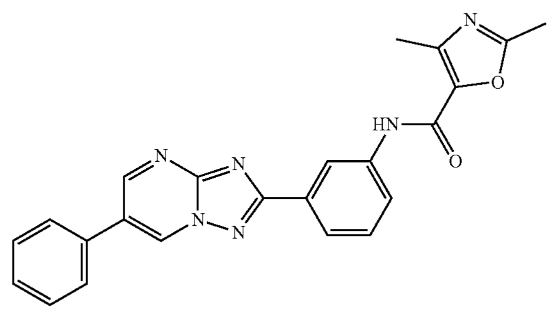 [SMILES: Cc1nc(C)c(C(=O)Nc2cccc(-c3nc4ncc(-c5ccccc5)cn4n3)c2)o1] | ¹H NMR (400 MHz, DMSO) 10.27-10.49 (m, 1H), 9.78 (s, 1H), 9.17-9.39 (m, 1H), 8.76-8.96 (m, 1H), 7.90 (d, J = 7.03, 4H), 7.40-7.70 (m, 4H), 2.51 (s, 3H), 2.41 (s, 3H). M/Z 411.0 (M + 1). RT = 0.98 min, Method 1 |
| 96 | 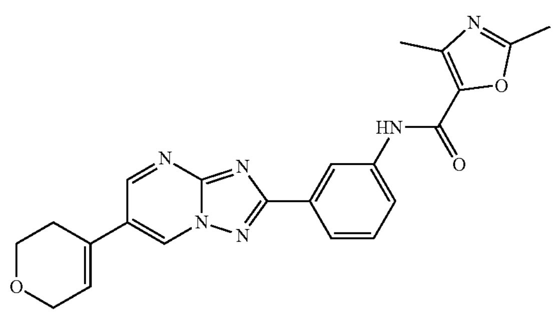 [SMILES: Cc1nc(C)c(C(=O)Nc2cccc(-c3nc4ncc(C5=CCOCC5)cn4n3)c2)o1] | ¹H NMR (400 MHz, DMSO) 10.30-10.45 (m, 1H), 9.42 (d, J = 1.76, 1H), 9.15 (d, J = 2.01, 1H), 8.81 (s, 1H), 7.91-8.02 (m, 1H), 7.85 (s, 1H), 7.52 (s, 1H), 6.64 (s, 1H), 4.28(d, J = 1.76, 2H), 3.87 (t, J = 5.27, 2H), 2.55 (s, 2H) 2.45-2.50 (m, 3H), 2.41 (s, 3H). M/Z 417.3 (M + 1). RT = 2.88 min, Method 2 |
| 97 | 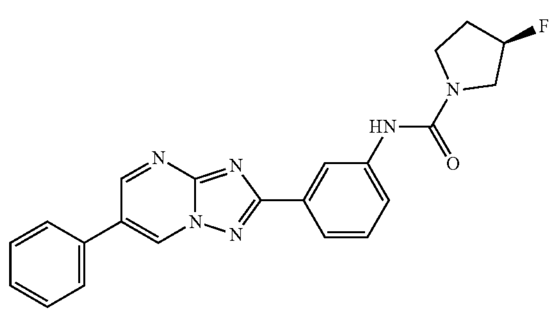 [SMILES: O=C(Nc1cccc(-c2nc3ncc(-c4ccccc4)cn3n2)c1)N1CC[C@@H](F)C1] | ¹H NMR (400 MHz, DMSO) 9.77 (s, 1H), 9.26 (s, 1H), 8.52 (d, J = 14.31, 2H), 7.89 (d, J = 7.28, 2H), 7.83 (d, J = 7.78, 1H), 7.74 (dd, J = 8.16, 1.13, 1H), 7.53-7.60 (m, 2H), 7.38-7.53 (m, 2H), 5.26-5.52 (m, 1H), 3.61-3.84 (m, 2H), 3.42-3.60 (m, 2H), 2.00-2.28 (m, 2H). M/Z 403.1 (M + 1). RT = 0.94 min, Method 1 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A method for treating Chagas disease, comprising administering to a subject in need thereof a therapeutically effective amount of N-(4-fluoro-3-(6-(3-methylpyridin-2-yl)-[1,2,4]triazolo[1,5-a]pyrimidin-2-yl)phenyl)-2,4-dimethyloxazole-5-carboxamide, or a pharmaceutically acceptable salt thereof; and optionally in combination with a second agent.

2. The method of claim 1, wherein said second agent is benznidazole, nifurtimox, amphotericin or a combination thereof.

3. The method of claim 1, wherein said second agent is benznidazole.

4. The method of claim 1, wherein said second agent is nifurtimox.

5. The method of claim 1, wherein said second agent is amphotericin.

* * * * *